US012753224B2

(12) United States Patent
Steffensen et al.

(10) Patent No.: US 12,753,224 B2
(45) Date of Patent: Oct. 6, 2026

(54) AGGRECAN BINDING IMMUNOGLOBULINS

(71) Applicants: Ablynx N.V., Zwijnaarde (BE); Merck Patent GmbH, Darmstadt (DE)

(72) Inventors: Soren Steffensen, Etterbeek (BE); Gerald Beste, Ghent (BE); Guy Hermans, Merelbeke (BE); Hans Gühring, Geisenheim (DE); Christoph Ladel, Darmstadt (DE); Lars Toleikis, Kleinniedesheim (DE)

(73) Assignees: Ablynx NV, Zwijnaarde (BE); Merck Patent GmbH, Darmstadt (DE)

( * ) Notice: Subject to any disclaimer, the term of this patent is extended or adjusted under 35 U.S.C. 154(b) by 256 days.

(21) Appl. No.: 18/145,989

(22) Filed: Dec. 23, 2022

(65) Prior Publication Data

US 2023/0312694 A1 Oct. 5, 2023

Related U.S. Application Data

(62) Division of application No. 16/617,025, filed as application No. PCT/EP2018/064608 on Jun. 4, 2018, now Pat. No. 11,603,401.

(60) Provisional application No. 62/514,180, filed on Jun. 2, 2017.

(51) Int. Cl.

| | |
|---|---|
| ***C07K 16/18*** | (2006.01) |
| ***A61P 19/02*** | (2006.01) |
| ***C07K 16/40*** | (2006.01) |

(52) U.S. Cl.

CPC .............. *C07K 16/18* (2013.01); *A61P 19/02* (2018.01); *C07K 16/40* (2013.01); *C07K 2317/22* (2013.01); *C07K 2317/24* (2013.01); *C07K 2317/31* (2013.01); *C07K 2317/33* (2013.01); *C07K 2317/569* (2013.01); *C07K 2317/92* (2013.01); *C07K 2317/94* (2013.01); *C07K 2319/00* (2013.01)

(58) Field of Classification Search

None

See application file for complete search history.

(56) References Cited

U.S. PATENT DOCUMENTS 11,603,401 B2 3/2023 Steffensen et al.

FOREIGN PATENT DOCUMENTS

| | | | | |
|---|---|---|---|---|
| CN | 101317089 A | | 12/2008 | |
| JP | 2012-531902 A | | 12/2012 | |
| WO | WO-2006122825 A2 | * | 11/2006 | ............. A61P 41/00 |
| WO | WO 2007/045661 A1 | | 4/2007 | |
| WO | WO 2010/054265 A2 | | 5/2010 | |
| WO | WO 2013/109829 A1 | | 7/2013 | |

OTHER PUBLICATIONS

Janeway et al., Immunobiology, 3rd edition, 1997, Garland Publishing Inc., pp. 3:1-3:11.*

Rudikoff et al., Proc Natl Acad Sci USA. Mar. 1982;79(6):1979-83.*

Edwards et al.,J Mol Biol. Nov. 14, 2003;334(1): 103-18.*

Llyod et al., Protein Eng Des Sel. Mar. 2009;22(3):159-68. doi: 10.1093/protein/gzn058. Epub Oct. 29, 2008.*

Goel et al., J Immunol. Dec. 15, 2004; 173(12):7358-67.*

Ghahroudi et al., FEBS Letters Sep. 15, 1997; 414(3): 521-526.*

Mateu et al., Eur J Immunol. Jun. 1992;22(6):1385-9. doi: 10.1002/eji.1830220609. PMID: 1376255.*

Winkler et al., J Immunol. Oct. 15, 2000;165(8):4505-14. doi: 10.4049/jimmunol.165.8.4505. PMID: 11035090.*

Clark et al., Protein Sci. May 2006;15(5):949-60. doi: 10.1110/ps.052030506. Epub Apr. 5, 2006. PMID: 16597831 PMCID: PMC2242497.*

Janeway et al., Immunobiology, 3rd edition, 1997, Curent Biology Ltd., New York, pp. 3:1 to 3:21.*

Dondelinger et al., Front Immunol. Oct. 16, 2018:9:2278. doi: 10.3389/fimmu.2018.02278. eCollection 2018. PMID: 30386328 PMCID: PMC6198058.*

[No Author Listed] Human Aggrecan G1-IGD-G2 Domains Antibody. Retrieved from https://resources.rndsystems.com/pdfs/datasheets/mab220.pdf on Jul. 20, 2018. 1 page.

Arbabi Ghahroudi et al., Selection and identification of single domain antibody fragments from camel heavy-chain antibodies. FEBS Lett. Sep. 15, 1997;414(3):521-6. doi: 10.1016/s0014-5793(97)01062-4.

Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.

George et al., Differential effects of anti-beta2-glycoprotein I antibodies on endothelial cells and on the manifestations of experimental antiphospholipid syndrome. Circulation. Mar. 10, 1998;97(9):900-6. doi: 10.1161/01.cir.97.9.900.

Goel et al., Plasticity within the antigen-combining site may manifest as molecular mimicry in the humoral immune response. J Immunol. Dec. 15, 2004;173(12):7358-67. doi: 10.4049/jimmunol.173.12.7358.

Harmsen et al., Properties, production, and applications of camelid single-domain antibody fragments. Appl Microbiol Biotechnol. 2007; 77(1): 13-22. EPub Aug. 18, 2007. doi: 10.1007/s00253-007-1142-2.

Janeway et al., Immunobiology. 3rd ed. Garland Publishing Inc. 1997. 3:1-3:11.

(Continued)

*Primary Examiner* — Michael Szperka

(74) *Attorney, Agent, or Firm* — Wolf, Greenfield & Sacks, P.C.

(57) ABSTRACT

The present invention relates to immunoglobulins that specifically bind Aggrecan and more in particular to polypeptides, nucleic acids encoding such polypeptides; to methods for preparing such polypeptides; to compositions and in particular to pharmaceutical compositions that comprise such polypeptides, for prophylactic, therapeutic or diagnostic purposes. In particular, the immunoglobulins of the present invention inhibit the activity of Aggrecan.

18 Claims, 7 Drawing Sheets

Figure 1:
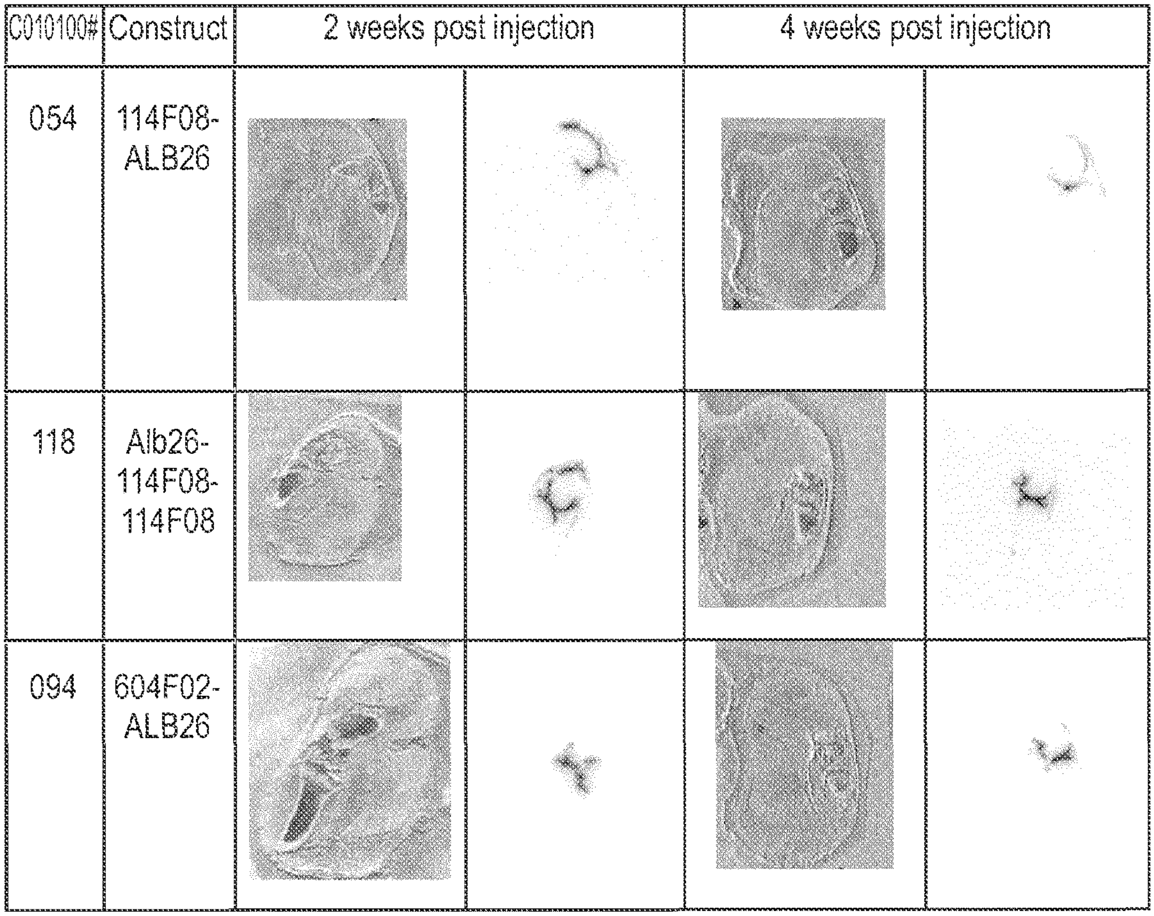

Specification includes a Sequence Listing.

(56) References Cited

OTHER PUBLICATIONS

Janune et al., Novel effects of CCN3 that may direct the differentiation of chondrocytes. FEBS Lett. 2011;585(19):3033-3040. doi:10.1016/j.febslet.2011.08.024.

Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.

Niwa et al., IgG subclass-independent improvement of antibody-dependent cellular cytotoxicity by fucose removal from Asn297-linked oligosaccharides. J Immunol Methods. Nov. 30, 2005;306(1-2):151-60. doi: 10.1016/j.jim.2005.08.009. Epub Sep. 22, 2005.

Pan et al., Research Progress in Single-Domain Antibody. Chinese Bulletin of Life Sciences. May 2012;24(5):404-10. doi: 10.13376/j.cbls/2012.05.001.

Roitt et al., Immunology. Moscow, Mir. 2000;110-111.

Rudikoff et al., Single amino acid substitution altering antigen-binding specificity. Proc Natl Acad Sci U S A. Mar. 1982;79(6):1979-83. doi: 10.1073/pnas.79.6.1979.

Siegwart Jr, et al., Selective modulation of scleral proteoglycan mRNA levels during minus lens compensation and recovery. Mol Vis. Oct. 4, 2007;13:1878-86.

Singer et al., Genes and Genomes. University Science Books. Mill Valley, CA. Section 8.3: Structure and Expression of Class II Genes. 1991. pp. 478-539. pp. 63-4 of 1998 Russian publication also included which correspond to pp. 506-509 of English language publication.

Sztrolovics et al., The mechanism of aggrecan release from cartilage differs with tissue origin and the agent used to stimulate catabolismiochem J. 2002;362(Pt 2):465-472. doi:10.1042/0264-6021:3620465.

Yamane-Ohnuki et al., Production of therapeutic antibodies with controlled fucosylation. MAbs. May-Jun. 2009;1(3):230-6. doi: 10.4161/mabs.1.3.8328. Epub May 28, 2009.

* cited by examiner

| Target | C010100 # | Construct | $T_0$ |
|---|---|---|---|
| G1 | 054 | 114F08-ALB26 |  |
| G1 | 118 | ALB26-114F08-114F08 | |
| G1-IGD-G2 | 094 | 604F02-ALB26 | |
| Dummy | 030 | ALB26-ALB26 | |

| Target | C010100 # | Construct | Intact surface |
|---|---|---|---|
| G1 | 054 | 114F08-ALB26 |  |
| G1 | 118 | ALB26-114F08-114F08 |  |
| G1-IGD-G2 | 094 | 60F02-ALB26 |  |
| Dummy | 030 | ALB26-ALB26 |  |

AGGRECAN BINDING IMMUNOGLOBULINS

RELATED APPLICATIONS

This Application is a divisional of U.S. Application Ser. No. 16/617,025, filed Nov. 26, 2019, now U.S. Pat. No. 11,603,401, which is a national stage filing under 35 U.S.C. 371 of International Application Serial No. PCT/EP2018/064608, filed Jun. 4, 2018, which claims priority under 35 U.S.C. § 119(e) of U.S. provisional Application Ser. No. 62/514,180, filed Jun. 2, 2017, the entire contents of each of which are incorporated by reference herein in its entirety.

REFERENCE TO AN ELECTRONIC SEQUENCE LISTING

The instant application contains a Sequence Listing which has been submitted in XML format and is hereby incorporated by reference in its entirety. Said Sequence Listing, created on Dec. 21, 2022, is named A084870206US02-SEQ-CRP, and is 235,984 bytes in size.

FIELD OF THE INVENTION

The present invention relates to immunoglobulins that bind Aggrecan and more in particular to polypeptides, that comprise or essentially consist of one or more such immunoglobulins (also referred to herein as “immunoglobulin(s) of the invention”, and “polypeptides of the invention”, respectively). The invention also relates to constructs comprising such immunoglobulins or polypeptides as well as nucleic acids encoding such immunoglobulins or polypeptides (also referred to herein as “nucleic acid(s) of the invention”; to methods for preparing such immunoglobulins, polypeptides and constructs; to host cells expressing or capable of expressing such immunoglobulins or polypeptides; to compositions, and in particular to pharmaceutical compositions, that comprise such immunoglobulins, polypeptides, constructs, nucleic acids and/or host cells; and to uses of immunoglobulins, polypeptides, constructs, nucleic acids, host cells and/or compositions, in particular for prophylactic and/or therapeutic purposes, such as the prophylactic and/or therapeutic purposes mentioned herein. Other aspects, embodiments, advantages and applications of the invention will become clear from the further description herein.

BACKGROUND

Osteoarthritis is one of the most common causes of disability worldwide. It affects 30 million Americans and is the most common joint disorder. It is projected to affect more than 20 percent of the U.S. population by 2025. The disease can occur in all joints, most often the knees, hips, hands and spine. Osteoarthritis (OA) can be defined as a diverse group of conditions characterised by a combination of joint symptoms, signs stemming from defects in the articular cartilage and changes in adjacent tissues including bone, tendons and muscle. OA is characterized by progressive erosion of articular cartilage (cartilage that covers the bones). Eventually, the disease leads to the total destruction of the articular cartilage, sclerosis of underlying bone, osteophyte formation etc., all leading to loss of movement and pain. Pain is the most prominent symptom of OA and this is most often the reason patients seek medical help.

Aggrecan is the major proteoglycan in the articular cartilage (Kiani et al. 2002 Cell Research 12:19-32). This molecule is important in the proper functioning of the articular cartilage because it provides a hydrated gel structure that endows the cartilage with load-bearing properties. Aggrecan is a large, multimodular molecule (2317 amino acids) expressed by chondrocytes. Its core protein is composed of three globular domains (G1, G2 and G3) and a large extended region between G2 and G3 for glycosaminoglycan chain attachment. This extended region comprises two domains, one substituted with keratan sulfate chains (KS domain) and one with chondroitin sulfate chains (CS domain). The CS domain has 100-150 glycosaminoglycan (GAG) chains attached to it. Aggrecan forms large complexes with Hyaluronan in which 50-100 Aggrecan molecules interact via the G1 domain and Link Protein with one Hyaluronan molecule. Upon uptake of water (due to the GAG content) these complexes form a reversibly deformable gel that resists compression. The structure, fluid retention and function of joint cartilage is linked to the matrix content of Aggrecan, and the amount of chondroitin sulfate bound to the intact core protein.

OA is characterized by 1) degradation of Aggrecan, progressively releasing domains G3 and G2 (resulting in ‘deflation’ of the cartilage) and eventually release of the G1 domain and 2) degradation of Collagen, irreversibly destroying the cartilage structure.

Although aging, obesity and joint injury have been identified as risk factors leading to osteoarthritis, the cause of OA is unknown and there are currently no pharmacological treatments that halt the disease progression or cure the joints. For large joints, a drug could be injected into the joint to help to limit potential side effects, like pain. Therapeutic strategies are primarily aimed at reducing pain and improving joint function. Fasinumab, a non-opioid anti-NGF pain treatment has been shown to give improvements on a key pain score during phase II/III trials. Duloxetine was approved for the treatment of chronic knee pain due to osteoarthritis and has been conditionally recommended by the American College of Rheumatology. Strontium ranelate was found to significantly decrease the rate of decline in joint space width as well as improve pain scores compared with placebo in a large multicenter study in patients with symptomatic knee osteoarthritis. However, at this moment the biologic agents interleukin-1 receptor antagonists and antitumor necrosis factor antibodies have neither been shown to be efficacious nor to alter the course of osteoarthritis (Smelter Hochberg 2013 Current Opin. Rheumatol. 25:310). Hence, many such therapies are ineffective and/or are associated with side effects. Ultimately patients will undergo total knee or hip replacement therapy if pain cannot be controlled.

Pharmacological therapy begins with oral administration of paracetamol either combined with NSAIDS or COX-2 inhibitors and a weak opioid. Major disadvantages of oral administration of drugs are the limited bio-availability at the site of interest and the risk of side effects, such as liver damage, Gastro-intestinal (GI)-ulcers, GI-bleeding and constipation.

As OA has a localized nature, intra-articular administration of drugs provides an excellent opportunity to improve treatment. However, most of the newly developed disease modifying osteoarthritis drugs (DMOADs) have a short residence time in the joint, even when administered intra-articularly (Edwards 2011 Vet. J. 190:15-21; Larsen et al. 2008 J Pham Sci 97:4622-4654). Intra-articular (IA) delivery of therapeutic proteins has been limited by their rapid clearance from the joint space and lack of retention within cartilage. Synovial residence time of a drug in the joint is often less than 24 h. Due to the rapid clearance of most IA injected drugs, frequent injections would be needed to maintain an effective concentration (Owen et al. 1994 Br. J. Clin Pharmacol. 38:349-355). However, frequent IA-injections are undesired due to the pain and discomfort they may cause challenging patient compliance, as well as the risk of introducing joint infections.

Loffredo et al. tested whether targeted delivery to cartilage by fusion with a heparin-binding domain would be sufficient to prolong the in vivo function of the insulin-like growth factor 1 (IGF-1). Heparin is present in mast cells. However, the natural role of Heparin is unknown, but it is widely used as a blood-thinner (Loffredo et al. 2014 Arthritis Rheumatol. 66:1247-1255).

There remains a need for further cartilage anchoring proteins (CAP).

SUMMARY OF THE INVENTION

The present inventors hypothesized that the efficacy of a therapeutic drug could be increased significantly by coupling the therapeutic drug to a moiety which would "anchor" the drug in the joint and consequently increase retention of the drug, but which should not disrupt the efficacy of said therapeutic drug (also indicated herein as "cartilage anchoring protein" or "CAP"). This anchoring concept would not only increase the efficacy of drug, but also the operational specificity for a diseased joint by decreasing toxicity and side-effects, thus widening the number of possible useful drugs. The present inventors further hypothesized that Aggrecan binders might potentially function as such an anchor, although Aggrecan is heavily glycosylated and degraded in various disorders affecting cartilage in joints. Moreover, in view of the costs and extensive testing in various animal models required before a drug can enter the clinic, such Aggrecan binders should preferentially have a broad cross-reactivity, e.g. the Aggrecan binders should bind to Aggrecan of various species.

Using various ingenious immunization, screening and characterization methods, the present inventors were able to identify a number of Aggrecan binders with superior selectivity, stability and/or specificity features, which enabled prolonged retention and activity in the joint.

Accordingly, the present invention relates to an immunoglobulin single variable domain (ISV) that specifically binds to Aggrecan, preferably said ISV specifically binds to human Aggrecan (SEQ ID NO: 125), and/or wherein said ISV specifically binds to dog Aggrecan (SEQ ID NO: 126), bovine Aggrecan (SEQ ID NO: 127), rat Aggrecan (SEQ ID NO: 128), pig (core) Aggrecan (SEQ ID NO: 129), mouse Aggrecan (SEQ ID NO: 130), rabbit Aggrecan (SEQ ID NO: 131), cynomolgus Aggrecan (SEQ ID NO: 132) and/or rhesus Aggrecan (SEQ ID NO: 133), even more preferably, wherein said ISV does not bind substantially to Neurocan (SEQ ID NO: 134) and/or Brevican (SEQ ID NO: 135).

In an aspect, the present invention relates to an ISV as described herein, wherein the ISV has more than fold, more than 100 fold, preferably more than 1000 fold selectivity over Neurocan and/or Brevican for binding to Aggrecan, and/or said ISV preferably binds to cartilaginous tissue such as cartilage and/or meniscus, and/or said ISV has a stability of at least 7 days, such as 14 days, 21 days, 1 month, 2 months or even 3 months in synovial fluid (SF) at 37° C., and/or said ISV has a cartilage retention of at least 2, such as at least, 3, 4, 5 or 6 RU in a cartilage retention assay, and/or said ISV penetrates into the cartilage by at least 5 μm, such as at least 10 μm, 20 μm, 30 μm, 40 μm, 50 am or even more, and/or said ISV essentially consists of a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation.

In an aspect, the present invention relates to an ISV as described herein, that essentially consists of 4 framework regions (FR1 to FR4, respectively) and 3 complementarity determining regions (CDR1 to CDR3, respectively), in which: CDR1 is chosen from the group consisting of SEQ ID NOs: 24, 20, 21, 22, 23, 25, 26, 27, 28, 29, 30, 31, 32, 33, 34, 35, 36, 37 and 109; CDR2 is chosen from the group consisting of SEQ ID NOs: 42, 38, 39, 40, 41, 43, 44, 45, 46, 47, 48, 49, 50, 51, 52, 53, 54, 55 and 110; and CDR3 is chosen from the group consisting of SEQ ID NOs: 60, 56, 57, 58, 59, 61, 62, 63, 64, 65, 66, 67, 68, 69, 70, 71, 72, 73, 74 and 111.

In an aspect, the present invention relates to an ISV as described herein, wherein said ISV binds to the G1 domain of Aggrecan, preferably said ISV has a pl of more than 8, and/or said ISV has a Koff of less than $2*10^{-2}$ $s^{-1}$, and/or said ISV has an $EC_{50}$ of less than $1*10^{-6}$M.

In an aspect, the present invention relates to an ISV as described herein, that essentially consists of 4 framework regions (FR1 to FR4, respectively) and 3 complementarity determining regions (CDR1 to CDR3, respectively), in which:

i) CDR1 is chosen from the group consisting of: a) SEQ ID NOs: 24, 20, or 21; or b) amino acid sequences that have 5, 4, 3, 2, or 1 amino acid(s) difference with the amino acid sequence of SEQ ID NO: 24, wherein at position 2 the S has been changed into R, F, I, or T; at position 3 the T has been changed into I; at position 5 the I has been changed into S; at position 6 the I has been changed into S, T, or M; at position 7 the N has been changed into Y, or R; at position 8 the V has been changed into A, Y, T, or G; at position 9 the V has been changed into M; and/or at position 10 the R has been changed into G, K, or A; and/or ii) CDR2 is chosen from the group consisting of: c) SEQ ID NOs: 42, 38, or 39; or d) amino acid sequences that have 5, 4, 3, 2, or 1 amino acid(s) difference with the amino acid sequence of SEQ ID NO: 42, wherein at position 1 the T has been changed into A, or G; an S or N is inserted between position 3 and position 4 (position 2a Table 1.3B); at position 3 the S has been changed into R, W, N, or T; at position 4 the S has been changed into T or G; at position 5 the G has been changed into S; at position 6 the G has been changed into S, or R; at position 7 the N has been changed into S, T, or R; at position 8 the A has been changed into T; and/or at position 9 the N has been changed into D or Y; and/or iii) CDR3 is chosen from the group consisting of: e) SEQ ID NO: 60, 56 or 57; or f) amino acid sequences that have 5, 4, 3, 2, or 1 amino acid(s) difference with the amino acid sequence of SEQ ID NO: 60, wherein at position 1 the P has been changed into G, R, D, or E, or is absent; at position 2 the T has been changed into R, L, P, or V, or is absent; at position 3 the T has been changed into M, S, or R, or is absent; at position 4 the H has been changed into D, Y, G, or T; at position 5 the Y has been changed into F, V, T or G; at position 6 the G has been changed into L, D, S, Y, or W; an R, T, Y or V is inserted between position 6 and position 7 (position 6a Table 1.3C); at position 7 the G has been changed into P, or S; at position 8 the V has been changed into G, T, H, R, L, or Y; at position 9 the Y has been changed into R, A, S, D or G; at position 10 the Y has been changed into N, E, G, W, or S; a W is inserted between position 10 and position 11 (position 10a Table 1.3C); at position 11 the G has been changed into S, K, or Y; at position 12 the P has been changed into E, or D, or is absent; and/or at position 13 the Y has been changed into L, or is absent.

In an aspect, the present invention relates to an ISV as described herein, wherein said ISV is chosen from the group of ISVs, wherein: CDR1 is chosen from the group consisting of SEQ ID NOs: 24, 20, 21, 25, 27, 29, 31, 34, 35, 36, 37 and 109; CDR2 is chosen from the group consisting of SEQ ID NOs: 42, 38, 39, 43, 45, 47, 49, 50, 53, 54, 55, and 110; and CDR3 is chosen from the group consisting of SEQ ID NOs: 60, 56, 57, 61, 63, 65, 67, 71, 72, 73, 74, and 111.

In an aspect, the present invention relates to an ISV as described herein, wherein said ISV is chosen from the group of ISVs, wherein:

CDR1 is SEQ ID NO: 24, CDR2 is SEQ ID NO: 42, and CDR3 is SEQ ID NO: 60;

CDR1 is SEQ ID NO: 20, CDR2 is SEQ ID NO: 38, and CDR3 is SEQ ID NO: 56;

CDR1 is SEQ ID NO: 21, CDR2 is SEQ ID NO: 39, and CDR3 is SEQ ID NO: 57;

CDR1 is SEQ ID NO: 25, CDR2 is SEQ ID NO: 43, and CDR3 is SEQ ID NO: 61;

CDR1 is SEQ ID NO: 27, CDR2 is SEQ ID NO: 45, and CDR3 is SEQ ID NO: 63;

CDR1 is SEQ ID NO: 29, CDR2 is SEQ ID NO: 47, and CDR3 is SEQ ID NO: 65;

CDR1 is SEQ ID NO: 31, CDR2 is SEQ ID NO: 49, and CDR3 is SEQ ID NO: 67;

CDR1 is SEQ ID NO: 34, CDR2 is SEQ ID NO: 50, and CDR3 is SEQ ID NO: 71;

CDR1 is SEQ ID NO: 35, CDR2 is SEQ ID NO: 53, and CDR3 is SEQ ID NO: 72;

CDR1 is SEQ ID NO: 36, CDR2 is SEQ ID NO: 54, and CDR3 is SEQ ID NO: 73; and

CDR1 is SEQ ID NO: 37, CDR2 is SEQ ID NO: 55, and CDR3 is SEQ ID NO: 74.

In an aspect, the present invention relates to an ISV as described herein, that essentially consists of 4 framework regions (FR1 to FR4, respectively) and 3 complementarity determining regions (CDR1 to CDR3, respectively), in which:

i) CDR1 is chosen from the group consisting of: a) SEQ ID NO: 24 and 109; or b) amino acid sequences that have 2, or 1 amino acid(s) difference with the amino acid sequence of SEQ ID NO: 24, wherein at position 7 the N has been changed into S; and/or at position 9 the V has been changed into M; and/or ii) CDR2 is chosen from the group consisting of: c) SEQ ID NO: 42 and 110; or d) amino acid sequences that have 5, 4, 3, 2, or 1 amino acid(s) difference with the amino acid sequence of SEQ ID NO: 42, wherein at position 1 the T has been changed into A; at position 3 the S has been changed into R; at position 4 the S has been changed into T; at position 8 the A has been changed into T; and/or at position 9 the N has been changed into D; and/or iii) CDR3 is chosen from the group consisting of: e) SEQ ID NO: 60 and 111; or f) amino acid sequences that have 2, or 1 amino acid(s) difference with the amino acid sequence of SEQ ID NO: 60, wherein at position 4 the H has been changed into R; and/or at position 8 the V has been changed into D.

In an aspect, the present invention relates to an ISV as described herein, wherein said ISV is chosen from the group of ISVs, wherein CDR1 is chosen from the group consisting of SEQ ID NOs: 24 and 109; CDR2 is chosen from the group consisting of SEQ ID NOs: 42 and 110; and CDR3 is chosen from the group consisting of SEQ ID NOs: 60 and 111.

In an aspect, the present invention relates to an ISV as described herein, wherein said ISV belongs to epitope bin 1 or epitope bin 4, preferably said ISV essentially consists of 4 framework regions (FR1 to FR4, respectively) and 3 complementarity determining regions (CDR1 to CDR3, respectively), in which:

i) CDR1 is chosen from the group consisting of: a) SEQ ID NO: 36; and b) amino acid sequences that have 2, or 1 amino acid(s) difference with the amino acid sequence of SEQ ID NO: 36, wherein at position 3 the T has been changed into S; at position 6 the T has been changed into S; at position 8 the T has been changed into A; and/or at position 9 the M has been changed into V; and/or ii) CDR2 is chosen from the group consisting of: c) SEQ ID NO: 54; and d) amino acid sequences that have 5, 4, 3, 2, or 1 amino acid(s) difference with the amino acid sequence of SEQ ID NO: 54, wherein at position 1 the A has been changed into I; at position 4 the W has been changed into R; at position 7 the G has been changed into R; and/or at position 8 the T has been changed into S; and/or iii) CDR3 is chosen from the group consisting of: e) SEQ ID NO: 73; and f) amino acid sequences that have 5, 4, 3, 2, or 1 amino acid(s) difference with the amino acid sequence of SEQ ID NO: 73, wherein at position 1 the R has been changed into G; at position 2 the P has been changed into R or L; at position 3 the R has been changed into L or S; at position 5 the Y has been changed into R; at position 6 the Y has been changed into S or A; at position 7 the Y has been changed into T, or is absent; at position 8 the S has been changed into P; at position 9 the L has been changed into H or R; at position the Y has been changed into P or A; at position 11 the S has been changed into A or Y; at position 12 the Y has been changed into D; at position 13 the D has been changed into F; at position 14 the Y has been changed into G, or is absent; and/or after position 14 an S is inserted.

In an aspect, the present invention relates to an ISV as described herein, wherein said ISV is chosen from the group of ISVs, wherein: CDR1 is chosen from the group consisting of SEQ ID NOs: 20, 29, and 36; CDR2 is chosen from the group consisting of SEQ ID NOs: 38, 47, and 54; and CDR3 is chosen from the group consisting of SEQ ID NOs: 56, 65, and 73.

In an aspect, the present invention relates to an ISV as described herein, wherein said ISV cross-blocks the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G1 domain of Aggrecan.

In an aspect, the present invention relates to an ISV, a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to epitope bin 1 of the G1-domain of Aggrecan, and which competes for binding to the G1 domain of Aggrecan with the ISV as described herein.

In an aspect, the present invention relates to an ISV as described herein, that essentially consists of 4 framework regions (FR1 to FR4, respectively) and 3 complementarity determining regions (CDR1 to CDR3, respectively), in which: i) CDR1 is chosen from the group consisting of: a) SEQ ID NO: 24; and b) amino acid sequences that have 2, or 1 amino acid(s) difference with the amino acid sequence of SEQ ID NO: 24, wherein at position 2 the S has been changed into I or F; at position 5 the I has been changed into S; at position 6 the I has been changed into S or M; at position 7 the N has been changed into R or Y; at position 8 the V has been changed into A or Y; at position 9 the V has been changed into M; and/or at position 10 the R has been changed into K; and/or ii) CDR2 is chosen from the group consisting of: c) SEQ ID NO: 42; and d) amino acid sequences that have 5, 4, 3, 2, or 1 amino acid(s) difference with the amino acid sequence of SEQ ID NO: 42, wherein at position 1 the T has been changed into A or G; an N is inserted between position 2 and position 3 (position 2a Table 2.3B); at position 7 the N has been changed into R; at position 8 the A has been changed into T; and/or at position 9 the N has been changed into D; and/or iii) CDR3 is chosen from the group consisting of: e) SEQ ID NO: 60; and f) amino acid sequences that have 5, 4, 3, 2, or 1 amino acid(s) difference with the amino acid sequence of SEQ ID NO: 60, wherein at position 1 the P is absent; at position 2 the T has been changed into R or is absent; at position 3 the T has been changed into M or is absent; at position 4 the H has been changed into D or Y; at position 5 the Y has been changed into F or V; at position 6 the G has been changed into L or D; at position 8 the V has been changed into G or T; at position 9 the Y has been changed into R; at position 10 the Y has been changed into N or E; at position 11 the G has been changed into S or K; at position 12 the P has been changed into E or is absent; and/or at position 13 the Y has been changed into L or is absent; preferably CDR1 is chosen from the group consisting of SEQ ID NOs: 24, 25, and 27; CDR2 is chosen from the group consisting of SEQ ID NOs: 42, 43, and 45; and CDR3 is chosen from the group consisting of SEQ ID NOs: 60, 61, and 63; even more preferably, wherein said ISV cross-blocks the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G1 domain of Aggrecan.

In an aspect, the present invention relates to an ISV as described herein, a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to epitope bin 4 of the G1-domain of Aggrecan, and which competes for binding to the G1 domain of Aggrecan with the ISV as described herein.

In an aspect, the present invention relates to an ISV as described herein, wherein said ISV is chosen from the group consisting of ISVs with SEQ ID NOs: 5, 1, 2, 6, 8, 10, 12, 16, 17, 18, and 19, and ISVs which have more than 80%, such as 90% or 95% sequence identity with any one of SEQ ID NOs: 5, 1, 2, 6, 8, 10, 12, 16, 17, 18, and 19.

In an aspect, the present invention relates to an ISV as described herein, wherein said ISV binds to the G1-IGD-G2 domain of Aggrecan, preferably wherein said ISV has a pI of more than 8 and/or has a Koff of less than $2*10^{-2}$ $s^{-1}$ and/or has an EC50 of less than $1*10^{-6}$M.

In an aspect, the present invention relates to an ISV as described herein, in which: i) CDR1 is chosen from the group consisting of: a) SEQ ID NO: 32, 30 and 23; and b) amino acid sequences that have 3, 2, or 1 amino acid(s) difference with the amino acid sequence of SEQ ID NO: 32, wherein at position 2 the R has been changed into L; at position 6 the S has been changed into T; and/or at position 8 the T has been changed into A; and/or ii) CDR2 is chosen from the group consisting of: c) SEQ ID NO: 50, 41, 48 and 51; and d) amino acid sequences that have 2, or 1 amino acid(s) difference with the amino acid sequence of SEQ ID NO: 50, wherein at position 7 the G has been changed into S or R; and/or at position 8 the R has been changed into T; and/or iii) CDR3 is chosen from the group consisting of: e) SEQ ID NO: 68, 59, 66 and 69; and f) amino acid sequences that have 5, 4, 3, 2, or 1 amino acid(s) difference with the amino acid sequence of SEQ ID NO: 68, wherein at position 4 the R has been changed into V, or P; at position 6 the A has been changed into Y; at position 7 the S has been changed into T; at position 8 the S is absent; at position 9 the N has been changed into P; at position 10 the R has been changed into T or L; at position 11 the G has been changed into E; and/or at position 12 the L has been changed into T or V, preferably, wherein said ISV is chosen from the group of ISVs, wherein: CDR1 is chosen from the group consisting of SEQ ID NOs: 32, 30 and 23; CDR2 is chosen from the group consisting of SEQ ID NOs: 50, 41, 48 and 51; and CDR3 is chosen from the group consisting of SEQ ID NOs: 68, 59, 66 and 69, even more preferably, wherein said ISV is chosen from the group of ISVs, wherein: CDR1 is SEQ ID NO: 32, CDR2 is SEQ ID NO: 50, and CDR3 is SEQ ID NO: 68; CDR1 is SEQ ID NO: 32, CDR2 is SEQ ID NO: 51, and CDR3 is SEQ ID NO: 69; CDR1 is SEQ ID NO: 30, CDR2 is SEQ ID NO: 48, and CDR3 is SEQ ID NO: 66; and CDR1 is SEQ ID NO: 23, CDR2 is SEQ ID NO: 41, and CDR3 is SEQ ID NO: 59.

In an aspect, the present invention relates to an ISV as described herein, wherein said ISV is chosen from the group consisting of ISVs with SEQ ID NOs: 13, 4, 11 and 14, and ISVs which have more than 80%, such as 90% or 95% sequence identity with any one of SEQ ID NOs: 13, 4, 11 and 14.

In an aspect, the present invention relates to an ISV as described herein, wherein said ISV cross-blocks the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G1-IGD-G2 domain of Aggrecan. In an aspect, the present invention relates to an ISV, a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to the G1-IGD-G2 domain of Aggrecan, and which competes for binding to the G1-IGD-G2 domain of Aggrecan with the ISV as described herein.

In an aspect, the present invention relates to an ISV as described herein, wherein said ISV binds to the G2 domain of Aggrecan, preferably wherein said ISV has a pl of more than 8, and/or has a Koff of less than $2*10^{-2}$ $s^{-1}$ and/or has an EC50 of less than $1*10^{-6}$M In an aspect, the present invention relates to an ISV as described herein, in which: i) CDR1 is chosen from the group consisting of: a) SEQ ID NO: 28; and b) amino acid sequences that have 5, 4, 3, 2, or 1 amino acid(s) difference with the amino acid sequence of SEQ ID NO: 28, wherein at position 1 the G has been changed into R; at position 2 the P has been changed into S or R; at position 3 the T has been changed into I; at position 5 the S has been changed into N; at position 6 the R has been changed into N, M, or S; at position 7 the Y has been changed into R or is absent; at position 8 the A has been changed into F or is absent; and/or at position 10 the G has been changed into Y; and/or ii) CDR2 is chosen from the group consisting of: c) SEQ ID NO: 46; and d) amino acid sequences that have 5, 4, 3, 2, or 1 amino acid(s) difference with the amino acid sequence of SEQ ID NO: 46, wherein at position 1 the A has been changed into S, or Y; at position 4 the W has been changed into L; at position 5 the S has been changed into N; at position 6 the S is absent; at position 7 the G is absent; at position 8 the G has been changed into A; at position 9 the R has been changed into S, D, or T; and/or at position 11 the Y has been changed into N or R; and/or iii) CDR3 is chosen from the group consisting of: e) SEQ ID NO: 64; and f) amino acid sequences that have 5, 4, 3, 2, or 1 amino acid(s) difference with the amino acid sequence of SEQ ID NO: 64, wherein at position 1 the A has been changed into R, or F; at position 2 the R has been changed into I, or L; at position 3 the I has been changed into H, or Q; at position 4 the P has been changed into G, or N; at position the V has been changed into S; at position 6 the R has been changed into G, N, or F; at position 7 the T has been changed into R, W, or Y; at position 8 the Y has been changed into R, or S, or is absent; at position 9 the T has been changed into S, or is absent; at position 10 the S has been changed into E, K or is absent; at position 11 the E has been changed into N, A, or is absent; at position 12 the W has been changed into D, or is absent; at position 13 the N has been changed into D, or is absent; at position 14 the Y is absent; and/or D and/or N are added after position 14 of SEQ ID NO: 64; preferably wherein said ISV is chosen from the group of ISVs, wherein: CDR1 is chosen from the group consisting of SEQ ID NOs: 28, 22, 26, and 33; CDR2 is chosen from the group consisting of SEQ ID NOs: 46, 40, 44, and 52; and CDR3 is chosen from the group consisting of SEQ ID NOs: 64, 58, 62, and 70; even more preferably, wherein said ISV is chosen from the group of ISVs, wherein: CDR1 is SEQ ID NO: 28, CDR2 is SEQ ID NO: 46, and CDR3 is SEQ ID NO: 64; CDR1 is SEQ ID NO: 22, CDR2 is SEQ ID NO: 40, and CDR3 is SEQ ID NO: 58; CDR1 is SEQ ID NO: 26, CDR2 is SEQ ID NO: 44, and CDR3 is SEQ ID NO: 62; and CDR1 is SEQ ID NO: 33, CDR2 is SEQ ID NO: 52, and CDR3 is SEQ ID NO: 70.

In an aspect, the present invention relates to an ISV as described herein, wherein said ISV is chosen from the group consisting of ISVs with SEQ ID NOs: 9, 3, 7 and 15, and ISVs which have more than 80%, such as 90% or 95% sequence identity with any one of SEQ ID NOs: 9, 3, 7 and 15.

In an aspect, the present invention relates to an ISV as described herein, wherein said ISV cross-blocks the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G2 domain of Aggrecan. In an aspect, the present invention relates to an ISV, a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to the G2-domain of Aggrecan, and which competes for binding to the G2 domain of Aggrecan with the ISV as described herein.

In an aspect, the present invention relates to an ISV as described herein, wherein said ISV is chosen from the group consisting of SEQ ID NO:s 1-19 and 114-118 and ISVs which have more than 80%, such as 90% or 95% sequence identity with any one of SEQ ID NOs: 1-19 and 114-118.

In an aspect, the present invention relates to a polypeptide comprising at least one ISV as described herein, preferably said comprises at least two ISVs as described herein, wherein said at least two ISVs can be the same or different. Preferably, said at least two ISVs are independently chosen from the group consisting of SEQ ID NOs: 1-19 and 114-118, more preferably wherein said at least two ISVs are chosen from the group consisting of SEQ ID NOs: 5, 6, 8 and 114-117 or wherein said at least two ISVs are chosen from the group consisting of SEQ ID NOs: 13 and 118.

Preferably, in an aspect, the polypeptide of the invention comprises at least one further ISV, e.g. a therapeutic ISV. Preferably, said at least one further ISV binds to a member of the serine protease family, cathepsins, matrix metalloproteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1) and/or ADAMTS11; wherein said at least one further ISV, e.g. a therapeutic ISV, preferably retains activity. Even more preferably, said at least one further ISV, such as an therapeutic ISV, inhibits an activity of a member of the serine protease family, cathepsins, matrix metalloproteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1) and/or ADAMTS11.

In an aspect, the present invention relates to a polypeptide as described herein, wherein said polypeptide has a stability of at least 7 days, such as at least 14 days, 21 days, 1 month, 2 months or even 3 months in synovial fluid (SF) at 37° C., and/or has a cartilage retention of at least 2, such as at least, 3, 4, 5 or 6 RU in a cartilage retention assay, and/or penetrates into the cartilage by at least 5 μm, such as at least 10 μm, 20 μm, 30 μm, 40 μm, 50 μm or even more.

In an aspect, the present invention relates to a polypeptide as described herein, further comprising a serum protein binding moiety or a serum protein, preferably said serum protein binding moiety binds serum albumin; even more preferably said serum protein binding moiety is an ISV binding serum albumin; even more preferably, said ISV binding serum albumin essentially consists of 4 framework regions (FR1 to FR4, respectively) and 3 complementarity determining regions (CDR1 to CDR3 respectively), in which CDR1 is SFGMS (SEQ ID NO: 151), CDR2 is SISGSGSDTLYADSVKG (SEQ ID NO: 152) and CDR3 is GGSLSR (SEQ ID NO: 153); even more preferably said ISV binding serum albumin comprises Alb8, Alb23, Alb129, Alb132, Alb135, Alb11, Alb11 (S112K)-A, Alb82, Alb82-A, Alb82-AA, Alb82-AAA, Alb82-G, Alb82-GG, Alb82-GGG (cf. Table C). In an aspect, the present invention relates to a polypeptide as described herein, further comprising a serum protein binding moiety or a serum protein, wherein said serum protein binding moiety is a non-antibody based polypeptide. In an aspect, the present invention relates to a polypeptide as described herein, further comprising PEG.

In an aspect, the present invention relates to a polypeptide as described herein, wherein said ISVs are directly linked to each other or are linked via a linker. In an aspect, the present invention relates to a polypeptide as described herein, wherein a first ISV and/or a second ISV and/or possibly a third ISV and/or possibly fourth ISV and/or possibly said ISV binding serum albumin are linked via a linker(s); preferably said linker is chosen from the group consisting of linkers of 5GS, 7GS, 9GS, 10GS, 15GS, 18GS, 20GS, 25GS, 30GS and 35GS (cf. Table D).

In an aspect, the present invention relates to a polypeptide as described herein, wherein said polypeptide is chosen from the group of polypeptides and/or constructs comprising an ISV binding a target as indicated and one or two ISVs binding Aggrecan as indicated in Table E-1 and Table E-2, respectively.

In an aspect, the present invention relates to a construct that comprises or essentially consists of an ISV as described herein, or a polypeptide as described herein, and which optionally further comprises one or more other groups, residues, moieties or binding units, optionally linked via one or more peptidic linkers; preferably said one or more other groups, residues, moieties or binding units is chosen from the group consisting of a polyethylene glycol molecule, serum proteins or fragments thereof, binding units that can bind to serum proteins, an Fc portion, and small proteins or peptides that can bind to serum proteins.

In an aspect, the present invention relates to a nucleic acid encoding an ISV as described herein, a polypeptide as described herein, or a construct as described herein.

In an aspect, the present invention relates to an expression vector comprising a nucleic acid as described herein.

In an aspect, the present invention relates to a host or host cell comprising a nucleic acid as described herein, or an expression vector as described herein.

In an aspect, the present invention relates to a method for producing an ISV as described herein or a polypeptide as described herein, said method at least comprising the steps of: a) expressing, in a suitable host cell or host organism or in another suitable expression system, a nucleic acid as described herein; optionally followed by: b) isolating and/or purifying the ISV as described herein, or the polypeptide as described herein.

In an aspect, the present invention relates to a composition comprising at least one ISV as described herein, a polypeptide as described herein, a construct as described herein, or a nucleic acid as described herein; preferably said composition is a pharmaceutical composition, which preferably further comprises at least one pharmaceutically acceptable carrier, diluent or excipient and/or adjuvant, and optionally comprises one or more further pharmaceutically active polypeptides and/or compounds.

In an aspect, the present invention relates to a composition as described herein, an ISV as described herein, a polypeptide as described herein, or a construct as described herein, for use as a medicament. Preferably, the composition, the ISV, the polypeptide, or the construct as described herein, is for use in preventing or treating arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis.

In an aspect, the present invention relates to a method for preventing or treating arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis, wherein said method comprises administering, to a subject in need thereof, a pharmaceutically active amount of at least a composition, an ISV, a polypeptide, or a construct as described herein to a person in need thereof.

In an aspect, the present invention relates to a method for reducing and/or inhibiting the efflux of a compound, a polypeptide or construct from cartilaginous tissue, wherein said method comprises administering pharmaceutically active amount of at least one polypeptide as described herein, a compound or construct as described herein, or a composition as described herein to a person in need thereof.

In an aspect, the present invention relates to a method for inhibiting and/or blocking ADAMTS5 activity and/or MMP13 activity, wherein said method comprises administering a pharmaceutically active amount of at least one polypeptide as described herein, a construct as described herein, or a composition as described herein to a person in need thereof.

In an aspect, the present invention relates to the use of an ISV as described herein, a polypeptide as described herein, a construct as described herein, or a composition as described herein, in the preparation of a pharmaceutical composition for treating or preventing arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis.

Other aspects, advantages, applications and uses of the polypeptides and compositions will become clear from the further disclosure herein. Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

FIGURE LEGENDS

FIG. 1: Examples of autoradiography images of sections of rat joints 2 or 4 weeks post injection with $^{125}$I-labeled ALB26-CAP constructs. For each of the 2 weeks post injection results and 4 weeks post injection results: Left panel: histological section; Right panel: autoradiography.

Figure 2:
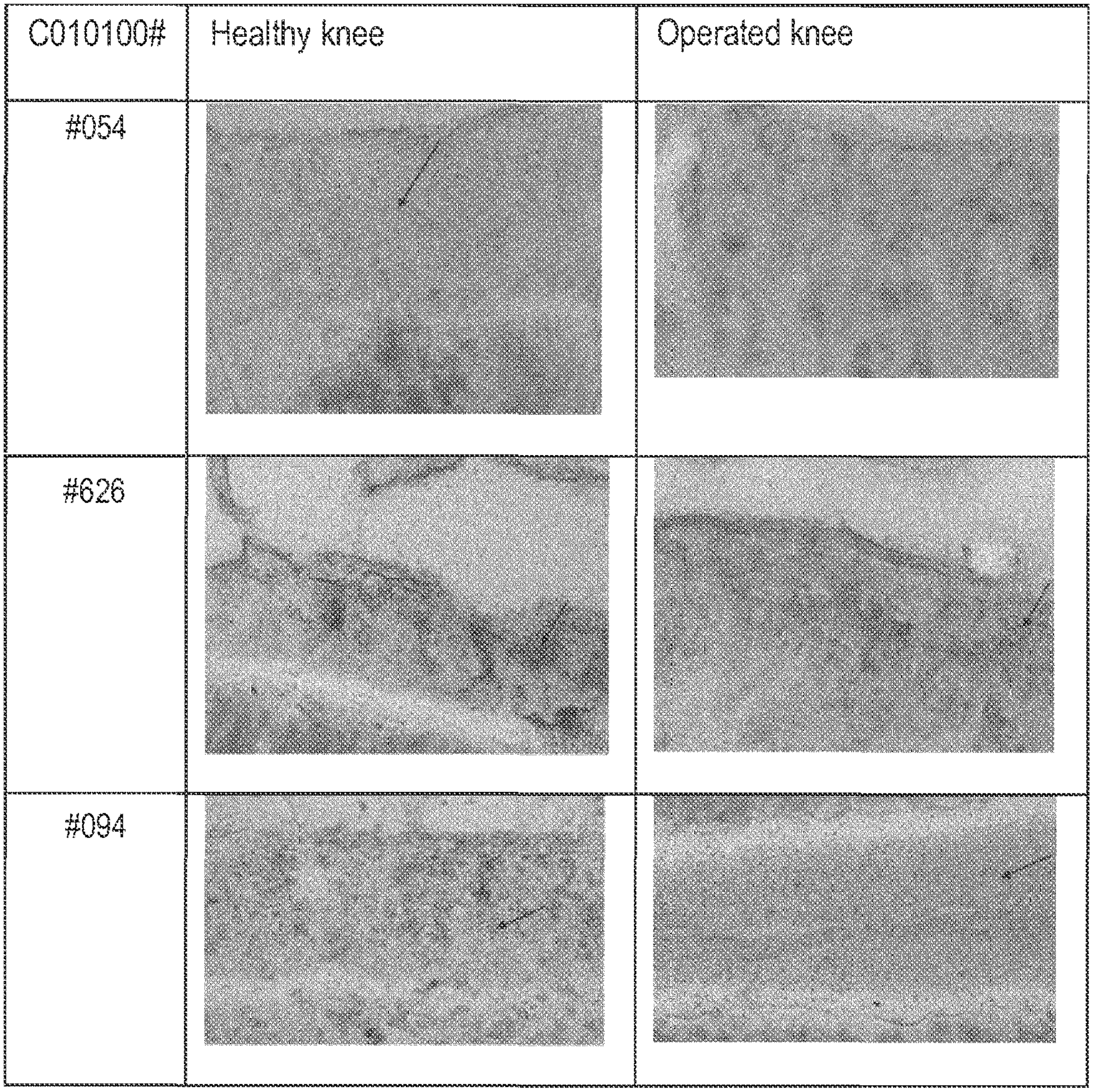

FIG. 2: Representative MARG images. Specific MARG staining appears as black grains on the images and is indicated by the arrows.

Figure 3:
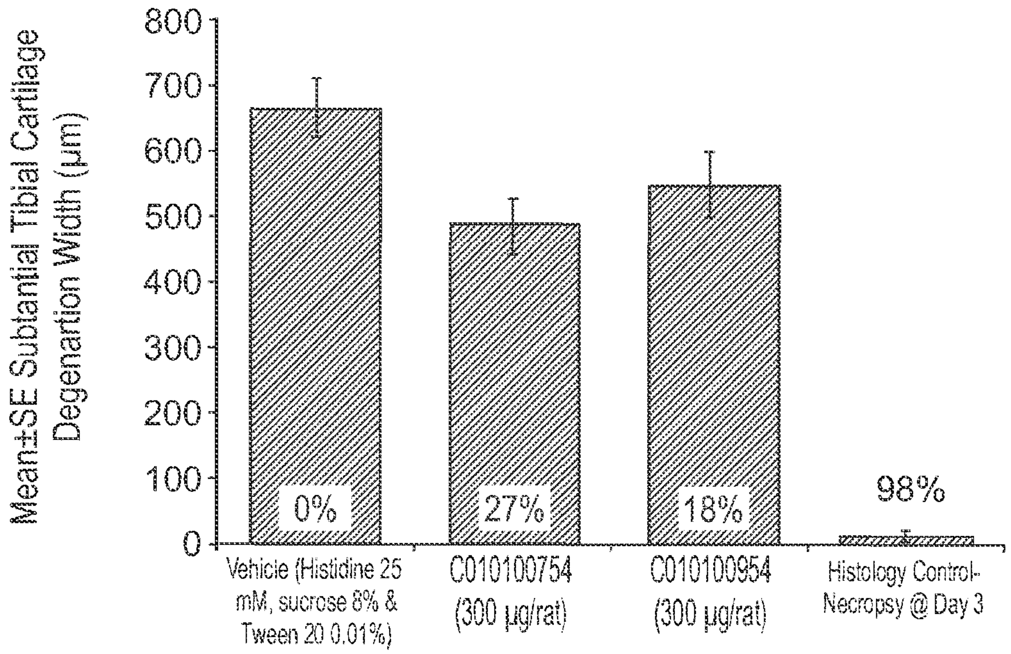

FIG. 3: Inhibition of cartilage degradation by Nanobodies in a rat MMT model using anti-MMP13-CAP Nanobody (C010100754) or an anti-ADAMTS5-CAP Nanobody (C010100954). Treatment started 3 days post-surgery by IA injection. Histopathology was performed at day 42 post surgery. The medial and total substantial cartilage degeneration width was determined, as well as the percentage reduction of cartilage degeneration. 20 animals were used per group.

Figure 4:
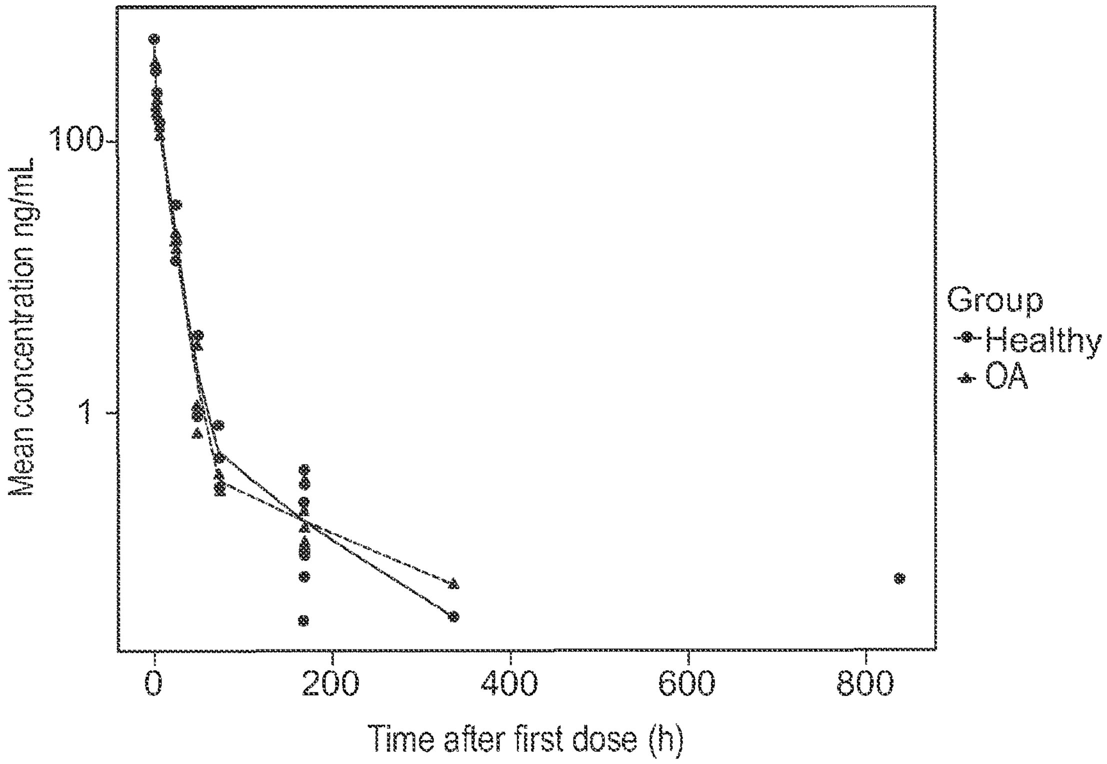

FIG. 4: Serum concentrations (mean concentration in ng/ml) versus time after first dose (h) of polypeptides in osteoarthritis rats and healthy rats, receiving a single intra-articular injection of 400 μg Nanobody per joint (right knee). Dots represent individual concentrations in healthy animals; triangles represent individual concentrations in OA animals; and lines represent mean concentrations.

Figure 5:
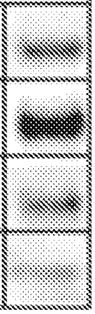

FIG. 5: Human ex vivo cartilage binding. The amount of construct bound to the cartilage after 30 minute wash (TO) was analysed by Western Blot.

Figure 6:
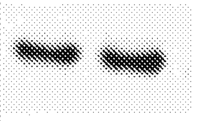
Figure 6:
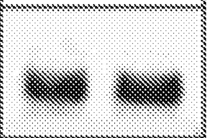
Figure 6:
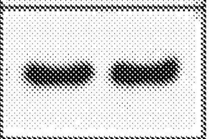
Figure 6:
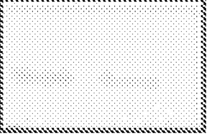

FIG. 6: Rat cartilage binding. Constructs were incubated with femural heads. Following Nanobody construct incubation, unbound construct was washed away and bound construct was analyzed by Western Blot.

Figure 7:
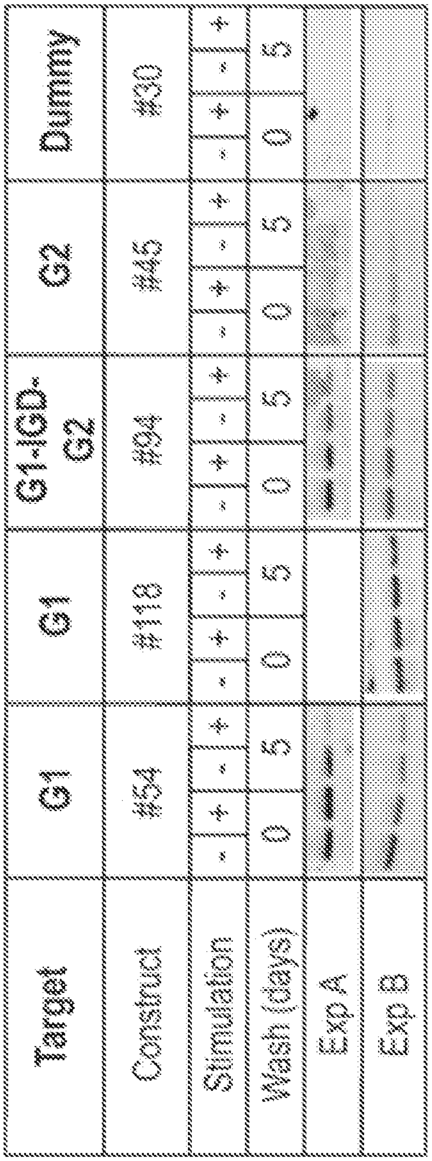

FIG. 7: Retention of ALB26-formatted Lead Panel in stimulated bovine cartilage explants. Two independent experiments were performed: A and B.

DETAILED DESCRIPTION

Unless indicated or defined otherwise, all terms used have their usual meaning in the art, which will be clear to the skilled person. Reference is for example made to the standard handbooks, such as Sambrook et al. (Molecular Cloning: A Laboratory Manual ($2^{nd}$ Ed.) Vols. 1-3, Cold Spring Harbor Laboratory Press, 1989), F. Ausubel et al. (Current protocols in molecular biology, Green Publishing and Wiley Interscience, New York, 1987), Lewin (Genes II, John Wiley & Sons, New York, N.Y., 1985), Old et al. (Principles of Gene Manipulation: An Introduction to Genetic Engineering ($2^{nd}$ edition) University of California Press, Berkeley, C A, 1981); Roitt et al. (Immunology ($6^{th}$ Ed.) Mosby/Elsevier, Edinburgh, 2001), Roitt et al. (Roitt's Essential Immunology ($10^{th}$ Ed.) Blackwell Publishing, U K, 2001), and Janeway et al. (Immunobiology ($6^{th}$ Ed.) Garland Science Publishing/Churchill Livingstone, New York, 2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta (Adv. Drug Deliv. Rev. 58 (5-6): 640-56, 2006), Levin and Weiss (Mol. Biosyst. 2(1): 49-57, 2006), Irving et al. (J. Immunol. Methods 248(1-2): 31-45, 2001), Schmitz et al. (Placenta 21 Suppl. A: S106-12, 2000), Gonzales et al. (Tumour Biol. 26(1): 31-43, 2005), which describe techniques for protein engineering, such as affinity maturation and other techniques for improving the specificity and other desired properties of proteins such as immunoglobulins.

The term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

Amino acid sequences are interpreted to mean a single amino acid or an unbranched sequence of two or more amino acids, depending of the context. Nucleotide sequences are interpreted to mean an unbranched sequence of 3 or more nucleotides.

Amino acids are those L-amino acids commonly found in naturally occurring proteins. Amino acid residues will be indicated according to the standard three-letter or one-letter amino acid code. Reference is for instance made to Table A-2 on page 48 of WO 08/020079. Those amino acid sequences containing D-amino acids are not intended to be embraced by this definition. Any amino acid sequence that contains post-translationally modified amino acids may be described as the amino acid sequence that is initially translated using the symbols shown in this Table A-2 with the modified positions; e.g., hydroxylations or glycosylations, but these modifications shall not be shown explicitly in the amino acid sequence. Any peptide or protein that can be expressed as sequence modified linkages, cross links and end caps, non-peptidyl bonds, etc., is embraced by this definition.

The terms "protein", "peptide", "protein/peptide", and "polypeptide" are used interchangeably throughout the disclosure and each has the same meaning for purposes of this disclosure. Each term refers to an organic compound made of a linear chain of two or more amino acids. The compound may have ten or more amino acids; twenty-five or more amino acids; fifty or more amino acids; one hundred or more amino acids, two hundred or more amino acids, and even three hundred or more amino acids. The skilled artisan will appreciate that polypeptides generally comprise fewer amino acids than proteins, although there is no art-recognized cut-off point of the number of amino acids that distinguish a polypeptide from a protein; that polypeptides may be made by chemical synthesis or recombinant methods; and that proteins are generally made in vitro or in vivo by recombinant methods, all as known in the art.

A nucleic acid or amino acid sequence is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid sequence is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined by using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of"

another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain ("ISV"), this may mean that said immunoglobulin single variable domain sequence has been incorporated into the sequence of the polypeptide of the invention, but more usually this generally means that the polypeptide of the invention contains within its sequence the sequence of the ISVs irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence). Also, when a construct of the invention is said to comprise a polypeptide or ISV, this may mean that said construct at least encompasses said polypeptide or ISV, respectively, but more usually this means that said construct encompasses groups, residues (e.g. amino acid residues), moieties and/or binding units in addition to said polypeptide or ISV, irrespective of how said polypeptide or ISV is connected to said groups, residues (e.g. amino acid residues), moieties and/or binding units and irrespective of how said construct has been generated or obtained.

By "essentially consist of" is meant that the ISV used in the method of the invention either is exactly the same as the ISV of the invention or corresponds to the ISV of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino-terminal end, at the carboxy-terminal end, or at both the amino terminal end and the carboxy-terminal end of the ISV.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as, e.g. NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 335768, WO 98/49185, WO 00/46383 and WO 01/09300; and (preferred) types and/or combinations of such substitutions may be selected on the basis of the pertinent teachings from, e.g. WO 04/037999 or e.g. WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into lie or into Val; Lys into Arg, into Gln or into Glu; Met into Leu, into Tyr or into Ile;

Phe into Met, into Leu or into Tyr; Ser into Thr; Thr into Ser; Trp into Tyr; Tyr into Trp; and/or Phe into Val, into lie or into Leu.

Any amino acid substitutions applied to the polypeptides described herein may also be based on the analysis of the frequencies of amino acid variations between homologous proteins of different species such as, for instance, developed by Schulz et al. ("Principles of Protein Structure", Springer-Verlag, 1978), on the analyses of structure forming potentials developed by, e.g. Chou and Fasman (Biochemistry 13: 211, 1974; Adv. Enzymol., 47: 45-149, 1978), and on the analysis of hydrophobicity patterns in proteins developed by e.g. Eisenberg et al. (Proc. Natl. Acad Sci. USA 81: 140-144, 1984), Kyte and Doolittle (J. Molec. Biol. 157: 105-132, 1981) or Goldman et al. (Ann. Rev. Biophys. Chem. 15: 321-353, 1986), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al. (Nature Structural Biology, 3: 803, 1996), Spinelli et al. (Natural Structural Biology, 3: 752-757, 1996) or Decanniere et al. (Structure, 7 (4): 361, 1999). Further information about some of the amino acid residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length.

When comparing two amino acid sequences, the term "amino acid(s) difference" refers to an insertion, deletion or substitution of a single amino acid residue on a position of the first sequence, compared to the second sequence; it being understood that two amino acid sequences can contain one, two or more such amino acid differences. More particularly, in the amino acid sequences and/or polypeptides of the present invention, the term "amino acid(s) difference" refers to an insertion, deletion or substitution of a single amino acid residue on a position of the CDR sequence specified in b), d) or f), compared to the CDR sequence of respectively a), c) or e); it being understood that the CDR sequence of b), d) and f) can contain one, two, three, four or maximal five such amino acid differences compared to the CDR sequence of respectively a), c) or e).

The "amino acid(s) difference" can be any one, two, three, four or maximal five substitutions, deletions or insertions, or any combination thereof, that either improve the properties of the Aggrecan binder of the invention, such as the polypeptide of the invention or that at least do not detract too much from the desired properties or from the balance or combination of desired properties of the Aggrecan binder of the invention, such as the polypeptide of the invention. In this respect, the resulting Aggrecan binder of the invention, such as the polypeptide of the invention should at least bind Aggrecan with the same, about the same, or a higher affinity compared to the polypeptide comprising the one or more CDR sequences without the one, two, three, four or maximal five substitutions, deletions or insertions, said affinity as measured by surface plasmon resonance (SPR).

In this respect, the amino acid sequence of the CDRs according to b), d) and/or f) may be an amino acid sequence that is derived from an amino acid sequence according to a), c) and/or e) respectively by means of affinity maturation using one or more techniques of affinity maturation known per se.

For example, and depending on the host organism used to express the polypeptide of the invention, such deletions and/or substitutions may be designed in such a way that one or more sites for post-translational modification (such as one or more glycosylation sites) are removed, as will be within the ability of the person skilled in the art.

A "Nanobody family", "$V_{HH}$ family" or "family" as used in the present specification refers to a group of Nanobodies and/or $V_{HH}$ sequences that have identical lengths (i.e. they have the same number of amino acids within their sequence) and of which the amino acid sequence between position 8 and position 106 (according to Kabat numbering) has an amino acid sequence identity of 89% or more.

The terms "epitope" and "antigenic determinant", which can be used interchangeably, refer to the part of a macromolecule, such as a polypeptide or protein that is recognized by antigen-binding molecules, such as immunoglobulins, conventional antibodies, ISVs and/or polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as an immunoglobulin, a conventional antibody, an ISV and/or a polypeptide of the invention) that recognizes the epitope is called a "paratope".

An amino acid sequence (such as an ISV, an antibody, a polypeptide of the invention, or generally an antigen binding protein or polypeptide or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g., "anti"-Aggrecan).

The affinity denotes the strength or stability of a molecular interaction. The affinity is commonly given as the $K_D$, or dissociation constant, which has units of mol/liter (or M). The affinity can also be expressed as an association constant, $K_A$, which equals $1/K_D$ and has units of $(mol/liter)^{-1}$ (or $M^{-1}$). In the present specification, the stability of the interaction between two molecules will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the change of free energy (DG) of binding by the well-known relation $DG=RT \cdot \ln(K_D)$ (equivalently $DG=-RT \cdot \ln(K_A)$), where R equals the gas constant, T equals the absolute temperature and ln denotes the natural logarithm.

The $K_D$ for biological interactions which are considered meaningful (e.g. specific) are typically in the range of $10^{-12}$ M (0.001 nM) to $10^{-5}$ M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has unit $s^{-1}$ (where s is the SI unit notation of second). The on-rate $k_{on}$ has units $M^{-1}s^{-1}$. The on-rate may vary between $10^2$ $M^{-1}s^{-1}$ to about $10^7$ $M^{-1}s^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$ $s^{-1}$ (near irreversible complex with a $t_{1/2}$ of multiple days) to 1 $s^{-1}$ ($t_{1/2=0.69}$ s).

Specific binding of an antigen-binding protein, such as an ISVD, to an antigen or antigenic determinant can be determined in any suitable manner known per se, including, for example, saturation binding assays and/or competitive binding assays, such as radio-immunoassays (RIA), enzyme immunoassays (EIA) and sandwich competition assays, and the different variants thereof known per se in the art; as well as the other techniques mentioned herein.

The affinity of a molecular interaction between two molecules can be measured via different techniques known per se, such as the well-known surface plasmon resonance (SPR) biosensor technique (see for example Ober et al. 2001, Intern. Immunology 13: 1551-1559) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE® instruments (Pharmacia Biosensor AB, Uppsala, Sweden). Kinetic Exclusion Assay (KINEXA®) (Drake et al. 2004, Analytical Biochemistry 328: 35-43) measures binding events in solution without labeling of the binding partners and is based upon kinetically excluding the dissociation of a complex. In-solution affinity analysis can also be performed using the GYROLAB® immunoassay system, which provides a platform for automated bioanalysis and rapid sample turnaround (Fraley et al. 2013, Bioanalysis 5: 1765-74), or ELISA.

It will also be clear to the skilled person that the measured $K_D$ may correspond to the apparent $K_D$ if the measuring process somehow influences the intrinsic binding affinity of the implied molecules for example by artifacts related to the coating on the biosensor of one molecule. Also, an apparent $K_D$ may be measured if one molecule contains more than one recognition site for the other molecule. In such situation the measured affinity may be affected by the avidity of the interaction by the two molecules. In particular, the accurate measurement of $K_D$ may be quite labor-intensive and as a consequence, often apparent $K_D$ values are determined to assess the binding strength of two molecules. It should be noted that as long as all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

The term "specificity" refers to the number of different types of antigens or antigenic determinants to which a particular antigen-binding molecule or antigen-binding protein (such as an ISVD or polypeptide of the invention) molecule can bind. The specificity of an antigen-binding protein can be determined based on affinity and/or avidity, for instance as described on pages 53-56 of WO 08/020079 (incorporated herein by reference), which also describes some preferred techniques for measuring binding between an antigen-binding molecule (such as a polypeptide or ISVD of the invention) and the pertinent antigen. Typically, antigen-binding proteins (such as the ISVDs and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^{5}$ to $10^{12}$ liter/moles or more, and preferably $10^{7}$ to $10^{12}$ liter/moles or more and more preferably $10^{8}$ to $10^{12}$ liter/moles). Any $K_D$ value greater than $10^{-4}$ mol/liter (or any $K_A$ value lower than 104 liter/mol) is generally considered to indicate non-specific binding. Preferably, a monovalent ISVD of the invention will bind to the desired antigen with an affinity less than 500 nM, preferably less than 200 nM, more preferably less than 10 nM, such as less than 500 pM, such as e.g., between 10 and 5 pM or less. Reference is also made to paragraph n) on pages 53-56 of WO 08/020079.

An ISV and/or polypeptide is said to be "specific for" a (first) target or antigen compared to another (second) target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times or more better than the affinity with which the ISVD and/or polypeptide binds to the second target or antigen. For example, the ISVD and/or polypeptide may bind to the first target or antigen with a $K_D$ value that is at least 10 times less, such as at least 100 times less, and preferably at least 1000 times less or even less than that, than the $K_D$ with which said ISV and/or polypeptide binds to the second target or antigen. Preferably, when an ISV and/or polypeptide is "specific for" a first target or antigen compared to a second target or antigen, it is directed against (as defined herein) said first target or antigen, but not directed against said second target or antigen.

Specific binding of an antigen-binding protein to an antigen or antigenic determinant can be determined in any suitable manner known per se, including, for example, saturation binding assays and/or competitive binding assays, such as radioimmunoassays (RIA), enzyme immunoassays (EIA) and the different variants thereof known in the art; as well as the other techniques mentioned herein.

A preferred approach that may be used to assess affinity is the 2-step ELISA (Enzyme-Linked Immunosorbent Assay) procedure of Friguet et al. 1985 (J. Immunol. Methods 77: 305-19). This method establishes a solution phase binding equilibrium measurement and avoids possible artifacts relating to adsorption of one of the molecules on a support such as plastic. As will be clear to the skilled person, the dissociation constant may be the actual or apparent dissociation constant. Methods for determining the dissociation constant will be clear to the skilled person, and for example include the techniques mentioned on pages 53-56 of WO 08/020079.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{Dref}$, the $K_D$ of the reference molecule, is known, as well as the total concentration $c_{ref}$ of the reference molecule, the apparent $K_D$ for the interaction A-B can be obtained from following formula: $K_D=IC_{50}/(1+c_{ref}/K_{Dref})$. Note that if $c_{ref} \ll K_{D\ ref}$, $K_D \approx IC_{50}$. Provided the measurement of the $IC_{50}$ is performed in a consistent way (e.g. keeping $c_{ref}$ fixed) for the binders that are compared, the difference in strength or stability of a molecular interaction can be assessed by comparing the $IC_{50}$ and this measurement is judged as equivalent to $K_D$ or to apparent $K_D$ throughout this text.

The half maximal inhibitory concentration ($IC_{50}$) can also be a measure of the effectiveness of a compound in inhibiting a biological or biochemical function, e.g. a pharmacological effect. This quantitative measure indicates how much of the polypeptide or ISV (e.g. a Nanobody) is needed to inhibit a given biological process (or component of a process, i.e. an enzyme, cell, cell receptor, chemotaxis, anaplasia, metastasis, invasiveness, etc.) by half. In other words, it is the half maximal (50%) inhibitory concentration (IC) of a substance (50% IC, or $IC_{50}$). $IC_{50}$ values can be calculated for a given antagonist such as the polypeptide or ISV (e.g. a Nanobody) of the invention by determining the concentration needed to inhibit half of the maximum biological response of the agonist. The $K_D$ of a drug can be determined by constructing a dose-response curve and examining the effect of different concentrations of antagonist such as the polypeptide or ISV (e.g. a Nanobody) of the invention on reversing agonist activity.

The term half maximal effective concentration ($EC_{50}$) refers to the concentration of a compound which induces a response halfway between the baseline and maximum after a specified exposure time. In the present context it is used as a measure of a polypeptide, ISV (e.g. a Nanobody) its potency. The $EC_{50}$ of a graded dose response curve represents the concentration of a compound where 50% of its maximal effect is observed. Concentration is preferably expressed in molar units.

In biological systems, small changes in ligand concentration typically result in rapid changes in response, following a sigmoidal function. The inflection point at which the increase in response with increasing ligand concentration begins to slow is the $EC_{50}$. This can be determined mathematically by derivation of the best-fit line. Relying on a graph for estimation is convenient in most cases. In case the $EC_{50}$ is provided in the examples section, the experiments were designed to reflect the $K_D$ as accurate as possible. In other words, the $EC_{50}$ values may then be considered as $K_D$ values. The term "average $K_D$" relates to the average $K_D$ value obtained in at least 1, but preferably more than 1, such as at least 2 experiments. The term "average" refers to the mathematical term "average" (sums of data divided by the number of items in the data).

It is also related to $IC_{50}$ which is a measure of a compound its inhibition (50% inhibition). For competition binding assays and functional antagonist assays $IC_{50}$ is the most common summary measure of the dose-response curve. For agonist/stimulator assays the most common summary measure is the $EC_{50}$.

The inhibition constant (Ki) is an indication of how potent an inhibitor is; it is the concentration required to produce half maximum inhibition. Unlike $IC_{50}$, which can change depending on the experimental conditions, Ki is an absolute value and is often referred to as the inhibition constant of a drug. The inhibition constant Ki can be calculated by using the Cheng-Prusoff equation:

$$K_i = \frac{IC50}{\frac{[L]}{K_D} + 1}$$

in which [L] is the fixed concentration of the ligand.

An ISV and/or polypeptide is said to be "specific for" a (first) target or antigen compared to another (second) target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times or more better than the affinity with which the ISV and/or polypeptide binds to the second target or antigen. For example, the ISV and/or polypeptide may bind to the first target or antigen with a $K_D$ value that is at least 10 times less, such as at least 100 times less, and preferably at least 1000 times less or even less than that, than the $K_D$ with which said ISV and/or polypeptide binds to the second target or antigen. Preferably, when an ISV and/or polypeptide is "specific for" a first target or antigen compared to a second target or antigen, it is directed against (as defined herein) said first target or antigen, but not directed against said second target or antigen.

The terms "(cross)-block", "(cross)-blocked", "(cross)-blocking", "competitive binding", "(cross)-compete", "(cross)-competing" and "(cross)-competition" are used interchangeably herein to mean the ability of an immunoglobulin, antibody, ISV, polypeptide or other binding agent to interfere with the binding of other immunoglobulins, antibodies, ISVs, polypeptides or binding agents to a given target. The extent to which an immunoglobulin, antibody, ISV, polypeptide or other binding agent is able to interfere with the binding of another to the target, and therefore whether it can be said to cross-block according to the invention, can be determined using competition binding assays, which are common in the art. Particularly suitable quantitative cross-blocking assays include an ELISA and a fluorescence-activated cell sorting (FACS) binding assay with Aggrecan expressed on cells. In a FACS set up, the extent of (cross)-blocking can be measured by the (reduced) channel fluorescence.

Methods for determining whether an immunoglobulin, antibody, ISV, polypeptide or other binding agent directed against a target (cross)-blocks, is capable of (cross)-blocking, competitively binds or is (cross)-competitive as defined herein are described e.g. in Xiao-Chi Jia et al. (Journal of Immunological Methods 288: 91-98, 2004), Miller et al. (Journal of Immunological Methods 365: 118-125, 2011) and/or the methods described herein (see e.g. Example 2.3).

An amino acid sequence is said to be "cross-reactive" for two different antigens or antigenic determinants (such as e.g., Aggrecan from different species of mammal, such as e.g., human Aggrecan, dog Aggrecan, bovine Aggrecan, rat Aggrecan, pig Aggrecan, mouse Aggrecan, rabbit Aggrecan, cynomolgus Aggrecan, and/or rhesus Aggrecan) if it is specific for (as defined herein) these different antigens or antigenic determinants.

In the context of the present invention, "modulating" or "to modulate" generally means reducing or inhibiting an activity of a member of the serine protease family, cathepsins, matrix metallo-proteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1), ADAMTS11 and/or pro-inflammatory cytokines, such as e.g. interleukin-1α, and -β, interleukin-6 and TNF-α, by an ISV, polypeptide or construct of the invention, as measured using a suitable in vitro, cellular, ex vivo or in vivo assay (such as those mentioned herein). In particular, "modulating" or "to modulate" may mean either reducing or inhibiting the activity of the aforementioned members as measured using a suitable in vitro, cellular, ex vivo or in vivo assay (such as those mentioned herein), by at least 1%, preferably at least 5%, such as at least 10% or at least 25%, for example by at least 50%, at least 60%, at least 70%, at least 80%, or 90% or more, compared to the activity of the aforementioned members in the same assay under the same conditions but without the presence of the immunoglobulin or polypeptide of the invention.

In the context of the present invention, "enhancing" or "to enhance" generally means increasing, potentiating or stimulating the activity of the polypeptides or constructs of the invention, as measured using a suitable in vitro, cellular, ex vivo or in vivo assay (such as those mentioned herein). In particular, increasing or enhancing the activity of a polypeptide or construct of the invention, as measured using a suitable in vitro, cellular, ex vivo or in vivo assay (such as those mentioned herein), by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, such as 100%, compared to the activity of the construct or polypeptide in the same assay under the same conditions but without the presence of the Aggrecan binder, e.g. ISV binding Aggrecan, of the invention.

A "synergistic effect" of two compounds is one in which the effect of the combination of the two agents is greater than the sum of their individual effects and is preferably statistically different from the controls and the single drugs.

The term "potency" of an ISV or polypeptide of the invention, as used herein, is a function of the amount of the ISV or polypeptide of the invention required for its specific effect, such as, e.g. penetration into the cartilage, specific binding to Aggrecan and/or cartilage retention, to occur. It can be measured simply by the methods known to the person skilled in the art, and for instance as used in the examples section.

In contrast, the "efficacy" of the ISV or polypeptide of the invention measures the maximum strength of the effect itself, at saturating ISV or polypeptide concentrations. Efficacy indicates the maximum response achievable from the ISV or polypeptide of the invention. It refers to the ability of an ISV or polypeptide to produce the desired (therapeutic) effect, such as, e.g. binding to Aggrecan or retention to Aggrecan, and/or inhibiting an activity of an ADAMTS family member or MMP family member.

The "half-life" of a polypeptide or construct of the invention refers to the time taken for the serum concentration of the construct or polypeptide to be reduced by 50%, in vivo, for example due to degradation of the construct or polypeptide and/or clearance or sequestration of the construct or polypeptide by natural mechanisms, see e.g. paragraph o) on page 57 of WO 08/020079. The in vivo half-life of a construct or polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t½-alpha, t½-beta and the area under the curve (AUC). Reference is for example made to the standard handbooks, such as Kenneth et al. (Chemical Stability of Pharmaceuticals: A Handbook for Pharmacists, John Wiley & Sons Inc, 1986) and M Gibaldi and D Perron ("Pharmacokinetics", Marcel Dekker, 2$^{nd}$ Rev. Edition, 1982). The terms "increase in half-life" or "increased half-life" refer to an increase in the t½-beta, either with or without an increase in the t½-alpha and/or the AUC or both, for instance as described in paragraph o) on page 57 of WO 08/020079.

Unless indicated otherwise, the terms "immunoglobulin" and "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H$/$V_L$ domains, respectively).

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site, and in particular CDR1, CDR2 and/or CDR3.

The term "immunoglobulin single variable domain" ("ISV" or "ISVD"), interchangeably used with "single variable domain", defines molecules wherein the antigen binding site is present on, and formed by, a single immunoglobulin domain. This sets ISVs apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an ISV, as, in these cases, binding to the respective epitope of an antigen would normally not occur by one (single) immunoglobulin domain but by a pair of (associating) immunoglobulin domains such as light and heavy chain variable domains, i.e., by a VH-VL pair of immunoglobulin domains, which jointly bind to an epitope of the respective antigen.

In contrast, ISVs are capable of specifically binding to an epitope of the antigen without pairing with an additional immunoglobulin variable domain. The binding site of an ISV is formed by a single VH/VHH or VL domain. Hence, the antigen binding site of an ISV is formed by no more than three CDRs.

As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the ISVs are heavy chain variable domain sequences (e.g., a VH-sequence); more specifically, the ISVs can be heavy chain variable domain sequences that are derived from a conventional four-chain antibody or heavy chain variable domain sequences that are derived from a heavy chain antibody.

For example, the ISV may be a (single) domain antibody, an amino acid that is suitable for use as a (single) domain antibody, an immunoglobulin that is suitable for use as a (single) domain antibody, a "dAb" or sdAb, or an amino acid that is suitable for use as a dAb, or a Nanobody (as defined herein, and including but not limited to a VHH); a humanized VHH sequence, a camelized VH sequence, a VHH sequence that has been obtained by affinity maturation, other single variable domains, an immunoglobulin single heavy chain variable domain or any suitable fragment of any one thereof.

In particular, the ISV may be a Nanobody® (as defined herein) or a suitable fragment thereof. [Note: Nanobody® and Nanobodies® are registered trademarks of Ablynx N.V.] For a general description of Nanobodies, reference is made to the further description below, as well as to the prior art cited herein, such as e.g. described in WO 08/020079 (page 16).

"VHH domains", also known as VHHs, $V_H$H domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al. Nature 363: 446-448, 1993). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). For a further description of VHHs and Nanobodies, reference is for instance made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, ISVs, Nanobodies (in particular VHH sequences and partially humanized Nanobodies) can in particular be characterized by the presence of one or more "Hallmark residues" in one or more of the framework sequences. A further description of the ISVs, Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the ISVs, Nanobodies and their preparations can be found e.g. in WO 08/101985 and WO 08/142164. For a further general description of Nanobodies, reference is made to the prior art cited herein, such as e.g., described in WO 08/020079 (page 16).

"Domain antibodies", also known as "Dab"(s), "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutic use in humans.

It should also be noted that, although less preferred in the context of the present invention because they are not of mammalian origin, single variable domains can be derived from certain species of shark (for example, the so-called "IgNAR domains", see for example WO 05/18629).

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g., described in Davies and Riechmann (FEBS 339: 285-290, 1994; Biotechnol. 13: 475-479, 1995; Prot. Eng. 9: 531-537, 1996) and Riechmann and Muyldermans (J. Immunol. Methods 231: 25-38, 1999).

The amino acid residues of a VHH domain are numbered according to the general numbering for $V_H$ domains given by Kabat et al. ("Sequence of proteins of immunological interest", US Public Health Services, NIH Bethesda, MD, Publication No. 91), as applied to VHH domains from Camelids, as shown e.g., in FIG. 2 of Riechmann and Muyldermans (J. Immunol. Methods 231: 25-38, 1999). Alternative methods for numbering the amino acid residues of $V_H$ domains, which methods can also be applied in an analogous manner to VHH domains, are known in the art. However, in the present description, claims and figures, the numbering according to Kabat applied to VHH domains as described above will be followed, unless indicated otherwise.

It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Determination of CDR regions may also be done according to different methods. In the CDR determination according to Kabat, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

In the present application, however, CDR sequences were determined according to Kontermann and Dubel (Eds., Antibody Engineering, vol 2, Springer Verlag Heidelberg Berlin, Martin, Chapter 3, pp. 33-51, 2010). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113 (according to Kabat numbering).

ISVs such as Domain antibodies and Nanobodies (including VHH domains) can be subjected to humanization. In particular, humanized immunoglobulin single variable domains, such as Nanobodies (including VHH domains) may be immunoglobulin single variable domains that are as generally defined for in the previous paragraphs, but in which at least one amino acid residue is present (and in particular, at least one framework residue) that is and/or that corresponds to a humanizing substitution (as defined herein). Potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domain, such as a Nanobody (including VHH domains) may be partially humanized or fully humanized.

ISVs such as Domain antibodies and Nanobodies (including VHH domains and humanized VHH domains), can also be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996).

The process of designing/selecting and/or preparing a polypeptide, starting from an ISV such as a Domain antibody or a Nanobody, is also referred to herein as "formatting" said ISV; and an ISV that is made part of a polypeptide is said to be "formatted" or to be "in the format of" said polypeptide. Examples of ways in which an ISV can be formatted and examples of such formats will be clear to the skilled person based on the disclosure herein; and such formatted ISV form a further aspect of the invention.

For example, and without limitation, one or more ISVs may be used as a "binding unit", "binding domain" or "building block" (these terms are used interchangeable) for the preparation of a polypeptide, which may optionally contain one or more further ISVs that can serve as a binding unit (i.e., against the same or another epitope on Aggrecan and/or against one or more other antigens, proteins or targets than Aggrecan).

The present invention provides Aggrecan binders, such as ISVs (also referred to herein as "ISVs of the invention") and/or polypeptides (also referred to herein as "polypeptides of the invention") that have specificity for and/or that bind Aggrecan.

Aggrecan is also known as aggrecan 1, ACAN, AGC1, AGCAN, CSPGCP, MSK16, SEDK, cartilage-specific proteoglycan core protein (CSPCP) or chondroitin sulfate proteoglycan 1 (CSPG1). Aggrecan is in humans encoded by the ACAN gene, which is located at chromosome Chr 15: q26.1.

Aggrecan is a large, multimodular molecule (2317 amino acids). Its core protein is composed of three globular domains (G1, G2 and G3) and a large extended region (CS) between G2 and G3 onto which a multitude of N-linked oligosaccharides and chondroitin sulfate chains and keratan sulfate chains are attached. Aggrecan is the major proteoglycan in the articular cartilage. It plays an important role in the proper functioning of articular cartilage by providing a hydrated gel structure through its interaction with hyaluronan and link proteins, which endows the cartilage with load-bearing properties. The G1 domain interacts with hyaluronan acid and link proteins, forming stable ternary complexes in the extracellular matrix (ECM). The G2 domain is homologous to the tandem repeats of G1 and link proteins, and is involved in product processing. G3 makes up the carboxyl terminus of the core protein, and enhances glycosaminoglycan modification and product secretion. Also, the G3 domain links the proteoglycan aggregates to the ECM proteins (fibulins and tenascins). Degradation of Aggrecan appears to initiate at the C-terminus. The population of Aggrecan molecules without the G3 domain increases with aging. Aggrecan interacts with laminin, fibronectin, tenascin, and collagen, but it is also an enzymatic substrate of various A Disintegrin And Metalloprotease with Thrombo-spondin Motifs (ADAMTSs) such as ADAMTS4, ADAMTS5 and ADAMTS11 and matrix metallo-proteinases (MMPs) such as MMP8, MMP13, MMP19 and MMP20.

In one aspect, the invention relates to Aggrecan binders such as ISVs and polypeptides that specifically bind Aggrecan.

The Aggrecan binders of the invention are eventually intended for use as medicaments in humans. Accordingly, in one aspect the invention relates to Aggrecan binders, such as ISVs and polypeptides that specifically bind human Aggrecan (SEQ ID NO: 125).

The inventors identified Aggrecan binders with highly improved interspecies cross-reactivity and exquisite selectivity properties.

Accordingly, in an aspect the invention relates to an Aggrecan binder, such as an ISV or polypeptide, wherein said Aggecan binder specifically binds to human Aggrecan (P16112; SEQ ID NO: 125), dog Aggrecan (Q28343; SEQ ID NO: 126), bovine Aggrecan (P13608; SEQ ID NO: 127), rat Aggrecan (P07897; SEQ ID NO: 128); pig Aggrecan (core; Q29011, SEQ ID NO: 129); mouse Aggrecan (Q61282; SEQ ID NO: 130), rabbit Aggrecan (G1U677-1; SEQ ID NO: 131); cynomolgus Aggrecan (XP_005560513.1; SEQ ID NO: 132) and/or rhesus Aggrecan (XP_002804990.1; SEQ ID NO: 133) (cf. Table B).

The present inventors surprisingly observed that the Aggrecan binders of the invention, such as the ISVs and/or polypeptides of the invention have favorable characteristics over the prior art molecules; they are stable in joints, they retain in the cartilage for prolonged times and they are specific for cartilaginous tissue, e.g. do not bind substantially to Neurocan (014594, SEQ ID NO: 134) and/or Brevican (Q96GW7, SEQ ID NO: 135) (cf. Table B).

Accordingly, in one aspect the invention relates to an Aggrecan binder, such as an ISV or polypeptide, wherein said Aggrecan binder does not bind substantially to Neurocan (014594, SEQ ID NO: 134) and/or Brevican (Q96GW7, SEQ ID NO: 135), preferably wherein said Aggrecan binds to Neurocan and/or Brevican with a $K_D$ value greater than $10^{-5}$ mol/liter, such as $10^{-4}$ mol/liter.

In one aspect the invention relates to an Aggrecan binder, such as an ISV, wherein said Aggrecan binder has more than 10 fold, more than 100 fold, preferably more than 1000 fold selectivity over Neurocan and/or Brevican for binding to Aggrecan.

Preferred Aggrecan binders of the invention include immunoglobulins (such as heavy chain antibodies, conventional 4-chain antibodies (such as IgG, IgM, IgA, IgD or IgE molecules), Fab fragments, F(ab')2 fragments, Fv fragments such as disulfide linked Fv or scFv fragments, or diabodies derived from such conventional 4-chain antibody, the individual chains thereof, as well as all parts, domains or fragments thereof (including but not limited to antigen-binding domains or fragments such as immunoglobulin single variable domains), monovalent polypeptides of the invention, or other binding agents).

It was observed that the Aggrecan binders of the invention had a pl over 8, with only one exception (cf. Table 2.2). Without being bound by theory, the present inventors hypothesized that the high positive charge of the Aggrecan may influence retention and cartilage penetration of the whole moiety, i.e. even when coupled to another building block such as in a multispecific polypeptide. Accordingly, the present invention relates to an Aggrecan binder, such as an ISV, polypeptide or construct of the invention, preferably an ISV of the invention, having a pl of more than 8, such as 8.1, 8.2, 8.3, 8.4, 8.5, 8.6, 8.7, 8.8, 8.9, 9.0 or even more, such as 9.1, 9.2, 9.3, 9.4, 9.5, 9.6, 9.7, 9.8 or even 9.8.

Binding of the Aggrecan binders of the invention, such as the ISVs and/or polypeptides of the invention, to Aggrecan can be measured in various binding assays, commonly known in the art. Typical assays include (without being limiting) Fluorescent ligand binding assays, Fluorescence-activated cell sorting (FACS), Radioligand binding assays, Surface plasmon resonance (SPR), Plasmon-waveguide resonance (PWR), SPR imaging for affinity-based biosensors, Whispering gallery microresonator (WGM), Resonant waveguide grating (RWG), Biolayer Interferometry Biosensor (BIB) assays, Nuclear magnetic resonance (NMR), X-ray crystallography, Thermal denaturation assays (TDA), Isothermal titration calorimetry (ITC), ELISA and Whole cell ligand-binding assays such as Surface acoustic wave (SAW) biosensor and RWG biosensor assays. A preferred assay for measuring binding of the Aggrecan binders of the invention, such as the ISVs and/or polypeptides of the invention, to Aggrecan is SPR, such as e.g. the SPR as described in the examples, wherein binding of the Aggrecan binders of the invention, such as the ISVs and/or polypeptides of the invention, to Aggrecan was determined. Some preferred KD values for binding of the Aggrecan binders of the invention, such as the ISVs and/or polypeptides of the invention, to Aggrecan will become clear from the further description and examples herein. Another particularly preferred assay is ELISA as detailed in the Examples (cf. Examples 1.2 and 2.4).

Binding of the Aggrecan binders of the invention to Aggrecan can also be measured in binding assays that preferably preserve the conformation of the Aggrecan target. Typical assays include (without being limiting) assays in which Aggrecan is exposed on a cell surface (such as e.g. CHO cells).

In an embodiment of the invention, the Aggrecan binders of the invention, such as the ISVs and/or polypeptides of the invention, have an on rate constant (Kon) for binding to said Aggrecan selected from the group consisting of at least about $10^2$ $M^{-1}s^{-1}$, at least about $10^3$ $M^{-1}s^{-1}$, at least about $10^4$ $M^{-1}s^{-1}$, at least about $10^5$ $M^{-1}s^{-1}$, at least about $10^6$ $M^{-1}s^{-1}$, $10^7$ $M^{-1}s^{-1}$, at least about $10^8$ $M^{-1}s^{-1}$, at least about $10^9$ $M^{-1}s^{-1}$, and at least about $10^{10}$ $M^{-1}s^{-1}$, preferably as measured by surface plasmon resonance.

In an embodiment of the invention, the Aggrecan binders of the invention, such as the ISVs and/or polypeptides of the invention, have an off rate constant (Koff) for binding to said Aggrecan selected from the group consisting of at most about $10^{-3}$ $s^{-1}$, at most about $10^{-4}$ $s^{-1}$, at most about $10^{-5}$ $s^{-1}$, at most about $10^{-6}$ $s^{-1}$, at most about $10^{-7}$ $s^{-1}$, at most about $10^{-8}$ $s^{-1}$, at most about $10^{-9}$ $s^{-1}$, and at most about $10^{-10}$ $s^{-1}$, preferably as measured by surface plasmon resonance.

In an embodiment of the invention, the Aggrecan binders of the invention, such as the ISVs and/or polypeptides of the invention, bind to said Aggrecan with an average KD value of between 100 nM and 10 pM, such as at an average KD value OF 90 nM or less, even more preferably at an average KD value OF 80 nM or less, such as less than 70, 60, 50, 40, 30, 20, 10, 5 nM or even less, such as less than 4, 3, 2, Or 1 nM, such as less than 500, 400, 300, 200, 100, 90, 80, 70, 60, 50, 40, 30, 20 pM, or even less such as less than 10 pM. Preferably, the KD is determined by SPR, for instance as determined by Proteon.

Some preferred EC50 values for binding of the immunoglobulins and/or polypeptides of the invention to Aggrecan will become clear from the further description and examples herein.

In an ELISA binding assay, the Aggrecan binders of the invention, such as ISVs and/or polypeptides of the present invention, preferably binding the G1 domain and/or G1-IGD-G2 domain, may have EC50 values in binding human Aggrecan of $10^{-8}$ M or lower, more preferably of $10^{-9}$ M or lower, or even of $10^{-10}$ M or lower. For example, in such ELISA binding assay, the immunoglobulins and/or polypeptides of the present invention may have EC50 values in binding human Aggrecan between $10^{-10}$ M and $10^{-8}$ M, such as between $10^{-9}$ M and $10^{-8}$ M or between $10^{-10}$ M and $10^{-9}$ M.

In such ELISA binding assay, the Aggrecan binders of the invention, such as ISVs and/or polypeptides of the present invention, preferably binding the G1 domain and/or G1-IGD-G2 domain, may have EC50 values in binding cynomolgus (cyno) Aggrecan of $10^{-7}$ M or lower, preferably of $10^{-8}$ M or lower, more preferably of $10^{-9}$ M or lower, or even of $10^{-10}$ M or lower. For example, in such ELISA binding assay, the polypeptides of the present invention may have EC50 values in binding cyno Aggrecan between $10^{-10}$ M and $10^{-7}$ M, such as between $10^{-10}$ M and $10^{-8}$ M, between $10^{-10}$ M and $10^{-9}$ M.

In such ELISA binding assay, the Aggrecan binders of the invention, such as ISVs and/or polypeptides of the present invention, preferably binding the G1 domain and/or G1-IGD-G2 domain, may have EC50 values in binding rat Aggrecan of $10^{-6}$ M or lower, preferably of $10^{-7}$ M or lower, preferably of $10^{-8}$ M or lower, more preferably of $10^{-9}$ M or lower, or even of $10^{-10}$ M or lower. For example, in such ELISA binding assay, the polypeptides of the present invention may have EC50 values in binding rat Aggrecan between $10^{-10}$ M and $10^{-6}$ M, such as between $10^{-10}$ M and $10^{-7}$ M, between $10^{-10}$ M and $10^{-8}$ M, between $10^{-10}$ M and $10^{-9}$ M.

In such ELISA binding assay, the Aggrecan binders of the invention, such as ISVs and/or polypeptides of the present invention, preferably binding the G1 domain and/or G1-IGD-G2 domain, may have EC50 values in binding dog Aggrecan of $10^{-6}$ M or lower, preferably of $10^{-7}$ M or lower, preferably of $10^{-8}$ M or lower, more preferably of $10^{-9}$ M or lower, or even of $10^{-10}$ M or lower. For example, in such ELISA binding assay, the polypeptides of the present invention may have EC50 values in binding dog Aggrecan between $10^{-10}$ M and $10^{-6}$ M, such as between $10^{-10}$ M and $10^{-7}$ M, between $10^{-10}$ M and $10^{-8}$ M, between $10^{-10}$ M and $10^{-9}$ M.

In such ELISA binding assay, the Aggrecan binders of the invention, such as ISVs and/or polypeptides of the present invention may, preferably binding the G1 domain and/or G1-IGD-G2 domain, have EC50 values in binding bovine Aggrecan of $10^{-6}$ M or lower, preferably of $10^{-7}$ M or lower, preferably of $10^{-8}$ M or lower, more preferably of $10^{-9}$ M or lower, or even of $10^{-10}$ M or lower. For example, in such ELISA binding assay, the polypeptides of the present invention may have EC50 values in binding bovine Aggrecan between $10^{-10}$ M and $10^{-6}$M, such as between $10^{-10}$M and $10^{-7}$M, between $10^{-10}$M and $10^{-8}$M, between $10^{-10}$M and $10^{-9}$M.

The term "cartilaginous tissue" as used herein, refers to cartilage, including elastic cartilage, hyaline cartilage and fibrocartilage, which are defined by the ratio of cells (chondrocytes) to intercellular space and relative amounts of collagen and proteoglycan. "Articular cartilage" is the cartilage found on the articular surface of bones and is mostly hyaline cartilage. Menisci are made entirely of fibrocartilage. Aggrecan is the main proteoglycan in the extracellular matrix (ECM) and accounts for ca. 50% of total protein content (the other ca. 50% are collagen II and some minor proteins, such as, e.g. collagen IX).

The Aggrecan binders of the invention demonstrated a preference to bind to cartilaginous tissues in a joint such as cartilage and meniscus over non-cartilaginous tissue such as synovial membrane, tendon, and/or epimysium. Accordingly, the present invention relates to an Aggrecan binder, such as an ISV or polypeptide, wherein said Aggrecan binder preferably binds to cartilaginous tissue such as cartilage and/or meniscus, preferably by at least a factor 1.5, a factor 2, a factor 3, a factor 4, a factor 5 or even more compared to non-cartilaginous tissue.

It is appreciated that joints are the areas where two or more bones meet. Most joints are mobile, allowing the bones to move. Joints consist of the following: cartilage, synovial membrane, ligaments, tendons, bursas and synovial fluid. Some joints also have a meniscus.

As demonstrated in the examples, the Aggrecan binders of the invention have various cartilage retention characteristics, which enables customizing retention in joints according to the specific needs (cf. Example 2.2). Preferably, the Aggrecan binders have the ability to retain in cartilage for prolonged periods of time following a relatively short exposure of the Aggrecan binders to the cartilage, which can be expected upon intra-articular injection. The cartilage retention can be measured via an ex vivo cartilage retention assay as set out in the examples section. The degree of retention can be measured by visual inspection of Western blots or via densitometric quantification. The scale used for determining the degree of retention can be defined by the person skilled in the art, for instance a scale from 0 to 6 RU (Retention Units), wherein 0 is no retention and 6 is full retention in this assay. If necessary, the scale can be quantified by using the Aggrecan binders of the invention in which each Aggrecan binder is assigned a score, e.g. full retention and no retention are fixed. In the alternative, the scale can be set by various intermediate scores, which are assigned via the Aggrecan binders of the invention, e.g. an Aggrecan binder comprising two 114F08=6 RU and a dummy Aggrecan binder, e.g. ALB26-ALB26=0 RU; or an Aggrecan binder comprising two 114F08=6; Aggrecan binders comprising 608A05=5; Aggrecan binder 604G01=4; Aggrecan binder comprising two 601D02=3; Aggrecan binder comprising two 606A07=2; Aggrecan binder 112A01=1; and a dummy Aggrecan binder, e.g. ALB26-ALB26=0 (cf. Table 2.2). Accordingly, the present invention relates to an Aggrecan binder, such as an ISV and/or polypeptide according to the invention wherein said Aggrecan binder has a cartilage retention of at least 2, such as at least, 3, 4, 5 or 6 RU in a cartilage retention assay.

The Aggrecan binders of the invention should preferably be stable. As a first prerequisite, the biophysical properties of the Aggrecan binders were tested as detailed in Example 3, in which it was demonstrated that these Aggrecan binders demonstrated favourable stability characteristics as shown by the high melting temperatures and the absence of signs of aggregation and multimerisation. Next, the Aggrecan binders were tested for their activity in the joints for prolonged periods by incubation in synovial fluids at 37° C. (cf. Example 6). No degradation of any of the constructs could be detected, indicating that the constructs were stable under circumstances mimicking the in vivo situation.

In an aspect the invention relates to Aggrecan binders, such as ISVs wherein said Aggrecan binder has a stability of at least 3 days, 4 days, 5 days, 6 days, 7 days, such as 14 days, 21 days, 1 month, 2 months or even 3 months in synovial fluid (SF) at 37° C.

The present invention provides stretches of amino acid residues (SEq ID NOs: 20-37 and 109, SEq ID NOs: 38-55 and 110, and SEq ID NOs: 56-74 and 111; Table A-2) that are particularly suited for binding to Aggrecan. In particular, the invention provides stretches of amino acid residues which bind to human Aggrecan and wherein the binding of said stretches to said Aggrecan retains the presence in cartilaginous tissue (as described above). These stretches of amino acid residues may be present in, and/or may be incorporated into, a construct or polypeptide of the invention, in particular in such a way that they form (part of) the antigen binding site of the polypeptide of the invention. These stretches of amino acid residues have been generated as CDR sequences of heavy chain antibodies or $V_{HH}$ sequences that were raised against Aggrecan. These stretches of amino acid residues are also referred to herein as "CDR sequence(s) of the invention" ("CDR1 sequence(s) of the invention", "CDR2 sequence(s) of the invention" and "CDR3 sequence(s) of the invention", respectively).

It should however be noted that the invention in its broadest sense is not limited to a specific structural role or function that these stretches of amino acid residues may have in a polypeptide of the invention, as long as these stretches of amino acid residues allow the polypeptide of the invention to bind to Aggrecan with a desired affinity and potency. Thus, generally, the invention in its broadest sense provides polypeptides (also referred to herein as "polypeptide(s) of the invention") that are capable of binding to Aggrecan with a certain specified affinity, avidity, efficacy and/or potency and that comprises one or more CDR sequences as described herein and, in particular a suitable combination of two or more such CDR sequences, that are suitably linked to each other via one or more further amino acid sequences, such that the entire polypeptide forms a binding domain and/or binding unit that is capable of binding to Aggrecan. It should however also be noted that the presence of only one such CDR sequence in a polypeptide of the invention may by itself already be sufficient to provide the polypeptide of the invention the capacity of binding to Aggrecan; reference is for example again made to the so-called "Expedite fragments" described in WO 03/050531.

In a specific, but non-limiting aspect, the Aggrecan binder of the invention such as the ISV and/or polypeptide of the invention, may essentially consist of or comprise at least one stretch of amino acid residues that is chosen from the group consisting of:

- i) CDR1 sequences:
  - a) SeQ ID NOs: 24, 32, 20, 21, 22, 23, 25, 26, 27, 28, 29, 30, 31, 33, 34, 35, 36, 37 and 109; and
  - b) amino acid sequences that have 4, 3, 2, or 1 amino acid(s) difference with the amino acid sequence of SEQ ID NO: 24;

and/or

- ii) CDR2 sequences:
  - c) SeQ ID NOs: 42, 50, 38, 39, 40, 41, 43, 44, 45, 46, 47, 48, 49, 51, 52, 53, 54, 55 and 110; and
  - d) amino acid sequences that have 4, 3, 2, or 1 amino acid(s) difference with the amino acid sequence of SEQ ID NO: 42;

and/or

- iii) CDR3 sequences:
  - e) SeQ ID NOs: 60, 68, 56, 57, 58, 59, 61, 62, 63, 64, 65, 66, 67, 69, 70, 71, 72, 73, 74 and 111; and
  - f) amino acid sequences that have 4, 3, 2, or 1 amino acid(s) difference with the amino acid sequence of SEQ ID NO: 60, preferably, the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In a further aspect, the Aggrecan binder of the invention, such as the polypeptide and/or ISV of the invention, may comprise at least one stretch of amino acid residues that is chosen from the group consisting of SeQ ID NOs: 20-74 and 109-111.

In particular, the Aggrecan binder of the invention, such as the polypeptide and/or ISV of the invention, may be an Aggrecan binder that comprises one antigen binding site, wherein said antigen binding site comprises at least one stretch of amino acid residues that is chosen from the group consisting of the CDR1 sequences, CDR2 sequences and CDR3 sequences as described above (or any suitable combination thereof). In a preferred aspect, however, the Aggrecan binder of the invention, such as the polypeptide and/or ISV of the invention, comprises more than one, such as two or more stretches of amino acid residues chosen from the group consisting of the CDR1 sequences of the invention, the CDR2 sequences of the invention and/or the CDR3 sequences of the invention. Preferably, the Aggrecan binder of the invention, such as the polypeptide and/or ISV of the invention, comprises three stretches of amino acid residues chosen from the group consisting of the CDR1 sequences of the invention, the CDR2 sequences of the invention and the CDR3 sequences of the invention, respectively. The combinations of CDR's that are mentioned herein as being preferred for the Aggrecan binder of the invention, such as the polypeptide and/or ISV of the invention, are listed in Table A-2, i.e. preferably the CDR combination shown on a single row in said table.

Representative polypeptides of the present invention having the CDRs described above are shown in Table A-1 (SEQ ID NO:s 1-19 and 114-118).

In a preferred embodiment, the present invention relates to an Aggrecan binder of the invention, such as an ISV and/or polypeptide of the invention, that comprises 3 complementarity determining regions (CDR1 to CDR3, respectively), wherein:

- CDR1 is chosen from the group consisting of SeQ ID NOs: 24, 32, 20, 21, 22, 23, 25, 26, 27, 28, 29, 30, 31, 33, 34, 35, 36, 37 and 109;
- CDR2 is chosen from the group consisting of SeQ ID NOs: 42, 50, 38, 39, 40, 41, 43, 44, 45, 46, 47, 48, 49, 51, 52, 53, 54, 55 and 110; and
- CDR3 is chosen from the group consisting of SeQ ID NOs: 60, 68, 56, 57, 58, 59, 61, 62, 63, 64, 65, 66, 67, 69, 70, 71, 72, 73, 74 and 111 preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In a preferred embodiment, the present invention relates to an Aggrecan binder of the invention, such as an ISV and/or polypeptide of the invention, that comprises 3 complementarity determining regions (CDR1 to CDR3, respectively), wherein:

CDR1 is SEQ ID NO: 24, CDR2 is SEQ ID NO: 42, and CDR3 is SEQ ID NO: 60;
CDR1 is SEQ ID NO: 32, CDR2 is SEQ ID NO: 50, and CDR3 is SEQ ID NO: 68;
CDR1 is SEQ ID NO: 20, CDR2 is SEQ ID NO: 38, and CDR3 is SEQ ID NO: 56;
CDR1 is SEQ ID NO: 21, CDR2 is SEQ ID NO: 39, and CDR3 is SEQ ID NO: 57;
CDR1 is SEQ ID NO: 22, CDR2 is SEQ ID NO: 40, and CDR3 is SEQ ID NO: 58;
CDR1 is SEQ ID NO: 23, CDR2 is SEQ ID NO: 41, and CDR3 is SEQ ID NO: 59;
CDR1 is SEQ ID NO: 25, CDR2 is SEQ ID NO: 43, and CDR3 is SEQ ID NO: 61;
CDR1 is SEQ ID NO: 26, CDR2 is SEQ ID NO: 44, and CDR3 is SEQ ID NO: 62;
CDR1 is SEQ ID NO: 27, CDR2 is SEQ ID NO: 45, and CDR3 is SEQ ID NO: 63;
CDR1 is SEQ ID NO: 28, CDR2 is SEQ ID NO: 46, and CDR3 is SEQ ID NO: 64;
CDR1 is SEQ ID NO: 29, CDR2 is SEQ ID NO: 47, and CDR3 is SEQ ID NO: 65;
CDR1 is SEQ ID NO: 30, CDR2 is SEQ ID NO: 48, and CDR3 is SEQ ID NO: 66;
CDR1 is SEQ ID NO: 31, CDR2 is SEQ ID NO: 49, and CDR3 is SEQ ID NO: 67;
CDR1 is SEQ ID NO: 32, CDR2 is SEQ ID NO: 51, and CDR3 is SEQ ID NO: 69;
CDR1 is SEQ ID NO: 33, CDR2 is SEQ ID NO: 52, and CDR3 is SEQ ID NO: 70;
CDR1 is SEQ ID NO: 34, CDR2 is SEQ ID NO: 50, and CDR3 is SEQ ID NO: 71;
CDR1 is SEQ ID NO: 35, CDR2 is SEQ ID NO: 53, and CDR3 is SEQ ID NO: 72;
CDR1 is SEQ ID NO: 36, CDR2 is SEQ ID NO: 54, and CDR3 is SEQ ID NO: 73;
CDR1 is SEQ ID NO: 37, CDR2 is SEQ ID NO: 55, and CDR3 is SEQ ID NO: 74; or
CDR1 is SEQ ID NO: 109, CDR2 is SEQ ID NO: 110, and CDR3 is SEQ ID NO: 111;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In a preferred embodiment, the present invention relates to an Aggrecan binder, such as an ISV, wherein said ISV has been chosen from the group consisting of SeQ ID NOs: 117, 5, 118, 13, 114-116, 1-4, 6-12 and 14-19.

It should be further noted that the invention is not limited as to the origin of the Aggrecan binder of the invention, such as the ISV and/or polypeptide of the invention, (or of the nucleic acid of the invention used to express it), nor as to the way that the Aggrecan binder of the invention, such as the ISV and/or polypeptide of the invention, or nucleic acid of the invention is (or has been) generated or obtained. Thus, the Aggrecan binder of the invention, such as the ISV and/or polypeptide of the invention, may be naturally occurring ISVs (from any suitable species) or synthetic or semi-synthetic ISVs and/or polypeptides.

Furthermore, it will also be clear to the skilled person that it is possible to "graft" one or more of the CDRs mentioned above onto other "scaffolds", including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0605522, EP 0460167, U.S. Pat. No. 7,054,297, Nicaise et al. (Protein Science 13: 1882-1891, 2004), Ewert et al. (Methods 34: 184-199, 2004), Kettleborough et al. (Protein Eng. 4: 773-783, 1991), O'Brien and Jones (Methods Mol. Biol. 207: 81-100, 2003), Skerra (J. Mol. Recognit. 13: 167-187, 2000) and Saerens et al. (J. Mol. Biol. 352: 597-607, 2005) and the further references cited therein. For example, techniques known per se for grafting mouse or rat CDR's onto human frameworks and scaffolds can be used in an analogous manner to provide chimeric proteins comprising one or more of the CDR sequences defined herein for the monovalent polypeptides of the invention and one or more human framework regions or sequences. Suitable scaffolds for presenting amino acid sequences will be clear to the skilled person, and for example comprise binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al. Nat Biotech 23:1257, 2005), and binding moieties based on DNA or RNA including but not limited to DNA or RNA aptamers (Ulrich et al. Com Chem High Throughput Screen 9:619-32, 2006).

In the Aggrecan binder of the invention, such as the ISV and/or polypeptide of the invention, the CDRs may be linked to further amino acid sequences and/or may be linked to each other via amino acid sequences, in which said amino acid sequences are preferably framework sequences or are amino acid sequences that act as framework sequences, or together form a scaffold for presenting the CDRs.

According to a preferred embodiment, the Aggrecan binders of the invention, such as the ISVs and/or polypeptides of the invention, comprise at least three CDR sequences linked to at least two framework sequences, in which preferably at least one of the three CDR sequences is a CDR3 sequence, with the other two CDR sequences being CDR1 or CDR2 sequences, and preferably being one CDR1 sequence and one CDR2 sequence. According to one specifically preferred, but non-limiting embodiment, the Aggrecan binders of the invention, such as the ISVs and/or polypeptides of the invention, have the structure FR1-CDR1-FR2-CDR2-FR3-CDR3-FR4, in which CDR1, CDR2 and CDR3 are as defined herein for the Aggrecan binders of the invention, such as the ISVs and/or polypeptides of the invention, and FR1, FR2, FR3 and FR4 are framework sequences. In such an Aggrecan binder of the invention, such as an ISV and/or polypeptide of the invention, the framework sequences may be any suitable framework sequence, and examples of suitable framework sequences will be clear to the skilled person, for example on the basis of the standard handbooks and the further disclosure and prior art mentioned herein.

Accordingly, an Aggrecan binder of the invention, such as an ISV and/or polypeptide of the invention, comprises 3 complementarity determining regions (CDR1 to CDR3, respectively), in which:

(i) CDR1 is chosen from the group consisting of:
(a) SeQ ID NOs: 24, 32, 20, 21, 22, 23, 25, 26, 27, 28, 29, 30, 31, 33, 34, 35, 36, 37 and 109; and
(b) amino acid sequences that have 4, 3, 2, or 1 amino acid(s) difference with the amino acid sequence of SEQ ID NO: 24 or with any of SeQ ID NOs: 20-23, 25-37 and 109; and/or
(ii) CDR2 is chosen from the group consisting of:
(c) SEQ ID NOs: 42, 50, 38, 39, 40, 41, 43, 44, 45, 46, 47, 48, 49, 51, 52, 53, 54, 55 and 110; and
(d) amino acid sequences that have 4, 3, 2, or 1 amino acid(s) difference with the amino acid sequence of SEQ ID NO: 42 or with any of SEQ ID NOs: 38-41, 43-55 and 110; and/or
(iii) CDR3 is chosen from the group consisting of:
(e) SEQ ID NOs: 60, 68, 56, 57, 58, 59, 61, 62, 63, 64, 65, 66, 67, 69, 70, 71, 72, 73, 74 and 111; and
(f) amino acid sequences that have 4, 3, 2, or 1 amino acid(s) difference with the amino acid sequence of SEQ ID NO: 60 or with any of SEQ ID NOs: 56-59, 61-74 and 111 preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

The Aggrecan binders of the invention could be mapped to the G1-region, the G1-IGD-G2 region or the G2 region of Aggrecan.

Accordingly, the present invention relates to Aggrecan binders of the invention, such as ISVs and/or polypeptides that bind to the G2 domain of Aggrecan. As set out in the examples, these Aggrecan binders of the invention, such as ISVs and/or polypeptides have various preferred characteristics. Preferably, the Aggrecan binders of the invention, such as ISVs and/or polypeptides, have a pl of more than 8, and/or have a Koff of less than $2*10^{-2}$ $s^{-1}$, and/or have an EC50 of less than $1*10^{-6}$M.

A comparison of the CDRs of the Aggrecan binders of the invention, such as the ISVs and/or polypeptides of the invention, revealed a number of permissible amino changes in the CDRs, while retaining binding to the G2 domain of Aggrecan. The sequence variability in the CDRs of all clones against the CDRs of 601D02, which was used as reference, is depicted in the Tables 1.5A, 1.5B and 1.5C.

In an embodiment, the present invention relates to Aggrecan binders of the invention, such as ISVs and/or polypeptides, in which:

i) CDR1 is chosen from the group consisting of:
a) SEQ ID NO:s 28, 22, 26, and 33; and
b) amino acid sequences that have 5, 4, 3, 2, or 1 amino acid(s) difference with the amino acid sequence of SEQ ID NO: 28, wherein the amino acid difference (s) are defined as follows:
at position 1 the G has been changed into R;
at position 2 the P has been changed into S or R;
at position 3 the T has been changed into I;
at position 5 the S has been changed into N;
at position 6 the R has been changed into N, M, or S;
at position 7 the Y has been changed into R or is absent;
at position 8 the A has been changed into F or is absent; and/or
at position 10 the G has been changed into Y;

and/or ii) CDR2 is chosen from the group consisting of:
c) SEQ ID NO: 46, 40, 44, and 52; and
d) amino acid sequences that have 5, 4, 3, 2, or 1 amino acid(s) difference with the amino acid sequence of SEQ ID NO: 46, wherein the amino acid difference (s) are defined as follows:
at position 1 the A has been changed into S, or Y;
at position 4 the W has been changed into L;
at position 5 the S has been changed into N;
at position 6 the S is absent;
at position 7 the G is absent;
at position 8 the G has been changed into A;
at position 9 the R has been changed into S, D, or T; and/or
at position 11 the Y has been changed into N or R;

and/or iii) CDR3 is chosen from the group consisting of:
e) SEQ ID NO: 64, 58, 62, and 70; and
f) amino acid sequences that have 5, 4, 3, 2, or 1 amino acid(s) difference with the amino acid sequence of SEQ ID NO: 64, wherein the amino acid difference (s) are defined as follows:
at position 1 the A has been changed into R, or F;
at position 2 the R has been changed into I, or L;
at position 3 the I has been changed into H, or Q;
at position 4 the P has been changed into G, or N;
at position 5 the V has been changed into S;
at position 6 the R has been changed into G, N, or F;
at position 7 the T has been changed into R, W, or Y;
at position 8 the Y has been changed into R, or S, or is absent;
at position 9 the T has been changed into S, or is absent;
at position 10 the S has been changed into E, K or is absent;
at position 11 the E has been changed into N, A, or is absent;
at position 12 the W has been changed into D, or is absent;
at position 13 the N has been changed into D, or is absent;
at position 14 the Y is absent; and/or
D and N are added after position 14 of SEQ ID NO: 64;

preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group of Aggrecan binders, wherein:

CDR1 is chosen from the group consisting of SEQ ID NOs: 28, 22, 26, and 33;
CDR2 is chosen from the group consisting of SEQ ID NOs: 46, 40, 44, and 52; and
CDR3 is chosen from the group consisting of SEQ ID NOs: 64, 58, 62, and 70;

preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group of Aggrecan binders, wherein:

CDR1 is SEQ ID NO: 28, CDR2 is SEQ ID NO: 46, and CDR3 is SEQ ID NO: 64;
CDR1 is SEQ ID NO: 22, CDR2 is SEQ ID NO: 40, and CDR3 is SEQ ID NO: 58;

CDR1 is SEQ ID NO: 26, CDR2 is SEQ ID NO: 44, and CDR3 is SEQ ID NO: 62; and

CDR1 is SEQ ID NO: 33, CDR2 is SEQ ID NO: 52, and CDR3 is SEQ ID NO: 70;

preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group of Aggrecan binders chosen from the group consisting of SEQ ID NOs: 9, 3, 7 and 15, and Aggrecan binders which have more than 80%, such as 90% or 95% sequence identity with any one of SEQ ID NOs: 9, 3, 7 and 15.

In an aspect, the present invention relates to Aggrecan binders of the invention, such as ISVs and/or polypeptides that cross-block the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G2 domain of Aggrecan.

In an aspect, the present invention relates to a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to G2-domain of Aggrecan, and which competes for binding to the G2 domain of Aggrecan with Aggrecan binders of the invention, such as ISVs and/or polypeptides of the invention, preferably represented by any one of SEQ ID NOs: 9, 3, 7 and 15.

The present invention also relates to Aggrecan binders of the invention, such as ISVs and/or polypeptides that bind to the G1-IGD-G2 domain of Aggrecan. As set out in the examples, these Aggrecan binders of the invention, such as ISVs and/or polypeptides have various preferred characteristics. Preferably, the Aggrecan binders of the invention, such as ISVs and/or polypeptides have a pI of more than 8, and/or have a Koff of less than $2*10^{-2}$ $s^{-1}$, and/or have an EC50 of less than $1*10^{-6}$M.

A comparison of the CDRs of the Aggrecan binders of the invention, such as the ISVs and/or polypeptides of the invention, revealed a number of permissible amino changes in the CDRs, while retaining binding to the G1-IGD-G2 domain of Aggrecan. The sequence variability in the CDRs of all clones against the CDRs of 604F02, which was used as reference, is depicted in the Tables 1.4A, 1.4B and 1.4C.

In an aspect the present invention also relates to Aggrecan binders of the invention, such as ISVs and/or polypeptides, in which:

i) CDR1 is chosen from the group consisting of:
   a) SEQ ID NOs: 32, 30 and 23; and
   b) amino acid sequences that have 3, 2, or 1 amino acid(s) difference with the amino acid sequence of SEQ ID NO: 32, wherein the amino acid difference (s) are defined as follows:
      at position 2 the R has been changed into L;
      at position 6 the S has been changed into T; and/or
      at position 8 the T has been changed into A;

and/or ii) CDR2 is chosen from the group consisting of:
   c) SEQ ID NOs: 50, 41, 48 and 51; and
   d) amino acid sequences that have 2, or 1 amino acid(s) difference with the amino acid sequence of SEQ ID NO: 50, wherein the amino acid difference(s) are defined as follows:
      at position 7 the G has been changed into S or R; and/or
      at position 8 the R has been changed into T;

and/or iii) CDR3 is chosen from the group consisting of:
   e) SEQ ID NOs: 68, 59, 66 and 69; and
   f) amino acid sequences that have 5, 4, 3, 2, or 1 amino acid(s) difference with the amino acid sequence of SEQ ID NO: 68, wherein the amino acid difference (s) are defined as follows:
      at position 4 the R has been changed into V, or P;
      at position 6 the A has been changed into Y;
      at position 7 the S has been changed into T;
      at position 8 the S is absent;
      at position 9 the N has been changed into P;
      at position 10 the R has been changed into T or L;
      at position 11 the G has been changed into E; and/or
      at position 12 the L has been changed into T or V;

preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides, wherein:

CDR1 is chosen from the group consisting of SEQ ID NOs: 32, 30 and 23;

CDR2 is chosen from the group consisting of SEQ ID NOs: 50, 41, 48 and 51; and

CDR3 is chosen from the group consisting of SEQ ID NOs: 68, 59, 66 and 69;

preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group of Aggrecan binders, wherein:

CDR1 is SEQ ID NO: 32, CDR2 is SEQ ID NO: 50, and CDR3 is SEQ ID NO: 68;

CDR1 is SEQ ID NO: 32, CDR2 is SEQ ID NO: 51, and CDR3 is SEQ ID NO: 69;

CDR1 is SEQ ID NO: 30, CDR2 is SEQ ID NO: 48, and CDR3 is SEQ ID NO: 66; and

CDR1 is SEQ ID NO: 23, CDR2 is SEQ ID NO: 41, and CDR3 is SEQ ID NO: 59;

preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group consisting of Aggrecan binders with SEQ ID NOs: 118, 13, 4, 11 and 14, and Aggrecan binders which have more than 80%, such as 90% or 95% sequence identity with any one of SEQ ID NOs: 118, 13, 4, 11 and 14.

In an aspect, the present invention relates to Aggrecan binders of the invention, such as ISVs and/or polypeptides that cross-block the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G1-IGD-G2 domain of Aggrecan.

In an aspect, the present invention relates to a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to the G1-IGD-G2 domain of Aggrecan, and which competes for binding to the G1-IGD-G2 domain of Aggrecan with the Aggrecan binder of the invention, such as the ISV and/or polypeptide of the invention, preferably represented by any one of SEQ ID NOs: 118, 13, 4, 11 and 14.

In a particularly preferred embodiment the present invention relates to Aggrecan binders of the invention, such as ISVs and/or polypeptides of the invention, which bind to the G1 domain of Aggrecan. As set out in the examples, these Aggrecan binders of the invention, such as the ISVs and/or polypeptides of the invention, have various preferred characteristics. Preferably, the Aggrecan binders of the invention, such as ISVs and/or polypeptides have a pI of more than 8, and/or have a Koff of less than $2*10^{-2}$ $s^{-1}$, and/or have an EC50 of less than $1*10^{-6}$M.

A comparison of the CDRs of the Aggrecan binders of the invention, such as the ISVs and/or polypeptides of the invention, revealed a number of permissible amino changes in the CDRs, while retaining binding to the G1 domain of Aggrecan. The sequence variability in the CDRs of all clones against the CDRs of 114F08, which was used as reference, is depicted in the Tables 1.3A, 1.3B and 1.3C.

In a preferred aspect, the present invention relates to Aggrecan binders of the invention, such as ISVs and/or polypeptides of the invention that comprises 3 complementarity determining regions (CDR1 to CDR3, respectively), in which:

i) CDR1 is chosen from the group consisting of:
  a) SEQ ID NOs: 24, 20, 21, 25, 27, 29, 31, 34, 35, 36, and 37; and
  b) amino acid sequences that have 5, 4, 3, 2, or 1 amino acid(s) difference with the amino acid sequence of SEQ ID NO: 24, wherein the amino acid difference(s) are defined as follows:
    at position 2 the S has been changed into R, F, I, or T;
    at position 3 the T has been changed into I;
    at position 5 the I has been changed into S;
    at position 6 the I has been changed into S, T, or M;
    at position 7 the N has been changed into Y, or R;
    at position 8 the V has been changed into A, Y, T, or G;
    at position 9 the V has been changed into M; and/or
    at position 10 the R has been changed into G, K, or A;

and/or ii) CDR2 is chosen from the group consisting of:
  c) SEQ ID NOs: 42, 38, 39, 43, 45, 47, 49, 50, 53, 54, and 55; and
  d) amino acid sequences that have 5, 4, 3, 2, or 1 amino acid(s) difference with the amino acid sequence of SEQ ID NO: 42, wherein the amino acid difference(s) are defined as follows:
    at position 1 the T has been changed into A, or G;
    an S or N is inserted between position 3 and position 4 (position 2a, Table 1.3B);
    at position 3 the S has been changed into R, W, N, or T;
    at position 4 the S has been changed into T or G;
    at position 5 the G has been changed into S;
    at position 6 the G has been changed into S, or R;
    at position 7 the N has been changed into S, T, or R;
    at position 8 the A has been changed into T; and/or
    at position 9 the N has been changed into D or Y;

and/or iii) CDR3 is chosen from the group consisting of:
  e) SEQ ID NOs: 60, 56, 57, 61, 63, 65, 67, 71, 72, 73 and 74; and
  f) amino acid sequences that have 5, 4, 3, 2, or 1 amino acid(s) difference with the amino acid sequence of SEQ ID NO: 60, wherein the amino acid difference(s) are defined as follows:
    at position 1 the P has been changed into G, R, D, or E, or is absent;
    at position 2 the T has been changed into R, L, P, or V, or is absent;
    at position 3 the T has been changed into M, S, or R, or is absent;
    at position 4 the H has been changed into D, Y, G, or T;
    at position 5 the Y has been changed into F, V, T or G;
    at position 6 the G has been changed into L, D, S, Y, or W;
    an R, T, Y or V is inserted between position 6 and position 7 (position 6a, Table 1.3C);
    at position 7 the G has been changed into P, or S;
    at position 8 the V has been changed into G, T, H, R, L, or Y;
    at position 9 the Y has been changed into R, A, S, D or G;
    at position 10 the Y has been changed into N, E, G, W, or S;
    a W is inserted between position 10 and position 11 (position 10a, Table 1.3C);
    at position 11 the G has been changed into S, K, or Y;
    at position 12 the P has been changed into E, or D, or is absent; and/or
    at position 13 the Y has been changed into L, or is absent;

preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In a preferred aspect, the present invention relates to Aggrecan binders of the invention, such as ISVs and/or polypeptides chosen from the group of Aggrecan binders, wherein: CDR1 is chosen from the group consisting of SEQ ID NOs: 24, 20, 21, 25, 27, 29, 31, 34, 35, 36, 37 and 109; CDR2 is chosen from the group consisting of SEQ ID NOs: 42, 38, 39, 43, 45, 47, 49, 50, 53, 54, 55, and 110; and CDR3 is chosen from the group consisting of SEQ ID NOs: 60, 56, 57, 61, 63, 65, 67, 71, 72, 73, 74, and 111; preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In a preferred aspect, the present invention relates to Aggrecan binders of the invention, such as ISVs and/or polypeptides chosen from the group of Aggrecan binders, wherein:

CDR1 is SEQ ID NO: 24, CDR2 is SEQ ID NO: 42, and CDR3 is SEQ ID NO: 60;

CDR1 is SEQ ID NO: 20, CDR2 is SEQ ID NO: 38, and CDR3 is SEQ ID NO: 56;

CDR1 is SEQ ID NO: 21, CDR2 is SEQ ID NO: 39, and CDR3 is SEQ ID NO: 57;

CDR1 is SEQ ID NO: 25, CDR2 is SEQ ID NO: 43, and CDR3 is SEQ ID NO: 61;

CDR1 is SEQ ID NO: 27, CDR2 is SEQ ID NO: 45, and CDR3 is SEQ ID NO: 63;

CDR1 is SEQ ID NO: 29, CDR2 is SEQ ID NO: 47, and CDR3 is SEQ ID NO: 65;

CDR1 is SEQ ID NO: 31, CDR2 is SEQ ID NO: 49, and CDR3 is SEQ ID NO: 67;

CDR1 is SEQ ID NO: 34, CDR2 is SEQ ID NO: 50, and CDR3 is SEQ ID NO: 71;

CDR1 is SEQ ID NO: 35, CDR2 is SEQ ID NO: 53, and CDR3 is SEQ ID NO: 72;

CDR1 is SEQ ID NO: 36, CDR2 is SEQ ID NO: 54, and CDR3 is SEQ ID NO: 73;

CDR1 is SEQ ID NO: 37, CDR2 is SEQ ID NO: 55, and CDR3 is SEQ ID NO: 74; and

CDR1 is SEQ ID NO: 109, CDR2 is SEQ ID NO: 110, and CDR3 is SEQ ID NO: 111;

preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

It has been demonstrated in the examples section that the exemplary clone 114F08 has particularly preferred characteristics. Clone 114F08 represents a family or set of clones, further comprising clone 114A09 (SEQ ID NO: 114) and 114B04 (SEQ ID NO: 115), which have been grouped based on similarities in the CDRs (cf. Table A-2 and Tables 3.3A, 3.3B, and 3.3C), which translates into similarities in functional characteristics. Hence, in another particularly preferred aspect, the present invention relates to Aggrecan binders of the invention, such as ISVs and/or polypeptides that comprises 3 complementarity determining regions (CDR1 to CDR3, respectively), in which:

i) CDR1 is chosen from the group consisting of:
   a) SEQ ID NO:s 24 and 109; and
   b) amino acid sequences that have 2, or 1 amino acid(s) difference with the amino acid sequence of SEQ ID NO: 24, wherein the amino acid difference(s) are defined as follows:
      at position 7 the N has been changed into S; and/or
      at position 9 the V has been changed into M;

and/or ii) CDR2 is chosen from the group consisting of:
   c) SEQ ID NO:s 42 and 110; and
   d) amino acid sequences that have 5, 4, 3, 2, or 1 amino acid(s) difference with the amino acid sequence of SEQ ID NO: 42, wherein the amino acid difference (s) are defined as follows:
      at position 1 the T has been changed into A;
      at position 3 the S has been changed into R;
      at position 4 the S has been changed into T;
      at position 8 the A has been changed into T; and/or
      at position 9 the N has been changed into D;
   and/or iii) CDR3 is chosen from the group consisting of:
   e) SEQ ID NO:s 60 and 111; and
   f) amino acid sequences that have 2, or 1 amino acid(s) difference with the amino acid sequence of SEQ ID NO: 60, wherein the amino acid difference(s) are defined as follows:
      at position 4 the H has been changed into R; and/or
      at position 8 the V has been changed into D;

preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides, chosen from the group of Aggrecan binders, wherein:

CDR1 is chosen from the group consisting of SEQ ID NOs: 24 and 109;

CDR2 is chosen from the group consisting of SEQ ID NOs: 42 and 110; and

CDR3 is chosen from the group consisting of SEQ ID NOs: 60 and 111 preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

It further has been demonstrated in the examples section that Aggrecan binders binding to the G1 region of Aggrecan and belonging to epitope bin 1 or epitope bin 4 are particularly effective in cartilage retention assays. In an aspect, the present invention relates to Aggrecan binders of the invention, such as ISVs and/or polypeptides that belong to epitope bin 1 or epitope bin 4.

A comparison of the CDRs of the Aggrecan binders of the invention, such as the ISVs and/or polypeptides of the invention, belonging to epitope bin 1 revealed a number of permissible amino changes in the CDRs, while retaining binding to the G1 domain of Aggrecan. The sequence variability in the CDRs of all clones against the CDRs of 608A05, which was used as reference, is depicted in the Tables 2.3D, 2.3E and 2.3F.

In a preferred aspect, the present invention relates to Aggrecan binders of the invention, such as ISVs and/or polypeptides that comprises 3 complementarity determining regions (CDR1 to CDR3, respectively), in which:

i) CDR1 is chosen from the group consisting of:
   a) SEQ ID NO:s 36, 20 and 29; and
   b) amino acid sequences that have 2, or 1 amino acid(s) difference with the amino acid sequence of SEQ ID NO: 36, wherein the amino acid difference(s) are defined as follows:
      at position 3 the T has been changed into S;
      at position 6 the T has been changed into S;
      at position 8 the T has been changed into A; and/or
      at position 9 the M has been changed into V;

and/or ii) CDR2 is chosen from the group consisting of:
   c) SEQ ID NO:s 54, 38 and 37; and
   d) amino acid sequences that have 2, or 1 amino acid(s) difference with the amino acid sequence of SEQ ID NO: 54, wherein the amino acid difference(s) are defined as follows:
      at position 1 the A has been changed into I;
      at position 4 the W has been changed into R;
      at position 7 the G has been changed into R; and/or
      at position 8 the T has been changed into S;

and/or iii) CDR3 is chosen from the group consisting of:
   e) SEQ ID NO: 73, 56 and 65; and f) amino acid sequences that have 5, 4, 3, 2, or 1 amino acid(s) difference with the amino acid sequence of SEQ ID NO: 73, wherein the amino acid difference(s) are defined as follows:
at position 1 the R has been changed into G;
at position 2 the P has been changed into R or L;
at position 3 the R has been changed into L or S;
at position 5 the Y has been changed into R;
at position 6 the Y has been changed into S or A;
at position 7 the Y has been changed into T, or is absent;
at position 8 the S has been changed into P;
at position 9 the L has been changed into H or R;
at position 10 the Y has been changed into P or A;
at position 11 the S has been changed into A or Y;
at position 12 the Y has been changed into D;
at position 13 the D has been changed into F;
at position 14 the Y has been changed into G, or is absent; and/or
after position 14 an S is inserted;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group of Aggrecan binders, wherein:
CDR1 is chosen from the group consisting of SEQ ID NOs: 20, 29, and 36;
CDR2 is chosen from the group consisting of SEQ ID NOs: 38, 47, and 54; and
CDR3 is chosen from the group consisting of SEQ ID NOs: 56, 65, and 73;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides belonging to epitope bin 1 that cross-block the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G1 domain of Aggrecan.

In an aspect, the present invention relates to a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to epitope bin 1 of the G1-domain of Aggrecan, and which competes for binding to the G1 domain of Aggrecan with the Aggrecan binders of the invention, such as ISVs and/or polypeptides that belong to epitope bin 1, preferably such as e.g. represented by any one of SEQ ID NO:s 1, 10 and 18.

A comparison of the CDRs of the Aggrecan binders of the invention, such as the ISVs and/or polypeptides of the invention, belonging to epitope bin 4 revealed a number of permissible amino changes in the CDRs, while retaining binding to the G1 domain of Aggrecan. The sequence variability in the CDRs of all clones against the CDRs of 114F08, which was used as reference, is depicted in the Tables 2.3A, 2.3B and 2.3C.

In an aspect, the present invention relates to Aggrecan binders of the invention, such as ISVs and/or polypeptides that comprises 3 complementarity determining regions (CDR1 to CDR3, respectively), in which:
i) CDR1 is chosen from the group consisting of:
a) SEQ ID NO: 24, 25 and 27; and
b) amino acid sequences that have 2, or 1 amino acid(s) difference with the amino acid sequence of SEQ ID NO: 24, wherein the amino acid difference(s) are defined as follows:
at position 2 the S has been changed into I or F;
at position 5 the I has been changed into S;
at position 6 the I has been changed into S or M;
at position 7 the N has been changed into R or Y;
at position 8 the V has been changed into A or Y;
at position 9 the V has been changed into M; and/or
at position 10 the R has been changed into K;
and/or
ii) CDR2 is chosen from the group consisting of:
c) SEQ ID NO: 42, 43 and 45; and
d) amino acid sequences that have 5, 4, 3, 2, or 1 amino acid(s) difference with the amino acid sequence of SEQ ID NO: 42, wherein the amino acid difference(s) are defined as follows:
at position 1 the T has been changed into A or G;
an N is inserted between position 2 and position 3 (position 2a Table 2.3B);
at position 7 the N has been changed into R;
at position 8 the A has been changed into T; and/or
at position 9 the N has been changed into D;
and/or
iii) CDR3 is chosen from the group consisting of:
e) SEQ ID NO: 60, 61 and 63; and
f) amino acid sequences that have 5, 4, 3, 2, or 1 amino acid(s) difference with the amino acid sequence of SEQ ID NO: 60, wherein the amino acid difference(s) are defined as follows:
at position 1 the P is absent;
at position 2 the T has been changed into R or is absent;
at position 3 the T has been changed into M or is absent;
at position 4 the H has been changed into D or Y;
at position 5 the Y has been changed into F or V;
at position 6 the G has been changed into L or D;
at position 8 the V has been changed into G or T;
at position 9 the Y has been changed into R;
at position 10 the Y has been changed into N or E;
at position 11 the G has been changed into S or K;
at position 12 the P has been changed into E or is absent; and/or
at position 13 the Y has been changed into L or is absent;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group of Aggrecan binders, wherein:
CDR1 is chosen from the group consisting of SEQ ID NOs: 24, 25, and 27;
CDR2 is chosen from the group consisting of SEQ ID NOs: 42, 43, and 45; and CDR3 is chosen from the group consisting of SEQ ID NOs: 60, 61, and 63;

preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides belonging to epitope bin 4 that cross-block the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G1 domain of Aggrecan.

In an aspect, the present invention relates to a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to epitope bin 4 of the G1-domain of Aggrecan, and which competes for binding to the G1 domain of Aggrecan with the Aggrecan binders of the invention, such as ISVs and/or polypeptides that belong to epitope bin 4, such as e.g. represented by any one of SEQ ID NO:s 117, 114, 115, 116, 5, 6 and 8.

In an aspect, the present invention relates to Aggrecan binders of the invention, such as ISVs and/or polypeptides chosen from the group consisting of Aggrecan binders represented by SEQ ID NOs: 117, 118, 116, 114, 115, 5, 13, 1, 2, 6, 8, 10, 12, 16, 17, 18, and 19, and ISVs which have more than 80%, such as 90% or 95%, or even more sequence identity with any one of SEQ ID NOs: 117, 118, 116, 114, 115, 5, 13, 1, 2, 6, 8, 10, 12, 16, 17, 18, and 19.

In a specific, but non-limiting aspect, the Aggrecan binder of the invention may be a stretch of amino acid residues that comprises an immunoglobulin fold or an Aggrecan binder that, under suitable conditions (such as physiological conditions) is capable of forming an immunoglobulin fold (i.e., by folding). Reference is inter alia made to the review by Halaby et al. (J. Protein Eng. 12: 563-71, 1999). Preferably, when properly folded so as to form an immunoglobulin fold, the stretches of amino acid residues may be capable of properly forming the antigen binding site for binding to Aggrecan. Accordingly, in a preferred aspect the Aggrecan binder of the invention is an immunoglobulin, such as e.g. an immunoglobulin single variable domain.

Accordingly, the framework sequences are preferably (a suitable combination of) immunoglobulin framework sequences or framework sequences that have been derived from immunoglobulin framework sequences (for example, by sequence optimization such as humanization or camelization). For example, the framework sequences may be framework sequences derived from an immunoglobulin single variable domain such as a light chain variable domain (e.g., a $V_L$-sequence) and/or from a heavy chain variable domain (e.g., a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences may preferably be such that the Aggrecan binder of the invention is an ISV such as a Domain antibody (or an amino acid sequence that is suitable for use as a domain antibody); a single domain antibody (or an amino acid that is suitable for use as a single domain antibody); a "dAb" (or an amino acid that is suitable for use as a dAb); a Nanobody®; a $V_{HH}$ sequence; a humanized $V_{HH}$ sequence; a camelized $V_H$ sequence; or a $V_{HH}$ sequence that has been obtained by affinity maturation. Again, suitable framework sequences will be clear to the skilled person, for example on the basis of the standard handbooks and the further disclosure and prior art mentioned herein.

Another particularly preferred class of ISVs of the invention comprises ISVs with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the description herein. Such "camelizing" substitutions are preferably inserted at amino acid positions that form and/or are present at the $V_H$-$V_L$ interface, and/or at the so-called Camelidae hallmark residues, well known to the person skilled in the art and which have been defined for example in WO 94/04678 and Davies and Riechmann (1994 and 1996). Preferably, the $V_H$ sequence that is used as a starting material or starting point for generating or designing the camelized ISVs is preferably a $V_H$ sequence from a mammal, more preferably the $V_H$ sequence of a human being, such as a $V_H3$ sequence. However, it should be noted that such camelized ISVs of the invention can be obtained in any suitable manner known per se and thus are not strictly limited to polypeptides that have been obtained using a polypeptide that comprises a naturally occurring $V_H$ domain as a starting material.

For example, again as further described herein, both "humanization" and "camelization" can be performed by providing a nucleotide sequence that encodes a naturally occurring $V_{HH}$ domain or $V_H$ domain, respectively, and then changing, in a manner known per se, one or more codons in said nucleotide sequence in such a way that the new nucleotide sequence encodes a "humanized" or "camelized" ISV of the invention, respectively. This nucleic acid can then be expressed in a manner known per se, so as to provide the desired ISVs of the invention. Alternatively, based on the amino acid sequence of a naturally occurring $V_{HH}$ domain or $V_H$ domain, respectively, the amino acid sequence of the desired humanized or camelized ISVs of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized ISVs of the invention, respectively, can be designed and then synthesized de novo using techniques for nucleic acid synthesis known per se, after which the nucleic acid thus obtained can be expressed in a manner known per se, so as to provide the desired ISVs of the invention.

In particular, the framework sequences present in the Aggrecan binders of the invention, such as the ISVs and/or polypeptides of the invention, may contain one or more of Hallmark residues for instance as defined in WO 08/020079 (Tables A-3 to A-8), such that the Aggrecan binder of the invention is a Nanobody. Some preferred, but non-limiting examples of (suitable combinations of) such framework sequences will become clear from the further disclosure herein (see e.g., Table A-2). Generally, Nanobodies (in particular $V_{HH}$ sequences and partially humanized Nanobodies) can in particular be characterized by the presence of one or more "Hallmark residues" in one or more of the framework sequences (as e.g., further described in WO 08/020079, page 61, line 24 to page 98, line 3). As used herein "represented by" in the context of any SEQ ID NO is equivalent to "comprises or consists of" said SEQ ID NO and preferably equivalent to "consists of" said SEQ ID NO.

More in particular, the invention provides Aggrecan binders comprising at least one ISV that is an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and which:

i) have at least 80%, more preferably 90%, even more preferably 95% amino acid identity with at least one of the amino acid sequences of SEQ ID NOs: 117, 116, 118, 116, 115, 114 and 1-19 (see Table A-2), in which for the purposes of determining the degree of amino acid identity, the amino acid residues that form the CDR sequences are disregarded. In this respect, reference is also made to Table A-2, which lists the framework 1 sequences (SEQ ID NOs: 119, 120 and 75-84), framework 2 sequences (SEQ ID NOs: 121 and 85-93), framework 3 sequences (SEQ ID NOs: 123, 124, 122, 94-104 and 112-113) and framework 4 sequences (SEQ ID NOs: 105-108) of the immunoglobulin single variable domains of SEQ ID NOs: 117, 118, 116, 115, 114 and 1-19; or ii) combinations of framework sequences as depicted in Table A-2;

and in which:

iii) preferably one or more of the amino acid residues at positions 11, 37, 44, 45, 47, 83, 84, 103, 104 and 108 according to the Kabat numbering are chosen from the Hallmark residues such as, e.g. mentioned in Table A-3 to Table A-8 of WO 08/020079.

Accordingly, the present invention relates to an ISV and/or polypeptide, wherein said ISV essentially consists of 4 framework regions (FR1 to FR4, respectively) and said 3 complementarity determining regions CDR1 to CDR3, e.g. the ISV that specifically binds Aggrecan consists of 4 framework regions (FR1 to FR4, respectively) and said 3 complementarity determining regions CDR1 to CDR3, the therapeutic ISV, e.g. the ISV that binds to a member of the serine protease family, cathepsins, matrix metalloproteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1) and/or ADAMTS11 consists of 4 framework regions (FR1 to FR4, respectively) and said 3 complementarity determining regions CDR1 to CDR3; the ISV binding serum albumin essentially consists of 4 framework regions (FR1 to FR4, respectively) and 3 complementarity determining regions (CDR1 to CDR3 respectively).

The Aggrecan binders of the invention, such as the ISVs and/or polypeptides of the invention, may also contain the specific mutations/amino acid residues described in the following co-pending US provisional applications, all entitled "Improved immunoglobulin variable domains": U.S. 61/994,552 filed May 16, 2014; U.S. 61/014,015 filed Jun. 18, 2014; U.S. 62/040,167 filed Aug. 21, 2014; and U.S. 62/047,560, filed Sep. 8, 2014 (all assigned to Ablynx N.V.).

In particular, the Aggrecan binders of the invention, such as the ISVs and/or polypeptides of the invention, may suitably contain (i) a K or Q at position 112; or (ii) a K or Q at position 110 in combination with a V at position 11; or (iii) a T at position 89; or (iv) an L on position 89 with a K or Q at position 110; or (v) a V at position 11 and an L at position 89; or any suitable combination of (i) to (v).

As also described in said co-pending US provisional applications, when the Aggrecan binder of the invention, such as the ISV and/or polypeptide of the invention, contain the mutations according to one of (i) to (v) above (or a suitable combination thereof):

the amino acid residue at position 11 is preferably chosen from L, V or K (and is most preferably V); and the amino acid residue at position 14 is preferably suitably chosen from A or P; and the amino acid residue at position 41 is preferably suitably chosen from A or P; and the amino acid residue at position 89 is preferably suitably chosen from T, V or L; and the amino acid residue at position 108 is preferably suitably chosen from Q or L; and the amino acid residue at position 110 is preferably suitably chosen from T, K or Q; and the amino acid residue at position 112 is preferably suitably chosen from S, K or Q.

As mentioned in said co-pending US provisional applications, said mutations are effective in preventing or reducing binding of so-called "pre-existing antibodies" to the ISVs, polypeptides and constructs of the invention. For this purpose, the Aggrecan binders of the invention, such as the ISVs and/or polypeptides of the invention, may also contain (optionally in combination with said mutations) a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I)), for which reference is again made to said US provisional applications as well as to WO 12/175741. In particular, an Aggrecan binder of the invention, such as an ISV and/or polypeptide of the invention, may contain such a C-terminal extension when it forms the C-terminal end of a protein, polypeptide or other compound or construct comprising the same (again, as further described in e.g. said US provisional applications as well as WO 12/175741).

An Aggrecan binder of the invention may be an immunoglobulin, such as an ISV, derived in any suitable manner and from any suitable source, and may for example be naturally occurring $V_{HH}$ sequences (i.e., from a suitable species of Camelid) or synthetic or semi-synthetic amino acid sequences, including but not limited to "humanized" (as defined herein) Nanobodies or VHH sequences, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when an immunoglobulin comprises a $V_{HH}$ sequence, said immunoglobulin may be suitably humanized, as further described herein, so as to provide one or more further (partially or fully) humanized immunoglobulins of the invention. Similarly, when an immunoglobulin comprises a synthetic or semi-synthetic sequence (such as a partially humanized sequence), said immunoglobulin may optionally be further suitably humanized, again as described herein, again so as to provide one or more further (partially or fully) humanized immunoglobulins of the invention.

In an aspect, the present invention provides an Aggrecan binder of the invention, such as an ISV, wherein said Aggrecan binder is chosen from the group consisting of SEQ ID NO:s 117, 118, 116, 115, 114 and 1-19.

The ISVs may be used as a "building block" for the preparation of a polypeptide, which may optionally contain one or more further "building blocks", such as ISVs, against the same or another epitope on Aggrecan and/or against one or more other antigens, proteins or targets than Aggrecan, e.g. building blocks having a therapeutic mode of action, e.g. therapeutic ISVs.

Generally, proteins or polypeptides or constructs that comprise or essentially consist of a single building block, single ISV or single Nanobody will be referred to herein as "monovalent" proteins or polypeptides or as "monovalent constructs", respectively. Polypeptides or constructs that comprise two or more building blocks or binding units (such as e.g., ISVs) will also be referred to herein as "multivalent" polypeptides or constructs, and the building blocks/ISVs present in such polypeptides or constructs will also be referred to herein as being in a "multivalent format". For example, a "bivalent" polypeptide may comprise two ISVs, optionally linked via a linker sequence, whereas a "trivalent" polypeptide may comprise three ISVs, optionally linked via two linker sequences; whereas a "tetravalent" polypeptide may comprise four ISVs, optionally linked via three linker sequences, etc.

In a multivalent polypeptide or construct, the two or more ISVs, such as Nanobodies may be the same or different, and may be directed against the same antigen or antigenic determinant (for example against the same part(s) or epitope(s) or against different parts or epitopes) or may alternatively be directed against different antigens or antigenic determinants; or any suitable combination thereof. Polypeptides or constructs that contain at least two building blocks (such as e.g., ISVs) in which at least one building block is directed against a first antigen (i.e., Aggrecan) and at least one building block is directed against a second antigen (i.e., different from Aggrecan, such as e.g. a therapeutic target) will also be referred to as "multispecific" polypeptides or multispecific constructs, respectively, and the building blocks (such as e.g., ISVs) present in such polypeptides or constructs will also be referred to herein as being in a "multispecific format". Thus, for example, a "bispecific" polypeptide of the invention is a polypeptide that comprises at least one ISV directed against a first antigen (i.e., Aggrecan) and at least one further ISV directed against a second antigen (i.e., different from Aggrecan, such as e.g. a therapeutic target), whereas a "trispecific" polypeptide of the invention is a polypeptide that comprises at least one ISV directed against a first antigen (i.e., Aggrecan), at least one further ISV directed against a second antigen (i.e., different from Aggrecan, such as e.g. a therapeutic target) and at least one further ISV directed against a third antigen (i.e., different from both Aggrecan and the second antigen); etc.

"Multiparatopic" polypeptides and "multiparatopic" constructs, such as e.g., "biparatopic" polypeptides or constructs and "triparatopic" polypeptides or constructs, comprise or essentially consist of two or more building blocks that each have a different paratope.

Accordingly, the ISVs of the invention that bind Aggrecan can be in essentially isolated form (as defined herein), or they may form part of a construct or polypeptide, which may comprise or essentially consist of one or more ISVs that bind Aggrecan and which may optionally further comprise one or more further amino acid sequences (all optionally linked via one or more suitable linkers). The present invention relates to a polypeptide or construct that comprises or essentially consists of at least one ISV according to the invention, such as one or more ISVs of the invention (or suitable fragments thereof), binding Aggrecan.

The one or more ISVs of the invention can be used as a binding unit or building block in such a polypeptide or construct, so as to provide a monovalent, multivalent or multiparatopic polypeptide or construct of the invention, respectively, all as described herein. The present invention thus also relates to a polypeptide which is a monovalent construct comprising or essentially consisting of one monovalent polypeptide or ISV of the invention. The present invention thus also relates to a polypeptide or construct which is a multivalent polypeptide or multivalent construct, respectively, such as e.g., a bivalent or trivalent polypeptide or construct comprising or essentially consisting of two or more ISVs of the invention (for multivalent and multispecific polypeptides containing one or more VHH domains and their preparation, reference is e.g. also made to Conrath et al. (J. Biol. Chem. 276: 7346-7350, 2001), as well as to for example WO 96/34103, WO 99/23221 and WO 2010/115998.

The invention further relates to a multivalent polypeptide (also referred to herein as a "multivalent polypeptide(s) of the invention") that comprises or (essentially) consists of at least one ISV, such as one or two ISVs (or suitable fragments thereof) directed against Aggrecan, preferably human Aggrecan, and one additional ISV.

In an aspect, in its simplest form, the multivalent polypeptide or construct of the invention is a bivalent polypeptide or construct of the invention comprising a first ISV, such as a Nanobody, directed against Aggrecan, and an identical second ISV, such as a Nanobody, directed against Aggrecan, wherein said first and said second ISVs, such as Nanobodies, may optionally be linked via a linker sequence (as defined herein). In another form, a multivalent polypeptide or construct of the invention may be a trivalent polypeptide or construct of the invention, comprising a first ISV, such as Nanobody, directed against Aggrecan, an identical second ISV, such as Nanobody, directed against Aggrecan and a third ISV, such as a Nanobody, directed against an antigen different from Aggrecan, such as e.g. a therapeutic target, in which said first, second and third ISVs, such as Nanobodies, may optionally be linked via one or more, and in particular two, linker sequences.

In another aspect, the multivalent polypeptide or construct of the invention may be a bispecific polypeptide or construct of the invention, comprising a first ISV, such as a Nanobody, directed against Aggrecan, and a second ISV, such as a Nanobody, directed against a second antigen, such as e.g. a therapeutic target, in which said first and second ISVs, such as Nanobodies, may optionally be linked via a linker sequence (as defined herein); whereas a multivalent polypeptide or construct of the invention may also be a trispecific polypeptide or construct of the invention, comprising a first ISV, such as a Nanobody, directed against Aggrecan, a second ISV, such as a Nanobody, directed against a second antigen, such as e.g. a therapeutic target, and a third ISV, such as a Nanobody, directed against a third antigen, such as e.g. also therapeutic target but different from said second antigen, in which said first, second and third ISVs, such as Nanobodies, may optionally be linked via one or more, and in particular two, linker sequences.

In a preferred aspect, the polypeptide or construct of the invention is a trivalent, bispecific polypeptide or construct, respectively. A trivalent, bispecific polypeptide or construct of the invention in its simplest form may be a trivalent polypeptide or construct of the invention (as defined herein), comprising two identical ISVs, such as Nanobodies, against Aggrecan and a third ISV, such as a Nanobody, directed against another antigen, such as e.g. a therapeutic target, in which said first, second and third ISVs, such as Nanobodies, may optionally be linked via one or more, and in particular two, linker sequences.

In a preferred aspect, the polypeptide or construct of the invention is a trivalent, bispecific polypeptide or construct, respectively. A trivalent, bispecific polypeptide or construct of the invention may be a trivalent polypeptide or construct of the invention (as defined herein), comprising two ISVs, such as Nanobodies, against Aggrecan, wherein said ISVs against Aggrecan may be the same or different and a third ISV, such as a Nanobody, directed against another antigen, such as e.g. a therapeutic target, in which said first, second and third ISVs, such as Nanobodies, may optionally be linked via one or more, and in particular two, linker sequences.

Particularly preferred trivalent, bispecific polypeptides or constructs in accordance with the invention are those shown in the Examples described herein and in Tables E-1 and E-2.

In another aspect, the polypeptide of the invention is a bispecific polypeptide or construct. A bispecific polypeptide or construct of the invention in its simplest form may be a bivalent polypeptide or construct of the invention (as defined herein), comprising an ISV, such as a Nanobody, against Aggrecan and a second ISV, such as a Nanobody, directed against another antigen, such as e.g. a therapeutic target, in which said first and second ISVs, such as Nanobodies, may optionally be linked via a linker sequence.

In a preferred aspect, the multivalent polypeptide or construct of the invention comprises or essentially consists of two or more ISVs directed against Aggrecan. In an aspect, the invention relates to a polypeptide or construct that comprises or essentially consists of at least two ISVs according to the invention, such as 2, 3 or 4 ISVs (or suitable fragments thereof), binding Aggrecan. The two or more ISVs may optionally be linked via one or more peptidic linkers.

The two or more ISVs present in the multivalent polypeptide or construct of the invention may consist of a light chain variable domain sequence (e.g., a $V_L$-sequence) or of a heavy chain variable domain sequence (e.g., a $V_H$-sequence); they may consist of a heavy chain variable domain sequence that is derived from a conventional four-chain antibody or of a heavy chain variable domain sequence that is derived from heavy chain antibody. In a preferred aspect, they consist of a Domain antibody (or an amino acid that is suitable for use as a domain antibody), of a single domain antibody (or an amino acid that is suitable for use as a single domain antibody), of a "dAb" (or an amino acid that is suitable for use as a dAb), of a Nanobody® (including but not limited to $V_{HH}$), of a humanized $V_{HH}$ sequence, of a camelized $V_H$ sequence; or of a $V_{HH}$ sequence that has been obtained by affinity maturation. The two or more ISVs may consist of a partially or fully humanized Nanobody or a partially or fully humanized VHH.

In an aspect of the invention, the first ISV and the second ISV present in the multiparatopic (preferably biparatopic or triparatopic) polypeptide or construct of the invention do not (cross)-compete with each other for binding to Aggrecan and, as such, belong to different families. Accordingly, the present invention relates to a multiparatopic (preferably biparatopic) polypeptide or construct comprising two or more ISVs wherein each ISV belongs to a different family. In an aspect, the first ISV of this multiparatopic (preferably biparatopic) polypeptide or construct of the invention does not cross-block the binding to Aggrecan of the second ISV of this multiparatopic (preferably biparatopic) polypeptide or construct of the invention and/or the first ISV is not cross-blocked from binding to Aggrecan by the second ISV. In another aspect, the first ISV of a multiparatopic (preferably biparatopic) polypeptide or construct of the invention cross-blocks the binding to Aggrecan of the second ISV of this multiparatopic (preferably biparatopic) polypeptide or construct of the invention and/or the first ISV is cross-blocked from binding to Aggrecan by the second ISV.

In a preferred aspect, the polypeptide or construct of the invention comprises or essentially consists of two or more ISVs, of which at least one ISV is directed against Aggrecan. In a particularly preferred aspect, the polypeptide or construct of the invention comprises or essentially consists of three or more ISVs, of which at least two ISVs are directed against Aggrecan. It will be appreciated that said at least two ISVs directed against Aggrecan can be the same or different, can be directed against the same epitope or different epitopes of Aggrecan, can belong to the same epitope bin or to different epitope bins, and/or can bind to the same or different domains of Aggrecan.

In a preferred aspect, the polypeptide or construct of the invention comprises or essentially consists of at least two ISVs, wherein said at least two ISVs can be the same or different, which are independently chosen from the group consisting of SEQ ID NOs: 117, 118, 116, 115 and 1-19, more preferably said at least two ISVs are chosen from the group consisting of SEQ ID NOs: 117, 5, 6, 8, 114-116 and/or said at least two ISVs are chosen from the group consisting of SEQ ID NOs: 118 and 13.

In a further aspect, the invention relates to a multiparatopic (preferably biparatopic) polypeptide or construct comprising two or more immunoglobulin single variable domains directed against Aggrecan that bind the same epitope(s) as is bound by any one of SEQ ID NOs: 117, 118, 114, 115, 116 and 1-19.

It is anticipated that the final format of a molecule for clinical use comprises one or two building blocks, such as ISVs, binding Aggrecan and one or more building blocks, such as ISVs, with a therapeutic mode of action, and possibly further moieties. In the examples section it is demonstrated that such formats retain both Aggrecan binding and retention properties as well as the therapeutic effect, e.g. enzymatic and/or inhibitory functions. The one or more building blocks, such as ISVs, with a therapeutic mode of action can be any building block having a therapeutic effect ("therapeutic building block" or "therapeutic ISV") in diseases in which Aggrecan is involved, such as arthritic disease, osteoarthritis, spondyloepimetaphyseal dysplasia, lumbar disk degeneration disease, Degenerative joint disease, rheumatoid arthritis, osteochondritis dissecans, aggrecanopathies and/or in which Aggrecan is used for directing, anchoring and/or retaining other, e.g. therapeutic, building blocks at the desired site, such as e.g. in a joint. The present invention thus pertains to a polypeptide or construct according to the invention, wherein the one or more further building block(s), e.g. further ISV(s), retain activity.

The present invention relates to a polypeptide or construct that comprises or essentially consists of at least one ISV according to the invention, such as one or more ISVs of the invention (or suitable fragments thereof), binding Aggrecan, and at least one further ISV, in particular a therapeutic ISV, wherein said at least one further ISV preferably binds to a therapeutic target, such as binds to a member of the serine protease family, cathepsins, matrix metalloproteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1) and/or ADAMTS11.

In an aspect the present invention relates to a polypeptide or construct of the invention essentially consisting of or comprising at least one ISV binding Aggrecan and at least one further ISV which has a therapeutic effect, e.g. a therapeutic building block. The therapeutic effect can be any desired effect which ameliorates, treats or prevents a disease as will be further detailed below. Preferably the further ISV, e.g. a therapeutic ISV, inhibits or decreases a protease activity, e.g. inhibits or decreases an activity of a therapeutic target, i.e. of a member of the serine protease family, cathepsins, matrix metalloproteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1) and/or ADAMTS11. Inhibiting or decreasing an activity may be achieved by binding to the active site or by modifying the structure of a protease or proteinase, thereby preventing and/or decreasing the hydrolysis of the target protein of the protease or proteinase.

In an aspect the present invention relates to a polypeptide or construct of the invention chosen from the polypeptides and constructs of Table E-1 and Table E-2.

In an aspect the present invention relates to an ISV, polypeptide or construct of the invention having a stability of at least 7 days, such as at least 14 days, 21 days, 1 month, 2 months or even 3 months in synovial fluid (SF) at 37° C.

In an aspect the present invention relates to an ISV, polypeptide or construct of the invention having cartilage retention of at least 2, such as at least, 3, 4, 5 or 6 RU in a cartilage retention assay.

In an aspect the present invention relates to an ISV, polypeptide or construct of the invention penetrating into the cartilage by at least 5 μm, such as at least 10 μm, 20 μm, 30 μm, 40 μm, 50 am or even more.

The stability of a polypeptide, construct or ISV of the invention can be measured by routine assays known to the person skilled in the art. Typical assays include (without being limiting) assays in which the activity of said polypeptide, construct or ISV is determined, followed by incubating in Synovial Fluid for a desired period of time, after which the activity is determined again, for instance as detailed in the examples section (cf. Example 6).

The desired activity of the therapeutic building block in the multivalent polypeptide or construct of the invention can be measured by routine assays known to the person skilled in the art. Typical assays include assays in which GAG release is assayed as detailed in the examples section (cf. Example 8).

The relative affinities may depend on the location of the ISVDs in the polypeptide. It will be appreciated that the order of the ISVDs in a polypeptide of the invention (orientation) may be chosen according to the needs of the person skilled in the art. The order of the individual ISVDs as well as whether the polypeptide comprises a linker is a matter of design choice. Some orientations, with or without linkers, may provide preferred binding characteristics in comparison to other orientations. For instance, the order of a first ISV (e.g. ISV 1) and a second ISV (e.g. ISV 2) in the polypeptide of the invention may be (from N-terminus to C-terminus): (i) ISV 1 (e.g. Nanobody 1)-[linker]-ISV 2 (e.g. Nanobody 2)-[C-terminal extension]; or (ii) ISV 2 (e.g. Nanobody 2)-[linker]-ISV 1 (e.g. Nanobody 1)-[C-terminal extension]; (wherein the moieties between the square brackets, i.e. linker and C-terminal extension, are optional). All orientations are encompassed by the invention. Polypeptides that contain an orientation of ISVs that provides desired binding characteristics may be easily identified by routine screening, for instance as exemplified in the examples section. A preferred order is from N-terminus to C-terminus: therapeutic ISV-[linker]-ISV binding Aggrecan-[C-terminal extension], wherein the moieties between the square brackets are optional.

Another preferred order is from N-terminus to C-terminus: therapeutic ISV-[linker]-ISV binding Aggrecan-[linker]-ISV binding Aggrecan-[C-terminal extension], wherein the moieties between the square brackets are optional.

The Aggrecan binders of the invention, such as the polypeptides and/or ISVs of the invention, may or may not further comprise one or more other groups, residues (e.g. amino acid residues), moieties or binding units (these Aggrecan binders, such as polypeptides and/or ISVs (with or without additional groups, residues, moieties or binding units) are all referred to as "compound(s) of the invention", "construct(s) of the invention" and/or "polypeptide(s) of the invention"). If present, such further groups, residues, moieties or binding units may or may not provide further functionality to the Aggrecan binder such as the polypeptide and/or ISV and may or may not modify the properties of the Aggrecan binder such as the polypeptide and/or ISV.

For example, such further groups, residues, moieties or binding units may be one or more additional amino acid sequences, such that the resulting polypeptide is a (fusion) polypeptide. In a preferred but non-limiting aspect, said one or more other groups, residues, moieties or binding units are immunoglobulins. Even more preferably, said one or more other groups, residues, moieties or binding units are ISVs chosen from the group consisting of Domain antibodies, amino acids that are suitable for use as a domain antibody, single domain antibodies, amino acids that are suitable for use as a single domain antibody, dAbs, amino acids that are suitable for use as a dAb, Nanobodies (such as e.g. VHH, humanized VHH or camelized VH sequences).

As described above, additional binding units, such as ISVs having different antigen specificity can be linked to form multispecific polypeptides. By combining ISVs of two or more specificities, bispecific, trispecific etc. polypeptides or constructs can be formed. For example, a polypeptide according to the invention may comprise one, two or more ISVs directed against Aggrecan and at least one ISV domain against another target. Such constructs and modifications thereof, which the skilled person can readily envisage, are all encompassed by the term "compound of the invention, construct of the invention and/or polypeptide of the invention" as used herein.

In the compounds, constructs and/or polypeptides described above, the one, two, three or more ISVs and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting polypeptide is a fusion (protein) or fusion (polypeptide).

The one or more further groups, residues, moieties or binding units may be any suitable and/or desired amino acid sequences. The further amino acid sequences may or may not change, alter or otherwise influence the (biological) properties of the polypeptide of the invention, and may or may not add further functionality to the polypeptide of the invention. Preferably, the further amino acid sequence is such that it confers one or more desired properties or functionalities to the polypeptide of the invention.

Examples of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson (Nature Biotechnology 23: 1126-1136, 2005).

For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the compound, construct and/or polypeptide of the invention, compared to polypeptide of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

In a specific aspect of the invention, a construct or polypeptide of the invention may have a moiety conferring an increased half-life, compared to the corresponding construct or polypeptide of the invention without said moiety. Some preferred, but non-limiting examples of such constructs and polypeptides of the invention will become clear to the skilled person based on the further disclosure herein, and for example comprise ISVs or polypeptides of the invention that have been chemically modified to increase the half-life thereof (for example, by means of pegylation); Aggrecan binders of the invention, such as ISVs and/or polypeptides of the invention that comprise at least one additional binding site for binding to a serum protein (such as serum albumin); or polypeptides of the invention which comprise at least one amino acid sequence of the invention that is linked to at least one moiety (and in particular at least one amino acid sequence) which increases the half-life of the amino acid sequence of the invention. Examples of constructs of the invention, such as polypeptides of the invention, which comprise such half-life extending moieties or ISVs will become clear to the skilled person based on the further disclosure herein; and for example include, without limitation, polypeptides in which the one or more ISVs of the invention are suitably linked to one or more serum proteins or fragments thereof (such as (human) serum albumin or suitable fragments thereof) or to one or more binding units that can bind to serum proteins (such as, for example, domain antibodies, ISVs that are suitable for use as a domain antibody, single domain antibodies, ISVs that are suitable for use as a single domain antibody, dAbs, ISVs that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an amino acid sequence of the invention is linked to an Fc portion (such as a human Fc) or a suitable part or fragment thereof; or polypeptides in which the one or more ISVs of the invention are suitable linked to one or more small proteins or peptides that can bind to serum proteins, such as, for instance, the proteins and peptides described in WO 91/01743, WO 01/45746, WO 02/076489, WO2008/068280, WO2009/127691 and PCT/EP2011/051559.

In an aspect the present invention provides a construct of the invention, such as a polypeptide, wherein said polypeptide further comprises a serum protein binding moiety or a serum protein.

Preferably, said serum protein binding moiety binds serum albumin, such as human serum albumin.

Generally, the constructs or polypeptides of the invention with increased half-life preferably have a half-life that is at least 1.5 times, preferably at least 2 times, such as at least 5 times, for example at least 10 times or more than 20 times, greater than the half-life of the corresponding constructs or polypeptides of the invention per se, i.e. without the moiety conferring the increased half-life. For example, the constructs or polypeptides of the invention with increased half-life may have a half-life e.g., in humans that is increased with more than 1 hours, preferably more than 2 hours, more preferably more than 6 hours, such as more than 12 hours, or even more than 24, 48 or 72 hours, compared to the corresponding constructs or polypeptides of the invention per se, i.e. without the moiety conferring the increased half-life.

In a preferred, but non-limiting aspect of the invention, the constructs of the invention, such as polypeptides of the invention, have a serum half-life e.g. in humans that is increased with more than 1 hours, preferably more than 2 hours, more preferably more than 6 hours, such as more than 12 hours, or even more than 24, 48 or 72 hours, compared to the corresponding constructs or polypeptides of the invention per se, i.e. without the moiety conferring the increased half-life.

In another preferred, but non-limiting aspect of the invention, such constructs of the invention, such as polypeptides of the invention, exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In a particularly preferred but non-limiting aspect of the invention, the invention provides a construct of the invention, such as a polypeptide of the invention, comprising besides the one or more building blocks binding Aggrecan and possibly the one or more therapeutic building blocks, at least one building block binding serum albumin, such as an ISV binding serum albumin, such as human serum albumin as described herein, wherein said ISV binding serum albumin comprises or essentially consists of 4 framework regions (FR1 to FR4, respectively) and 3 complementarity determining regions (CDR1 to CDR3 respectively), in which CDR1 is SFGMS (SEQ ID NO: 151), CDR2 is SISGSGSDTLYADSVKG (SEQ ID NO: 152) and CDR3 is GGSLSR (SEQ ID NO: 153). Preferably, said ISV binding human serum albumin is chosen from the group consisting of Alb8, Alb23, Alb129, Alb132, Alb135, Alb11, Alb11 (S112K)-A, Alb82, Alb82-A, Alb82-AA, Alb82-AAA, Alb82-G, Alb82-GG, Alb82-GGG, Alb92 or Alb223 (cf. Table C).

In an embodiment, the present invention relates to construct of the invention, such as a polypeptide comprising a serum protein binding moiety, wherein said serum protein binding moiety is a non-antibody based polypeptide.

In an aspect, the present invention relates to a compound or construct as described herein comprising one or more other groups, residues, moieties or binding units, preferably chosen from the group consisting of a polyethylene glycol molecule, serum proteins or fragments thereof, binding units that can bind to serum proteins, an Fc portion, and small proteins or peptides that can bind to serum proteins.

In an embodiment, the present invention relates to construct of the invention, such as a polypeptide comprising a moiety conferring half-life extension, wherein said moiety is a PEG. Hence, the present invention relates to a construct or polypeptide of the invention comprising PEG.

The further amino acid residues may or may not change, alter or otherwise influence other (biological) properties of the polypeptide of the invention and may or may not add further functionality to the polypeptide of the invention. For example, such amino acid residues:

a) can comprise an N-terminal Met residue, for example as result of expression in a heterologous host cell or host organism.
b) may form a signal sequence or leader sequence that directs secretion of the polypeptide from a host cell upon synthesis (for example to provide a pre-, pro- or prepro-form of the polypeptide of the invention, depending on the host cell used to express the polypeptide of the invention). Suitable secretory leader peptides will be clear to the skilled person, and may be as further described herein. Usually, such a leader sequence will be linked to the N-terminus of the polypeptide, although the invention in its broadest sense is not limited thereto;
c) may form a "tag", for example an amino acid sequence or residue that allows or facilitates the purification of the polypeptide, for example using affinity techniques directed against said sequence or residue. Thereafter, said sequence or residue may be removed (e.g. by chemical or enzymatical cleavage) to provide the polypeptide (for this purpose, the tag may optionally be linked to the amino acid sequence or polypeptide sequence via a cleavable linker sequence or contain a cleavable motif). Some preferred, but non-limiting examples of such residues are multiple histidine residues, glutathione residues and a myc-tag such as AAAEQKLISEEDLNGAA (SEQ ID NO: 172);
d) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the polypeptides of the invention.

In the constructs of the invention, such as the polypeptides of the invention, the two or more building blocks, such as e.g. ISVs, and the optionally one or more other groups, drugs, agents, residues, moieties or binding units may be directly linked to each other (as for example described in WO 99/23221) and/or may be linked to each other via one or more suitable spacers or linkers, or any combination thereof. Suitable spacers or linkers for use in multivalent and multispecific polypeptides will be clear to the skilled person, and may generally be any linker or spacer used in the art to link amino acid sequences. Preferably, said linker or spacer is suitable for use in constructing constructs, proteins or polypeptides that are intended for pharmaceutical use.

For instance, the polypeptide of the invention may, for example, be a trivalent, trispecific polypeptide, comprising one building block, such as an ISV, binding Aggrecan, one therapeutic building block, such as an ISV, and one building block, such as an ISV, binding (human) serum albumin, in which said first, second and third building blocks, such as ISVs, may optionally be linked via one or more, and in particular two, linker sequences. Also, the present invention provides a construct or polypeptide of the invention comprising a first ISV binding Aggrecan and/or a second ISV and/or possibly a third ISV and/or possibly an ISV binding serum albumin, wherein said first ISV and/or said second ISV and/or possibly said third ISV and/or possibly said ISV binding serum albumin are linked via a linker.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each ISV, such as a Nanobody, by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4 ser)_3$ or $(gly_3 ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as for instance described in WO 94/04678). Preferred linkers are depicted in Table D (SEQ ID NO:s 154-170).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final the construct of the invention, such as the polypeptide of the invention, including but not limited to the affinity, specificity or avidity for a chemokine, or for one or more of the other antigens. Based on the disclosure herein, the skilled person will be able to determine the optimal linker(s) for use in a specific construct of the invention, such as the polypeptide of the invention, optionally after some limited routine experiments.

For example, in multivalent polypeptides of the invention that comprise building blocks, ISVs or Nanobodies directed against Aggrecan and another target, the length and flexibility of the linker are preferably such that it allows each building block, such as an ISV, of the invention present in the polypeptide to bind to its cognate target, e.g. the antigenic determinant on each of the targets. Again, based on the disclosure herein, the skilled person will be able to determine the optimal linker(s) for use in a specific construct of the invention, such as a polypeptide of the invention, optionally after some limited routine experiments.

It is also within the scope of the invention that the linker(s) used, confer one or more other favourable properties or functionality to the constructs of the invention, such as the polypeptides of the invention, and/or provide one or more sites for the formation of derivatives and/or for the attachment of functional groups (e.g. as described herein for the derivatives of the ISVs of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the constructs such as polypeptides of the invention, these linkers may be the same or different. Again, based on the disclosure herein, the skilled person will be able to determine the optimal linkers for use in a specific construct or polypeptide of the invention, optionally after some limited routine experiments.

Usually, for the ease of expression and production, a construct of the invention, such as a polypeptide of the invention, will be a linear polypeptide. However, the invention in its broadest sense is not limited thereto. For example, when a construct of the invention, such as a polypeptide of the invention, comprises three of more building blocks, ISVs or Nanobodies, it is possible to link them by use of a linker with three or more "arms", which each "arm" being linked to a building block, ISV or Nanobody, so as to provide a "star-shaped" construct. It is also possible, although usually less preferred, to use circular constructs.

Accordingly, the present invention relates to a construct of the invention, such as a polypeptide of the invention, wherein said ISVs are directly linked to each other or are linked via a linker.

Accordingly, the present invention relates to a construct of the invention, such as a polypeptide of the invention, wherein a first ISV and/or a second ISV and/or possibly an ISV binding serum albumin are linked via a linker.

Accordingly, the present invention relates to a construct of the invention, such as a polypeptide of the invention, wherein said linker is chosen from the group consisting of linkers of 5GS, 7GS, 9GS, 10GS, 15GS, 18GS, 20GS, 25GS, 30GS, 35GS, poly-A, 8GS, 40GS, G1 hinge, 9GS-G1 hinge, llama upper long hinge region, and G3 hinge.

Accordingly, the present invention relates to a construct of the invention, such as a polypeptide of the invention, wherein said polypeptide is chosen from the group consisting of polypeptides of Table E-1 and Table E-2.

Also encompassed in the present invention are compounds, constructs and/or polypeptides that comprise an ISV or polypeptide of the invention and further comprise tags or other functional moieties, e.g., toxins, labels, radiochemicals, etc.

The other groups, residues, moieties or binding units may for example be chemical groups, residues, moieties, which may or may not by themselves be biologically and/or pharmacologically active. For example, and without limitation, such groups may be linked to the one or more ISVs or polypeptides of the invention so as to provide a "derivative" of the polypeptide of the invention.

Accordingly, the invention in its broadest sense also comprises compounds, constructs and/or polypeptides that are derivatives of the polypeptides of the invention. Such derivatives can generally be obtained by modification, and in particular by chemical and/or biological (e.g., enzymatic) modification, of the polypeptides of the invention and/or of one or more of the amino acid residues that form a polypeptide of the invention.

Examples of such modifications, as well as examples of amino acid residues within the polypeptide sequences that can be modified in such a manner (i.e. either on the protein backbone but preferably on a side chain), methods and techniques that can be used to introduce such modifications and the potential uses and advantages of such modifications will be clear to the skilled person (see also Zangi et al., Nat Biotechnol 31(10):898-907, 2013).

For example, such a modification may involve the introduction (e.g., by covalent linking or in any other suitable manner) of one or more (functional) groups, residues or moieties into or onto the polypeptide of the invention, and in particular of one or more functional groups, residues or moieties that confer one or more desired properties or functionalities to the polypeptide of the invention. Examples of such functional groups will be clear to the skilled person.

For example, such modification may comprise the introduction (e.g., by covalent binding or in any other suitable manner) of one or more functional groups that increase the half-life, the solubility and/or the absorption of the polypeptide of the invention, that reduce the immunogenicity and/or the toxicity of the polypeptide of the invention, that eliminate or attenuate any undesirable side effects of the polypeptide of the invention, and/or that confer other advantageous properties to and/or reduce the undesired properties of the polypeptide of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington (Pharmaceutical Sciences, $16^{th}$ ed., Mack Publishing Co., Easton, P A, 1980). Such functional groups may for example be linked directly (for example covalently) to a polypeptide of the invention, or optionally via a suitable linker or spacer, as will again be clear to the skilled person.

One specific example is a derivative polypeptide of the invention wherein the polypeptide of the invention has been chemically modified to increase the half-life thereof (for example, by means of pegylation). This is one of the most widely used techniques for increasing the half-life and/or reducing the immunogenicity of pharmaceutical proteins and comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments, such as e.g. (single) domain antibodies and ScFv's; reference is made to for example Chapman (Nat. Biotechnol. 54: 531-545, 2002), Veronese and Harris (Adv. Drug Deliv. Rev. 54: 453-456, 2003), Harris and Chess (Nat. Rev. Drug. Discov. 2: 214-221, 2003) and WO 04/060965. Various reagents for pegylation of proteins are also commercially available, for example from Nektar Therapeutics, USA.

Preferably, site-directed pegylation is used, in particular via a cysteine-residue (see for example Yang et al. (Protein Engineering 16: 761-770, 2003). For example, for this purpose, PEG may be attached to a cysteine residue that naturally occurs in a polypeptide of the invention, a polypeptide of the invention may be modified so as to suitably introduce one or more cysteine residues for attachment of PEG, or an amino acid sequence comprising one or more cysteine residues for attachment of PEG may be fused to the N- and/or C-terminus of a polypeptide of the invention, all using techniques of protein engineering known per se to the skilled person.

Preferably, for the polypeptides of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the polypeptide of the invention.

Yet another modification may comprise the introduction of one or more detectable labels or other signal-generating groups or moieties, depending on the intended use of the labelled polypeptide of the invention. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals, such as, $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes (such as $^{3}$H, $^{125}$I $^{32}$P, $^{35}$S, $^{14}$C, $^{51}$Cr, $^{36}$Cl, $^{57}$Co, $^{58}$Co, $^{59}$Fe, and $^{75}$Se), metals, metal chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe)), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the polypeptide of the invention to another protein, polypeptide or chemical compound that is bound to the other half of the binding pair, i.e. through formation of the binding pair. For example, a polypeptide of the invention may be conjugated to biotin, and linked to another protein, polypeptide, compound or carrier conjugated to avidin or streptavidin. For example, such a conjugated polypeptide of the invention may be used as a reporter, for example in a diagnostic system where a detectable signal-producing agent is conjugated to avidin or streptavidin. Such binding pairs may for example also be used to bind the polypeptide of the invention to a carrier, including carriers suitable for pharmaceutical purposes. See, for instance, the liposomal formulations described by Cao and Suresh (Journal of Drug Targeting 8: 257, 2000). Such binding pairs may also be used to link a therapeutically active agent to the polypeptide of the invention.

Other potential chemical and enzymatical modifications will be clear to the skilled person. Such modifications may also be introduced for research purposes (e.g. to study function-activity relationships). Reference is for example made to Lundblad and Bradshaw (Biotechnol. Appl. Biochem. 26: 143-151, 1997).

Preferably, the compounds, constructs, polypeptides and/or derivatives are such that they bind to Aggrecan, with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein (i.e. as defined for the polypeptides of the invention).

Such compounds, constructs and/or polypeptides of the invention and derivatives thereof may also be in essentially isolated form.

In an aspect, the present invention relates to a construct of the invention, that comprises or essentially consists of an ISV according to the invention or a polypeptide according to the invention, and which further comprises one or more other groups, residues, moieties or binding units, optionally linked via one or more peptidic linkers.

In an aspect, the present invention relates to a construct of the invention, in which one or more other groups, residues, moieties or binding units are chosen from the group consisting of a polyethylene glycol molecule, serum proteins or fragments thereof, binding units that can bind to serum proteins, an Fc portion, and small proteins or peptides that can bind to serum proteins.

The invention further relates to methods for preparing the compounds, constructs, polypeptides, nucleic acids, host cells, and compositions described herein.

The multivalent polypeptides of the invention can generally be prepared by a method which comprises at least the step of suitably linking the ISV and/or monovalent polypeptide of the invention to one or more further ISVs, optionally via the one or more suitable linkers, so as to provide the multivalent polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

A method for preparing multivalent polypeptides of the invention may comprise at least the steps of linking two or more ISVs of the invention and for example one or more linkers together in a suitable manner. The ISVs of the invention (and linkers) can be coupled by any method known in the art and as further described herein. Preferred techniques include the linking of the nucleic acid sequences that encode the ISVs of the invention (and linkers) to prepare a genetic construct that expresses the multivalent polypeptide. Techniques for linking amino acids or nucleic acids will be clear to the skilled person, and reference is again made to the standard handbooks, such as Sambrook et al. and Ausubel et al., mentioned above, as well as the examples below.

Accordingly, the present invention also relates to the use of an ISV of the invention in preparing a multivalent polypeptide of the invention. The method for preparing a multivalent polypeptide will comprise the linking of an ISV of the invention to at least one further ISV of the invention, optionally via one or more linkers. The ISV of the invention is then used as a binding domain or building block in providing and/or preparing the multivalent polypeptide comprising 2 (e.g., in a bivalent polypeptide), 3 (e.g., in a trivalent polypeptide), 4 (e.g., in a tetravalent) or more (e.g., in a multivalent polypeptide) building blocks. In this respect, the ISV of the invention may be used as a binding domain or binding unit in providing and/or preparing a multivalent, such as bivalent, trivalent or tetravalent polypeptide of the invention comprising 2, 3, 4 or more building blocks.

Accordingly, the present invention also relates to the use of an ISV polypeptide of the invention (as described herein) in preparing a multivalent polypeptide. The method for the preparation of the multivalent polypeptide will comprise the linking of the ISV of the invention to at least one further ISV of the invention, optionally via one or more linkers.

The polypeptides and nucleic acids of the invention can be prepared in a manner known per se, as will be clear to the skilled person from the further description herein. For example, the polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the polypeptides and nucleic acids include the methods and techniques described herein.

The method for producing a polypeptide of the invention may comprise the following steps:

the expression, in a suitable host cell or host organism (also referred to herein as a "host of the invention") or in another suitable expression system of a nucleic acid that encodes said polypeptide of the invention (also referred to herein as a "nucleic acid of the invention"), optionally followed by:

isolating and/or purifying the polypeptide of the invention thus obtained.

In particular, such a method may comprise the steps of:

cultivating and/or maintaining a host of the invention under conditions that are such that said host of the invention expresses and/or produces at least one polypeptide of the invention; optionally followed by:

isolating and/or purifying the polypeptide of the invention thus obtained.

Accordingly, the present invention also relates to a nucleic acid or nucleotide sequence that encodes a polypeptide, ISV or construct of the invention (also referred to as "nucleic acid of the invention").

A nucleic acid of the invention can be in the form of single or double stranded DNA or RNA. According to one embodiment of the invention, the nucleic acid of the invention is in essentially isolated from, as defined herein. The nucleic acid of the invention may also be in the form of, be present in and/or be part of a vector, e.g. expression vector, such as for example a plasmid, cosmid or YAC, which again may be in essentially isolated form. Accordingly, the present invention also relates to an expression vector comprising a nucleic acid or nucleotide sequence of the invention.

The nucleic acids of the invention can be prepared or obtained in a manner known per se, based on the information on the polypeptides of the invention given herein, and/or can be isolated from a suitable natural source. Also, as will be clear to the skilled person, to prepare a nucleic acid of the invention, also several nucleotide sequences, such as at least two nucleic acids encoding ISVs of the invention and for example nucleic acids encoding one or more linkers can be linked together in a suitable manner. Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as to the Examples below.

In a preferred but non-limiting embodiment, a genetic construct of the invention comprises a) at least one nucleic acid of the invention;
b) operably connected to one or more regulatory elements, such as a promoter and optionally a suitable terminator; and optionally also
c) one or more further elements of genetic constructs known per se;

in which the terms "regulatory element", "promoter", "terminator" and "operably connected" have their usual meaning in the art.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

The nucleic acids of the invention and/or the genetic constructs of the invention may be used to transform a host cell or host organism, i.e., for expression and/or production of the polypeptide of the invention. Suitable hosts or host cells will be clear to the skilled person, and may for example be any suitable fungal, prokaryotic or eukaryotic cell or cell line or any suitable fungal, prokaryotic or (non-human) eukaryotic organism as well as all other host cells or (non-human) hosts known per se for the expression and production of antibodies and antibody fragments (including but not limited to (single) domain antibodies and ScFv fragments), which will be clear to the skilled person. Reference is also made to the general background art cited hereinabove, as well as to, for example, WO 94/29457; WO 96/34103; WO 99/42077; Frenken et al. (Res Immunol. 149: 589-99, 1998); Riechmann and Muyldermans (1999), supra; van der Linden (J. Biotechnol. 80: 261-70, 2000); Joosten et al. (Microb. Cell Fact. 2: 1, 2003); Joosten et al. (Appl. Microbiol. Biotechnol. 66: 384-92, 2005); and the further references cited herein. Furthermore, the polypeptides of the invention can also be expressed and/or produced in cell-free expression systems, and suitable examples of such systems will be clear to the skilled person. Suitable techniques for transforming a host or host cell of the invention will be clear to the skilled person and may depend on the intended host cell/host organism and the genetic construct to be used. Reference is again made to the handbooks and patent applications mentioned above. The transformed host cell (which may be in the form or a stable cell line) or host organisms (which may be in the form of a stable mutant line or strain) form further aspects of the present invention. Accordingly, the present invention relates to a host or host cell comprising a nucleic acid according to the invention, or an expression vector according to the invention. Preferably, these host cells or host organisms are such that they express, or are (at least) capable of expressing (e.g., under suitable conditions), a polypeptide of the invention (and in case of a host organism: in at least one cell, part, tissue or organ thereof). The invention also includes further generations, progeny and/or offspring of the host cell or host organism of the invention, which may for instance be obtained by cell division or by sexual or asexual reproduction.

To produce/obtain expression of the polypeptides of the invention, the transformed host cell or transformed host organism may generally be kept, maintained and/or cultured under conditions such that the (desired) polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g., using a specific, cleavable amino acid sequence fused with the polypeptide of the invention) and/or preparative immunological techniques (i.e. using antibodies against the polypeptide to be isolated).

In an aspect the invention relates to method for producing a construct, polypeptide or ISV according to the invention comprising at least the steps of: (a) expressing, in a suitable host cell or host organism or in another suitable expression system, a nucleic acid sequence according to the invention; optionally followed by (b) isolating and/or purifying the construct, polypeptide or ISV according to the invention.

In an aspect the invention relates to a composition comprising a construct, polypeptide, ISV or nucleic acid according to the invention.

Generally, for pharmaceutical use, the constructs, polypeptides and/or ISVDs of the invention may be formulated as a pharmaceutical preparation or composition comprising at least one construct, polypeptide and/or ISVD of the invention and at least one pharmaceutically acceptable carrier, diluent or excipient and/or adjuvant, and optionally one or more pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration (such as intra-articular administration), for administration by inhalation, by a skin patch, by an implant, by a suppository, etc., wherein the intra-articular administration is preferred. Such suitable administration forms—which may be solid, semi-solid or liquid, depending on the manner of administration—as well as methods and carriers for use in the preparation thereof, will be clear to the skilled person, and are further described herein. Such a pharmaceutical preparation or composition will generally be referred to herein as a "pharmaceutical composition".

Thus, in a further aspect, the invention relates to a pharmaceutical composition that contains at least at least one construct of the invention, at least one polypeptide of the invention, at least one ISV of the invention, or at least one nucleic acid of the invention and at least one suitable carrier, diluent or excipient (i.e., suitable for pharmaceutical use), and optionally one or more further active substances. In a particular aspect, the invention relates to a pharmaceutical composition that comprises a construct, polypeptide, ISV or nucleic acid according to the invention, preferably at least one of Table E-1 or Table E-2 and at least one suitable carrier, diluent or excipient (i.e., suitable for pharmaceutical use), and optionally one or more further active substances.

Generally, the constructs, polypeptides, and/or ISVs of the invention can be formulated and administered in any suitable manner known per se. Reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, $18^{th}$ Ed., Mack Publishing Company, USA (1990), Remington, the Science and Practice of Pharmacy, $21^{st}$ Edition, Lippincott Williams and Wilkins (2005); or the Handbook of Therapeutic Antibodies (S. Dubel, Ed.), Wiley, Weinheim, 2007 (see for example pages 252-255).

In a particular aspect, the invention relates to a pharmaceutical composition that comprises a construct, polypeptide, ISV or nucleic acid according to the invention, and which further comprises at least one pharmaceutically acceptable carrier, diluent or excipient and/or adjuvant, and optionally comprises one or more further pharmaceutically active polypeptides and/or compounds.

The constructs, polypeptides, and/or ISVs of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (e.g. intravenous, intraperitoneal, subcutaneous, intramuscular, intraluminal, intra-arterial or intrathecal administration) or for topical (e.g., intra-articular, transdermal or intradermal) administration.

Preparations for parenteral administration may for example be sterile solutions, suspensions, dispersions or emulsions that are suitable for infusion or injection. Suitable carriers or diluents for such preparations for example include those mentioned on page 143 of WO 08/020079. Usually, aqueous solutions or suspensions will be preferred.

The constructs, polypeptides, and/or ISVs of the invention can also be administered using methods of delivery known from gene therapy, see, e.g., U.S. Pat. No. 5,399,346, which is incorporated by reference for its gene therapy delivery methods. Using a gene therapy method of delivery, primary cells transfected with the gene encoding a construct, polypeptide, and/or ISV of the invention can additionally be transfected with tissue specific promoters to target specific organs, tissue, grafts, tumors, joints or cells and can additionally be transfected with signal and stabilization sequences for subcellularly localized expression.

The constructs, polypeptides, and/or ISVs of the invention may also be administered intravenously, intra-articularly or intraperitoneally by infusion or injection. Particular examples are as further described on pages 144 and 145 of WO 08/020079 or in PCT/EP2010/062975 (entire document).

Useful dosages of the constructs, polypeptides, and/or ISVs of the invention can be determined by comparing their in vitro activity, and in vivo activity in animal models. Methods for the extrapolation of effective dosages in mice, and other animals, to humans are known to the art; see for example U.S. Pat. No. 4,938,949.

The amount of the constructs, polypeptides, and/or ISVs of the invention required for use in treatment will vary not only with the particular ISV, polypeptide, compound and/or construct selected but also with the route of administration, the nature of the condition being treated and the age and condition of the patient and will be ultimately at the discretion of the attendant physician or clinician. Also the dosage of the constructs, polypeptides, and/or ISVs of the invention varies depending on the target cell, tumor, joint, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. Preferably, the dose is administered once per week or even less frequent, such as once per two weeks, once per three weeks, once per month or even once per two months.

An administration regimen could include long-term treatment. By "long-term" is meant at least two weeks and preferably, several weeks, months, or years of duration. Necessary modifications in this dosage range may be determined by one of ordinary skill in the art using only routine experimentation given the teachings herein. See for instance Remington's Pharmaceutical Sciences (Martin, E. W., ed. $4^{th}$), Mack Publishing Co., Easton, PA. The dosage can also be adjusted by the individual physician in the event of any complication.

The art is in need of more effective therapies for disorders affecting cartilage in joints, such as osteoarthritis. Even when administered intra-articularly, the residence time of most drugs for treating affected cartilage is insufficient. The present inventors hypothesized that the efficacy of a therapeutic drug could be increased significantly by coupling the therapeutic drug to a moiety which would "anchor" the drug in the joint and consequently increase retention of the drug, but which should not disrupt the efficacy of said therapeutic drug (also indicated as "cartilage anchoring protein" or "CAP"). This anchoring concept not only increases the efficacy of drug, but also the operational specificity for a diseased joint by decreasing toxicity and side-effects, thus widening the number of possible useful drugs. The present inventors further hypothesized that Aggrecan binders might potentially function as such an anchor, although Aggrecan is heavily glycosylated and degraded in various disorders affecting cartilage in joints. Moreover, in view of the costs and extensive testing in various animal models required before a drug can enter the clinic, such Aggrecan binders should preferentially have a broad cross-reactivity, e.g. the Aggrecan binders should bind to Aggrecan of various species. Using various ingenious immunization, screening and characterization methods, the present inventors were able to identify various Aggrecan binders with superior selectivity, stability and specificity features, which enabled prolonged retention and activity in the joint.

In an aspect the present invention relates to a composition according to the invention, an ISV according to the invention, a polypeptide according to the invention, and/or a construct according to the invention for use as a medicament.

In an aspect the present invention relates to a method for reducing and/or inhibiting the efflux of a composition, a polypeptide or a construct from a joint, wherein said method comprises administering a pharmaceutically active amount of at least one polypeptide according to the invention, a construct according to the invention, or a composition according to the invention to a person in need thereof.

In the present invention the term "reducing and/or inhibiting the efflux" means reducing and/or inhibiting the outward flow of the composition, polypeptide or construct from within a joint to the outside. Preferably, the efflux is reduced and/or inhibited by at least 10% such as at least 20%, 30%, 40% or 50% or even more such as at least 60%, 70%, 80%, 90% or even 100%, compared to the efflux of the aforementioned composition, polypeptide or construct in a joint under the same conditions but without the presence of the Aggrecan binder of the invention, e.g. ISV(s) binding Aggrecan.

It is anticipated that the Aggrecan binders of the invention can be used in various diseases affecting cartilage, such as arthropathies and chondrodystrophies, arthritic disease, such as osteoarthritis, rheumatoid arthritis, gouty arthritis, psoriatic arthritis, traumatic rupture or detachment, achondroplasia, costochondritis, Spondyloepimetaphyseal dysplasia, spinal disc herniation, lumbar disk degeneration disease, degenerative joint disease, and relapsing polychondritis (commonly indicated herein as "Aggrecan associated diseases").

In an aspect the present invention relates to a composition, an ISV, a polypeptide, and/or a construct according to the invention for use in preventing or treating an Aggrecan associated disease, such as e.g. arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis.

In an aspect the present invention relates to a method for preventing or treating arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis wherein said method comprises administering, to a subject in need thereof, a pharmaceutically active amount of at least a composition, ISV, polypeptide, or construct according to the invention to a person in need thereof.

In an aspect the present invention relates to the use of an ISV, polypeptide, composition or construct according to the invention, in the preparation of a pharmaceutical composition for treating or preventing arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis.

It is expected that by binding to Aggrecan, the Aggrecan binders of the invention may reduce or inhibit an activity of a member of the serine protease family, cathepsins, matrix metallo-proteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1) and/or ADAMTS11 in degrading Aggrecan.

Accordingly, in an aspect the invention relates to a method for reducing or inhibiting an activity of a member of the serine protease family, cathepsins, matrix metallo-proteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1) and/or ADAMTS11 in degrading Aggrecan, wherein said method comprises administering a pharmaceutically active amount of at least an ISV, polypeptide, construct or composition according to the invention to a person in need thereof.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases, disorders and conditions mentioned herein.

Generally, the treatment regimen will comprise the administration of one or more ISVs, polypeptides, compounds and/or constructs of the invention, or of one or more compositions comprising the same, in one or more pharmaceutically effective amounts or doses. The specific amount(s) or doses to be administered can be determined by the clinician, again based on the factors cited above.

Generally, depending on the specific disease, disorder or condition to be treated, the potency of the specific ISV, polypeptide, compound and/or construct of the invention to be used, the specific route of administration and the specific pharmaceutical formulation or composition used, the clinician will be able to determine a suitable daily dose.

Usually, in the above method, an ISV, polypeptide, compound and/or construct of the invention will be used. It is however within the scope of the invention to use two or more ISVs, polypeptides and/or constructs of the invention in combination.

The ISVs, polypeptides and/or constructs of the invention may be used in combination with one or more further pharmaceutically active compounds or principles, i.e., as a combined treatment regimen, which may or may not lead to a synergistic effect.

Again, the clinician will be able to select such further compounds or principles, as well as a suitable combined treatment regimen, based on the factors cited above and his expert judgment.

In particular, the ISVs, polypeptides and/or constructs of the invention may be used in combination with other pharmaceutically active compounds or principles that are or can be used for the prevention and/or treatment of the diseases, disorders and conditions cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease, disorder or condition involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of an ISV, polypeptide, compound and/or construct of the invention in the preparation of a pharmaceutical composition for prevention and/or treatment of at least an Aggrecan associated disease; and/or for use in one or more of the methods of treatment mentioned herein.

The invention also relates to the use of an ISV, polypeptide, compound and/or construct of the invention in the preparation of a pharmaceutical composition for the prevention and/or treatment of at least one disease or disorder that can be prevented and/or treated by modulating Aggrecan, e.g. inhibiting Aggrecan degradation.

The invention also relates to the use of an ISV, polypeptide, compound and/or construct of the invention in the preparation of a pharmaceutical composition for the prevention and/or treatment of at least one disease, disorder or condition that can be prevented and/or treated by administering an ISV, polypeptide, compound and/or construct of the invention to a patient.

The invention further relates to an ISV, polypeptide, compound and/or construct of the invention or a pharmaceutical composition comprising the same for use in the prevention and/or treatment of at least one Aggrecan associated disease.

The subject to be treated may be any warm-blooded animal, but is in particular a mammal, and more in particular a human being. In veterinary applications, the subject to be treated includes any animal raised for commercial purposes or kept as a pet. As will be clear to the skilled person, the subject to be treated will in particular be a person suffering from, or at risk of, the diseases, disorders and conditions mentioned herein.

Again, in such a pharmaceutical composition, the one or more ISVs, polypeptides, compounds and/or constructs of the invention, or nucleotide encoding the same, and/or a pharmaceutical composition comprising the same, may also be suitably combined with one or more other active principles, such as those mentioned herein.

The invention also relates to a composition (such as, without limitation, a pharmaceutical composition or preparation as further described herein) for use, either in vitro (e.g. in an in vitro or cellular assay) or in vivo (e.g. in an a single cell or multi-cellular organism, and in particular in a mammal, and more in particular in a human being, such as in a human being that is at risk of or suffers from a disease, disorder or condition of the invention).

It is to be understood that reference to treatment includes both treatment of established symptoms and prophylactic treatment, unless explicitly stated otherwise.

Sequences are disclosed in the main body of the description and in a separate sequence listing according to WIPO standard ST.25. A SEQ ID specified with a specific number should be the same in the main body of the description and in the separate sequence listing. By way of example SEQ ID NO.: 1 should define the same sequence in both, the main body of the description and in the separate sequence listing. Should there be a discrepancy between a sequence definition in the main body of the description and the separate sequence listing (if e.g. SEQ ID NO.: 1 in the main body of the description erroneously corresponds to SEQ ID NO.: 2 in the separate sequence listing) then a reference to a specific sequence in the application, in particular of specific embodiments, is to be understood as a reference to the sequence in the main body of the application and not to the separate sequence listing. In other words a discrepancy between a sequence definition/designation in the main body of the description and the separate sequence listing is to be resolved by correcting the separate sequence listing to the sequences and their designation disclosed in the main body of the application which includes the description, examples, figures and claims.

The invention will now be further described by means of the following non-limiting preferred aspects, examples and figures.

The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1 Immunization of Llamas with Aggrecan, Cloning of the Heavy Chain-Only Antibody Fragment Repertoires and Preparation of Phage The present inventors realized that the purpose of animal models of OA is to controllably reproduce the scale and progression of joint damage, so that opportunities to detect and modulate symptoms and disease progression can be identified and new therapies developed. An ideal animal model is of relatively low cost and displays reproducible disease progression with a magnitude of effect large enough to detect differences within a short period of time. If the model progresses too rapidly to end-stage degeneration, intermediate time points, which are representative of OA pathophysiology, may not be obtainable and in the absence of this information, subtle effects of potential interventions may be missed. Recognizing that OA is an end-stage phenotype, the result of an interaction of mechanical and biochemical processes, animal models allow these factors to be studied in a controlled environment (cf. Teeple et al. 2013 AAPS J. 15: 438-446).

The final goal of animal models is to reproduce human diseases (cf. Cohen-Solal et al. 2013 Bonekey Rep. 2: 422). Given the heterogeneity of profiles in human OA, many models are needed. They are either spontaneous or induced. Most of them focus on one factor that favors the development of OA such as aging, mechanical stress (surgery), chemical defect (enzyme) or in genetic factors. All of them differ in terms of severity, localization of lesions and pathogenesis. However, no animal model addresses all aspects of developing OA.

Thus, in order to be useful in different animal models as well as ultimately in the human patient, the CAP-binder preferably has a broad cross-reactivity, e.g. binds to Aggrecan of more than one species. Preferably, the Aggrecan binder binds to human Aggrecan, as well as one or more of dog Aggrecan, bovine Aggrecan, rat Aggrecan, pig Aggrecan, mouse Aggrecan, rabbit Aggrecan, cynomolgus Aggrecan and/or rhesus Aggrecan.

Moreover, the present inventors realized that degradation of Aggrecan appears to initiate within the C-terminal region. The population of Aggrecan molecules without the G3 domain increases also with aging. A major feature of cartilage degeneration associated with arthritis is the loss of Aggrecan due to proteolytic cleavage within the interglobular region between the G1 and G2 domains. Hence, preferably, the Aggrecan binder binds to the N-terminal region of Aggrecan, i.e., a region other than the CS or G3 domain, such as the G1-IGD-G2 region, or the G1-domain, the IGD, or the G2 domain. Most preferably, the Aggrecan binder would bind to the G1 domain, which remains present in chondrocytes and the ECM.

1.1 Immunizations

Five llamas were immunized with recombinant (rec) human Aggrecan (G1-IGD-G2 domains, R&D Systems #1220-PG) (see Example 1.2). Serum samples were taken after antigen administrations and titers were determined by ELISA against human recombinant Aggrecan G1-IGD-G2. All llamas gave specific serum titers.

1.2 Primary Screening

RNA was extracted from PBLs (primary blood lymphocytes) and used as template for RT-PCR to amplify ISV encoding gene fragments. These fragments were cloned into phagemid vector pAX212 enabling production of phage particles displaying ISVs fused with His6- and FLAG3-tags. Phages were prepared and stored according to standard protocols (cf. Phage Display of Peptides and Proteins: A Laboratory Manual 1st Edition, Brian K. Kay, Jill Winter, John McCafferty, Academic Press, 1996).

Phage Display selections were performed with five immune libraries and two synthetic ISV libraries. The libraries were subjected to two to three rounds of enrichment against different combinations of recombinant human and (biotin-)rat Aggrecan G1-IGD-G2 domain, full length extracted bovine Aggrecan or intact bovine cartilage. Individual clones from the selection outputs were screened for binding in ELISA (using periplasmic extracts from *E. coli* cells expressing the ISVs) against the human G1-IGD-G2 domain. Sequencing of 542 ELISA-positive clones identified 144 unique ISV sequences. ISVs were assessed for species cross-reactivity and mapped by ELISA for binding to the individual human G1, IGD and G2 domains. Only a few ISVs showed similar binding levels to recombinant human, rat, dog and bovine Aggrecan G1-IGD-G2. The limited species cross-reactivity was particularly evident for G1 domain binders, for which binding to especially bovine and dog Aggrecan was poor. To identify more species cross-reactive G1 domain-binding ISVs, Phage Display selections against bovine G1-IGD-G2, dog G1-IGD-G2 and human G1 domains were performed. Of 1245 clones screened in ELISA for binding to human, cynomolgus, rat, dog and bovine G1-IGD-G2, only 15 novel species cross-reactive ISVs were identified of which nine could be mapped to the G1-domain.

A total of 19 unique clones were selected as 'Lead panel' for further characterization. An overview of the domain-mapping and species cross-reactivity data for this lead panel is provided in Table 1.2.

TABLE 1.2

Overview of periplasmic extract-based screening data for the lead panel.

| | | Periplasmic extract ELISA. OD 450 nm | | | | |
|---|---|---|---|---|---|---|
| Mapping | Clone | Hu G1-IGD-G2 | Cy G1-IGD-G2 | Rat G1-IGD-G2 | Dog G1-IGD-G2 | Bov G1-IGD-G2 |
| G1 | C0101PMP601E08 | 2.28 | 1.32 | 2.49 | 0.57 | 1.68 |
| G1 | C0101PMP102G11 | 1.69 | 0.60 | 0.16 | 1.02 | 0.32 |
| G1 | C0101PMP114F08 | 2.38 | 2.32 | 2.05 | 1.90 | 1.18 |
| G1 | C0101PMP112A01 | 2.50 | 2.50 | 2.03 | 1.57 | 2.41 |
| G1 | C0101PMP115B08 | 1.65 | 1.18 | 1.85 | 1.80 | 0.84 |
| G1 | C0101PMP117G09 | 2.21 | 2.21 | 2.29 | 1.68 | 0.76 |
| G1 | C0101PMP604B05 | 2.48 | 2.04 | 1.98 | 1.27 | 1.63 |
| G1 | C0101PMP606A05 | 0.25 | 1.24 | 0.93 | 0.51 | 0.19 |
| G1 | C0101PMP606A07 | 0.71 | 2.41 | 2.31 | 1.47 | 0.10 |
| G1 | C0101PMP608A05 | 2.33 | 2.48 | 2.39 | 0.86 | 2.27 |
| G1 | C0101PMP609C09 | 2.10 | 1.83 | 0.97 | 1.52 | 1.08 |
| G2 | C0101PMP112A03 | 2.51 | 2.36 | 1.69 | 1.47 | 0.73 |
| G2 | C0101PMP117D05 | 2.25 | 2.12 | 2.35 | 1.53 | 1.92 |
| G2 | C0101PMP604G09 | 2.41 | 1.57 | 1.40 | 1.16 | 1.21 |
| G1-IGD-G2 | C0101PMP113A01 | 2.56 | 2.57 | 2.53 | 2.51 | 2.54 |
| G1-IGD-G2 | C0101PMP601D02 | 2.58 | nd | 2.59 | 2.58 | nd |
| G1-IGD-G2 | C0101PMP601E09 | 2.59 | nd | 2.61 | 2.57 | nd |
| G1-IGD-G2 | C0101PMP604F02 | 2.41 | 1.37 | 0.78 | 1.04 | 0.82 |
| G1-IGD-G2 | C0101PMP604G01 | 2.27 | 1.25 | 0.60 | 1.55 | 0.68 |
| control | cAbLys3 | 0.05 | 0.06 | 0.06 | 0.06 | 0.06 |
| control | cAbLys3 | 0.05 | 0.05 | 0.06 | 0.06 | 0.05 |

Nd: not determined.

1.3 GI Binders

The sequence variability in the CDRs of the G1-binders has been determined against clone 114F08. The amino acid sequences of the CDRs of clone 114F08 were used as reference, against which the CDRs of all other clones (G1-binders) were compared, and are depicted in the Tables 1.3A, 1.31B and 1.3C below (CDR1 starts at Kabat position 26, CDR2 starts at Kabat position 50, and CDR3 starts at Kabat position 95).

TABLE 1.3A

G1 CDR1*

| | absolute numbering | | | | | | | | | |
|---|---|---|---|---|---|---|---|---|---|---|
| | 1 | 2 | 3 | 4 | 5 | 6 | 7 | 8 | 9 | 10 |
| wildtype sequence | G | S | T | F | I | I | N | V | V | R |
| mutation | | R | I | | S | S | Y | A | M | G |
| mutation | | F | | | | M | R | G | | K |
| mutation | | I | | | | T | | Y | | A |
| mutation | | T | | | | | | T | | |

*up to 2 CDR1 mutations in one clone

TABLE 1.3B

G1 CDR2*

| | absolute numbering | | | | | | | | | |
|---|---|---|---|---|---|---|---|---|---|---|
| | 1 | 2 | 2a | 3 | 4 | 5 | 6 | 7 | 8 | 9 |
| wildtype sequence | T | I | — | S | S | G | G | N | A | N |
| mutations | A | | S | R | T | S | S | S | T | D |
| | G | | N | W | G | | R | T | | Y |
| | | | | T | | | | R | | |
| | | | | N | | | | | | |

*up to 5 CDR2 mutations in one clone

TABLE 1.3C

G1 CDR3*

| | absolute numbering | | | | | | | | | | | | | | |
|---|---|---|---|---|---|---|---|---|---|---|---|---|---|---|---|
| | 1 | 2 | 3 | 4 | 5 | 6 | 6a | 7 | 8 | 9 | 10 | 10a | 11 | 12 | 13 |
| wildtype sequence | P | T | T | H | Y | G | — | G | V | Y | Y | — | G | P | Y |
| mutations | — | — | — | D | F | L | R | P | G | R | N | W | S | — | — |
| | G | R | M | Y | V | D | T | S | T | A | E | | K | E | L |
| | D | L | S | G | T | S | Y | | H | S | G | | Y | D | |
| | R | P | R | T | G | Y | V | | R | D | W | | | | |
| | E | V | | | | W | | | L | G | S | | | | |
| | | | | | | | | | Y | | | | | | |

*up to 5 CDR3 mutations in one clone

1.4 G1-IGD-G2 Binders

The sequence variability in the CDRs of the G1-IGD-G2 (GIG) binders has been determined against clone 604F02. The amino acid sequences of the CDRs of clone 604F02 were used as reference, against which the CDRs of all other clones (GIG binders) were compared, and are depicted in the Tables 1.4A, 1.4B and 1.4C below (CDR1 starts at Kabat position 26, CDR2 starts at Kabat position 50, and CDR3 starts at Kabat position 95).

TABLE 1.4A

GIG CDR1*

| | absolute numbering | | | | | | | | | |
|---|---|---|---|---|---|---|---|---|---|---|
| | 1 | 2 | 3 | 4 | 5 | 6 | 7 | 8 | 9 | 10 |
| wildtype sequence | G | R | T | F | S | S | Y | T | M | G |
| mutation | | L | | | | T | | A | | |

*up to 2 CDR1 mutations in one clone

TABLE 1.4B

GIG CDR2*

| | absolute numbering | | | | | | | | | |
|---|---|---|---|---|---|---|---|---|---|---|
| | 1 | 2 | 3 | 4 | 5 | 6 | 7 | 8 | 9 | 10 |
| wildtype sequence | A | I | S | W | S | G | G | R | T | Y |
| mutations | | | | | | | S | T | | |
| | | | | | | | R | | | |

*up to 2 CDR2 mutations in one clone

TABLE 1.4C

GIG CDR3*

| | absolute numbering | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| wildtype sequence | Y | R | R | R | R | A | S | S | N | R | G | L | W | D | Y |
| mutations | | | | V | | Y | T | — | P | T | E | T | | | |
| | | | | P | | | | | | L | | V | | | |

*up to 5 CDR3 mutations in one clone

1.5 G2 Binders

The sequence variability in the CDRs of the G2-binders has been determined against clone 601D02. The amino acid sequences of the CDRs of clone 601D02 were used as reference, against which the CDRs of all other clones (G2 binders) were compared, and are depicted in the Tables 1.5A, 1.5B and 1.5C below (CDR1 starts at Kabat position 26, CDR2 starts at Kabat position 50, and CDR3 starts at Kabat position 95).

TABLE 1.5A

G2 CDR1*

| | absolute numbering | | | | | | | | | |
|---|---|---|---|---|---|---|---|---|---|---|
| | 1 | 2 | 3 | 4 | 5 | 6 | 7 | 8 | 9 | 10 |
| wildtype sequence | G | P | T | F | S | R | Y | A | M | G |
| mutation | R | S | I | | N | N | R | F | | Y |
| mutation | | R | | | | M | — | — | | |
| | | | | | | S | | | | |

*up to 5 CDR1 mutations in one clone

TABLE 1.5B

| G2 CDR2* | | | | | | | | | | | |
|---|---|---|---|---|---|---|---|---|---|---|---|
| | absolute numbering | | | | | | | | | | |
| | 1 | 2 | 3 | 4 | 5 | 6 | 7 | 8 | 9 | 10 | 11 |
| wildtype sequence | A | I | T | W | S | S | G | G | R | T | Y |
| mutations | S | | | L | N | | | A | S | | N |
| | Y | | | | | | | | D | | R |
| | | | | | | | | | T | | |

*up to 5 CDR2 mutations in one clone

TABLE 1.5C

| G2 CDR3* | | | | | | | | | | | | | | | | |
|---|---|---|---|---|---|---|---|---|---|---|---|---|---|---|---|---|
| | absolute numbering | | | | | | | | | | | | | | | |
| | 1 | 2 | 3 | 4 | 5 | 6 | 7 | 8 | 9 | 10 | 11 | 12 | 13 | 14 | 15 | 16 |
| wildtype sequence | A | R | I | P | V | R | T | Y | T | S | E | W | N | Y | — | — |
| mutations | R | I | H | G | S | G | R | R | S | E | N | D | D | — | D | N |
| | F | L | Q | N | | N | W | S | — | K | A | — | — | | | |
| | | | | | | F | Y | — | | — | — | | | | | |

*up to 5 CDR3 mutations in one clone 1.6 Sequence Optimization of ISVs

Various ISVs were subjected to a sequence optimisation process. Sequence optimisation is a process in which a parental ISV sequence is mutated. This process covers the humanisation (i) of the ISV and knocks-out post-translational modifications (ii) as well as epitopes for potential pre-existing antibodies (iii).

(i) for humanisation purposes the parental ISV sequence is mutated to yield a ISV sequence which is more identical to the human IGHV3-IGHJ germline consensus sequence. Specific amino acids in the framework regions (with the exception of the so-called hallmark residues) that differ between the ISV and the human IGHV3-IGHJ germline consensus are altered to the human counterpart in such a way that the protein structure, activity and stability are kept intact. A handful of hallmark residues are known to be critical for the stability, activity and affinity of the ISV and are therefore not mutated.

(ii) the amino acids present in the CDRs and for which there is experimental evidence that they are sensitive to post-translational modifications (PTM) are altered in such a way that the PTM site is inactivated while the protein structure, activity and stability are kept intact.

(iii) the sequence of the ISV is optimised, without affecting protein structure, activity and stability, to minimise binding of any naturally occurring pre-existing antibodies and reduce the potential to evoke a treatment-emergent immunogenicity response.

For the generation of sequence optimised formatted ISVs, the ISV building were produced in *Pichia pastoris* as tagless proteins and purified via Protein A affinity chromatography, followed by desalting, all according to standard protocols.

Various sequence optimised formatted ISVs are shown in Tables A-1 and A-2.

Example 2 Characterization of the Lead Panel (Purified ISVs)—Aggrecan

After the primary screening, initial assessment of binding via ELISA, determination of off-rate and species cross-reactivity, the ISVs of the Lead panel were subjected to further characterization. 2.1 Formatting Aggrecan Lead Panels with ALB26 (n=19) It is anticipated that the final format of a molecule for clinical use comprises one or two Aggrecan binding ISVs ("anchors") and also one, two or more ISVs or other moieties with a therapeutic mode of action. Hence, the 19 selected clones were fused in monovalent or bivalent format to ALB26 (CAP-ALB26 or ALB26-CAP-CAP) and expressed in *P. pastoris*. ALB26 is a variant of ALB11 (Albumin binding ISV) with two mutations in CDR1, which completely abolish binding to Albumin from different species. The fusion to ALB26 was performed in order to mimic the size of a final polypeptide format comprising an Aggrecan binder. Without being bound by any theory, the inventors hypothesized that the pl may influence cartilage penetration and retention. As negative control, or 'dummy', bivalent ALB26 (C01010030) was used.

2.2 Ex Vivo Bovine Cartilage Retention

Since there is no established assay for assessing cartilage retention, the inventors developed reliable and reproducible ex vivo cartilage retention assay using bovine cartilage.

Bovine bones were typically collected from the local slaughter house. Cartilage was cut off the bones in ~1 mm thick strips and further cut into circular discs with a diameter of 3 mm with biopsy cutters. The cartilage discs were preferentially taken from fresh cartilage.

The ability of the ISVs to be retained in the cartilage for a prolonged period of time, following a relatively short exposure of the Nanobody to the cartilage (which can be expected upon intra-articular injection), was determined. The assay consisted of incubating ex vivo cartilage, typically 3 mm bovine discs (~10 mg wet weight) with 10 μg/mL Nanobody (100 μL) ON, followed by washing for up to 5 days (PBS/0.1% BSA/0.1% $NaN_3$/100 mM NaCl). Hereafter, bound (retained) Nanobody was released from the cartilage in SDS-containing SDS-PAGE sample buffer (LDS sample buffer Invitrogen) and analysed by Western Blot (WB). The assay was typically performed with 4 cartilage discs per Nanobody sample; 2 discs were analysed right after the Nanobody incubation ($t_0$) to determine the initial amount of bound Nanobody; 2 discs were analysed after washing ($t_{15\ days}$). The degree of retention was defined as the ratio of the amount of Nanobody detected at $t_{1\text{-}5\ days}$ and $t_0$. To increase the throughput of the assay, the determination of this ratio was performed by visual inspection of the Western Blots giving a score from 0-6, where 0 is no retention and 6 is full retention.

A summary of the results is shown in Table 2.2.

TABLE 2.2

Epitope binning and cartilage retention of the ALB26-formatted Aggrecan Lead Panel.

| Target | Epitope bin | C01010# | Construct | pI | Cartilage retention * |
|---|---|---|---|---|---|
| G1 | 4 | 118 | ALB26-114F08-114F08 | 9.09 | 6.00 |
| G1 | 1 | 131 | ALB26-601E08-601E08 | 9.00 | 6.00 |
| G1-IGD-G2 | 8 | 106 | ALB26-604F02-604F02 | 9.61 | 6.00 |
| G1-IGD-G2 | 8 | 94 | 604F02-ALB26 | 9.47 | 5.33 |
| G1 | 4 | 54 | 114F08-ALB26 | 9.02 | 5.00 |
| G1 | 4 | 93 | 117G09-ALB26 | 9.13 | 5.00 |
| G1 | 1 | 97 | 608A05-ALB26 | 9.09 | 5.00 |
| G1 | 1 | 109 | ALB26-608A05-608A05 | 8.95 | 5.00 |
| G2 | 7 | 115 | ALB26-117D05-117D05 | 8.73 | 5.00 |
| G1-IGD-G2 | 8 | 47 | 601E09-ALB26 | 9.13 | 4.83 |
| G2 | 6 | 108 | ALB26-604G09-604G09 | 9.13 | 4.00 |
| G1-IGD-G2 | 8 | 95 | 604G01-ALB26 | 6.96 | 4.00 |
| G1-IGD-G2 | 8 | 116 | ALB26-113A01-113A01 | 8.73 | 4.00 |
| G1-IGD-G2 | 8 | 88 | 113A01-ALB26 | 8.53 | 3.50 |
| G2 | 6 | 45 | 601D02-ALB26 | 9.15 | 3.40 |
| G2 | 7 | 99 | 117D05-ALB26 | 9.10 | 3.33 |
| G2 | 6 | 96 | 604G09-ALB26 | 8.99 | 3.00 |
| G2 | 6 | 130 | ALB26-601D02-601D02 | 9.24 | 3.00 |
| G1 | 1 | 46 | 601E08-ALB26 | 8.96 | 2.60 |
| G1 | 5 | 60 | 606A07-ALB26 | 9.09 | 2.25 |
| G1 | 5 | 113 | ALB26-606A07-606A07 | 8.62 | 2.00 |
| G1 | 4 | 119 | ALB26-115B08-115B08 | 9.49 | 2.00 |
| G2 | 6 | 117 | ALB26-112A03-112A03 | 9.12 | 2.00 |
| G2 | 6 | 62 | 112A03-ALB26 | 9.21 | 1.66 |
| G1 | 4 | 104 | 115B08-ALB26 | 8.66 | 1.50 |
| G1 | 1 | 40 | 102G11-ALB26 | 9.20 | 1.33 |
| G1 | 2 | 53 | 112A01-ALB26 | 9.17 | 1.00 |
| G1 | 2 | 111 | ALB26-112A01-112A01 | 8.64 | 1.00 |
| G1 | 3 | 56 | 604B05-ALB26 | 9.89 | 0.66 |
| G1 | 3 | 59 | 606A05-ALB26 | 9.19 | 0.33 |
| G1 | 2 | 98 | 609C09-ALB26 | 9.72 | 0.33 |
| G1 | 2 | 110 | ALB26-609C09-609C09 | 8.13 | 0.00 |
| G1 | 3 | 112 | ALB26-604B05-604B05 | 9.06 | 0.00 |
| G1 | 3 | 114 | ALB26-606A05-606A05 | 9.03 | 0.00 |
| Dummy | | 30 | ALB26-ALB26 | 8.75 | 0.00 |

* The table lists average scores from a number (n) of independent ex vivo bovine cartilage retention assays on a scale from 0-6, in which 0 is no retention and 6 is full retention.

It was found that 9 constructs were retained very well (scores 5-6) in the cartilage. This 'top-9' included both monovalent and bivalent constructs for the Aggrecan binding moiety binding to all of the recombinant G1, G2 or G1-IGD-G2 domains. 14 constructs showed moderate retention (scores between <5 and 2) and 5 constructs showed low albeit detectable retention (scores between <2 and 1) in this assay. It is notable that all Aggrecan constructs, except one, had pI values ranging from 8 to above 9.

2.3 Epitope Binning

For epitope-binning the purified ALB26-fused Nanobodies constructs were screened against the same set of Nanobodies fused with a FLAG-tag in a competition ELISA.

In short, the assay set up was as follows. Monoclonal phage ELISA were incubated at half-saturating dilution of phage with or without 1 μM purified Nanobody (or 5 μg/mL mAb). The ratio between the absorbance at 450 nm in the presence and absence of purified Nanobody (or mAb) was used to determine if the Nanobodies recognised overlapping or non-overlapping epitopes.

The resulting epitope bins are shown in Table 2.2 (above). Constructs in epitope bins 2 and 3 (on the G1-domain) had low cartilage retention scores (0-1) in the ex vivo bovine cartilage retention assay. There appears to be, however, no direct correlation between binding to bovine Aggrecan G1-IGD-G2 as measured by ELISA and bovine cartilage retention. Without being bound to any theory, the inventors hypothesized that these epitopes may not be easily accessible in the native cartilage tissue.

The sequence variability of the CDRs of clones belonging to a bin is depicted below and above (i.e. bin 8 with 604F02 as reference compound; Tables 1.4A-C).

The sequence variability of the G1-binders of epitope bin 4 against 114F08 is depicted in the Tables 2.3A, 2.3B and 2.3C below. The amino acid sequences of the CDRs of clone 114F08 were used as reference, against which the CDRs of all other clones (epitope bin 4 binders) were compared (CDR1 starts at Kabat position 26, CDR2 starts at Kabat position 50, and CDR3 starts at Kabat position 95).

TABLE 2.3A (114F08)
G1 bin 4 CDR1*

| | absolute numbering | | | | | | | | | |
|---|---|---|---|---|---|---|---|---|---|---|
| | 1 | 2 | 3 | 4 | 5 | 6 | 7 | 8 | 9 | 10 |
| wildtype sequence | G | S | T | F | I | I | N | V | V | R |
| mutations | | I | | | S | S | R | Y | M | K |
| | | F | | | | M | Y | A | | |

*Up to 2 CDR1 mutations in one clone

TABLE 2.3B (114F08)
G1 bin 4 CDR2*

| | absolute numbering | | | | | | | | | |
|---|---|---|---|---|---|---|---|---|---|---|
| | 1 | 2 | 2a | 3 | 4 | 5 | 6 | 7 | 8 | 9 |
| wildtype sequence | T | I | — | S | S | G | G | N | A | N |
| mutations | A | | N | | | | | R | T | D |
| | G | | | | | | | | | |

*Up to 2 CDR2 mutations in one clone

TABLE 2.3C (114F08)
G1 bin 4 CDR3*

| | absolute numbering | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| wildtype sequence | P | T | T | H | Y | G | G | V | Y | Y | G | P | V |
| muta-tions | — | — | — | D | F | L | | G | R | N | S | — | — |
| | | R | M | Y | V | D | | T | | E | K | E | L |

*Up to 5 CDR3 mutations in one clone

The sequence variability of the G1-binders of epitope bin 1 against 608A05 is depicted in the Tables 2.3D, 2.3E and 2.3F below. The amino acid sequences of the CDRs of clone 608A05 were used as reference, against which the CDRs of all other clones (epitope bin 1 binders) were compared (CDR1 starts at Kabat position 26, CDR2 starts at Kabat position 50, and CDR3 starts at Kabat position 95).

TABLE 2.3D (608A05)
G1 bin 1 CDR1*

| | absolute numbering | | | | | | | | | |
|---|---|---|---|---|---|---|---|---|---|---|
| | 1 | 2 | 3 | 4 | 5 | 6 | 7 | 8 | 9 | 10 |
| wildtype sequence | G | R | T | F | S | T | Y | T | M | G |
| mutation | | | S | | | S | | A | V | |

*up to 2 CDR1 mutations in one clone

TABLE 2.3E

| (608A05) G1 bin 1 CDR2* | | | | | | | | | | |
|---|---|---|---|---|---|---|---|---|---|---|
| | absolute numbering | | | | | | | | | |
| | 1 | 2 | 3 | 4 | 5 | 6 | 7 | 8 | 9 | 10 |
| wildtype sequence | A | I | S | W | S | G | G | T | T | Y |
| mutations | I | | | R | | | R | S | | |

*up to 2 CDR2 mutations in one clone

TABLE 2.3F

| (608A05) G1 bin1 CDR3* | | | | | | | | | | | | | | | |
|---|---|---|---|---|---|---|---|---|---|---|---|---|---|---|---|
| | absolute numbering | | | | | | | | | | | | | | |
| | 1 | 2 | 3 | 4 | 5 | 6 | 7 | 8 | 9 | 10 | 11 | 12 | 13 | 14 | 15 |
| wildtype sequence | R | P | R | Y | Y | Y | Y | S | L | Y | S | Y | D | Y | — |
| mutations | G | L | L | | R | S | T | P | H | P | Y | D | F | G | S |
| | | R | S | | | A | — | | R | A | A | | | | |

*up to 5 CDR3 mutations in one clone 2.4 Binding Characteristics—ELISA and SPR

Based on the ex vivo bovine cartilage retention and the epitope binning data, some exemplary constructs from different epitope bins were selected for further characterization. Binders to the G2-domain were excluded from further characterization at this stage for the reasons set out before.

The selected constructs were characterized in ELISA on the recombinant G1-IGD-G2 region from human, cynomolgus, rat, dog and bovine Aggrecan to determine their species cross-reactivity and on recombinant human Neurocan and Brevican to determine selectivity. The determined $EC_{50}$ values are listed in Table 2.4A.

SPR (ProteOn) experiments were carried out for the "monovalent" Aggrecan-ALB26 formats in order to determine off-rates. The interaction of the Nanobodies with the Aggrecan surface was found to be heterogeneous. The heterogeneity could be due to re-binding events, a heterogeneous population of immobilized Aggrecan and/or heterogeneous glycosylation patterns. As a consequence, the calculated off-rates are only indicative. Overall it appears that the dissociation kinetics were fast for the Aggrecan comprising Nanobodies (Table 2.4B).

TABLE 2.4A

Characterization of the ALB26-formatted Aggrecan Lead panel by ELISA.

| | | | | EC50 (M) | | | | | | |
|---|---|---|---|---|---|---|---|---|---|---|
| Target | Epitope bin | C01010 # | Construct | Hu | Cy | Rat | Dog | Bov | Neurocan | Brevican |
| G1 | 4 | 54 | 114F08-ALB26 | 6.0E-09 | 4.4E-09 | 7.6E-09 | 3.0E-09 | 5.6E-09 | No bind | No bind |
| G1 | 4 | 118 | ALB26-114F08-114F08 | 1.1E-10 | 7.6E-11 | 1.9E-10 | 2.4E-10 | 3.7E-10 | No bind | No bind |
| G1 | 1 | 97 | 608A05-ALB26 | 2.4E-10 | 2.1E-10 | 3.3E-10 | 2.5E-08 | 2.8E-10 | No bind | No bind |
| G1 | 1 | 109 | ALB26-608A05-608A05 | 1.0E-10 | 9.1E-11 | 9.5E-11 | 3.3E-10 | 7.7E-11 | No bind | No bind |
| G1 | 1 | 46 | 601E08-ALB26 | 5.1E-09 | 6.8E-09 | 3.2E-10 | 6.1E-10 | 1.2E-09 | No bind | No bind |
| G1 | 5 | 60 | 606A07-ALB26 | 1.2E-08 | 5.4E-09 | 8.4E-09 | 6.9E-09 | No fit | No fit | No bind |
| G1 | 5 | 113 | AL326-606A07-606A07 | 6.7E-10 | 3.0E-10 | 1.2E-10 | 3.0E-09 | No fit | 8.7E-10 | No bind |
| G1-IGD-G2 | 8 | 94 | 604F02-ALB26 | 1.2E-09 | 2.2E-09 | 5.9E-09 | 2.6E-09 | 1.6E-09 | No bind | No bind |
| G1-IGD-G2 | 8 | 106 | ALB26-604F02-604F02 | 6.6E-11 | 6.8E-11 | 1.0E-10 | 9.7E-11 | No fit | No bind | No bind |
| Dummy | | 30 | ALB26-ALB26 | No bind | No bind | No bind | No bind | No bind | No bind | No bind |

TABLE 2.4B

Characterization of the 'monovalent' ALB26-formatted Aggrecan Lead Panel (n = 5) by SPR (off-rate). Off-rates are only indicative due to heterogeneous binding patterns.

| | C01010 | | G1-IGD-G2 (kd 1/s) | | | | |
|---|---|---|---|---|---|---|---|
| Target | # | Construct | human | Cyno | Rat | Dog | Bovine |
| G1 | 54 | 114F08-ALB26 | 1.3E-02 | 6.9E-03 | 6.5E-01 | 1.1E-02 | 4.7E-01 |
| G1 | 97 | 608A05-ALB26 | 2.5E-03 | 1.8E-03 | 1.5E-03 | 8.3E-02 | 2.7E-03 |
| G1 | 46 | 601E08-ALB26 | 3.4E-03 | 3.1E-03 | 2.5E-04 | 7.1E-03 | 1.3E-03 |
| G1 | 60 | 606A07-ALB26 | 2.1E-02 | 2.0E-02 | 2.1E-02 | 3.8E-02 | 2.7E-02 |
| G1-IGD-G2 | 94 | 604F02-ALB26 | 1.7E-01 | 1.5E-01 | 2.6E-01 | 1.2E-01 | 2.6E-01 |

Example 3 Biophysical Characterization of Monovalent Lead Constructs—Aggrecan Since all selected constructs demonstrated various favourable characteristics, whether or not in combination, the ISVs 114F08 and 604F02 and their corresponding ALB26-formats (C010100054, -118 and -094) were used as exemplary constructs representing the Lead panel for further characterization.

3.1 Expression of Monovalent 114F08 and 604F02 in *E. coli* and *P. pastoris*

For biophysical characterization, the monovalent Nanobodies 114F08 and 604F02 were expressed with $FLAG_3$-$His_6$-tags in *E. coli* and/or *P. pastoris* and purified according to standard protocols (e.g. Maussang et al. 2013 J Biol Chem 288(41): 29562-72).

3.2 pl, Tm and Analytical SEC of 114F08 and 604F02

For the Thermal shift assay (TSA), 5 µL purified monovalent Nanobody (800 µg/ml) was incubated with 5 µL of the fluorescent probe Sypro Orange (Invitrogen, S6551) (final concentration 10 x) in 10 µL buffer (100 mM phosphate, 100 mM borate, 100 mM citrate, 115 mM NaCl, buffered at different pH ranging from 3.5 to 9). The samples were heated in a LightCycler 48011 machine (Roche), from 37 to 99° C. at the rate of 4.4° C./s, after which they were cooled down to 37° C. at a rate of 0.03° C./s. Upon heat-induced unfolding, hydrophobic patches of the proteins are exposed to which the Sypro Orange binds resulting in an increase in fluorescence intensity (Ex/Em=465/580 nm). The inflection point of the first derivative of the fluorescence intensity curve serves as a measure of the melting temperature (Tm), essentially according to Ericsson et al. 2006 (Anals of Biochemistry, 357: 289-298).

The Analytical size exclusion chromatography (Analytical SEC) experiments were performed on an Ultimate 3000 machine (Dionex) in combination with a Biosep-SEC-3 (Agilent) column using 10 mM phosphate, 300 mM Arg-HCl, pH 6.0 as mobile phase. 8 µg of Nanobody sample (0.5 mg/mL in d-PBS) were injected.

The isoelectric points of the two Aggrecan ISVs are relatively basic. The sequences are shown in Table A-1). The melting temperature was determined to be 61.0° C. for 114F08 and 70.0° C. for 604F02. None of the clones showed signs of aggregation or multimerisation as determined by analytical SEC.

Accordingly, next to the positive functional properties, the ISVs demonstrate favourable biophysical properties.

3.3 114F08 Family Members

The sequence variability in the CDRs of the family members of 114F08 is depicted in the Tables 3.3A, 3.3B and 3.3C below. The amino acid sequences of the CDRs of clone 114F08 were used as reference, against which the CDRs of all other clones (114F08 family members) were compared (CDR1 starts at Kabat position 26, CDR2 starts at Kabat position 50, and CDR3 starts at Kabat position 95).

TABLE 3.3A

| 114F08 CDR1* | | | | | | | | | | |
|---|---|---|---|---|---|---|---|---|---|---|
| | Kabat numbering | | | | | | | | | |
| | 26 | 27 | 28 | 29 | 30 | 31 | 32 | 33 | 34 | 35 |
| absolute numbering | 1 | 2 | 3 | 4 | 5 | 6 | 7 | 8 | 9 | 10 |
| wildtype sequence | G | S | T | F | I | I | N | V | V | R |
| mutations | | | | | | | S | | M | |

*Up to 2 CDR1 mutations in one clone

TABLE 3.3B

| 114F08 CDR2* | | | | | | | | | |
|---|---|---|---|---|---|---|---|---|---|
| | Kabat numbering | | | | | | | | |
| | 50 | 51 | 52 | 53 | 54 | 55 | 56 | 57 | 58 |
| absolute numbering | 1 | 2 | 3 | 4 | 5 | 6 | 7 | 8 | 9 |

TABLE 3.3B-continued

| 114F08 CDR2* | | | | | | | | | |
|---|---|---|---|---|---|---|---|---|---|
| | Kabat numbering | | | | | | | | |
| | 50 | 51 | 52 | 53 | 54 | 55 | 56 | 57 | 58 |
| wildtype sequence | T | I | S | S | G | G | N | A | N |
| mutations | A | | R | T | | | | T | D |

*Up to 5 CDR2 mutations in one done

TABLE 3.3C

| 114F08 CDR3* | | | | | | | | | | | | | |
|---|---|---|---|---|---|---|---|---|---|---|---|---|---|
| | Kabat numbering | | | | | | | | | | | | |
| | 95 | 96 | 97 | 98 | 99 | 100 | 100a | 100b | 100c | 100d | 100e | 100f | 100g |
| absolute numbering | 1 | 2 | 3 | 4 | 5 | 6 | 7 | 8 | 9 | 10 | 11 | 12 | 13 |
| wildtype sequence | P | T | T | H | Y | G | G | V | Y | Y | G | P | Y |
| mutations | . | . | . | R | . | . | . | D | . | . | . | . | . |

*Up to 2 CDR3 mutations in one clone

Example 4 Ex Vivo Binding to Cartilage from Various Species

The exemplary CAP comprising polypeptides (also designated herein as "CAP comprising constructs" or "constructs") were shown to bind recombinant/extracted human proteins and bovine cartilage in the bovine ex vivo cartilage retention assay. In order to demonstrate that these exemplary CAP comprising constructs also bind to cartilage from other species, experiments as set out above with bovine cartilage were repeated in essence with human cartilage and rat cartilage.

4.1 Binding to Ex Vivo Human Cartilage

In order to confirm that the exemplary CAP comprising constructs also bind to human cartilage, selected constructs were tested in the ex vivo cartilage binding assay using frozen human cartilage chips. Binding was determined after a 30 min wash by means of Western Blot.

The results are summarized in FIG. 5.

It was found that all constructs bound better to the human cartilage than the Dummy construct.

4.2 Binding to Ex Vivo Rat Cartilage

To facilitate testing of constructs in a rat in vivo model, binding to rat cartilage was assessed. Therefore, an assay was set up using femurs from rat with intact cartilage. Exemplary constructs C010100054, -118, and -094 were incubated with the rat cartilage overnight, followed by a 30 min wash, release of bound constructs followed by Western Blot analysis.

The results are shown in FIG. 6.

It was found that all the tested constructs bound well to Rat cartilage.

Example 5 Tissue Specificity

It was demonstrated above that the constructs of the invention bind specifically to Aggrecan both in vitro and ex vivo. In addition, these constructs should also bind preferably to the cartilage of a joint, while not or less to other tissues in a joint.

Binding of exemplary CAP comprising constructs to synovial membrane, tendon, epimysium and meniscus was assessed using the same set up as for the ex vivo cartilage binding assay. Construct release and Western Blot analysis were performed following a brief wash of the tissues (30 min) after ON incubation with the constructs.

The results are summarized in Table 5.

The results show that CAP binders show preferential binding to the cartilaginous tissues, including meniscus, over the other tissues found in the joint.

TABLE 5

Tissue specificity. Binding of the ALB26-formatted Lead Panel (n = 10) to articular cartilage, synovial membrane, tendon, epimysium and meniscus.

| Target | C010100 # | Construct | Cartilage | Synovial Membrane | Tendon | Epimysium | Meniscus |
|---|---|---|---|---|---|---|---|
| G1 | 054 | 114F08-AB26 | +++++ | +/- | + | +/- | nd |
| G1 | 118 | ALB26-114F08-114F08 | +++++ | + | + | + | nd |

TABLE 5-continued

Tissue specificity. Binding of the ALB26-formatted Lead Panel (n = 10) to articular cartilage, synovial membrane, tendon, epimysium and meniscus.

| Target | C010100 # | Construct | Carti-lage | Synovial Membrane | Tendon | Epimysium | Meniscus |
|---|---|---|---|---|---|---|---|
| G1-IGD-G2 | 094 | 604F02-ALB26 | +++++ | + | + | +/- | nd |
| G1 | 046 | 601E08-ALB26 | ++++ | +/- | + | nd | +++ |
| Dummy | 030 | ALB26-ALB26 | +/- | +/- | +/- | - | - |

Example 6 Nanobody Stability in Bovine Synovial Fluid

For various reasons, including patient convenience and safety, it is preferred that the constructs remain stable for longer periods in the synovium.

Accordingly, the stability of the exemplary ALB26-fused CAP constructs in Synovial Fluid (SF) was assessed by incubation of the constructs in non-arthritic bovine SF for up to 7 days at 37° C.

The results are summarized in Table 6.

TABLE 6

Stability of ALB26-formatted Lead Panel in bovine SF.

| Target | C010100# | Construct | Stability in Bovine SF, 37° C. |
|---|---|---|---|
| G1 | 054 | 114F08-ALB26 | >7 days |
| G1 | 118 | ALB26-114F08-114F08 | >7 days |
| G1-IGD-G2 | 094 | 604F02-ALB26 | >7 days |
| Dummy | 030 | ALB26-ALB26 | >7 days |

No degradation of any of the constructs could be detected.

Example 7 Retention in IL-1α-Stimulated Explant Cartilage

Up to this point, all experiments addressing cartilage binding and retention of the CAP comprising Nanobodies were performed in healthy (non-arthritic) ex vivo cartilage. Arthritic cartilage is characterized by degraded Collagen and Aggrecan. It is therefore of relevance to also assess binding and retention of the Aggrecan-binders in cartilage where degradation of these proteins has taken place. To this end, the exemplary ALB26-fused CAP constructs were tested in a cartilage explant assay in which cartilage was stimulated to induce degradation.

In short, the exemplary CAP comprising constructs were incubated overnight (ON) with bovine cartilage explants that were cultured with, or without, IL-1α and Oncostatin M, followed by 5 days of culture with daily change of medium (wash). IL-1α and Oncostatin M primarily induce the degradation of Aggrecan within the 6 days of the experiment. The cartilage explants were analysed for construct binding and retention by WB. Two independent experiments were performed (Exp A and Exp B).

The results of the Western Blots are depicted in FIG. 7.

The results of the CAP comprising construct retention in stimulated cartilage explants are summarized in Table 7.

TABLE 7

Summary of CAP binding and retention in stimulated bovine cartilage explant assay.

| Target | C010100# | Construct | Binding stimulated vs non-stimulated | Retention day 5 |
|---|---|---|---|---|
| G1 | 054 | 114F08-ALB26 | Reduced | Partial |
| G1 | 118 | ALB26-114F08-114F08 | Equal | Full |
| G1-IGD-G2 | 094 | 604F02-ALB26 | Reduced | Partial |
| G1 | 045 | 601D02-ALB26 | Reduced | Partial |
| Dummy | 030 | ALB26-ALB26 | No binding | No binding |

The results show that the constructs C01010054 ("054" or "54") and C01010045 ("045" or "45") have reduced retention in stimulated cartilage after 5 days of wash as compared to non-stimulated cartilage, while constructs C01010118 ("118") and C01010094 ("094" or "94") showed little sensitivity to stimulation.

It further appears that binding to the G2 Aggrecan domain (as exemplified by C01010045) is reduced more than binding to the other domains, which would be consistent with the hypothesis that Aggrecan degradation proceeds from the C-terminus.

Example 8 ADAMTS5-CAP GAG-Release Assay

In order to address the possible impact of CAP, the cartilage anchoring moiety, on the potency of a protease inhibiting Nanobody in cartilage tissue, the exemplary CAP constructs were fused to an ADAMTS5 (ATS5) blocking ISV and tested in a GAG (GlycosAminoGlycan)-release cartilage explant assay.

Before testing the constructs in the GAG-release cartilage explant assay, the in vitro cartilage binding and ADAMTS5 inhibiting properties were confirmed. For the latter, an enzymatic peptide assay was performed that showed that the enzyme-blocking function of the ADAMTS5 ISV was not impaired in any of the CAP-fusion constructs in vitro.

In the GAG-release assay, bovine cartilage explants were cultured for 5 days in the presence of IL-1α and Oncostatin M (for induction of ADAMTS5) and a dose range of constructs followed by quantification of the released GAG content in the culture supernatant.

The tested constructs and the results of the GAG-release assay are summarized in Table 8.

TABLE 8

Summary of ADAMTS5-CAP GAG-release assay.

| Target | ID | Construct | IC50 (nM) Peptide assay | GAG-release |
|---|---|---|---|---|
| ADAMTS-5-G1 | C010100270 | ATS5-114F08 | 0.11 | 4.17 |
| ADAMTS-5-G1 | C010100276 | ATS5-114F08-114F08 | 0.06 | 19.15 |
| ADAMTS-5-G1-IGD-G2 | C010100271 | ATS5-604F02 | 0.19 | 2.15 |
| ADAMTS-5-G1 | C011400510 | ATS5 (Tag-less) | 0.12 | 0.87 |

The results show that adding the anchoring arm (CAP-ISV construct) to the ADAMTS5 inhibitor still allowed for efficient inhibition of GAG-release.

Example 9 In Vivo Bio-Imaging of CAP-Constructs

In parallel to the in vitro and ex vivo characterization of the exemplary Aggrecan CAP constructs, in vivo bio-distribution was determined for several of the ALB26-fusion constructs, in order to confirm the retention properties.

9.1 Biodistribution Studies of ALB26-CAP Constructs

The Nanobodies were labeled with $^{125}$I (via Lysine coupling of $^{125}$I-SIB). The constructs were injected into the knee joints of healthy rats. Autoradiography images of the joints were produced for different time points up to 4 weeks post injection. These images allowed assessing the retention and the tissue (cartilage) specificity of the constructs in an in vivo-setting.

Representative images are shown in FIG. 1.

From the results it can be concluded that all constructs showed specific binding to the cartilage. A clear staining—even 4 weeks post injection—was observed for both 'monovalent' and 'bivalent' Aggrecan binders.

9.2 MARG of ALB26-CAP Constructs

The biodistribution study described above (Example 9.1) demonstrated specific retention in the cartilage of the ALB26-CAP constructs. However, the resolution of the images did not allow investigation of the depth of penetration into the cartilage. In order to increase the resolution of the imaging and thus to be able to evaluate penetration into the cartilage, MARG (Micro-Auto-Radio-Graphy) was used.

The exemplary constructs that went into the study are listed in Table 9.2A. For this study, the Nanobodies were labelled with $^{3}$H (via lysine coupling of $^{3}$H-NSP (N-Succinimidyl propionate)) and injected into the healthy and osteoarthritic (surgically induced via transection of the anterior cruciate ligament) rat joints; 8 rats per group. 7 to 14 days after injection the rats were sacrificed and the injected healthy and OA-induced joints were processed for MARG.

Representative MARG images are shown in FIG. 2.

TABLE 9.2A

Exemplary Nanobody constructs tested

| Target | C010100# | Construct |
|---|---|---|
| Aggrecan | #54 | 114F08-ALB26 |
| Aggrecan | #626 | ALB26-114F08-114F08 SO |
| Aggrecan | #94 | 604F02-ALB26 |
| Dummy | #30 | ALB26-ALB26 |

All of the Aggrecan binders generally showed penetration into the healthy cartilage. Construct 626 occasionally also showed some more intense staining on the surface. Various degrees of cartilage staining and penetration were seen in the operated knee: no staining was observed with monovalent construct 054; staining was absent or mild with monovalent construct 094 while the bivalent construct 626 resulted in a somewhat more consistent staining albeit with varying depths of penetration (see Table 9.2B)

TABLE 9.2B

Summary MARG staining results.

| Construct* | Healthy Knee joint: Silver grain evaluation | Healthy Knee joint: Penetration Depth | Operated Knee joint: Silver grain evaluation | Operated Knee joint: Penetration Depth |
|---|---|---|---|---|
| 030 | 0% of samples stained | na | 0% of samples stained | na |
| 054 | 100% samples with minimal staining | C | 0% of samples stained | na |
| 094 | 83% samples with mostly mild staining | C | 60% samples with mostly mild staining | C |
| 626 | 100% samples with mostly mild staining | B-C | 100% samples with minimal to mild staining | A-B-C |

*Overall results of 8 animals are presented, based on a silver grain evaluation.

Scoring of distribution: A = surface of cartilage with virtually no deeper staining, B = Surface of cartilage with some deeper staining, C = Staining in deeper layers of cartilage with no accumulation at surface

Example 10 In Vivo Rat MMT DMOAD Demonstrated a Statistical Significant Effect In order to further demonstrate the in vivo efficacy of the CAP binders of the invention, a surgically induced Medial Meniscal Tear (MMT) model in rats was used. In short, CAP binders of the invention were coupled to an anti-MMP13 ISV (designated as "0754" or "C010100754") or an anti-ADAMTS5 ISV (designated as "0954" or "C010100954"). Rats were operated in one knee to induce OA-like symptoms. Treatment started 3 days post-surgery by IA injection. Histopathology was performed at day 42 post surgery. Interim and terminal serum samples were taken for exploratory biomarker analysis. The medial and total substantial cartilage degeneration width was determined, as well as the percentage reduction of cartilage degeneration. 20 animals were used per group.

The inhibition of cartilage degradation by Nanobodies in the medial tibia is shown in FIG. 3.

The results demonstrate that the cartilage width was substantially reduced by the ADAMTS5-CAP construct and the MMP13-CAP construct after 42 days compared to the vehicle. These results suggest that the CAP-moiety (a) has no negative impact on the activity of either the anti-MMP13 ISV (0754) or the anti-ADAMTS5 ISV (0954); and (b) enables the retention of these constructs for prolonged extension of time in the joints.

Example 11 Retention of CAP Binders in Healthy and Osteoarthritic Rats is Similar In Vivo It was demonstrated in a cartilage retention study in healthy rats that the polypeptides of the invention were measurable in cartilage up to 112 days after intra-articular (I.A.) injection (data not shown). Since the cartilage composition can have an influence on cartilage binding and absorption in systemic circulation, the pharmacokinetics of the polypeptides of the invention were compared in diseased osteoarthritis and healthy rats in vivo by following the serum level of the polypeptides in time.

In particular, the surgically induced Medial Meniscal Tear (MMT) model in rats was used as described in Example 10, but with some modifications. In short, the polypeptides of the invention were coupled to an anti-MMP13 ISV and an anti-ADAMTS5 ISV, resulting in an MMP13-ADAMTS5-CAP-CAP construct (designated as "0949" or "C010100949" Nanobodies). Rats were operated in one knee to induce OA-like symptoms (OA-group). Each treatment group (healthy and OA) comprised of 15 animals, and received a single I.A. injection of 400 μg/30 μl Nanobody at day 7 (healthy) or 7 days post-surgery (MMT). Serum samples were collected from anesthetized rats at day 0, at day 7 (at 0 h=pre-dose sample) at day 8 (at different times post treatment up to 24 h), day 9 (48 h post-treatment), d10 (3 days post-treatment), d14 (7 days post-treatment), d21 (14 days post-treatment) and d42 (35 days post-treatment). Collected serum samples were used for the determination of the polypeptide concentrations in an electrochemoluminescence (ECL) based total PK assay format, followed by a non-compartmental analysis.

The retention of the polypeptides in the serum of healthy and OA rats is shown in FIG. 4.

The results demonstrate that no obvious differences can be seen in the serum concentrations of the polypeptides in healthy rats and OA rats. These results suggest that cartilage degradation has no influence on the pharmacokinetics of the polypeptides of the invention.

TABLE A-1

Amino acid sequences of monovalent Aggrecan binders ("ID" refers to the SEQ ID NO as used herein)

| Name | ID | Amino acid sequence |
|---|---|---|
| 102G11 | 1 | EVQLVESGGGLVQAGGSLRLSCAASGRSFSSYAMGWFRQAPGKEREFVSIISWSGGSTVYADSVKGRFTISRDNAKNTVYLQMNSLKPEDTAIYYCAAGRLYRATPRPADFGSWGQGTQVTVSS |
| 112A01 | 2 | EVQLVESGGGLVQTGGSLRLSCVASGRAFSNYIMGWFRQAPGKERDFVAAINWNGVTTHYTDSVKGRFTISRDNAKSTSYLQMDSLKPDDTAVYFCAARGTVYSRTYGVSEEGYMYWGQGTQVTVSS |
| 112A03 | 3 | EVQLVESGGGLVQPGGSLRLSCAASGSIFSNRFMYWYRQAPGKQRELVASITLSGSTNYADSVKGRFTISRDNAKNTVYLQMNSLKPEDTAVYYCNTFLQNSFYWGQGTQVTVSS |
| 113A01 | 4 | EVQLVESGGGLVQPGGSLRLSCSASGFTFSGSWMFWVRQAPGKDYEWVASINSSGGRTYYDDSVKGRFTISRDSAKNTLYLEMNNLKPEDTALYFCARSPRVGSWGQGTQVTVSS |
| 114F08 | 5 | EVQLVESGGGLVQAGGSLRLSCAASGSTFIINVVRWYRRTPGKQRELVATISSGGNANYVDSVRGRFSISRDGAKNAVDLQMNGLKPEDTAVYYCNVPTTHYGGVYYGPYWGQGTQVTVSS |
| 115B08 | 6 | KVQLVESGGGLVQPGGSLRLSCAASGFTFSMYAMKWVRQAPGKGLEWVSGINSSGGRTNYAGSVKGRFTISRDNAKNTLYLQMNSLKPEDTAVYYCATDFLGGRNSRGQGTQVTVSS |
| 117D05 | 7 | KVQLVESGGGLVQAGGSLRLSCAASRRTFNMMGWFRQAPGKEREFVAYITWNGGDTRYAESVKGRFTVSDRDVKNTMALQMNRLDPLDTAVYYCGVRIHGSNWSTKADDYDNWGQGTQVTVSS |
| 117G09 | 8 | EVQLVESGGGSALPGGSLRLSCAASGITFSSRYMRWYRQAPGRQRELVAAISSGGRTDYVDSVRGRFTLSINNAKNTVYLQMNDLKPEDTAVYYCYRPRMYVDGTYEKELWGQGTLVTVSS |
| 601D02 | 9 | DVQLVESGGGLVQPGGSLRLSCAASGPTFSRYAMGWFRQAPGKEREFVAAITWSSGGRTYYADSVKGRFTISRDNSKNTVYLQMNSLRPEDTAVYYCAAARIPVRTYTSEWNYWGQGTLVTVSS |
| 601E08 | 10 | DVQLVESGGGLVQPGGSLRLSCTASGRTFSSYAVGWFRQAPGKEREFVAAISRSGRSTYYADSVKGRFTISRDNSKNTVYLQMNSLRPEDTAVYYCAAGLSYYSPHAYYDYWGQGTLVTVSS |
| 601E09 | 11 | DVQLVESGGGLVQPGGSLRLSCAASGLTFSTYAMGWFRQAPGKEREFVAAISWSGSRTYYADSVKGRFTISRDNSKNTVYLQMNSLRPEDTAVYYCAAYRRPRYSPTGTWDYWGQGTLVTVSS |
| 604B05 | 12 | DVQLVESGGGLVQPGGSLRLSCVASGRTFSIYTMAWFRQAPGKEREFVAAISWSSGRTYYADSVKGRFTISRDNSKNTVYLQMNSLRPEDTAVYYCTAYTGPRSGYDYWGQGTLVTVSS |
| 604F02 | 13 | DVQLVESGGGLVQPGGSLRLSCAASGRTFSSYTMGWFRQAPGKEREFVAAISWSGGRTYYADSVKGRFTISRDNSKNTVYLQMNSLRPEDTAVYYCAAYRRRRASSNRGLWDYWGQGTLVTVSS |
| 604G01 | 14 | DVQLVESGGGLVQPGGSLRLSCAASGRTFSSYTMGWFRQAPGKEREFVAAISWSGRTTYYADSVKGRFTISRDNSKNTVYLQMNSLRPEDTAVYYCAAYRRVRYTNLEVWDYWGQGTLVTVSS |
| 604G09 | 15 | DVQLVESGGGLVQPGGSLRLSCVASGRTFSSYAMGWFRQAPGKEREFVAAITWSSATTYYADSVKGRFTISRDNSKNTVYLQMNSLRPEDTAVYYCAAARIPVGRRSENWDYWGQGTLVTVSS |
| 606A05 | 16 | DVQLVESGGGLVQPGGSLRLSCVASGRTFSIYTMGWFRQAPGKEREFVAAISWSGGRTYYADSVYGRFTISRDNSKNTVYLQMNSLRPEDTAVYYCTAYTGRSYGSYDYWGQGTLVTVSS |
| 606A07 | 17 | DVQLVESGGGLVQPGGSLRLSCVASGRTFSIYGMGWFRQAPGKEREFVAAINGGSRTYYADSVKGRFTISRDNSKNTVYLQMNSLRPEDTAVYYCAADRSGYGTSLDWWYDYWGQGTLVTVSS |
| 608A05 | 18 | DVQLVESGGGLVQPGGSLRLSCAASGRTFSTYTMGWFRQAPGKEREFVAAISWSGGTTYYADSVKGRFTISRDNSKNTVYLQMNSLRPEDTAVYYCAARPRYYYYSLYSYDYWGQGTLVTVSS |
| 609C09 | 19 | DVQLVESGGGLVQPGGSLRLSCAASGTIFSINVMGWYRQAPGKEREFVAAITTGGRTNYADSVKGRFTISRDNSKNTVYLQMNSLRPEDTAVYYCNAEVTTGWVGYSWYDYWGQGTMVTVSS |

TABLE A-1-continued

Amino acid sequences of monovalent Aggrecan binders ("ID" refers to the SEQ ID NO as used herein)

| Name | ID | Amino acid sequence |
|---|---|---|
| 114A09 | 114 | EVQLVESGGGLVQAGGSLRLSCAASGSTFIISVMRWYRQAPGKQRELVAAIRTGGNTDYAGPVRGRFSI SRDGAKNAVDLQMNGLKPEDTAVYYCNVPTTRYGGDYYGPYWGQGTQVTVSS |
| 114B04 | 115 | EVQLVESGGGLVQAGGSLRLSCAASGSTFIISVMRWYRQAPGKQRELVAAIRTGGNTDYAGPVRGRFSI SRDGAKDAVDLQMNGLKPEDTAVYYCNVPTTRYGGDYYGPYWGQGTQVTVSS |
| 00269 SO114F08 | 116 | EVQLVESGGGLVQPGGSLRLSCAASGSTFIINVVRWYRRAPGKQRELVATISSGGNANYVDSVRGRFTI S RDNSKNTVYLQMNSLRPEDTAVYYCNVPTTHYGGVYYGPYWGQGTLVTVSS |
| 00745 PEA114F08 | 117 | EVQLVESGGGVVQPGGSLRLSCAASGSTFIINVVRWYRRAPGKQRELVATISSGGNANYVDSVRGRFTI SRDNSKNTVYLQMNSLRPEDTALYYCNVPTTHYGGVYYGPYWGQGTLVTVSSA |
| 00747 PEA604F02 | 118 | EVQLVESGGGVVQPGGSLRLSCAASGRTFSSYTMGWFRQAPGKEREFVAAISWSGGRTYYADSVKGRFT ISRDNSKNTVYLQMNSLRPEDTALYYCAAYRRRRASSNRGLWDYWGQGTLVTVSSA |

TABLE A-2

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 1 | 102G11 | 75 | EVQLVESGGGLVQAGGSLRLSCAAS | 20 | GRSFSSYAMG | 85 | WFRQAPGKEREFVS | 38 | IISWSGGSTV | 94 | YADSVKGRFTISRDNAKNTVYLQMNSLKPEDTAIYYCAA | 56 | GRLYRATPRPADFGS | 105 | WGQGTQVTVSS |
| 2 | 112A01 | 76 | EVQLVESGGGLVQTGGSLRLSCVAS | 21 | GRAFSNYIMG | 86 | WFRQAPGKERDFVA | 39 | AINWNGVTTH | 95 | YTDSVKGRFTISRDNAKSTSYLQMDSLKPDDTAVYFCAA | 57 | RGTVYSRTYGVSEEGYMY | 105 | WGQGTQVTVSS |
| 3 | 112A03 | 77 | EVQLVESGGGLVQPGGSLRLSCAAS | 22 | GSIFSNRFMY | 87 | WYRQAPGKQRELVA | 40 | SITLSGSTN | 96 | YADSVKGRFTISRDNAKNTVYLQMNSLKPEDTAVYYCNT | 58 | FLQNSFY | 105 | WGQGTQVTVSS |
| 4 | 113A01 | 78 | EVQLVESGGGLVQPGGSLRLSCSAS | 23 | GFTFSGSWMF | 88 | WVRQAPGKDYEWVA | 41 | SINSSGGRTY | 97 | YDDSVKGRFTISRDSAKNTLYLEMNNLKPEDTALYFCAR | 59 | SPRVGS | 105 | WGQGTQVTVSS |
| 5 | 114F08 | 75 | EVQLVESGGGLVGAGGSLRLSCAAS | 24 | GSTFIINVVR | 89 | WYRRTPGKQRELVA | 42 | TISSGGNAN | 98 | YVDSVRGRFSISRDGAKNAVDLQMNGLKPEDTAVYYCNV | 60 | PTTHYGGVYYGPY | 105 | WGQGTQVTVSS |
| 6 | 115B08 | 79 | KVQLVESGGGLVQPGGSLRLSCAAS | 25 | GFTFSMYAMK | 90 | WVRQAPOKGLEWVS | 43 | GINSSGGRTN | 99 | YAGSVKGRFTISRDNAKNTLYLQMNSLKPEDTAVYYCAT | 61 | DFLGGRNS | 106 | RGQGTQVTVSS |
| 7 | 117D05 | 80 | KVQLVESGGGLVQAGGSLRLSCAAS | 26 | RRTFNMMG | 91 | WFRQAPGKEREFVA | 44 | YITWNGGDTR | 100 | YAESVKGRFTVSRDDVKNTMALQMNRLDPLDTAVYYCGV | 62 | RIHGSNWSTKADDYDN | 105 | WGQGTQVTVSS |
| 8 | 117G09 | 81 | EVQLVESGGGSALPGGSLRLSCAAS | 27 | GITFSSRYMR | 92 | WYRQAPGRQRELVA | 45 | AISSGGRTD | 101 | YVDSVRGRFTLSINNAKNTVYLQMNDLKPEDTAVYYCYR | 63 | PRMYVDGTYEKEL | 107 | WGQGTLVTVSS |
| 9 | 601D02 | 82 | DVQLVESGGGLVQPGGSLRLSCAAS | 28 | GPTFSRYAMG | 91 | WFRQAPGKEREFVA | 46 | AITWSSGGRTY | 102 | YADSVKGRFTISRDNSKNTVYLQMNSLRPEDTAVYYCAA | 64 | ARIPVRTYTSEWNY | 107 | WGQGTLVTVSS |
| 10 | 601E08 | 83 | DVQLVESGGGLVQPGGSLRLSCTAS | 29 | GRTFSSYAVG | 91 | WFRQAPGKEREFVA | 47 | AISRSGRSTY | 102 | YADSVKGRFTISRDNSKNTVYLQMNSLRPEDTAVYYCAA | 65 | GLSYYSPHAYYDY | 107 | WGQGTLVTVSS |
| 11 | 601E09 | 82 | DVQLVESGGGLVQPGGSLRLSCAAS | 30 | GLTFSTYAMG | 91 | WFRQAPGKEREFVA | 48 | AISWSGSRTY | 102 | YADSVKGRFTISRDNSKNTVYLQMNSLRPEDTAVYYCAA | 66 | YRRPRYSPTGTWDY | 107 | WGQGTLVTVSS |
| 12 | 604B05 | 84 | DVQLVESGGGLVQPGGSLRLSCVAS | 31 | GRTFSIYTMA | 91 | WFRQAPGKEREFVA | 49 | AISWSSGRTY | 183 | YADSVKGRFTISRDNSKNTVYLQMNSLRPEDTAVYYCTA | 67 | YTGPRSGYDY | 107 | WGQGTLVTVSS |
| 13 | 604F02 | 82 | DVQLVESGGGLVQPGGSLRLSCAAS | 32 | GRTFSSYTMG | 91 | WFRQAPGKEREFVA | 50 | AISWSGGRTY | 102 | YADSVKGRFTISRDNSKNTVYLQMNSLRPEDTAVYYCAA | 68 | YRRRRASSNRGLWDY | 107 | WGQGTLVTVSS |
| 14 | 604G01 | 82 | DVQLVDSGGGLVQPGGSLRLSCAAS | 32 | GRTFSSYTMG | 91 | WFRQAPGKEREFVA | 51 | AISWSGRTTY | 102 | YADSVKGRFTISRDNSKNTVYLQMNSLRPEDTAVYYCAA | 69 | YRRVRYTNLEVWDY | 107 | WGQGTLVTVSS |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 15 | 604G09 | 84 | DVQLVESGGGLVQ PGGSDRLSCVAS | 33 | GRTFSSYAMG | 91 | WFRQAPGKEREEVA | 52 | AITWSSATTY | 102 | YADSVKGRFTISRDNSKNTV YLQMNSLRPEDTAVYYCAA | 70 | ARIPVGRRSENWDY | 107 | WGQGTLVTV SS |
| 16 | 606A05 | 84 | DVQLVESGGGLVQ PGGSLRLSCVAS | 34 | GRTFSIYTMG | 91 | WFRQAPGKEREFVA | 50 | AISWSGGRTY | 103 | YADSVKGRFTISRDNSKNTV YLQMNSLRPEDTAVYYCTA | 71 | YTGRSYGSYDY | 107 | WGQGTLVTV SS |
| 17 | 606A07 | 84 | DVQLVESGGGLVQ PGGSLRLSCVAS | 35 | GRTFSIYGMG | 91 | WFRQAPGKEREFVA | 53 | AINGGSRTY | 102 | YADSVKGRFTISRDNSKNTV YLQMNSLRPEDTAVYYCAA | 72 | DRSGYGTSLDWWYDY | 107 | WGQGTLVTV SS |
| 18 | 608A05 | 82 | DVQLVESGGGLVQ PGGSLRLSCAAS | 36 | GRTFSTYTMG | 91 | WFRQAPGKEREFVA | 54 | AISWSGGTTY | 102 | YADSVKGRFTISRDNSKNTV YLQMNSLRPEDTAVYYCAA | 73 | RPRYYYYSLYSYDY | 107 | WGQGTLVTV SS |
| 19 | 609C09 | 82 | DVQLVESGGGLVQ PGGSLRLSCAAS | 37 | GTIFSINVMG | 93 | WYRQAPGKEREEVA | 55 | AITTGGRTN | 104 | YADSVKGRFTISRDNSKNTV YLQMNSLRPEDTAVYYCNA | 74 | EVTTGWVGYSWYDY | 108 | WGQGTMVTV SS |
| 114 | 114A09 | 75 | EVQLVESGGGLVQ AGGSLRLSCAAS | 109 | GSTFIISVMR | 87 | WYRQAPGKQRELVA | 110 | AIRTGGNTD | 112 | YAGPVRGRFSISRDGAKNAV DLQMNGLKPEDTAVYYCNV | 111 | PTTRYGGDYYGPY | 105 | WGQGTQVTV SS |
| 115 | 114B04 | 75 | EVQLVESGGGLVQ AGGSLRLSCAAS | 109 | GSTFIISVMR | 87 | WYRQAPGKQRELVA | 110 | AIRTGGNTD | 113 | YAGPVRGRFSISRDGAKDAV DLQMNGLKPEDTAVYYCNV | 111 | PTTRYGGDYYGPY | 105 | WGQGTQVTV SS |
| 116 | 0269 | 77 | EVQLVESGGGLVQ PGGSLRLSCAAS | 24 | GSTFIINVVR | 121 | WYRRAPGKQRELVA | 42 | TISSGGNAN | 122 | YVDSVRGRFTISRDNSKNTV YLQMNSLRPEDTAVYYCNV | 60 | PTTHYGGVYYGPY | 107 | WGQGTLVTV SS |
| 117 | 0745 | 119 | EVQLVESGGGVVQ PGGSLRLSCAAS | 24 | GSTFIINVVR | 121 | WYRRAPGKQRELVA | 42 | TISSGGNAN | 123 | YVDSVRGRFTISMNSKNTV YLQMNSLRPEDTALYYCNV | 60 | PTTHYGGVYYGPY | 107 | WGQGTLVTV SS |
| 118 | 0747 | 120 | DVQLVESGGGVVQ PGGSLRLSCAAS | 32 | GRTFSSYTMG | 91 | WFRQAPGKEREFVA | 50 | AISWSGGRTY | 124 | YADSVKGRFTISRDNSKNTV YLQMNSLRPEDTALYYCAA | 68 | YRRRRASSNRGLWDY | 107 | WGQGTLVTV SS |

TABLE B

Aggrecan sequences and others from various species
("ID" refers to the SEQ ID NO as used herein)

| Name | ID | Amino acid sequence |
|---|---|---|
| human<br>Aggrecan | 125 | MTTLLWVFVTLRVITAAVTVETSDHDNSLSVSIPQSPLRVLLGTSLTIPCYFIDPMHPVTTAPSTAPLA<br>PRIKWSRVSKEKEVVLLVATEGRVRVNSAYQDKVSLPNYPAIPSDATLEVQSLRSNDSGVYRCEVMHGIE<br>DSEATLEVVVKGIVFHYRAISTRYTLDFDRAQRACLQNSAIIATPEQLQAAYEDGFHQCDAGWLADQTVR<br>YPIHTPREGCYGDKDEFPGVRTYGIRDTNETYDVYCFAEEMEGEVFYATSPEKFTFQEAANECRRLGARL<br>ATTGHVYLAWQAGMDMCSAGWLADRSVRYPISKARPNCGGNLLGVRTVYVHANQTGYPDPSSRYDAICYT<br>GEDFVDIPENFFGVGGEEDITVQTVTWPDMELPLPRNITEGEARGSVILTVKPIFEVSPSPLEPEEPFTF<br>APEIGATAFAEVENETGEATRPWGFPTPGLGPATAFTSEDLVVQVTAVPGQPHLPGGVVFHYRPGPTRYS<br>LTFEEAQQACPGTGAVIASPEQLQAAYEAGYEQCDAGWLRDQTVRYPIVSPRTPCVGDKDSSPGVRTYGV<br>RPSTETYDVYCFVDRLEGEVFFATRLEQFTFQEALEFCESHNATATTGQLYAAWSRGLDKCYAGWLADGS<br>LRYPIVTPRPACGGDKPGVRTVYLYPNQTGLPDPLSRHHAFCFRGISAVPSPGEEEGGITTSPSGVEEWI<br>VTQVVPGVAAVPVEEETTAVPSGETTAILEFTTEPENQTEWEPAYTPVGTSPLPGILPTWPPTGAETEES<br>TEGPSATEVPSASEEPSPSEVPFPSEEPSPSEEPFPSVRPFPSVELFPSEEPFPSKEPSPSEEPSASEEP<br>YTPSPPEPSWTELPSSGEESGAPDVSGDFTGSGDVSGHLDFSGQLSGDRASGLPSGDLDSSGLTSTVGSG<br>LTVESGLPSGDEERIEWPSTPTVGELPSGAEILEGSASGVGDLSGLPSGEVLETSASGVGDLSGLPSGEV<br>LETTAPGVEDISGLPSGEVLETTAPGVEDISGLPSGEVLETTAPGVEDISGLPSGEVLETTAPGVEDISG<br>LPSGEVLETTAPGVEDISGLPSGEVLETAAPGVEDISGLPSGEVLETAAPGVEDISGLPSGEVLETAAPG<br>VEDISCLPSGEVLETAAPGVEDISGLPSGEVLETAAPGVEDISGLPSGEVLETAAPGVEDISGLPSGEVL<br>ETAAPGVEDISGLPSGEVLETAAPGVEDISGLPSGEVLETAAPGVEDISGLPSGEVLETAAPGVEDISGL<br>PSGEVLETAAPGVEDISGLPSGEVLETTAPGVERISGLPSGEVLETTAPGVDEISGLPSGEVLETTAPGV<br>EEISGLPSGEVLETSTSAVGDLSGLPSGGEVLEISVSGVEDISGLPSGEVVETSASGIEDVSELPSGEGL<br>ETSASGVEDLSRLPSGEEVLEISASGFGDLSGVPSGGEGLETSASEVGTDLSGLPSGREGLETSASGAED<br>LSGLPSGKEDLVGSASGDLDLGKLPSGTLGSGQAPETSGLPSGFSGEYSGVDLGSGPPSGLPDFSGLPSG<br>FPTVSLVDSTLVEVVTASTASELEGRGTIGISGAGEISGLPSSELDISGRASGLPSGTELSGQASGSPDV<br>SGEIPGLFGVSGQPSGFPDTSGETSGVTELSGLSSGQPGVSGEASGVLYGTSQPFGITDLSGETSGVPDL<br>SGQPSGLPGFSGATSGVPDLVSGTTSGSGESSGITFVDTSLVEVAPTTFKEEEGLGSVELSGLPSGEADL<br>SGKSGMVDVSGQFSGTVDSSGFTSQTPEFSGLPSGIAEVSGESSRAEIGSSLPSGAYYGSGTPSSFPTVS<br>LVDRTLVESVTQAPTAQEAGEGPSGILELSGAHSGAPDMSGEHSGFLDLSGLQSGLIEPSGEPPGTPYFS<br>GDFASTTNVSGESSVAMGTSGEASGLPEVTLITSEFVEGVTEPTISQELGQRPPVTHTPQLFESSGKVST<br>AGDISGATPVLPGSGVEVSSVPESSSETSAYPEAGFGASAAPEASREDSGSPDLSETTSAFHEANLERSS<br>GLGVSGSTLTFQEGEASAAPEVSGESTTTSDVGTEAPGLPSATPTASGDRTEISGDLSGHTSQLGVVIST<br>SIPESEWTQQTQRPAETHLEIESSSLLYSGEETHTVETATSPTDASIPASPEWKRESESTAAAPARSCAE<br>EPCGAGTCKETEGHVICLCPPGYTGEHCNIDQEVCEEGWNKYQGHCYRHFPDRETWVDAERRCREQQSHL<br>SSIVTPEEQEFVNNNAQDYQWIGLNDRTIEGDFRWSDGHPMQFENWRPNQPDNFFAAGEDCVVMIWHEKG<br>EWNDVPCNYHLPFTCKKGTVACGEPPVVEHARTFGQKKDRYEINSLVRYQCTEGFVQRHMPTIRCQPSGH<br>WEEPRITCTDATTYKRRLQKRSSRHPRRSRPSTAH |
| dog<br>Aggrecan | 126 | MTTLLWVFVTLRVITAASSEETSDHDNSLSVSIPEPSPMRVLLGSSLTIPCYFIDPMHPVTTAPSTAPLA<br>PRIKWSRITKEKEVVLLVATEGQVRINSAYQDKVSLPNYPAIPSDATLEIQNLRSNDSGIYRCEVMHGIE<br>DSEATLEVVVKGIVFHYRAISTRYTLDFDRAQRACLQNSAIIATPEQLQAAYEDGFHQCDAGWLADQTVR<br>YPIHTPREGCYGDKDEFPGVRTYGIRDTNETYDVYCFAEEMEGEVLYATSPEKFTFQEAANECRRLGARL<br>ATTGQLYLAWQGGMDMCSAGWLADRSVRYPISKARPNCGGNLLGVRTVYLHANQTGYPDPSSRYDAICYT<br>GEDFVDIPENFFGVGGEEDITIQTVTWPDVELPLPRNITEGEARGNVILTVKPIFDLSPTAPEPEEPFTF<br>VPEPEKPFTFATDVGVTAFPEAENRTGEATRPWGVPEESTPGPAFTAFTSEDHVVQVTAVPGAAEVPGQP<br>RLPGGVVFHYRPGSARYSLTFEEAQQACLRTGAVIASPEQLQAAYEAGYEQCDAGWLQDQTVRYPIVSPR<br>TPCVGDKDSSPGVRTYGVRPPSETYDVYCYVDKLEGEVFFITRLEQFTFQEALAFCESHNATLASTGQLY<br>AAWRQGLDKCYAGWLSDGSLRYPIVTPRPSCGGDKPGVRTVYLYPNQTGLPDPLSRHHVFCFRGVSGVPS<br>PGEEEGGTPTPSVVEDWIPTQVGPVVPSVPMGEETTAILDFTIEPENQTEWEPAYSPAGTSPLPGIPPTW<br>PPTSTATEESTEGPSGTEVPSVSEEPSPSEEPFPWEELSTLSPPGPSGTELPGSGEASGVPEVSGDFTGS<br>GEVSGHPDSSGQLSGESASGLPSEDLDSSGLTSAVGSGLASGDEDRITLSSIPKVEGEGLETSASGVEDL<br>SGLPSGREGLETSTSGVGDLSGLPSGEGLEVSASGVEDLSGLPSGEGPETSTSGVGDLSRLPSGEGPEVS<br>ASGVGDLSGLPSGREGLETSTSGVEDLSGLPSGEGPEASTSGVGDLSRLPSGEGPEVSASGVEDLSGLPS<br>GEGLEASASGVGDLSGLPSGEGPEASASGVGDLSRLPSGEGPEVSASGVEDLSGLSSGESPEASASGVGD<br>LSGLPSGREGLETSASGVGDLSGLPSGEGQEASASGVEDLSRLPSGEGPEASASGVGELSGLPSGREGLE<br>TSASGVGDLSGLPSGEGPEAFASGVEDLSILPSGEGPEASASGVGDLSGLPSGREGLETSTSGVGDLSGL<br>PSGREGLETSTSGVGDLSGLPSGEGPEASASGIGDISGLPSGREGLETSSSGVEDHPETSASGVEDLSGL<br>PSGVEGHPETSASGVEDLSDLSEGGEGLETSASGAEDLSGFPSGKEDLIGSASGALDFGRIPSGTLGSGQ<br>APEASSLPSGFSGEYSGVDFGSGPISGLPDFSGLPSGFPTISLVDTTLVEVITTTSASELEGRGTIGISG<br>AGETSGLPVSELDISGAVSGLPSGAELSGQASGSPDMSGETSGFFGVSGQPSGFPDISGGTSGLFEVSGQ<br>PSGFSGETSGVTELSGLYSGQPDVSGEASGVPSGSGQPFGMTDLSGETSGVPDISGQPSGLPEFSGTTSG<br>IPDLVSSTMSGSGESSGITFVDTSLVEVTPTTFKEKKRLGSVELSGLPSGEVDLSGASGTMDISGQSSGA<br>TDSSGLTSHLPKFSGLPSGAAEVSGESSGAEVGSSLPSGTYEGSGNFHPAFPTVFLVDRTLVESVTQAPT<br>AQEAGEGPSGILELSGAHSGAPDVSGDHSGSLDLSGMQSGLVEPSGEPSSTPYFSGDFSGTMDVTGEPST<br>AMSASGEASGLLEVTLITSEFVEGVTEPTVSQELAQRPPVTHTPQLFESSGEASASGEISGATPAFPGSG<br>LEASSVPESSSETSDFPERAVGVSAAPEASGGASGAPDVSEATSTFPEADVEGASGLGVSGGTSAFPEAP<br>REGSATPEVQEEPTTSYDVGREALGWPSATPTASGDRIEVSGDLSGHTSGLDVVISTSVPESEWIQQTQR<br>PAEAHLEIEASSPLHSGEETQTAETATSPTDDASIPTSPSGTDESAPAIPDIDECLSSPCLNGATCVDAI<br>DSFTCLCLPSYRGDLCEIDQELCEEGWTKFQGHCYRYFPDRESWVDAESRCRAQQSHLSSIVTPEEQEFV<br>NNNAQDYQWIGLNDRTIEGDFRWSDGHSLQFENWRPNQPDNFFVSGEDCVVMIWHEKGEWNDVPCNYYLP<br>FTCKKGTVACGDPPVVEHARTEGQKKDRYEINSLVRYQCTEGFVQRHVPTIRCQPSGHWEKPRITCTDPS<br>TYKRRLQKRSSRAPRRSRPSTAH |
| bovine<br>Aggrecan | 127 | MTTLLLVFVTLRVITAAISVEVSEPDNSLSVSIPEPSPLRVLLGSSLTIPCYFIDPMHPVTTAPSTAPLA<br>PRIKWSRISKEKEVVLLVATEGRVRVNSAYQDKVTLPNYPAIPSDATLEIQNMRSNDSGILRCEVMHGIE<br>DSQATLEVVVKGIVFHYRAISTRYTLDFDRAQRACLQNSAIIATPEQLQAAYEDGFHQCDAGWLADQTVR<br>YPIHTPREGCYGDKDEFPGVRTYGIRDTNETYDVYCFAEEMEGEVFYATSPEKFTFQEAANECRRLGARL |

TABLE B-continued

Aggrecan sequences and others from various species
("ID" refers to the SEQ ID NO as used herein)

| Name | ID | Amino acid sequence |
|---|---|---|
| | | ATTGQLYLAWQGGMDMCSAGWLADRSVRYPISKARPNCGGNLLGVRTVYLHANQTGYPDPSSRYDAICYT<br>GEDFVDIPESFFGVGGEEDITIQTVTWPDVELPLPRNITEGEARGSVILTAKPDFEVSPTAPEPEEPFTF<br>VPEVRATAFPEVENRTEEATRPWAFPRESTPGLGAPTAFTSEDLVVQVTLAPGAAEVPGQPRLPGGVVFH<br>YRPGSSRYSLTFEEAKQACLRTGAIIASPEQLQAAYEAGYEQCDAGWLQDQTVRYPIVSPRTPCVGDKDS<br>SPGVRTYGVRPPSETYDVYCYVDRLEGEVFFATRLEQFTFWEAQEFCESQNATLATTGQLYAAWSRGLDK<br>CYAGWLADGSLRYPIVTPRPACGGDKPGVRTVYLYPNQTGLLDPLSRHHAFCFRGVSAAPSPEEEEGSAP<br>TAGPDVEEWMVTQVGPGVAAVPIGEETTAIPGFTVEPENKTEWELAYTPAGTLPLPGIPPTWPPTGEATE<br>EHTEGPSATEVPSASEKPFPSEEPFPPEEPFPSEKPFPPEELFPSEKPFPSEKPFPSEEPFPSEKPFPPE<br>ELFPSEKPIPSEEPFPSEEPFPSEKPFPPEEPFPSEKPIPSEEPFPSEKPFPSEEPFPSEEPSTLSAPVP<br>SRTELFSSGEVSGVPEISGDFTGSGEISGHLDFSGQPSGESASGLPSEDLDSSGLTSTVGSGLPVESGLP<br>SGEEERITWTSAPKVDRLPSGGEGPEVSGVEDISGLPSGGEVHLEISASGVEDISGLPSGGEVHLEISAS<br>GVEDLSRIPSGEGPEISASGVEDISGLPSGEEGHLEISASGVEDLSGIPSGEGPEVSASGVEDLIGLPSG<br>EGPEVSASGVEDLSRLPSGEGPEVSASGVEDLSGLPSGEGPEVSVSGVEDLSRLPSGEGPEVSASGVEDL<br>SRLPSGEGPEISVSGVEDISILPSGEGPEVSASGVEDLSVLPSGEGHLEISTSGVEDLSVLPSGEGHLET<br>SSGVEDISRLPSGEGPEVSASGVEDLSVLPSGEDHLEISASGVEDLGVLPSGEDHLEISASGVEDISRLP<br>SGEGPEVSASGVEDLSVLPSGEGHLEISASGVEDLSRLPSGGEDHLETSASGVGDLSGLPSGREGLEISA<br>SGAGDLSGLTSGKEDLTGSASGALDLGRIPSVTLGSGQAPEASGLPSGFSGEYSGVDLESGPSSGLPDFS<br>GLPSGFPTVSLVDTTLVEVVTATTAGELEGRGTIDISGAGETSGLPFSELDISGGASGLSSGAELSGQAS<br>GSPDISGETSGLFGVSGQPSGFPDISGETSGLLEVSGQPSGFYGEISGVTELSGLASGQPEISGEASGIL<br>SGLGPPFGITDLSGEAPGIPDLSGQPSGLPEFSGTASGIPDLVSSAVSGSGESSGITFVDTSLVEVTPTT<br>FKEEEGLGSVELSGLPSGELGVSGTSGLADVSGLSSGAIDSSGFTSQPPEFSGLPSGVTEVSGEASGAES<br>GSSLPSGAYDSSGLPSGFPTVSFVDRTLVESVTQAPTAQEAGEGPSGILELSGAPSGAPDMSGDHLGSLD<br>QSGLQSGLVEPSGEPASTPYFSGDFSGTTDVSGESSAATSTSGEASGLPEVTLITSELVEGVTEPTVSQE<br>LGQRPPVTYTPQLFESSGEASASGDVPRFPGSGVEVSSVPESSGETSAYPEAEVGASAAPEASGGASGSP<br>NLSETTSTFHEADLEGTSGLGVSGSPSAFPEGPTEGLATPEVSGESTTAFDVSVEASGSPSATPLASGDR<br>TDTSGDLSGHTSGLDIVISTTIPESEWTQQTQRPAEARLEIESSSPVHSGEESQTADTATSPTDASIPAS<br>AGGTDDSEATTTDIDECLSSPCLNGATCVDAIDSFTCLCLPSYQGDVCEIQKLCEEGWTKFQGHCYRHFP<br>DRATWVDAESQCRKQQSHLSSIVTPEEQEFVNNNAQDYQWIGLNDKTIEGDFRWSDGHSLQFENWRPNQP<br>DNFFATGEDCVVMIWHEKGEWNDVPCNYQLPFTCKKGTVACGEPPVVEHARIFGQKKDRYEINALVRYQC<br>TEGFIQGHVPTIRCQPSGHWEEPRITCTDPATYKRRLQKRSSRPLRRSHPSTAH |
| rat Aggrecan | 128 | MTTLLLVFVTLRVIAAVISEEVPDHDNSLSVSIPQPSPLKALLGTSLTIPCYFIDPMHPVTTAPSTAPLT<br>PRIKWSRVSKEKEVVLLVATEGQVRVNSIYQDKVSLPNYPAIPSDATLEIQNLRSNDSGIYRCEVMHGIE<br>DSEATLEVIVKGIVFHYRAISTRYTLDFDRAQRACLQNSAIIATPEQLQAAYEDGFHQCDAGWLADQTVR<br>YPIHTPREGCYGDKDEFPGVRTYGIRDTNETYDVYCFAEEMEGEVFYATSPEKFTFQEAANECRTVGARL<br>ATTGQLYLAWQGGMDMCSAGWLADRSVRYPISKARPNCGGNLLGVRTVYLHANQTGYPDPSSRYDAICYT<br>GEDFVDIPENFFGVGGEEDITIQTVTWPDLELPLPRNITEGEARGNVILTAKPIFDMSPTVSEPGEALTL<br>APEVGTTVFPEAGERTEKTTRPWGFPEEATRGPDSATAFASEDLVVRVTISPGAVEVPGQPRLPGGVVFH<br>YRPGSTRYSLTFEEAQQACIRTGAAIASPEQLQAAYEAGYEQCDAGWLQDQTVRYPIVSPRTPCVGDKDS<br>SPGVRTYGVRPSSETYDVYCYVDKLEGEVFFATQMEQFTFQEAQAFCAAQNATLASTGQLYAAWSQGLDK<br>CYAGWLADGTLRYPIVNPRPACGGDKPGVRTVYLYPNQTGLPDPLSKHHAFCFRGVSVVPSPGGTPTSPS<br>DIEDWIVTRVEPGVDAVPLEPETTEVPYFTTEPEKQTEWEPAYTPVGTSPLPGIPPTWLPTVPAAEEHTE<br>SPSASQEPSASQVPSTSEEPYTPSLAVPSGTELPSSGDTSGAPDLSGDFTGSTDTSGRLDSSGEPSGGSE<br>SGLPSGDLDSSGLGPTVSSGLPVESGSASGDGEIPWSSTPTVDRLPSGGESLEGSASASGTGDLSGLPSG<br>GEITETSASGTEEISGLPSGGDDLETSTSGIDGASVLPTGRGGLETSASGVEDLSGLPSGEEGSETSTSG<br>IEDISVLPTGESPETSASGVGDLSGLPSGGESLETSASGVEDVTQLPTERGGLETSASGIEDITVLPTGR<br>ENLETSASGVEDVSGLPSGKEGLETSASGIEDISVFPTEAEGLETSASGGYVSGIPSGEDGTETSTSGVE<br>GVSGLPSGGEGLETSASGVEDLGLPTRDSLETSASGVDVTGYPSGREDTETSVPGVGDDLSGLPSGQEGL<br>ETSASGAEDLGGLPSGKEDLVGSASGALDFGKLPSGTLGSGQTPEASGLPSGFSGEYSGVDIGSGPSSGL<br>PDFSGLPSGFPTVSLVDSTLVEVITATTASELEGRGTISVSGSGEESGPPLSELDSSADISGLPSGTELS<br>GQTSGSLDVSGETSGFFDVSGQPFGSSGTGEGTSGIPEVSGQAVRSPDTTEISELSGLSSGQPDVSGEGS<br>GILFGSGQSSGITSVSGETSGISDLSGQPSGFPVLSGTTPGTPDLASGANSGSGDSSGITFVDTSLIEVT<br>PTTFREEEGLGSVELSGLPSGETDLSGTSGMVDVSGQSSGAIDSSGLISPTPEFSGLPSGVAEVSGEVSG<br>VETGSSLSSGAFDGSGLVSGFPTVSLVDRTLVESITLAPTAQEAGEGPSSILEFSGAHSGTPDISGDLSG<br>SLDQSTWQPGWTEASTEPPSSPYFSGDFSSTTDASGESITAPTGSGETSGLPEVTLITSELVEGVTEPTV<br>SQELGEGPSMTYTPRLFEASGEASASGDLGGPVTIFPGSGVEASVPEGSSDPSAYPEAGVGVSAAPEASS<br>QLSEFPDLHGITSASRETDLEMTTPGTEVSSNPWTFQEGTREGSAAPEVSGESSTTSDIDAGTSGVPFAT<br>PMTSGDRTEISGEWSDHTSEVNVTVSTTVPESRWAQSTQHPTETLQEIGSPNPSYSGEETQTAETAKSLT<br>DTPTLASPEGSGETESTAADQEQCEEGWTKFQGHCYRHFPDRETWVDAERRCREQQSHLSSIVTPEEQEF<br>VNKNAQDYQWIGLNDRTIEGDFRWSDGHSLQFEKWRPNQPDNFFATGEDCVVMIWHERGEWNDVPCNYQL<br>PFTCKKGTVACGEPPAVEHARTLGQKKDRYEISSLVRYQCTEGFVQRHVPTIRCQPSADWEEPRITCTDP<br>NTYKHRLQKRTMRPTRRSRPSMAH |
| Pig Aggrecan (core) | 129 | AISVEVSEPDNSLSVSIPQPSPLRVLLGGSLTIPCYFIDPMHPVXTAPXTAPLAPRIKWSRVSKEKEVVL<br>LVATEGQVRVNSAYQDRVTLPNYPAIPSDATLEIQNLRSNDSGIYRCEVMHGIEDSEATLEVVVKGIVFH<br>YRAISXRYTLDFDRAQRACLQNSAIIATPEQLQAAYEDGFHQCDAGWLADQTVRYPIHTPREGCYGDKDE<br>FPGVITYGIRDTNETYDVYCFAEEMEGEVFYATSPEKFTFQEAANECRRLGARLATTGQLYLAWRGGMDM<br>CSAGWLADRSVRYPISKARPNCGGNLLGVRTVYLHANQTGYPDPSSRYDAICYTGEDFVDIPENFFGVGG<br>EEDITIQTVTWPDVELPLPRNITEGEARGTVILTVKPVFEFSPTAPEPEEPFTFAPGTGATAFPEAENRT<br>GEATRPWAFPEESTPGLGAPTAFTSEDLVVQVTSAATEEGTEGPSATEAPSTSEEPFPSEKPFPSEEPFP<br>SEEPFPSEKPSASEEPFPSEQPSTLSAPVPSRTELPGSGEVSGAPEV |
| mouse Aggrecan | 130 | MTTLLLVFVTLRVIAAVISEEVPDHDNSLSVSIPQPSPLKVLLGSSLTIPCYFIDPMHPVTTAPSTAPLT<br>PRIKWSRVSKEKEVVLLVATEGQVRVNSIYQDKVSLPNYPAIPSDATLEIQNLRSNDSGIYRCEVMHGIE<br>DSEATLEVIVKGIVFHYRAISTRYTLDFDRAQRACLQNSAIIATPEQLQAAYEDGFHQCDAGWLADQTVR |

TABLE B-continued

Aggrecan sequences and others from various species ("ID" refers to the SEQ ID NO as used herein)

| Name | ID | Amino acid sequence |
|---|---|---|
| | | YPIHTPREGCYGDKDEFPGVRTYGIRDTNETYDVYCFAEEMEGEVFYATSPEKFTFQEAANECRRLGARL<br>ATTGQLYLAWQGGMDMCSAGWLADRSVRYPISKARPNCGGNLLGVRTVYLHANQTGYPDPSSRYDAICYT<br>GEDFVDIPENFFGVGGEDDITIQTVTWPDLELPLPRNVTEGEALGSVILTAKPIFDLSPTISEPGEALTL<br>APEVGSTAFPEAEERTGEATRPWGEPAEVTRGPDSATAFASEDLVVRVTISPGAAEVPGQPRLPGGVVFH<br>YRPGSTRYSLTFEEAQQACMHTGAVIASPEQLQAAYEAGYEQCDAGWLQDQTVRYPIVSPRTPCVGDKDS<br>SPGVRTYGVRPSSETYDVYCYVDKLEGEVFFATRLEQFTFQEARAFCAAQNATLASTGQLYAAWSQGLDK<br>CYAGWLADGTLRYPIITPRPACGGDKPGVRTVYLYPNQTGLPDPLSKHHAFCFRGVSVAPSPGEEGGSTP<br>TSPSDIEDWIVTQVGPGVDAVPLEPKTTEVPYFTTEPRKQTEWEPAYTPVGTSPQRGIPPTWLPTLPAAE<br>EHTESPSASEEPSASAVPSTSEEPYTSSFAVPSMTELPGSGEASGAPDLSGDFTGSGDASGRLDSSGQPS<br>GGIESGLPSGDLDSSGLSPTVSSGLPVESGSASGDGEVPWSHTPTVGRLPSGGESPEGSASASGTGDLSG<br>LPSGGEITETSTSGAEETSGLPSGGDGLETSTSGVDDVSGIPTGREGLETSASGVEDLSGLPSGEEGSET<br>STSGIEDISVLPTGGESLETSASGVGDLSGLPSGGESLETSASGAEDVTQLPTERGGLETSASGVEDITV<br>LPTGRESLETSASGVEDVSGLPSGREGLETSASGIEDISVFPTEAEGLDTSASGGYVSGIPSGGDGTETS<br>ASGVEDVSGLPSGGEGLETSASGVEDLGPSTRDSLETSASGVDVTGFPSGRGDPETSVSGVGDDFSGLPS<br>GKEGLETSASGAEDLSGLPSGKEDLVGSASGALDFGKLPPGTLGSGQTPEVNGFPSGFSGEYSGADIGSG<br>PSSGLPDFSGLPSGFPTVSLVDSTLVEVITATTSSELEGRGTIGISGSGEVSGLPLGELDSSADISGLPS<br>GTELSGQASGSPDSSGETSGFFDVSGQPFGSSGVSEETSGIPEISGQPSGTPDTTATSGVTELNELSSGQ<br>PDVSGDGSGILFGSGQSSGITSVSGETSGISDLSGQPSGFPVFSGTATRTPDLASGTISGSGESSGITFV<br>DTSFVEVTPTTFREEEGLGSVELSGFPSGETELSGTSGTVDVSEQSSGAIDSSGLTSPTPEFSGLPSGVA<br>EVSGEFSGVETGSSLPSGAFDGSGLVSGFPTVSLVDRTLVESITQAPTAQEAGEGPSGILEFSGAHSGTP<br>DISGELSGSLDLSTLQSGQMETSTETPSSPYFSGDFSSTTDVSGESIAATTGSGESSGLPEVTLNTSELV<br>EGVTEPTVSQELGHGPSMTYTPRLFEASGDASASGDLGGAVTNFPGSGIEASVPEASSDLSAYPEAGVGV<br>SAAPEASSKLSEFPDLHGITSAFHETDLEMTTPSTEVNSNPWTFQEGTREGSAAPEVSGESSTTSDIDTG<br>TSGVPSATPMASGDRTEISGEWSDHTSEVNVAISSTITESEWAQPTRYPTETLQEIESPNPSYSGEETQT<br>AETTMSLTDAPTLSSSEGSGETESTVADQEQCEEGWTKFQGHCYRHFHDRETWVDAERRCREQQSHLSSI<br>VTPEEQEFVNKNAQDYQWIGLNDRTIEGDFRWSDGHSLQFEKWRPNQPDNFFAIGEDCVVMIWHERGEWN<br>DVPCNYQLPFTCKKGTVACGDPPVVEHARTLGQKKDRYEISSLVRYQCTEGFVQRHVPTIRCQPSGHWEE<br>PRITCTDPNTYKHRLQKRSMRPTRRSRPSMAH |
| rabbit Aggrecan | 131 | MTTLLLVLVALRVIAAAISGDVSDLDNALSVSIPQPSPVRALLGTSLTIPCYFIDPVHPVTTAPSTAPLT<br>PRIKWSRISKDKEVVLLVANEGRVRINSAYQDKVSLPNYPAIPSDATLEIQSLRSNDSGIYRCEVMHGLE<br>DSEATLEVVVKGVVFHYRAISTRYTLDFDRAQRACLQNSAIIATPEQLQAAYEDGFHQCDAGWLADQTVR<br>YPIHTPREGCYGDKDEFPGVRTYGIRDTNETYDVYCFAEEMEGEVFYATSPEKFTFQEAASECRRLGARL<br>ATTGQLYLAWQAGMDMCSAGWLADRSVRYPISKARPNCGGNLLGVRTVYVHANQTGYPDPSSRYDAICYT<br>GEDFMDIPENFFGVGGEEDITVQTVTWPDVELPVPRNITEGEARGSVVLTAKPVLDVSPTAPQPEETFAP<br>GVGATAFPGVENGTEEATRPRGFADEATLGPSSATAFTSADLVVQVTAAPGVAEVPGQPRLPGGVVFHYR<br>PGPTRYSLTFEEAQQACLRTGAAMASAEQLQAAYEAGYEQCDAGWLQDQTVRYPIVSPRTPCVGDKDSSP<br>GVRTYGVRPPSETYDVYCYVDRLEGEVFFATRLEQFTFQEALESCESHNATLASTGQLYAAWSRGLDRCY<br>AGWLADGSLRYPIVTPRPACGGDKPGVRTVYLYPNQTGLPDPLSRHHAFCFRGTSEAPSPGPEEGGTATP<br>ASGLEDWIVTQVGPGVAATPRAEERTAVPSFATEPGNQTGWEAASSPVGTSLLPGIPPTWPPTGTAAEGT<br>TEGLSTAAMPSASEGPYTPSSLVARETELPGLGVTSVPPDISGDLTSSGEASGLFGPTGQPLGGSASGLP<br>SGELDSGSLTPTVGSGLPIGSGLASGDEDRIQWSSSTEVGGVTSGAEIPETSASGVGTDLSGLPSGAEIP<br>ETFASGVGTDLSGLPSGAEIPETFASGVGTDLSGLPSGAEILETSASGVGTDLSGLPSGAEILETSASGV<br>GTDLSGLPSGAEILETSASGVGTDLSGLPSGAEIPETFASGVGTDLSGLPSGAEILETSASGVGTDLSGL<br>PSGAEIPETSASGVGTDLSGLPSGAEILETSASGVGTDLSGLPSGAEILETSASGVGTDLSGLPSGAEIL<br>ETSASGVGTDLSGLPSGAEILETSASGVGTDLSGLPSGAEILETSASGVGTDLSGLPSGGEIPETFASGV<br>GDLSGLPPGREDLETLTSGVGDLSGLSSGKDGLVGSASGALDFGGTLGSGQIPETSGLPSGYSGEYSEVD<br>LGSGPSSGLPDFSGLPSGFPTVSLVDTPLVEVVTATTARELEGRGTIGISGAGEISGLPSSELDVSGGTS<br>GADISGEADVGGEASGLIVRGQPSGFPDTSGEAFGVTEVSGLSSGQPDLSGEASGVLFGSGPPFGITDLS<br>GEPSGQPSGLPEFSGTTHRIPDLVSGATSGSGESSGIAFVDTSVVEVTPTTLREEEGLGSVEFSGFPSGE<br>TGLSGTPETIDVSGQSSGTIDSSGFTSLAPEVSGSPSGVAEVSGEASCTEITSGLPSGVFDSSGLPSGFP<br>TVSLVDRTLVESVTQAPTAQEAEGPSDILELSGVHSGLPDVSGAHSGFLDPSGLQSGLVEPSGEPPRTPY<br>FSGDFPSTPDVSGEASAATSSSGDISGLPEVTLVTSEFMEGVTRPTVSQELGQGPPMTHVPKLFESSGEA<br>LASGDTSGAAPAFPGSGLEASSVPESHGETSAYAEPGTKAAAAPDASGEASGSPDSGEITSVFREAAGEG<br>ASGLEVSSSSLASQQGPREGSASPEVSGESTTSYEIGTETSGLPLATPAASEDRAEVSGDLSGRTPVPVD<br>VVTNVPEAEWIQHSQRPAEMWPETKSSSPSYSGEDTAGTAASPASADTPGEPGPTTAAPRSCAEEPCGPG<br>TCQETEGRVTCLCPPGHTGEYCDIDIDECLSSPCVNGATCVDASDSFTCLCLPSYGGDLCETDQEVCEEG<br>WTKFQGHCYRHFPDRETWVDAEGRCREQQSHLSSIVTPEEQEFVNNNAQDYQWIGLNDRTIEGDFRWSDG<br>HPLQFENWRPNQPDNFFATGEDCVVMIWHEKGEWNDVPCNYHLPFTCKKGTVACGDPPVVEHARTFGQKK<br>DRYEINSLVRYQCAEGFTQRHVPTIRCQPSGHWEEPRITCTHPTTYKRRVQKRSSRTLQRSQASSAP |
| cynomolgus Aggrecan | 132 | MTTLLWVFVTLRVIAAAVTVETSDHDNSLSVSIPQPSPLRVLLGTSLTIPCYFIDPMHPVTTAPSTAPLA<br>PRIKWSRVSKEKEVVLLVATEGRVRVNSAYQDKVSLPNYPAIPSDATLEIQSLRSNDSGVYRCEVMHGIE<br>DSEATLEVVVKGIVFHYRAISTRYTLDFDRAQRACLQNSAIIATPEQLQAAYEDGFHQCDAGWLADQTVR<br>YPIHTPREGCYGDKDEFPGVRTYGIRDTNETYDVYCFAEEMEGEVFYATSPEKFTFQEAANECRRLGARL<br>ATTGQLYLAWQAGMDMCSAGWLADRSVRYPISKARPNCGGNLLGVRTVYLHANQTGYPDPSSRYDAICYT<br>GEDFVDIPENFFGVGGEEDTTVQTVTWPDMELPLPRNITEGEARGSVILTVKPIFDVSPSPLEPEEPFTF<br>APEIGATAFPEVENETGEATRPWGFPTPGLGPATAFTSEDLVVQVTAVPGQPHLPGGVVFHYRPGSTRYS<br>LTFEEAQQACLRTGAVIASPEQLQAAYEAGYEQCDAGWLRDQTVRYPIVSPRTPCVGDKDSSPGVRTYGV<br>RPSTETYDVYCYVDRLEGEVFFATRLEQFTFQEALEFCESHNATLATTGQLYAAWSRGLDKCYAGWLADG<br>SLRYPIVTPRPACGGDKPGVRTVYLYPNQTGLPDPLSRHHAFCFRGVSAVPSPGEEEGGTPTSPSGVEDW<br>IATQVVPGVAAVPVEEETTAVPLGETTAILEFTTEPENQTEWEPAYTPMGTSPLPGILPTWPPTGTATEE<br>STEGPSATEVLTASKEPSPPEVPFPSEEPSPSEEPFPSVRPFPSVEPSPSEEPFPSVEPSPSEEPSASEE<br>PYTPSPPVPSWTELPGSGEESGAPDVSGDFIGSGDVSGHLDFSGQLSGDRISGLPSGDLDSSGLTSTVGS<br>GLPVDSGLASGDEERIEWSSTPTVGELPSGAEILEGSASEVGDLSGLPSGDVLETSASGVGDLSGLPSGE |

TABLE B-continued

Aggrecan sequences and others from various species ("ID" refers to the SEQ ID NO as used herein)

| Name | ID | Amino acid sequence |
|---|---|---|
| | | VLETSASGVGDLSGLPSGEVLETSTSGVGDLSGLPSGEVLETSTSGVGDLSGLPSAGEVLETTASGVEDI<br>SGLPSGEVLETTASGVEDISGFPSGEVLETTASGVEDISGLPSGEVLETTASGVEDISGLPSGEVLETTA<br>SGVGDLGGLPSGEVLETSTSGVGDLSGLPSGEVVETSTSGVEDLSGLPSGGEVLETSTSGVEDISGLPSG<br>EVLETTASGIEDVSELPSGEGLETSASGVEDLSRLPSGEVLETSASGVGDISGLPSGGEVLETSASGVGD<br>LSGLPSGGEGLETSASGVGTDLSGLPSGREGLETSASGAEDLSGLPSGKEDLVGPASGDLDLGKLPSGTL<br>RSGQAPETSGLPSGFSGEYSGVDLGSGPPSGLPDFSGLPSGFPTVSLVDSTLVEVVTASTASELEGRGTI<br>GISGAGEISGLPSSELDISGEASGLPSGTELSGQASGSPDVSRETPGLFDVSGQPSGFPDISGGTSGISE<br>VSGQPSGFPDTSGETSGVTELSGLPSGQPGVSGEASGVPYGSSQPFGITDLSGETSGVPDLSGQPSGLPG<br>FSGATSGVPDLVSGATSGSGESSGITFVDTSLVEVTPTTFKEEEGLGSVELSGLPSGEADLSGRSGMVDV<br>SGQFSGTVDSSGFTSQTPEFSGLPIGIAEVSGESSGAETGSSLPSGAYYGSGLPSGFPTVSLVDRTLVES<br>VTQAPTAQEAGEGPPGILELSGTHSGAPDMSGDHSGFLDVSGLQFGLVEPSGEPPSTPYFSGDFASTTDV<br>SGESSAAMGTSGEASGLPGVTLITSEFMEGVTEPTVSQELGQRPPVTHTPQLFESSGEASAAGDISGATP<br>VLPGSGVEVSSVPESSSETSAYPEAGVGASAAPETSGEDSGSPDLSETTSAFHEADLERSSGLGVSGSTL<br>TFQEGEPSASPEVSGESTTTGDVGTEAPGLPSATPTASGDRTEISGDLSGHTSGLGVVISTSIPESEWTQ<br>QTQRPAEAHLETESSSLLYSGEETHTAETATSPTDASIPASPEWTGESESTVADIDECLSSPCLNGATCV<br>DAIDSFTCLCLPSYGGDLCEIDQEVCEEGWTKYQGHCYRHFPDRETWVDAERRCREQQSHLSSIVTPEEQ<br>EFVNNNAQDYQWIGLNDRTIEGDFRWSDGHPMQFENWRPNQPDNFFAAGEDCVVMIWHEKGEWNDVPCNY<br>HLPFTCKKGTVACGEPPMVQHARTFGQKKDRYEINSLVRYQCTEGFVQRHVPTIRCQPSGHWEEPRITCT<br>DATAYKRRLQKRSSRHPRRSRPSTAH |
| rhesus Aggrecan XM_ 002804944.1 | 133 | MTTLLWVFVTLRVIAAAVTVETSDHDNSLSVSIPQPSPLRVLLGTSLTIPCYFIDPMHPVTTAPSTAPLA<br>PRIKWSRVSKEKEVVLLVATEGRVRVNSAYQDKVSLPNYPAIPSDATLEIQSLRSNDSGVYRCEVMHGIE<br>DSEATLEVVVKGIVFHYRAISTRYTLDFDRAQRACLQNSAIIATPEQLQAAYEDGFHQCDAGWLADQTVR<br>YPIHTPREGCYGDKDEFPGVRTYGIRDTNETYDVYCFAEEMEGEVFYATSPEKFTFQEAANECRRLGARL<br>ATTGQLYLAWQAGMDMCSAGWLADRSVRYPISKARPNCGGNLLGVRTVYLHANQTGYPDPSSRYDAICYT<br>GEDFVDIPENFFGVGGEEDITVQTVTWPDMELPLPRNITEGEARGSVILTVKPIFDVSPSPLEPEEPFTF<br>APEIGATAFPEVENETGEATRPWGFPTPGLGPATAFTSEDLVVQVTAVPGQPHLPGGVVFHYRPGSTRYS<br>LTFEEAQQACLRTGAVIASPEQLQAAYEAGYEQCDAGWLRDQTVRYPIVSPRTPCVGDKDSSPGVRTYGV<br>RPSTETYDVYCYVDRLEGEVFFATRLEQFTFQEALEFCESHNATLATTGQLYAAWSRGLDKCYAGWLADG<br>SLRYPIVTPRPACGGDKPGVRTVYLYPNQTGLPDPLSRHHAFCFRGVSAVPSPGEEEGGTPTSPSGVEDW<br>IATQVVPGVAAVPVEEETTAVPLGETTAILEFTTEPENQTEWEPAYTPMGTSPLPGILPTWPPTGTATEE<br>STEGPSATEVLTASKEPSPPEVPFPSEEPSPSEEPFPSVRPFPSVEPSPSEEPFPSVEPSPSEEPSASEE<br>PYTPSPPVPSWTELPGSGEESGAPDVSGDFIGSGDVSGHLDFSGQLSGDRISGLPSGDLDSSGLTSTVGS<br>GLPVDSGLASGDEERIEWSSTPTVGELPSGAEILEGSASEVGDLSGLPSGDVLETSASGVGDLSGLPSGE<br>VLETSVSGVGDLSGLPSGEVLETSTSGVGDLSGLPSGEVLETSTSGVGDLSGLPSAGEVLETTASGVEDI<br>SGLPSGEVLETTASGVEDISGFPSGEVLETTASGVEDISGLPSGEVLETTASGVEDISGLPSGEVLETTA<br>SGVGDLGGLPSGEVLETSTSGVGDLSGLPSGEVVETSTSGVEDLSGLPSGGEVLETSTSGVEDISGLPSG<br>EVLETTASGIEDVSELPSGEGLETSASGVEDLSRLPSGEVLETSASGVGDISGLPSGGEVLEISASGVGD<br>LSGLPSGGEGLETSASGVGTDLSGLPSGREGLETSASGAEDLSGLPSGKEDLVGPASGDLDLGKLPSGTL<br>GSGQAPETSGLPSGFSGEYSGVDLGSGPPSGLPDFSGLPSGFPTVSLVDSTLVEVVTASTASELEGRGTI<br>GISGAGEISGLPSSELDISGEASGLPSGTELSGQASGSPDVSRETSGLFDVSGQPSGFPDTSGETSGVTE<br>LSGLPSGQPGVSGEASGVPYGSSQPFGITDLSGETSGVPDLSGQPSGLPGFSGATSGVPDLVSGATSGSG<br>ESSDITFVDTSLVEVTPTTFKEEEGLGSVELSGLPSGEADLSGRSGMVDVSGQFSGTVDSSGFTSQTPEF<br>SGLPIGIAEVSGESSGAETGSSLPSGAYYGSELPSGFPTVSLVDRTLVESVTQAPTAQEAGEGPPGILEL<br>SGTHSGAPDMSGDHSGFLDVSGLQFGLVEPSGEPPSTPYFSGDFASTTDVSGESSAAMGTNGEASGLPEV<br>TLITSEFMEGVTEPTVSQELGQRPPVTHTPQLFESSGEASAAGDISGATPVLPGSGVEVSSVPESSSETS<br>AYPEAGVGASAAPETSGEDSGSPDLSETTSAFHEADLERSSGLGVSGSTLTFQEGEPSASPEVSGESTTT<br>GDVGTEAPGLPSATPTASGXXXXXXPTRSCAEEPCGAGTCKETEGHVICLCPPGYTGEHCNIDQEVCEEG<br>WTKYQGHCYRHFPDRETWVDAERRCREQQSHLSSIVTPEEQEFVNNNAQDYQWIGLNDRTIEGDFRWSDG<br>HPMQFENWRPNQPDNFFAAGEDCVVMIWHEKGEWNDVPCNYHLPFTCKKGTVACGEPPMVQHARTFGQKK<br>DRYEINSLVRYQCTEGFVQRHVPTIRCQPSGHWEEPRITCTDATAYKRRLQKRSSRHPRRSRPSTAH |
| human neurocan | 134 | MGAPFVWALGLLMLQMLLFVAGEQGTQDITDASERGLHMQKLGSGSVQAALAELVALPCLFTLQPRPSAA<br>RDAPRIKWTKVRTASGQRQDLPILVAKDNVVRVAKSWQGRVSLPSYPRRRANATLLLGPLRASDSGLYRC<br>QVVRGIEDEQDLVPLEVTGVVFHYRSARDRYALTFAEAQEACRLSSAIIAAPRHLQAAFEDGFDNCDAGW<br>LSDRTVRYPITQSRPGCYGDRSSLPGVRSYGRRNPQELYDVYCFARELGGEVFYVGPARRLTLAGARAQC<br>RRQGAALASVGQLHLAWHEGLDQCDPGWLADGSVRYPIQTPRRRCGGPAPGVRTVYRFANRTGFPSPAER<br>FDAYCFRAHHPTSQHGDLETPSSGDEGEILSAEGPPVRELEPTLEEEEVVTPDFQEPLVSSGEEETLILE<br>EKQESQQTLSPTPGDPMLASWPTGEVWLSTVAPSPSDMGAGTAASSHTEVAPTDPMPRRRGRFKGLNGRY<br>FQQQEPEPGLQGGMEASAQPPTSEAAVNQMEPPLAMAVTEMLGSGQSRSPWADLTNEVDMPGAGSAGGKS<br>SPEPWLWPPTMVPPSISGHSRAPVLELEKAEGPSARPATPDLFWSPLEATVSAPSPAPWEAFPVATSPDL<br>PMMAMLRGPKEWMLPHPTPISTEANRVEAHGEATATAPPSPAAETKVYSLPLSLTPTGQGGEAMPTTPES<br>PRADFRETGETSPAQVNKAEHSSSSPWPSVNRNVAVGFVPTETATEPTGLRGIPGSESGVEDTAESPTSG<br>LQATVDEVQDPWPSVYSKGLDASSPSAPLGSPGVFLVPKVTPNLEPWVATDEGPTVNPMDSTVTPAPSDA<br>SGIWEPGSQVFEEAESTTLSPQVALDTSIVTPLTTLEQGDKVGVPAMSTLGSSSSQPHPEPEDQVETQGT<br>SGASVPPHQSSPLGKPAVPPGTPTAASVGESASVSSGEPTVPWDPSSTLLPVTLGIEDFELEVLAGSPGV<br>ESFWEEVASGEEPALPGTPMNAGAEEVHSDPCENNPCLHGGTCNANGTMYGCSCDQGFAGENCEIDIDDC<br>LCSPCENGGTCIDEVNGFVCLCLPSYGGSFCEKDTEGCDRGWHKFQGHCYRYFAHRRAWEDAEKDCRRRS<br>GHLTSVHSPEEHSFINSFGHENTWIGLNDRIVERDFQWTDNTGLQFENWRENQPDNFFAGGEDCVVMVAH<br>ESGRWNDVPCNYNLPYVCKKGTVLCGPPPAVENASLIGARKAKYNVHATVRYQCNEGFAQHHVATIRCRS<br>NGKWDRPQIVCTKPRRSHRMRRHHHHHQHHHQHHHHKSRKERRKHKKHPTEDWEKDEGNFC |
| human brevican | 135 | MAQLFLPLLAALVLAQAPAALADVLEGDSSEDRAFRVRIAGDAPLQGVLGGALTIPCHVHYLRPPPSRRA<br>VLGSPRVKWTFLSRGREAEVLVARGVRVKVNEAYRFRVALPAYPASLTDVSLALSELRPNDSGIYRCEVQ<br>HGIDDSSDAVEVKVKGVVFLYREGSARYAFSFSGAQEACARIGAHIATPEQLYAAYLGGYEQCDAGWLSD |

TABLE B-continued

| Aggrecan sequences and others from various species ("ID" refers to the SEQ ID NO as used herein) | | |
|---|---|---|
| Name | ID | Amino acid sequence |
| | | QTVRYPIQTPREACYGDMDGFPGVRNYGVVDPDDLYDVYCYAEDLNGELFLGDPPEKLTLEEARAYCQERGAEIATTGQLYAAWDGGLDHCSPGWLADGSVRYPIVTPSQRCGGGLPGVKTLFLFPNQTGFPNKHSRFNVYCFRDSAQPSAIPEASNPASNPASDGLEAIVTVTETLEELQLPQEATESESRGAIYSIPIMEDGGGGSSTPEDPAEAPRTLLEFETQSMVPPTGFSEEEGKALEEEEKYEDEEEKEEEEEEEEVEDEALWAWPSELSSPGPEASLPTEPAAQESSLSQAPARAVLQPGASPLPDGESEASRPPRVHGPPTETLPTPRERNLASPSPSTLVEAREVGEATGGPELSGVPRGESEETGSSEGAPSLLPATRAPEGTRELEAPSEDNSGRTAPAGTSVQAQPVLPTDSASRGGVAVVPASGDCVPSPCHNGGTCLEEEEGVRCLCLPGYGGDLCDVGLRFCNPGWDAFQGACYKHFSTRRSWEEAETQCRMYGAHLASISTPEEQDFINNRYREYQWIGLNDRTIEGDFLWSDGVPLLYENWNPGQPDSYFLSGENCVVMVWHDQGQWSDVPCNYHLSYTCKMGLVSCGPPPELPLAQVFGRPRLRYEVDTVLRYRCREGLAQRNLPLIRCQENGRWEAPQISCVPRRPARALHPEEDPEGRQGRLLGRWKALLIPPSSPMPGP |

TABLE C

| Serum albumin binding ISV sequences ("ID" refers to the SEQ ID NO as used herein) | | |
|---|---|---|
| Name | ID | Amino acid sequence |
| Alb8 | 136 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| Alb23 | 137 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| Alb129 | 138 | EVQLVESGGGVVQPGNSLRLSCAASGFTFSSFGMSWVRQAPGKGLEWVSSISGSGSDTLYADSVKGRFTISRDNAKTTLYLQMNSLRPEDIATYYCTIGGSLSRSSQGTLVTVSSA |
| Alb132 | 139 | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIOGSLSRSSQGTLVTVSSA |
| Alb11 | 140 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCIIGGSLSRSSQGTLVTVSS |
| Alb11 (S112K)-A | 141 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVKVSSA |
| Alb82 | 142 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSS |
| Alb82-A | 143 | EVQLVESGGGVVQPGNSLRLSCAASGFTFSSFGMSWVRQAPGKGLEMVSSISGSGSDTLYADSVKGRFTISRDNAKTTLYLQMNSLRPEDTALYYCTIGGSLSRSSQGTLVTVSSA |
| Alb82-AA | 144 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSAA |
| Alb82-AAA | 145 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSAAA |
| Alb82-G | 146 | EVQLVESGGGVVQPGNSLRLSCAASGFTFSSFGMSWVRQAPGKGLEWVSSISGSGSDTLYADSVKGRFTISRDNAKTTLYLQMNSLRPEDIALYYCTIGGSLSRSSQGTLVTVSSG |
| Alb82-GG | 147 | EVQLVESGGGVVQPGNSLRLSCAASGFTFSSFGMSWVRQAPGKGLEWVSSISGSGSDTLYADSVKGRFTISRDNAKTTLYLQMNSLRPEDTALTYCITGGSLSRSSQGTLVTVSSGG |
| Alb82-GGG | 148 | EVQLVESGGGVVQPGNSLRLSCAASGFTFSSFGMSWVRQAPGKGLEWVSSISGSGSDTLYADSVKGRFTISRDNAKTTLYLQMNSLRPEDTALTYCTIGGSLSRSSQGTLVTVSSGGG |
| Alb92 | 149 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSS |
| Alb223 | 150 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSSA |
| ALB-CDR1 | 151 | SFGMS |
| ALB-CDR2 | 152 | SISGSGSDTLYADSVKG |
| ALB-CDR3 | 153 | GGSLSR |
| Alb135 | 171 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVKSA |

TABLE D

Linker sequences ("ID" refers to the SEQ ID NO as used herein)

| Name | ID | Amino acid sequence |
|---|---|---|
| 3A linker (Poly-A) | 154 | AAA |
| 5GS linker | 155 | GGGGS |
| 7GS linker | 156 | SGGSGGS |
| 8GS linker | 157 | GGGGGGGS |
| 9GS linker | 158 | GGGGSGGGS |
| 10GS linker | 159 | GGGGSGGGGS |
| 15GS linker | 160 | GGGGSGGGGSGGGGS |
| 18GS linker | 161 | GGGGSGGGGSGGGGGGGS |
| 20GS linker | 162 | GGGGSGGGGSGGGGSGGGGS |
| 25GS linker | 163 | GGGGSGGGGSGGGGSGGGGSGGGGS |
| 30GS linker | 164 | GGGGSGGGGSGGGGSGGGGSGGGGSGGGGS |
| 35GS linker | 165 | GGGGSGGGGSGGGGSGGGGSGGGGSGGGGSGGGGS |
| 40GS linker | 166 | GGGGSGGGGSGGGGSGGGGSGGGGSGGGGSGGGGSGGG GS |
| G1 hinge | 167 | EPKSCDKTHTCPPCP |
| 9GS-G1 hinge | 168 | GGGGSGGGSEPKSCDKTHTCPPCP |
| Llama upper long hinge region | 169 | EPKTPKPQPAAA |
| G3 hinge | 170 | ELKTPLGDTTHTCPRCPEPKSCDTPPPCPRCPEPKSCDTPPPCP RCPEPKSCDTPPPCPRCP |

TABLE E-1

Polypeptides/constructs comprising a therapeutic ISV as indicated and an ISV binding Aggrecan as indicated

| Target (ISV binding) | CAP (ISV) | Target (ISV binding) | CAP (ISV) | Target (ISV binding) | CAP (ISV) |
|---|---|---|---|---|---|
| Cathepsin A | 604F02 | ADAMTS1 | 604F02 | MMP1 | 604F02 |
| Cathepsin B | 604F02 | ADAMTS2 | 604F02 | MMP2 | 604F02 |
| Cathepsin C | 604F02 | ADAMTS3 | 604F02 | MMP3 | 604F02 |
| Cathepsin D | 604F02 | ADAMTS4 | 604F02 | MMP7 | 604F02 |
| Cathepsin E | 604F02 | ADAMTS5 | 604F02 | MMP8 | 604F02 |
| Cathepsin F | 604F02 | ADAMTS6 | 604F02 | MMP9 | 604F02 |
| Cathepsin G | 604F02 | ADAMTS7 | 604F02 | MMP10 | 604F02 |
| Cathepsin H | 604F02 | ADAMTS8 | 604F02 | MMP11 | 604F02 |
| Cathepsin K | 604F02 | ADAMTS9 | 604F02 | MMP12 | 604F02 |
| Cathepsin L1 | 604F02 | ADAMTS10 | 604F02 | MMP13 | 604F02 |
| Cathepsin L2 (or V) | 604F02 | ADAMTS11 | 604F02 | MMP14 | 604F02 |
| Cathepsin O | 604F02 | ADAMTS12 | 604F02 | MMP15 | 604F02 |
| Cathepsin S | 604F02 | ADAMTS13 | 604F02 | MMP16 | 604F02 |

TABLE E-1-continued

Polypeptides/constructs comprising a therapeutic ISV as indicated and an ISV binding Aggrecan as indicated

| Target (ISV binding) | CAP (ISV) | Target (ISV binding) | CAP (ISV) | Target (ISV binding) | CAP (ISV) |
|---|---|---|---|---|---|
| Cathepsin W | 604F02 | ADAMTS14 | 604F02 | MMP17 | 604F02 |
| Cathepsin Z (or X) | 604F02 | ADAMTS15 | 604F02 | MMP18 | 604F02 |
| | | ADAMTS16 | 604F02 | MMP19 | 604F02 |
| | | ADAMTS17 | 604F02 | MMP20 | 604F02 |
| | | ADAMTS18 | 604F02 | MMP21 | 604F02 |
| | | ADAMTS19 | 604F02 | MMP23A | 604F02 |
| | | ADAMTS20 | 604F02 | MMP23B | 604F02 |
| | | | | MMP24 | 604F02 |
| | | | | MMP25 | 604F02 |
| | | | | MMP26 | 604F02 |
| | | | | MMP27 | 604F02 |
| | | | | MMP28 | 604F02 |

TABLE E-2

Polypeptides/constructs comprising a therapeutic ISV as indicated and two ISVs binding Aggrecan as indicated

| Target (ISV binding) | CAP (ISV) | Target (ISV binding) | CAP (ISV) | Target (ISV binding) | CAP (ISV) |
|---|---|---|---|---|---|
| Cathepsin A | 114F08-114F08 | ADAMTS1 | 114F08-114F08 | MMP1 | 114F08-114F08 |
| Cathepsin B | 114F08-114F08 | ADAMTS2 | 114F08-114F08 | MMP2 | 114F08-114F08 |

TABLE E-2-continued

Polypeptides/constructs comprising a therapeutic ISV as indicated and two ISVs binding Aggrecan as indicated

| Target (ISV binding) | CAP (ISV) | Target (ISV binding) | CAP (ISV) | Target (ISV binding) | CAP (ISV) |
|---|---|---|---|---|---|
| Cathepsin C | 114F08-114F08 | ADAMTS3 | 114F08-114F08 | MMP3 | 114F08-114F08 |
| Cathepsin D | 114F08-114F08 | ADAMTS4 | 114F08-114F08 | MMP7 | 114F08-114F08 |
| Cathepsin E | 114F08-114F08 | ADAMTS5 | 114F08-114F08 | MMP8 | 114F08-114F08 |
| Cathepsin F | 114F08-114F08 | ADAMTS6 | 114F08-114F08 | MMP9 | 114F08-114F08 |
| Cathepsin G | 114F08-114F08 | ADAMTS7 | 114F08-114F08 | MMP10 | 114F08-114F08 |
| Cathepsin H | 114F08-114F08 | ADAMTS8 | 114F08-114F08 | MMP11 | 114F08-114F08 |
| Cathepsin K | 114F08-114F08 | ADAMTS9 | 114F08-114F08 | MMP12 | 114F08-114F08 |
| Cathepsin L1 | 114F08-114F08 | ADAMTS10 | 114F08-114F08 | MMP13 | 114F08-114F08 |
| Cathepsin L2 (or V) | 114F08-114F08 | ADAMTS11 | 114F08-114F08 | MMP14 | 114F08-114F08 |
| Cathepsin O | 114F08-114F08 | ADAMTS12 | 114F08-114F08 | MMP15 | 114F08-114F08 |
| Cathepsin S | 114F08-114F08 | ADAMTS13 | 114F08-114F08 | MMP16 | 114F08-114F08 |
| Cathepsin W | 114F08-114F08 | ADAMTS14 | 114F08-114F08 | MMP17 | 114F08-114F08 |
| Cathepsin Z (or X) | 114F08-114F08 | ADAMTS15 | 114F08-114F08 | MMP18 | 114F08-114F08 |
| | | ADAMTS16 | 114F08-114F08 | MMP19 | 114F08-114F08 |
| | | ADAMTS17 | 114F08-114F08 | MMP20 | 114F08-114F08 |
| | | ADAMTS18 | 114F08-114F08 | MMP21 | 114F08-114F08 |
| | | ADAMTS19 | 114F08-114F08 | MMP23A | 114F08-114F08 |
| | | ADAMTS20 | 114F08-114F08 | MMP23B | 114F08-114F08 |
| | | | | MMP24 | 114F08-114F08 |
| | | | | MMP25 | 114F08-114F08 |
| | | | | MMP26 | 114F08-114F08 |
| | | | | MMP27 | 114F08-114F08 |
| | | | | MMP28 | 114F08-114F08 |

The invention claimed is:

1. A polypeptide comprising an immunoglobulin single variable domain (ISV) that specifically binds to Aggrecan, wherein the ISV that specifically binds Aggrecan essentially consists of 4 framework regions (FR1 to FR4, respectively) and 3 complementarity determining regions (CDR1 to CDR3, respectively), in which:

i) CDR1 is chosen from the group consisting of:
  a) SEQ ID NO: 32; and
  b) amino acid sequences that have 3, 2, or 1 amino acid(s) difference with the amino acid sequence of SEQ ID NO: 32, wherein
    at position 2 the R has been changed into L;
    at position 6 the S has been changed into T; and/or
    at position 8 the T has been changed into A;

and ii) CDR2 is chosen from the group consisting of:
  c) SEQ ID NO: 50; and
  d) amino acid sequences that have 2 or 1 amino acid(s) difference with the amino acid sequence of SEQ ID NO: 50, wherein
    at position 7 the G has been changed into S or R; and/or
    at position 8 the R has been changed into T;

and iii) CDR3 is chosen from the group consisting of:
  e) SEQ ID NO: 68; and
  f) amino acid sequences that have 5, 4, 3, 2, or 1 amino acid(s) difference with the amino acid sequence of SEQ ID NO: 68, wherein
    at position 4 the R has been changed into V, or P;
    at position 6 the A has been changed into Y;
    at position 7 the S has been changed into T;
    at position 8 the S is absent;
    at position 9 the N has been changed into P;
    at position 10 the R has been changed into T or L;
    at position 11 the G has been changed into E; and/or
    at position 12 the L has been changed into T or V;

wherein:
  CDR1 is SEQ ID NO: 32, CDR2 is SEQ ID NO: 50, and CDR3 is SEQ ID NO: 68;
  CDR1 is SEQ ID NO: 32, CDR2 is SEQ ID NO: 51, and CDR3 is SEQ ID NO: 69;
  CDR1 is SEQ ID NO: 30, CDR2 is SEQ ID NO: 48, and CDR3 is SEQ ID NO: 66; or
  CDR1 is SEQ ID NO: 23, CDR2 is SEQ ID NO: 41, and CDR3 is SEQ ID NO: 59; and
  wherein the polypeptide does not comprise an ISV that binds to matrix metalloproteinase 13 (MMP13).

2. The polypeptide according to claim 1, wherein CDR1 is SEQ ID NO: 32, CDR2 is SEQ ID NO: 50, and CDR3 is SEQ ID NO: 68.

3. The polypeptide according to claim 1, wherein said ISV that specifically binds to Aggrecan is chosen from the group consisting of SEQ ID NO: 118 and ISVs which have more than 80% sequence identity with SEQ ID NO: 118.

4. The polypeptide according to claim 1, wherein said ISV that specifically binds to Aggrecan is chosen from the group consisting of SEQ ID NO: 13 and ISVs which have more than 80% sequence identity with SEQ ID NO: 13.

5. The polypeptide according to claim 1, wherein said polypeptide comprises two or more ISVs.

6. The polypeptide according to claim 1, wherein said polypeptide comprises at least two ISVs that specifically bind Aggrecan, wherein the at least two ISVs are the same.

7. The polypeptide according to claim 1, wherein said polypeptide comprises at least two ISVs that specifically bind Aggrecan, wherein the at least two ISVs are different.

8. The polypeptide according to claim 1, wherein said polypeptide comprises two or more ISVs, wherein at least two ISVs are independently chosen from the group consisting of SEQ ID NOs: 13 and 118.

9. The polypeptide according to claim 1, wherein said polypeptide comprises two or more ISVs, wherein at least one ISV binds to a member of the serine protease family, cathepsins, matrix metalloproteinases (MMPs)/Matrixins or A Disintegrin and Metalloproteinase with Thrombospondin motifs (ADAMTS).

10. The polypeptide according to claim 1, wherein said polypeptide further comprises a serum protein binding moiety or a serum protein.

11. A construct that comprises or essentially consists of the polypeptide of claim 1.

12. A composition comprising a polypeptide according to claim 1.

13. The composition according to claim 12, which is a pharmaceutical composition, wherein said composition further comprises a pharmaceutically acceptable carrier, a diluent, an excipient, an adjuvant, and/or one or more further pharmaceutically active polypeptides and/or compounds.

14. The polypeptide according to claim 1, wherein the polypeptide comprises at least one ISV that binds to MMP8, MMP19, MMP20, ADAMTS4, ADAMTS5, or ADAMTS11.

15. The construct according to claim 11, wherein said construct further comprises one or more other groups, residues, moieties or binding units.

16. The construct according to claim 15, wherein said one or more other groups, residues, moieties or binding units are linked via one or more peptidic linkers.

17. A polypeptide comprising an immunoglobulin single variable domain (ISV) that specifically binds to Aggrecan, wherein the ISV that specifically binds Aggrecan essentially consists of 4 framework regions (FR1 to FR4, respectively)

and 3 complementarity determining regions (CDR1 to CDR3, respectively), wherein:

CDR1 has the amino acid sequence of the CDR1 of an ISVD comprising the amino acid sequence of SEQ ID NO: 118, CDR2 has the amino acid sequence of the CDR2 of an ISVD comprising the amino acid sequence of SEQ ID NO: 118, and CDR3 has the amino acid sequence of the CDR3 of an ISVD comprising the amino acid sequence of SEQ ID NO: 118;

CDR1 has the amino acid sequence of the CDR1 of an ISVD comprising the amino acid sequence of SEQ ID NO: 13, CDR2 has the amino acid sequence of the CDR2 of an ISVD comprising the amino acid sequence of SEQ ID NO: 13, and CDR3 has the amino acid sequence of the CDR3 of an ISVD comprising the amino acid sequence of SEQ ID NO: 13;

CDR1 has the amino acid sequence of the CDR1 of an ISVD comprising the amino acid sequence of SEQ ID NO: 4, CDR2 has the amino acid sequence of the CDR2 of an ISVD comprising the amino acid sequence of SEQ ID NO: 4, and CDR3 has the amino acid sequence of the CDR3 of an ISVD comprising the amino acid sequence of SEQ ID NO: 4;

CDR1 has the amino acid sequence of the CDR1 of an ISVD comprising the amino acid sequence of SEQ ID NO: 11, CDR2 has the amino acid sequence of the CDR2 of an ISVD comprising the amino acid sequence of SEQ ID NO: 11, and CDR3 has the amino acid sequence of the CDR3 of an ISVD comprising the amino acid sequence of SEQ ID NO: 11; or CDR1 has the amino acid sequence of the CDR1 of an ISVD comprising the amino acid sequence of SEQ ID NO: 14, CDR2 has the amino acid sequence of the CDR2 of an ISVD comprising the amino acid sequence of SEQ ID NO: 14, and CDR3 has the amino acid sequence of the CDR3 of an ISVD comprising the amino acid sequence of SEQ ID NO: 14;

wherein the CDRs are numbered according to the same antibody numbering system; and wherein the polypeptide does not comprise an ISV that binds to matrix metalloproteinase 13 (MMP13).

18. The polypeptide according to claim 17, wherein the CDRs are numbered according to Kabat.

* * * * *

SEQUENCE LISTING

```
Sequence total quantity: 172
SEQ ID NO: 1            moltype = AA  length = 124
FEATURE                 Location/Qualifiers
REGION                  1..124
                        note = Nanobody Sequence
source                  1..124
                        mol_type = protein
                        organism = synthetic construct
SEQUENCE: 1
EVQLVESGGG LVQAGGSLRL SCAASGRSFS SYAMGWFRQA PGKEREFVSI ISWSGGSTVY  60
ADSVKGRFTI SRDNAKNTVY LQMNSLKPED TAIYYCAAGR LYRATPRPAD FGSWGQGTQV  120
TVSS                                                               124

SEQ ID NO: 2            moltype = AA  length = 127
FEATURE                 Location/Qualifiers
REGION                  1..127
                        note = Nanobody Sequence
source                  1..127
                        mol_type = protein
                        organism = synthetic construct
SEQUENCE: 2
EVQLVESGGG LVQTGGSLRL SCVASGRAFS NYIMGWFRQA PGKERDFVAA INWNGVTTHY  60
TDSVKGRFTI SRDNAKSTSY LQMDSLKPDD TAVYFCAARG TVYSRTYGVS EEGYMYWGQG  120
TQVTVSS                                                            127

SEQ ID NO: 3            moltype = AA  length = 115
FEATURE                 Location/Qualifiers
REGION                  1..115
                        note = Nanobody Sequence
source                  1..115
                        mol_type = protein
                        organism = synthetic construct
SEQUENCE: 3
EVQLVESGGG LVQPGGSLRL SCAASGSIFS NRFMYWYRQA PGKQRELVAS ITLSGSTNYA  60
DSVKGRFTIS RDNAKNTVYL QMNSLKPEDT AVYYCNTFLQ NSFYWGQGTQ VTVSS       115

SEQ ID NO: 4            moltype = AA  length = 115
FEATURE                 Location/Qualifiers
REGION                  1..115
                        note = Nanobody Sequence
source                  1..115
                        mol_type = protein
                        organism = synthetic construct
```

```
SEQUENCE: 4
EVQLVESGGG LVQPGGSLRL SCSASGFTFS GSWMFWVRQA PGKDYEWVAS INSSGGRTYY  60
DDSVKGRFTI SRDSAKNTLY LEMNNLKPED TALYFCARSP RVGSWGQGTQ VTVSS       115

SEQ ID NO: 5            moltype = AA  length = 121
FEATURE                 Location/Qualifiers
REGION                  1..121
                        note = Nanobody Sequence
source                  1..121
                        mol_type = protein
                        organism = synthetic construct
SEQUENCE: 5
EVQLVESGGG LVQAGGSLRL SCAASGSTFI INVVRWYRRT PGKQRELVAT ISSGGNANYV  60
DSVRGRFSIS RDGAKNAVDL QMNGLKPEDT AVYYCNVPTT HYGGVYYGPY WGQGTQVTVS  120
S                                                                  121

SEQ ID NO: 6            moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 6
KVQLVESGGG LVQPGGSLRL SCAASGFTFS MYAMKWVRQA PGKGLEWVSG INSSGGRTNY  60
AGSVKGRFTI SRDNAKNTLY LQMNSLKPED TAVYYCATDF LGGRNSRGQG TQVTVSS     117

SEQ ID NO: 7            moltype = AA  length = 123
FEATURE                 Location/Qualifiers
REGION                  1..123
                        note = Nanobody Sequence
source                  1..123
                        mol_type = protein
                        organism = synthetic construct
SEQUENCE: 7
KVQLVESGGG LVQAGGSLRL SCAASRRTFN MMGWFRQAPG KEREFVAYIT WNGGDTRYAE  60
SVKGRFTVSR DDVKNTMALQ MNRLDPLDTA VYYCGVRIHG SNWSTKADDY DNWGQGTQVT  120
VSS                                                                123

SEQ ID NO: 8            moltype = AA  length = 121
FEATURE                 Location/Qualifiers
REGION                  1..121
                        note = Nanobody Sequence
source                  1..121
                        mol_type = protein
                        organism = synthetic construct
SEQUENCE: 8
EVQLVESGGG SALPGGSLRL SCAASGITFS SRYMRWYRQA PGRQRELVAA ISSGGRTDYV  60
DSVRGRFTLS INNAKNTVYL QMNDLKPEDT AVYYCYRPRM YVDGTYEKEL WGQGTLVTVS  120
S                                                                  121

SEQ ID NO: 9            moltype = AA  length = 124
FEATURE                 Location/Qualifiers
REGION                  1..124
                        note = Nanobody Sequence
source                  1..124
                        mol_type = protein
                        organism = synthetic construct
SEQUENCE: 9
DVQLVESGGG LVQPGGSLRL SCAASGPTFS RYAMGWFRQA PGKEREFVAA ITWSSGGRTY  60
YADSVKGRFT ISRDNSKNTV YLQMNSLRPE DTAVYYCAAA RIPVRTYTSE WNYWGQGTLV  120
TVSS                                                               124

SEQ ID NO: 10           moltype = AA  length = 122
FEATURE                 Location/Qualifiers
REGION                  1..122
                        note = Nanobody Sequence
source                  1..122
                        mol_type = protein
                        organism = synthetic construct
SEQUENCE: 10
DVQLVESGGG LVQPGGSLRL SCTASGRTFS SYAVGWFRQA PGKEREFVAA ISRSGRSTYY  60
ADSVKGRFTI SRDNSKNTVY LQMNSLRPED TAVYYCAAGL SYYSPHAYYD YWGQGTLVTV  120
SS                                                                 122

SEQ ID NO: 11           moltype = AA  length = 123
FEATURE                 Location/Qualifiers
REGION                  1..123
                        note = Nanobody Sequence
```

```
source                  1..123
                        mol_type = protein
                        organism = synthetic construct
SEQUENCE: 11
DVQLVESGGG LVQPGGSLRL SCAASGLTFS TYAMGWFRQA PGKEREFVAA ISWSGSRTYY  60
ADSVKGRFTI SRDNSKNTVY LQMNSLRPED TAVYYCAAYR RPRYSPTGTW DYWGQGTLVT  120
VSS                                                                123

SEQ ID NO: 12           moltype = AA  length = 119
FEATURE                 Location/Qualifiers
REGION                  1..119
                        note = Nanobody Sequence
source                  1..119
                        mol_type = protein
                        organism = synthetic construct
SEQUENCE: 12
DVQLVESGGG LVQPGGSLRL SCVASGRTFS IYTMAWFRQA PGKEREFVAA ISWSSGRTYY  60
ADSVKGRFTI SRDNSKNTVY LQMNSLRPED TAVYYCTAYT GPRSGYDYWG QGTLVTVSS   119

SEQ ID NO: 13           moltype = AA  length = 124
FEATURE                 Location/Qualifiers
REGION                  1..124
                        note = Nanobody Sequence
source                  1..124
                        mol_type = protein
                        organism = synthetic construct
SEQUENCE: 13
DVQLVESGGG LVQPGGSLRL SCAASGRTFS SYTMGWFRQA PGKEREFVAA ISWSGGRTYY  60
ADSVKGRFTI SRDNSKNTVY LQMNSLRPED TAVYYCAAYR RRRASSNRGL WDYWGQGTLV  120
TVSS                                                               124

SEQ ID NO: 14           moltype = AA  length = 123
FEATURE                 Location/Qualifiers
REGION                  1..123
                        note = Nanobody Sequence
source                  1..123
                        mol_type = protein
                        organism = synthetic construct
SEQUENCE: 14
DVQLVESGGG LVQPGGSLRL SCAASGRTFS SYTMGWFRQA PGKEREFVAA ISWSGRTTYY  60
ADSVKGRFTI SRDNSKNTVY LQMNSLRPED TAVYYCAAYR RVRYTNLEVW DYWGQGTLVT  120
VSS                                                                123

SEQ ID NO: 15           moltype = AA  length = 123
FEATURE                 Location/Qualifiers
REGION                  1..123
                        note = Nanobody Sequence
source                  1..123
                        mol_type = protein
                        organism = synthetic construct
SEQUENCE: 15
DVQLVESGGG LVQPGGSLRL SCVASGRTFS SYAMGWFRQA PGKEREFVAA ITWSSATTYY  60
ADSVKGRFTI SRDNSKNTVY LQMNSLRPED TAVYYCAAAR IPVGRRSENW DYWGQGTLVT  120
VSS                                                                123

SEQ ID NO: 16           moltype = AA  length = 120
FEATURE                 Location/Qualifiers
REGION                  1..120
                        note = Nanobody Sequence
source                  1..120
                        mol_type = protein
                        organism = synthetic construct
SEQUENCE: 16
DVQLVESGGG LVQPGGSLRL SCVASGRTFS IYTMGWFRQA PGKEREFVAA ISWSGGRTYY  60
ADSVKGRFTI SRDNSKNTVY LQMNSLRPED TAVYYCTAYT GRSYGSYDYW GQGTLVTVSS  120

SEQ ID NO: 17           moltype = AA  length = 123
FEATURE                 Location/Qualifiers
REGION                  1..123
                        note = Nanobody Sequence
source                  1..123
                        mol_type = protein
                        organism = synthetic construct
SEQUENCE: 17
DVQLVESGGG LVQPGGSLRL SCVASGRTFS IYGMGWFRQA PGKEREFVAA INGGSRTYYA  60
DSVKGRFTIS RDNSKNTVYL QMNSLRPEDT AVYYCAADRS GYGTSLDWWY DYWGQGTLVT  120
VSS                                                                123

SEQ ID NO: 18           moltype = AA  length = 123
```

```
FEATURE                Location/Qualifiers
REGION                 1..123
                       note = Nanobody Sequence
source                 1..123
                       mol_type = protein
                       organism = synthetic construct
SEQUENCE: 18
DVQLVESGGG LVQPGGSLRL SCAASGRTFS TYTMGWFRQA PGKEREFVAA ISWSGGTTYY  60
ADSVKGRFTI SRDNSKNTVY LQMNSLRPED TAVYYCAARP RYYYYSLYSY DYWGQGTLVT  120
VSS                                                               123

SEQ ID NO: 19          moltype = AA  length = 122
FEATURE                Location/Qualifiers
REGION                 1..122
                       note = Nanobody Sequence
source                 1..122
                       mol_type = protein
                       organism = synthetic construct
SEQUENCE: 19
DVQLVESGGG LVQPGGSLRL SCAASGTIFS INVMGWYRQA PGKEREFVAA ITTGGRTNYA  60
DSVKGRFTIS RDNSKNTVYL QMNSLRPEDT AVYYCNAEVT TGWVGYSWYD YWGQGTMVTV  120
SS                                                                122

SEQ ID NO: 20          moltype = AA  length = 10
FEATURE                Location/Qualifiers
REGION                 1..10
                       note = CDR1
source                 1..10
                       mol_type = protein
                       organism = synthetic construct
SEQUENCE: 20
GRSFSSYAMG                                                        10

SEQ ID NO: 21          moltype = AA  length = 10
FEATURE                Location/Qualifiers
REGION                 1..10
                       note = CDR1
source                 1..10
                       mol_type = protein
                       organism = synthetic construct
SEQUENCE: 21
GRAFSNYIMG                                                        10

SEQ ID NO: 22          moltype = AA  length = 10
FEATURE                Location/Qualifiers
REGION                 1..10
                       note = CDR1
source                 1..10
                       mol_type = protein
                       organism = synthetic construct
SEQUENCE: 22
GSIFSNRFMY                                                        10

SEQ ID NO: 23          moltype = AA  length = 10
FEATURE                Location/Qualifiers
REGION                 1..10
                       note = CDR1
source                 1..10
                       mol_type = protein
                       organism = synthetic construct
SEQUENCE: 23
GFTFSGSWMF                                                        10

SEQ ID NO: 24          moltype = AA  length = 10
FEATURE                Location/Qualifiers
REGION                 1..10
                       note = CDR1
source                 1..10
                       mol_type = protein
                       organism = synthetic construct
SEQUENCE: 24
GSTFIINVVR                                                        10

SEQ ID NO: 25          moltype = AA  length = 10
FEATURE                Location/Qualifiers
REGION                 1..10
                       note = CDR1
source                 1..10
                       mol_type = protein
```

```
                        organism = synthetic construct
SEQUENCE: 25
GFTFSMYAMK                                                                  10

SEQ ID NO: 26           moltype = AA  length = 8
FEATURE                 Location/Qualifiers
REGION                  1..8
                        note = CDR1
source                  1..8
                        mol_type = protein
                        organism = synthetic construct
SEQUENCE: 26
RRTFNMMG                                                                    8

SEQ ID NO: 27           moltype = AA  length = 10
FEATURE                 Location/Qualifiers
REGION                  1..10
                        note = CDR1
source                  1..10
                        mol_type = protein
                        organism = synthetic construct
SEQUENCE: 27
GITFSSRYMR                                                                  10

SEQ ID NO: 28           moltype = AA  length = 10
FEATURE                 Location/Qualifiers
REGION                  1..10
                        note = CDR1
source                  1..10
                        mol_type = protein
                        organism = synthetic construct
SEQUENCE: 28
GPTFSRYAMG                                                                  10

SEQ ID NO: 29           moltype = AA  length = 10
FEATURE                 Location/Qualifiers
REGION                  1..10
                        note = CDR1
source                  1..10
                        mol_type = protein
                        organism = synthetic construct
SEQUENCE: 29
GRTFSSYAVG                                                                  10

SEQ ID NO: 30           moltype = AA  length = 10
FEATURE                 Location/Qualifiers
REGION                  1..10
                        note = CDR1
source                  1..10
                        mol_type = protein
                        organism = synthetic construct
SEQUENCE: 30
GLTFSTYAMG                                                                  10

SEQ ID NO: 31           moltype = AA  length = 10
FEATURE                 Location/Qualifiers
REGION                  1..10
                        note = CDR1
source                  1..10
                        mol_type = protein
                        organism = synthetic construct
SEQUENCE: 31
GRTFSIYTMA                                                                  10

SEQ ID NO: 32           moltype = AA  length = 10
FEATURE                 Location/Qualifiers
REGION                  1..10
                        note = CDR1
source                  1..10
                        mol_type = protein
                        organism = synthetic construct
SEQUENCE: 32
GRTFSSYTMG                                                                  10

SEQ ID NO: 33           moltype = AA  length = 10
FEATURE                 Location/Qualifiers
REGION                  1..10
                        note = CDR1
source                  1..10
```

```
                        mol_type = protein
                        organism = synthetic construct
SEQUENCE: 33
GRTFSSYAMG                                              10

SEQ ID NO: 34           moltype = AA  length = 10
FEATURE                 Location/Qualifiers
REGION                  1..10
                        note = CDR1
source                  1..10
                        mol_type = protein
                        organism = synthetic construct
SEQUENCE: 34
GRTFSIYTMG                                              10

SEQ ID NO: 35           moltype = AA  length = 10
FEATURE                 Location/Qualifiers
REGION                  1..10
                        note = CDR1
source                  1..10
                        mol_type = protein
                        organism = synthetic construct
SEQUENCE: 35
GRTFSIYGMG                                              10

SEQ ID NO: 36           moltype = AA  length = 10
FEATURE                 Location/Qualifiers
REGION                  1..10
                        note = CDR1
source                  1..10
                        mol_type = protein
                        organism = synthetic construct
SEQUENCE: 36
GRTFSTYTMG                                              10

SEQ ID NO: 37           moltype = AA  length = 10
FEATURE                 Location/Qualifiers
REGION                  1..10
                        note = CDR1
source                  1..10
                        mol_type = protein
                        organism = synthetic construct
SEQUENCE: 37
GTIFSINVMG                                              10

SEQ ID NO: 38           moltype = AA  length = 10
FEATURE                 Location/Qualifiers
REGION                  1..10
                        note = CDR2
source                  1..10
                        mol_type = protein
                        organism = synthetic construct
SEQUENCE: 38
IISWSGGSTV                                              10

SEQ ID NO: 39           moltype = AA  length = 10
FEATURE                 Location/Qualifiers
REGION                  1..10
                        note = CDR2
source                  1..10
                        mol_type = protein
                        organism = synthetic construct
SEQUENCE: 39
AINWNGVTTH                                              10

SEQ ID NO: 40           moltype = AA  length = 9
FEATURE                 Location/Qualifiers
REGION                  1..9
                        note = CDR2
source                  1..9
                        mol_type = protein
                        organism = synthetic construct
SEQUENCE: 40
SITLSGSTN                                               9

SEQ ID NO: 41           moltype = AA  length = 10
FEATURE                 Location/Qualifiers
REGION                  1..10
                        note = CDR2
```

```
source                  1..10
                        mol_type = protein
                        organism = synthetic construct
SEQUENCE: 41
SINSSGGRTY                                                                  10

SEQ ID NO: 42           moltype = AA  length = 9
FEATURE                 Location/Qualifiers
REGION                  1..9
                        note = CDR2
source                  1..9
                        mol_type = protein
                        organism = synthetic construct
SEQUENCE: 42
TISSGGNAN                                                                   9

SEQ ID NO: 43           moltype = AA  length = 10
FEATURE                 Location/Qualifiers
REGION                  1..10
                        note = CDR2
source                  1..10
                        mol_type = protein
                        organism = synthetic construct
SEQUENCE: 43
GINSSGGRTN                                                                  10

SEQ ID NO: 44           moltype = AA  length = 10
FEATURE                 Location/Qualifiers
REGION                  1..10
                        note = CDR2
source                  1..10
                        mol_type = protein
                        organism = synthetic construct
SEQUENCE: 44
YITWNGGDTR                                                                  10

SEQ ID NO: 45           moltype = AA  length = 9
FEATURE                 Location/Qualifiers
REGION                  1..9
                        note = CDR2
source                  1..9
                        mol_type = protein
                        organism = synthetic construct
SEQUENCE: 45
AISSGGRTD                                                                   9

SEQ ID NO: 46           moltype = AA  length = 11
FEATURE                 Location/Qualifiers
REGION                  1..11
                        note = CDR2
source                  1..11
                        mol_type = protein
                        organism = synthetic construct
SEQUENCE: 46
AITWSSGGRT Y                                                                11

SEQ ID NO: 47           moltype = AA  length = 10
FEATURE                 Location/Qualifiers
REGION                  1..10
                        note = CDR2
source                  1..10
                        mol_type = protein
                        organism = synthetic construct
SEQUENCE: 47
AISRSGRSTY                                                                  10

SEQ ID NO: 48           moltype = AA  length = 10
FEATURE                 Location/Qualifiers
REGION                  1..10
                        note = CDR2
source                  1..10
                        mol_type = protein
                        organism = synthetic construct
SEQUENCE: 48
AISWSGSRTY                                                                  10

SEQ ID NO: 49           moltype = AA  length = 10
FEATURE                 Location/Qualifiers
REGION                  1..10
```

```
                        note = CDR2
source                  1..10
                        mol_type = protein
                        organism = synthetic construct
SEQUENCE: 49
AISWSSGRTY                                                                10

SEQ ID NO: 50           moltype = AA  length = 10
FEATURE                 Location/Qualifiers
REGION                  1..10
                        note = CDR2
source                  1..10
                        mol_type = protein
                        organism = synthetic construct
SEQUENCE: 50
AISWSGGRTY                                                                10

SEQ ID NO: 51           moltype = AA  length = 10
FEATURE                 Location/Qualifiers
REGION                  1..10
                        note = CDR2
source                  1..10
                        mol_type = protein
                        organism = synthetic construct
SEQUENCE: 51
AISWSGRTTY                                                                10

SEQ ID NO: 52           moltype = AA  length = 10
FEATURE                 Location/Qualifiers
REGION                  1..10
                        note = CDR2
source                  1..10
                        mol_type = protein
                        organism = synthetic construct
SEQUENCE: 52
AITWSSATTY                                                                10

SEQ ID NO: 53           moltype = AA  length = 9
FEATURE                 Location/Qualifiers
REGION                  1..9
                        note = CDR2
source                  1..9
                        mol_type = protein
                        organism = synthetic construct
SEQUENCE: 53
AINGGSRTY                                                                 9

SEQ ID NO: 54           moltype = AA  length = 10
FEATURE                 Location/Qualifiers
REGION                  1..10
                        note = CDR2
source                  1..10
                        mol_type = protein
                        organism = synthetic construct
SEQUENCE: 54
AISWSGGTTY                                                                10

SEQ ID NO: 55           moltype = AA  length = 9
FEATURE                 Location/Qualifiers
REGION                  1..9
                        note = CDR2
source                  1..9
                        mol_type = protein
                        organism = synthetic construct
SEQUENCE: 55
AITTGGRTN                                                                 9

SEQ ID NO: 56           moltype = AA  length = 15
FEATURE                 Location/Qualifiers
REGION                  1..15
                        note = CDR3
source                  1..15
                        mol_type = protein
                        organism = synthetic construct
SEQUENCE: 56
GRLYRATPRP ADFGS                                                          15

SEQ ID NO: 57           moltype = AA  length = 18
FEATURE                 Location/Qualifiers
```

```
REGION                1..18
                      note = CDR3
source                1..18
                      mol_type = protein
                      organism = synthetic construct
SEQUENCE: 57
RGTVYSRTYG VSEEGYMY                                                    18

SEQ ID NO: 58         moltype = AA  length = 7
FEATURE               Location/Qualifiers
REGION                1..7
                      note = CDR3
source                1..7
                      mol_type = protein
                      organism = synthetic construct
SEQUENCE: 58
FLQNSFY                                                                7

SEQ ID NO: 59         moltype = AA  length = 6
FEATURE               Location/Qualifiers
REGION                1..6
                      note = CDR3
source                1..6
                      mol_type = protein
                      organism = synthetic construct
SEQUENCE: 59
SPRVGS                                                                 6

SEQ ID NO: 60         moltype = AA  length = 13
FEATURE               Location/Qualifiers
REGION                1..13
                      note = CDR3
source                1..13
                      mol_type = protein
                      organism = synthetic construct
SEQUENCE: 60
PTTHYGGVYY GPY                                                         13

SEQ ID NO: 61         moltype = AA  length = 8
FEATURE               Location/Qualifiers
REGION                1..8
                      note = CDR3
source                1..8
                      mol_type = protein
                      organism = synthetic construct
SEQUENCE: 61
DFLGGRNS                                                               8

SEQ ID NO: 62         moltype = AA  length = 16
FEATURE               Location/Qualifiers
REGION                1..16
                      note = CDR3
source                1..16
                      mol_type = protein
                      organism = synthetic construct
SEQUENCE: 62
RIHGSNWSTK ADDYDN                                                      16

SEQ ID NO: 63         moltype = AA  length = 13
FEATURE               Location/Qualifiers
REGION                1..13
                      note = CDR3
source                1..13
                      mol_type = protein
                      organism = synthetic construct
SEQUENCE: 63
PRMYVDGTYE KEL                                                         13

SEQ ID NO: 64         moltype = AA  length = 14
FEATURE               Location/Qualifiers
REGION                1..14
                      note = CDR3
source                1..14
                      mol_type = protein
                      organism = synthetic construct
SEQUENCE: 64
ARIPVRTYTS EWNY                                                        14

SEQ ID NO: 65         moltype = AA  length = 13
```

```
FEATURE                Location/Qualifiers
REGION                 1..13
                       note = CDR3
source                 1..13
                       mol_type = protein
                       organism = synthetic construct
SEQUENCE: 65
GLSYYSPHAY YDY                                                    13

SEQ ID NO: 66          moltype = AA  length = 14
FEATURE                Location/Qualifiers
REGION                 1..14
                       note = CDR3
source                 1..14
                       mol_type = protein
                       organism = synthetic construct
SEQUENCE: 66
YRRPRYSPTG TWDY                                                   14

SEQ ID NO: 67          moltype = AA  length = 10
FEATURE                Location/Qualifiers
REGION                 1..10
                       note = CDR3
source                 1..10
                       mol_type = protein
                       organism = synthetic construct
SEQUENCE: 67
YTGPRSGYDY                                                        10

SEQ ID NO: 68          moltype = AA  length = 15
FEATURE                Location/Qualifiers
REGION                 1..15
                       note = CDR3
source                 1..15
                       mol_type = protein
                       organism = synthetic construct
SEQUENCE: 68
YRRRRASSNR GLWDY                                                  15

SEQ ID NO: 69          moltype = AA  length = 14
FEATURE                Location/Qualifiers
REGION                 1..14
                       note = CDR3
source                 1..14
                       mol_type = protein
                       organism = synthetic construct
SEQUENCE: 69
YRRVRYTNLE VWDY                                                   14

SEQ ID NO: 70          moltype = AA  length = 14
FEATURE                Location/Qualifiers
REGION                 1..14
                       note = CDR3
source                 1..14
                       mol_type = protein
                       organism = synthetic construct
SEQUENCE: 70
ARIPVGRRSE NWDY                                                   14

SEQ ID NO: 71          moltype = AA  length = 11
FEATURE                Location/Qualifiers
REGION                 1..11
                       note = CDR3
source                 1..11
                       mol_type = protein
                       organism = synthetic construct
SEQUENCE: 71
YTGRSYGSYD Y                                                      11

SEQ ID NO: 72          moltype = AA  length = 15
FEATURE                Location/Qualifiers
REGION                 1..15
                       note = CDR3
source                 1..15
                       mol_type = protein
                       organism = synthetic construct
SEQUENCE: 72
DRSGYGTSLD WWYDY                                                  15
```

```
SEQ ID NO: 73          moltype = AA  length = 14
FEATURE                Location/Qualifiers
REGION                 1..14
                       note = CDR3
source                 1..14
                       mol_type = protein
                       organism = synthetic construct
SEQUENCE: 73
RPRYYYYSLY SYDY                                                    14

SEQ ID NO: 74          moltype = AA  length = 14
FEATURE                Location/Qualifiers
REGION                 1..14
                       note = CDR3
source                 1..14
                       mol_type = protein
                       organism = synthetic construct
SEQUENCE: 74
EVTTGWVGYS WYDY                                                    14

SEQ ID NO: 75          moltype = AA  length = 25
FEATURE                Location/Qualifiers
REGION                 1..25
                       note = FR1
source                 1..25
                       mol_type = protein
                       organism = synthetic construct
SEQUENCE: 75
EVQLVESGGG LVQAGGSLRL SCAAS                                        25

SEQ ID NO: 76          moltype = AA  length = 25
FEATURE                Location/Qualifiers
REGION                 1..25
                       note = FR1
source                 1..25
                       mol_type = protein
                       organism = synthetic construct
SEQUENCE: 76
EVQLVESGGG LVQTGGSLRL SCVAS                                        25

SEQ ID NO: 77          moltype = AA  length = 25
FEATURE                Location/Qualifiers
REGION                 1..25
                       note = FR1
source                 1..25
                       mol_type = protein
                       organism = synthetic construct
SEQUENCE: 77
EVQLVESGGG LVQPGGSLRL SCAAS                                        25

SEQ ID NO: 78          moltype = AA  length = 25
FEATURE                Location/Qualifiers
REGION                 1..25
                       note = FR1
source                 1..25
                       mol_type = protein
                       organism = synthetic construct
SEQUENCE: 78
EVQLVESGGG LVQPGGSLRL SCSAS                                        25

SEQ ID NO: 79          moltype = AA  length = 25
FEATURE                Location/Qualifiers
REGION                 1..25
                       note = FR1
source                 1..25
                       mol_type = protein
                       organism = synthetic construct
SEQUENCE: 79
KVQLVESGGG LVQPGGSLRL SCAAS                                        25

SEQ ID NO: 80          moltype = AA  length = 25
FEATURE                Location/Qualifiers
REGION                 1..25
                       note = FR1
source                 1..25
                       mol_type = protein
                       organism = synthetic construct
SEQUENCE: 80
KVQLVESGGG LVQAGGSLRL SCAAS                                        25
```

```
SEQ ID NO: 81          moltype = AA  length = 25
FEATURE                Location/Qualifiers
REGION                 1..25
                       note = FR1
source                 1..25
                       mol_type = protein
                       organism = synthetic construct
SEQUENCE: 81
EVQLVESGGG SALPGGSLRL SCAAS                                       25

SEQ ID NO: 82          moltype = AA  length = 25
FEATURE                Location/Qualifiers
REGION                 1..25
                       note = FR1
source                 1..25
                       mol_type = protein
                       organism = synthetic construct
SEQUENCE: 82
DVQLVESGGG LVQPGGSLRL SCAAS                                       25

SEQ ID NO: 83          moltype = AA  length = 25
FEATURE                Location/Qualifiers
REGION                 1..25
                       note = FR1
source                 1..25
                       mol_type = protein
                       organism = synthetic construct
SEQUENCE: 83
DVQLVESGGG LVQPGGSLRL SCTAS                                       25

SEQ ID NO: 84          moltype = AA  length = 25
FEATURE                Location/Qualifiers
REGION                 1..25
                       note = FR1
source                 1..25
                       mol_type = protein
                       organism = synthetic construct
SEQUENCE: 84
DVQLVESGGG LVQPGGSLRL SCVAS                                       25

SEQ ID NO: 85          moltype = AA  length = 14
FEATURE                Location/Qualifiers
REGION                 1..14
                       note = FR2
source                 1..14
                       mol_type = protein
                       organism = synthetic construct
SEQUENCE: 85
WFRQAPGKER EFVS                                                   14

SEQ ID NO: 86          moltype = AA  length = 14
FEATURE                Location/Qualifiers
REGION                 1..14
                       note = FR2
source                 1..14
                       mol_type = protein
                       organism = synthetic construct
SEQUENCE: 86
WFRQAPGKER DFVA                                                   14

SEQ ID NO: 87          moltype = AA  length = 14
FEATURE                Location/Qualifiers
REGION                 1..14
                       note = FR2
source                 1..14
                       mol_type = protein
                       organism = synthetic construct
SEQUENCE: 87
WYRQAPGKQR ELVA                                                   14

SEQ ID NO: 88          moltype = AA  length = 14
FEATURE                Location/Qualifiers
REGION                 1..14
                       note = FR2
source                 1..14
                       mol_type = protein
                       organism = synthetic construct
SEQUENCE: 88
```

```
WVRQAPGKDY EWVA                                                    14

SEQ ID NO: 89          moltype = AA  length = 14
FEATURE                Location/Qualifiers
REGION                 1..14
                       note = FR2
source                 1..14
                       mol_type = protein
                       organism = synthetic construct
SEQUENCE: 89
WYRRTPGKQR ELVA                                                    14

SEQ ID NO: 90          moltype = AA  length = 14
FEATURE                Location/Qualifiers
REGION                 1..14
                       note = FR2
source                 1..14
                       mol_type = protein
                       organism = synthetic construct
SEQUENCE: 90
WVRQAPGKGL EWVS                                                    14

SEQ ID NO: 91          moltype = AA  length = 14
FEATURE                Location/Qualifiers
REGION                 1..14
                       note = FR2
source                 1..14
                       mol_type = protein
                       organism = synthetic construct
SEQUENCE: 91
WFRQAPGKER EFVA                                                    14

SEQ ID NO: 92          moltype = AA  length = 14
FEATURE                Location/Qualifiers
REGION                 1..14
                       note = FR2
source                 1..14
                       mol_type = protein
                       organism = synthetic construct
SEQUENCE: 92
WYRQAPGRQR ELVA                                                    14

SEQ ID NO: 93          moltype = AA  length = 14
FEATURE                Location/Qualifiers
REGION                 1..14
                       note = FR2
source                 1..14
                       mol_type = protein
                       organism = synthetic construct
SEQUENCE: 93
WYRQAPGKER EFVA                                                    14

SEQ ID NO: 94          moltype = AA  length = 39
FEATURE                Location/Qualifiers
REGION                 1..39
                       note = FR3
source                 1..39
                       mol_type = protein
                       organism = synthetic construct
SEQUENCE: 94
YADSVKGRFT ISRDNAKNTV YLQMNSLKPE DTAIYYCAA                         39

SEQ ID NO: 95          moltype = AA  length = 39
FEATURE                Location/Qualifiers
REGION                 1..39
                       note = FR3
source                 1..39
                       mol_type = protein
                       organism = synthetic construct
SEQUENCE: 95
YTDSVKGRFT ISRDNAKSTS YLQMDSLKPD DTAVYFCAA                         39

SEQ ID NO: 96          moltype = AA  length = 39
FEATURE                Location/Qualifiers
REGION                 1..39
                       note = FR3
source                 1..39
                       mol_type = protein
                       organism = synthetic construct
```

```
SEQUENCE: 96
YADSVKGRFT ISRDNAKNTV YLQMNSLKPE DTAVYYCNT                         39

SEQ ID NO: 97          moltype = AA  length = 39
FEATURE                Location/Qualifiers
REGION                 1..39
                       note = FR3
source                 1..39
                       mol_type = protein
                       organism = synthetic construct
SEQUENCE: 97
YDDSVKGRFT ISRDSAKNTL YLEMNNLKPE DTALYFCAR                         39

SEQ ID NO: 98          moltype = AA  length = 39
FEATURE                Location/Qualifiers
REGION                 1..39
                       note = FR3
source                 1..39
                       mol_type = protein
                       organism = synthetic construct
SEQUENCE: 98
YVDSVRGRFS ISRDGAKNAV DLQMNGLKPE DTAVYYCNV                         39

SEQ ID NO: 99          moltype = AA  length = 39
FEATURE                Location/Qualifiers
REGION                 1..39
                       note = FR3
source                 1..39
                       mol_type = protein
                       organism = synthetic construct
SEQUENCE: 99
YAGSVKGRFT ISRDNAKNTL YLQMNSLKPE DTAVYYCAT                         39

SEQ ID NO: 100         moltype = AA  length = 39
FEATURE                Location/Qualifiers
REGION                 1..39
                       note = FR3
source                 1..39
                       mol_type = protein
                       organism = synthetic construct
SEQUENCE: 100
YAESVKGRFT VSRDDVKNTM ALQMNRLDPL DTAVYYCGV                         39

SEQ ID NO: 101         moltype = AA  length = 39
FEATURE                Location/Qualifiers
REGION                 1..39
                       note = FR3
source                 1..39
                       mol_type = protein
                       organism = synthetic construct
SEQUENCE: 101
YVDSVRGRFT LSINNAKNTV YLQMNDLKPE DTAVYYCYR                         39

SEQ ID NO: 102         moltype = AA  length = 39
FEATURE                Location/Qualifiers
REGION                 1..39
                       note = FR3
source                 1..39
                       mol_type = protein
                       organism = synthetic construct
SEQUENCE: 102
YADSVKGRFT ISRDNSKNTV YLQMNSLRPE DTAVYYCAA                         39

SEQ ID NO: 103         moltype = AA  length = 39
FEATURE                Location/Qualifiers
REGION                 1..39
                       note = FR3
source                 1..39
                       mol_type = protein
                       organism = synthetic construct
SEQUENCE: 103
YADSVKGRFT ISRDNSKNTV YLQMNSLRPE DTAVYYCTA                         39

SEQ ID NO: 104         moltype = AA  length = 39
FEATURE                Location/Qualifiers
REGION                 1..39
                       note = FR3
source                 1..39
                       mol_type = protein
```

```
                      organism = synthetic construct
SEQUENCE: 104
YADSVKGRFT ISRDNSKNTV YLQMNSLRPE DTAVYYCNA                   39

SEQ ID NO: 105        moltype = AA  length = 11
FEATURE               Location/Qualifiers
REGION                1..11
                      note = FR4
source                1..11
                      mol_type = protein
                      organism = synthetic construct
SEQUENCE: 105
WGQGTQVTVS S                                                 11

SEQ ID NO: 106        moltype = AA  length = 11
FEATURE               Location/Qualifiers
REGION                1..11
                      note = FR4
source                1..11
                      mol_type = protein
                      organism = synthetic construct
SEQUENCE: 106
RGQGTQVTVS S                                                 11

SEQ ID NO: 107        moltype = AA  length = 11
FEATURE               Location/Qualifiers
REGION                1..11
                      note = FR4
source                1..11
                      mol_type = protein
                      organism = synthetic construct
SEQUENCE: 107
WGQGTLVTVS S                                                 11

SEQ ID NO: 108        moltype = AA  length = 11
FEATURE               Location/Qualifiers
REGION                1..11
                      note = FR4
source                1..11
                      mol_type = protein
                      organism = synthetic construct
SEQUENCE: 108
WGQGTMVTVS S                                                 11

SEQ ID NO: 109        moltype = AA  length = 10
FEATURE               Location/Qualifiers
REGION                1..10
                      note = CDR1
source                1..10
                      mol_type = protein
                      organism = synthetic construct
SEQUENCE: 109
GSTFIISVMR                                                   10

SEQ ID NO: 110        moltype = AA  length = 9
FEATURE               Location/Qualifiers
REGION                1..9
                      note = CDR2
source                1..9
                      mol_type = protein
                      organism = synthetic construct
SEQUENCE: 110
AIRTGGNTD                                                    9

SEQ ID NO: 111        moltype = AA  length = 13
FEATURE               Location/Qualifiers
REGION                1..13
                      note = CDR3
source                1..13
                      mol_type = protein
                      organism = synthetic construct
SEQUENCE: 111
PTTRYGGDYY GPY                                               13

SEQ ID NO: 112        moltype = AA  length = 39
FEATURE               Location/Qualifiers
REGION                1..39
                      note = FR3
source                1..39
```

```
                        mol_type = protein
                        organism = synthetic construct
SEQUENCE: 112
YAGPVRGRFS ISRDGAKNAV DLQMNGLKPE DTAVYYCNV                          39

SEQ ID NO: 113          moltype = AA  length = 39
FEATURE                 Location/Qualifiers
REGION                  1..39
                        note = FR3
source                  1..39
                        mol_type = protein
                        organism = synthetic construct
SEQUENCE: 113
YAGPVRGRFS ISRDGAKDAV DLQMNGLKPE DTAVYYCNV                          39

SEQ ID NO: 114          moltype = AA  length = 121
FEATURE                 Location/Qualifiers
REGION                  1..121
                        note = Nanobody Sequence
source                  1..121
                        mol_type = protein
                        organism = synthetic construct
SEQUENCE: 114
EVQLVESGGG LVQAGGSLRL SCAASGSTFI ISVMRWYRQA PGKQRELVAA IRTGGNTDYA  60
GPVRGRFSIS RDGAKNAVDL QMNGLKPEDT AVYYCNVPTT RYGGDYYGPY WGQGTQVTVS  120
S                                                                   121

SEQ ID NO: 115          moltype = AA  length = 121
FEATURE                 Location/Qualifiers
REGION                  1..121
                        note = Nanobody Sequence
source                  1..121
                        mol_type = protein
                        organism = synthetic construct
SEQUENCE: 115
EVQLVESGGG LVQAGGSLRL SCAASGSTFI ISVMRWYRQA PGKQRELVAA IRTGGNTDYA  60
GPVRGRFSIS RDGAKDAVDL QMNGLKPEDT AVYYCNVPTT RYGGDYYGPY WGQGTQVTVS  120
S                                                                   121

SEQ ID NO: 116          moltype = AA  length = 121
FEATURE                 Location/Qualifiers
REGION                  1..121
                        note = Nanobody Sequence
source                  1..121
                        mol_type = protein
                        organism = synthetic construct
SEQUENCE: 116
EVQLVESGGG LVQPGGSLRL SCAASGSTFI INVVRWYRRA PGKQRELVAT ISSGGNANYV  60
DSVRGRFTIS RDNSKNTVYL QMNSLRPEDT AVYYCNVPTT HYGGVYYGPY WGQGTLVTVS  120
S                                                                   121

SEQ ID NO: 117          moltype = AA  length = 122
FEATURE                 Location/Qualifiers
REGION                  1..122
                        note = Nanobody Sequence
source                  1..122
                        mol_type = protein
                        organism = synthetic construct
SEQUENCE: 117
EVQLVESGGG VVQPGGSLRL SCAASGSTFI INVVRWYRRA PGKQRELVAT ISSGGNANYV  60
DSVRGRFTIS RDNSKNTVYL QMNSLRPEDT ALYYCNVPTT HYGGVYYGPY WGQGTLVTVS  120
SA                                                                  122

SEQ ID NO: 118          moltype = AA  length = 125
FEATURE                 Location/Qualifiers
REGION                  1..125
                        note = Nanobody Sequence
source                  1..125
                        mol_type = protein
                        organism = synthetic construct
SEQUENCE: 118
EVQLVESGGG VVQPGGSLRL SCAASGRTFS SYTMGWFRQA PGKEREFVAA ISWSGGRTYY  60
ADSVKGRFTI SRDNSKNTVY LQMNSLRPED TALYYCAAYR RRRASSNRGL WDYWGQGTLV  120
TVSSA                                                               125

SEQ ID NO: 119          moltype = AA  length = 25
FEATURE                 Location/Qualifiers
REGION                  1..25
                        note = FR1
```

```
source                  1..25
                        mol_type = protein
                        organism = synthetic construct
SEQUENCE: 119
EVQLVESGGG VVQPGGSLRL SCAAS                                    25

SEQ ID NO: 120          moltype = AA  length = 25
FEATURE                 Location/Qualifiers
REGION                  1..25
                        note = FR1
source                  1..25
                        mol_type = protein
                        organism = synthetic construct
SEQUENCE: 120
DVQLVESGGG VVQPGGSLRL SCAAS                                    25

SEQ ID NO: 121          moltype = AA  length = 14
FEATURE                 Location/Qualifiers
REGION                  1..14
                        note = FR2
source                  1..14
                        mol_type = protein
                        organism = synthetic construct
SEQUENCE: 121
WYRRAPGKQR ELVA                                                14

SEQ ID NO: 122          moltype = AA  length = 39
FEATURE                 Location/Qualifiers
REGION                  1..39
                        note = FR3
source                  1..39
                        mol_type = protein
                        organism = synthetic construct
SEQUENCE: 122
YVDSVRGRFT ISRDNSKNTV YLQMNSLRPE DTAVYYCNV                     39

SEQ ID NO: 123          moltype = AA  length = 39
FEATURE                 Location/Qualifiers
REGION                  1..39
                        note = FR3
source                  1..39
                        mol_type = protein
                        organism = synthetic construct
SEQUENCE: 123
YVDSVRGRFT ISRDNSKNTV YLQMNSLRPE DTALYYCNV                     39

SEQ ID NO: 124          moltype = AA  length = 39
FEATURE                 Location/Qualifiers
REGION                  1..39
                        note = FR3
source                  1..39
                        mol_type = protein
                        organism = synthetic construct
SEQUENCE: 124
YADSVKGRFT ISRDNSKNTV YLQMNSLRPE DTALYYCAA                     39

SEQ ID NO: 125          moltype = AA  length = 2415
FEATURE                 Location/Qualifiers
source                  1..2415
                        mol_type = protein
                        organism = Homo sapiens
SEQUENCE: 125
MTTLLWVFVT LRVITAAVTV ETSDHDNSLS VSIPQPSPLR VLLGTSLTIP CYFIDPMHPV  60
TTAPSTAPLA PRIKWSRVSK EKEVVLLVAT EGRVRVNSAY QDKVSLPNYP AIPSDATLEV  120
QSLRSNDSGV YRCEVMHGIE DSEATLEVVV KGIVFHYRAI STRYTLDFDR AQRACLQNSA  180
IIATPEQLQA AYEDGFHQCD AGWLADQTVR YPIHTPREGC YGDKDEFPGV RTYGIRDTNE  240
TYDVYCFAEE MEGEVFYATS PEKFTFQEAA NECRRLGARL ATTGHVYLAW QAGMDMCSAG  300
WLADRSVRYP ISKARPNCGG NLLGVRTVYV HANQTGYPDP SSRYDAICYT GEDFVDIPEN  360
FFGVGGEEDI TVQTVTWPDM ELPLPRNITE GEARGSVILT VKPIFEVSPS PLEPEEPFTF  420
APEIGATAFA EVENETGEAT RPWGFPTPGL GPATAFTSED LVVQVTAVPG QPHLPGGVVF  480
HYRPGPTRYS LTFEEAQQAC PGTGAVIASP EQLQAAYEAG YEQCDAGWLR DQTVRYPIVS  540
PRTPCVGDKD SSPGVRTYGV RPSTETYDVY CFVDRLEGEV FFATRLEQFT FQEALEFCES  600
HNATATTGQL YAAWSRGLDK CYAGWLADGS LRYPIVTPRP ACGGDKPGVR TVYLYPNQTG  660
LPDPLSRHHA FCFRGISAVP SPGEEEGGTP TSPSGVEEWI VTQVVPGVAA VPVEEETTAV  720
PSGETTAILE FTTEPENQTE WEPAYTPVGT SPLPGILPTW PPTGAETEES TEGPSATEVP  780
SASEEPSPSE VPFPSEEPSP SEEPFPSVRP FPSVELFPSE EPFPSKEPSP SEEPSASEEP  840
YTPSPPEPSW TELPSSGEES GAPDVSGDFT GSGDVSGHLD FSGQLSGDRA SGLPSGDLDS  900
SGLTSTVGSG LTVESGLPSG DEERIEWPST PTVGELPSGA EILEGSASGV GDLSGLPSGE  960
VLETSASGVG DLSGLPSGEV LETTAPGVED ISGLPSGEVL ETTAPGVEDI SGLPSGEVLE  1020
```

TTAPGVEDIS GLPSGEVLET TAPGVEDISG LPSGEVLETT APGVEDISGL PSGEVLETAA 1080
PGVEDISGLP SGEVLETAAP GVEDISGLPS GEVLETAAPG VEDISGLPSG EVLETAAPGV 1140
EDISGLPSGE VLETAAPGVE DISGLPSGEV LETAAPGVED ISGLPSGEVL ETAAPGVEDI 1200
SGLPSGEVLE TAAPGVEDIS GLPSGEVLET AAPGVEDISG LPSGEVLETA APGVEDISGL 1260
PSGEVLETAA PGVEDISGLP SGEVLETTAP GVEEISGLPS GEVLETTAPG VDEISGLPSG 1320
EVLETTAPGV EEISGLPSGE VLETSTSAVG DLSGLPSGGE VLEISVSGVE DISGLPSGEV 1380
VETSASGIED VSELPSGEGL ETSASGVEDL SRLPSGEEVL EISASGFGDL SGVPSGGEGL 1440
ETSASEVGTD LSGLPSGREG LETSASGAED LSGLPSGKED LVGSASGDLD LGKLPSGTLG 1500
SGQAPETSGL PSGFSGEYSG VDLGSGPPSG LPDFSGLPSG FPTVSLVDST LVEVVTASTA 1560
SELEGRGTIG ISGAGEISGL PSSELDISGR ASGLPSGTEL SGQASGSPDV SGEIPGLFGV 1620
SGQPSGFPDT SGETSGVTEL SGLSSGQPGV SGEASGVLYG TSQPFGITDL SGETSGVPDL 1680
SGQPSGLPGF SGATSGVPDL VSGTTSGSGE SSGITFVDTS LVEVAPTTFK EEEGLGSVEL 1740
SGLPSGEADL SGKSGMVDVS GQFSGTVDSS GFTSQTPEFS GLPSGIAEVS GESSRAEIGS 1800
SLPSGAYYGS GTPSSFPTVS LVDRTLVESV TQAPTAQEAG EGPSGILELS GAHSGAPDMS 1860
GEHSGFLDLS GLQSGLIEPS GEPPGTPYFS GDFASTTNVS GESSVAMGTS GEASGLPEVT 1920
LITSEFVEGV TEPTISQELG QRPPVTHTPQ LFESSGKVST AGDISGATPV LPGSGVEVSS 1980
VPESSSETSA YPEAGFGASA APEASREDSG SPDLSETTSA FHEANLERSS GLGVSGSTLT 2040
FQEGEASAAP EVSGESTTTS DVGTEAPGLP SATPTASGDR TEISGDLSGH TSQLGVVIST 2100
SIPESEWTQQ TQRPAETHLE IESSSLLYSG EETHTVETAT SPTDASIPAS PEWKRESEST 2160
AAAPARSCAE EPCGAGTCKE TEGHVICLCP PGYTGEHCNI DQEVCEEGWN KYQGHCYRHF 2220
PDRETWVDAE RRCREQQSHL SSIVTPEEQE FVNNNAQDYQ WIGLNDRTIE GDFRWSDGHP 2280
MQFENWRPNQ PDNFFAAGED CVVMIWHEKG EWNDVPCNYH LPFTCKKGTV ACGEPPVVEH 2340
ARTFGQKKDR YEINSLVRYQ CTEGFVQRHM PTIRCQPSGH WEEPRITCTD ATTYKRRLQK 2400
RSSRHPRRSR PSTAH 2415

SEQ ID NO: 126 moltype = AA length = 2333
FEATURE Location/Qualifiers
source 1..2333
mol_type = protein
organism = Canis lupus
SEQUENCE: 126
MTTLLWVFVT LRVITAASSE ETSDHDNSLS VSIPEPSPMR VLLGSSLTIP CYFIDPMHPV 60
TTAPSTAPLA PRIKWSRITK EKEVVLLVAT EGQVRINSAY QDKVSLPNYP AIPSDATLEI 120
QNLRSNDSGI YRCEVMHGIE DSEATLEVVV KGIVFHYRAI STRYTLDFDR AQRACLQNSA 180
IIATPEQLQA AYEDGFHQCD AGWLADQTVR YPIHTPREGC YGDKDEFPGV RTYGIRDTNE 240
TYDVYCFAEE MEGEVLYATS PEKFTFQEAA NECRRLGARL ATTGQLYLAW QGGMDMCSAG 300
WLADRSVRYP ISKARPNCGG NLLGVRTVYL HANQTGYPDP SSRYDAICYT GEDFVDIPEN 360
FFGVGGEEDI TIQTVTWPDV ELPLPRNITE GEARGNVILT VKPIFDLSPT APEPEEPFTF 420
VPEPEKPFTF ATDVGVTAFP EAENRTGEAT RPWGVPEEST PGPAFTAFTS EDHVVQVTAV 480
PGAAEVPGQP RLPGGVVFHY RPGSARYSLT FEEAQQACLR TGAVIASPEQ LQAAYEAGYE 540
QCDAGWLQDQ TVRYPIVSPR TPCVGDKDSS PGVRTYGVRP PSETYDVYCY VDKLEGEVFF 600
ITRLEQFTFQ EALAFCESHN ATLASTGQLY AAWRQGLDKC YAGWLSDGSL RYPIVTPRPS 660
CGGDKPGVRT VYLYPNQTGL PDPLSRHHVF CFRGVSGVPS PGEEEGGTPT PSVVEDWIPT 720
QVGPVVPSVP MGEETTAILD FTIEPENQTE WEPAYSPAGT SPLPGIPPTW PPTSTATEES 780
TEGPSGTEVP SVSEEPSPSE EPFPWEELST LSPPGPSGTE LPGSGEASGV PEVSGDFTGS 840
GEVSGHPDSS GQLSGESASG LPSEDLDSSG LTSAVGSGLA SGDEDRITLS SIPKVEGEGL 900
ETSASGVEDL SGLPSGREGL ETSTSGVGDL SGLPSGEGLE VSASGVEDLS GLPSGEGPET 960
STSGVGDLSR LPSGEGPEVS ASGVGDLSGL PSGREGLETS TSGVEDLSGL PSGEGPEAST 1020
SGVGDLSRLP SGEGPEVSAS GVEDLSGLPS GEGLEASASG VGDLSGLPSG EGPEASASGV 1080
GDLSRLPSGE GPEVSASGVE DLSGLSSGES PEASASGVGD LSGLPSGREG LETSASGVGD 1140
LSGLPSGEGQ EASASGVEDL SRLPSGEGPE ASASGVGELS GLPSGREGLE TSASGVGDLS 1200
GLPSGEGPEA FASGVEDLSI LPSGEGPEAS ASGVGDLSGL PSGREGLETS TSGVGDLSGL 1260
PSGREGLETS TSGVGDLSGL PSGEGPEASA SGIGDISGLP SGREGLETSS SGVEDHPETS 1320
ASGVEDLSGL PSGVEGHPET SASGVEDLSD LSSGGEGLET SASGAEDLSG FPSGKEDLIG 1380
SASGALDFGR IPSGTLGSGQ APEASSLPSG FSGEYSGVDF GSGPISGLPD FSGLPSGFPT 1440
ISLVDTTLVE VITTTSASEL EGRGTIGISG AGETSGLPVS ELDISGAVSG LPSGAELSGQ 1500
ASGSPDMSGE TSGFFGVSGQ PSGFPDISGG TSGLFEVSGQ PSGFSGETSG VTELSGLYSG 1560
QPDVSGEASG VPSGSGQPFG MTDLSGETSG VPDISGQPSG LPEFSGTTSG IPDLVSSTMS 1620
GSGESSGITF VDTSLVEVTP TTFKEKKRLG SVELSGLPSG EVDLSGASGT MDISGQSSGA 1680
TDSSGLTSHL PKFSGLPSGA AEVSGESSGA EVGSSLPSGT YEGSGNFHPA FPTVFLVDRT 1740
LVESVTQAPT AQEAGEGPSG ILELSGAHSG APDVSGDHSG SLDLSGMQSG LVEPSGEPSS 1800
TPYFSGDFSG TMDVTGEPST AMSASGEASG LLEVTLITSE FVEGVTEPTV SQELAQRPPV 1860
THTPQLFESS GEASASGEIS GATPAFPGSG LEASSVPESS SETSDFPERA VGVSAAPEAS 1920
GGASGAPDVS EATSTFPEAD VEGASGLGVS GGTSAFPEAP REGSATPEVQ EEPTTSYDVG 1980
REALGWPSAT PTASGDRIEV SGDLSGHTSG LDVVISTSVP ESEWIQQTQR PAEAHLEIEA 2040
SSPLHSGEET QTAETATSPT DDASIPTSPS GTDESAPAIP DIDECLSSPC LNGATCVDAI 2100
DSFTCLCLPS YRGDLCEIDQ ELCEEGWTKF QGHCYRYFPD RESWVDAESR CRAQQSHLSS 2160
IVTPEEQEFV NNNAQDYQWI GLNDRTIEGD FRWSDGHSLQ FENWRPNQPD NFFVSGEDCV 2220
VMIWHEKGEW NDVPCNYYLP FTCKKGTVAC GDPPVVEHAR TFGQKKDRYE INSLVRYQCT 2280
EGFVQRHVPT IRCQPSGHWE KPRITCTDPS TYKRRLQKRS SRAPRRSRPS TAH 2333

SEQ ID NO: 127 moltype = AA length = 2364
FEATURE Location/Qualifiers
source 1..2364
mol_type = protein
organism = Bos taurus
SEQUENCE: 127
MTTLLLVFVT LRVITAAISV EVSEPDNSLS VSIPEPSPLR VLLGSSLTIP CYFIDPMHPV 60
TTAPSTAPLA PRIKWSRISK EKEVVLLVAT EGRVRVNSAY QDKVTLPNYP AIPSDATLEI 120

```
QNMRSNDSGI LRCEVMHGIE DSQATLEVVV KGIVFHYRAI STRYTLDFDR AQRACLQNSA  180
IIATPEQLQA AYEDGFHQCD AGWLADQTVR YPIHTPREGC YGDKDEFPGV RTYGIRDTNE  240
TYDVYCFAEE MEGEVFYATS PEKFTFQEAA NECRRLGARL ATTGQLYLAW QGGMDMCSAG  300
WLADRSVRYP ISKARPNCGG NLLGVRTVYL HANQTGYPDP SSRYDAICYT GEDFVDIPES  360
FFGVGGEEDI TIQTVTWPDV ELPLPRNITE GEARGSVILT AKPDFEVSPT APEPEEPFTF  420
VPEVRATAFP EVENRTEEAT RPWAFPREST PGLGAPTAFT SEDLVVQVTL APGAAEVPGQ  480
PRLPGGVVFH YRPGSSRYSL TFEEAKQACL RTGAIIASPE QLQAAYEAGY EQCDAGWLQD  540
QTVRYPIVSP RTPCVGDKDS SPGVRTYGVR PPSETYDVYC YVDRLEGEVF FATRLEQFTF  600
WEAQEFCESQ NATLATTGQL YAAWSRGLDK CYAGWLADGS LRYPIVTPRP ACGGDKPGVR  660
TVYLYPNQTG LLDPLSRHHA FCFRGVSAAP SPEEEEGSAP TAGPDVEEWM VTQVGPGVAA  720
VPIGEETTAI PGFTVEPENK TEWELAYTPA GTLPLPGIPP TWPPTGEATE EHTEGPSATE  780
VPSASEKPFP SEEPFPPEEP FPSEKPFPPE ELFPSEKPFP SEKPFPSEEP FPSEKPFPPE  840
ELFPSEKPIP SEEPFPSEEP FPSEKPFPPE EPFPSEKPIP SEEPFPSEKP FPSEEPFPSE  900
EPSTLSAPVP SRTELPSSGE VSGVPEISGD FTGSGEISGH LDFSGQPSGE SASGLPSEDL  960
DSSGLTSTVG SGLPVESGLP SGEEERITWT SAPKVDRLPS GGEGPEVSGV EDISGLPSGG  1020
EVHLEISASG VEDISGLPSG GEVHLEISAS GVEDLSRIPS GEGPEISASG VEDISGLPSG  1080
EEGHLEISAS GVEDLSGIPS GEGPEVSASG VEDLIGLPSG EGPEVSASGV EDLSRLPSGE  1140
GPEVSASGVE DLSGLPSGEG PEVSVSGVED LSRLPSGEGP EVSASGVEDL SRLPSGEGPE  1200
ISVSGVEDIS ILPSGEGPEV SASGVEDLSV LPSGEGHLEI STSGVEDLSV LPSGEGHLET  1260
SSGVEDISRL PSGEGPEVSA SGVEDLSVLP SGEDHLEISA SGVEDLGVLP SGEDHLEISA  1320
SGVEDISRLP SGEGPEVSAS GVEDLSVLPS GEGHLEISAS GVEDLSRLPS GGEDHLETSA  1380
SGVGDLSGLP SGREGLEISA SGAGDLSGLT SGKEDLTGSA SGALDLGRIP SVTLGSGQAP  1440
EASGLPSGFS GEYSGVDLES GPSSGLPDFS GLPSGFPTVS LVDTTLVEVV TATTAGELEG  1500
RGTIDISGAG ETSGLPFSEL DISGGASGLS SGAELSGQAS GSPDISGETS GLFGVSGQPS  1560
GFPDISGETS GLLEVSGQPS GFYGEISGVT ELSGLASGQP EISGEASGIL SGLGPPFGIT  1620
DLSGEAPGIP DLSGQPSGLP EFSGTASGIP DLVSSAVSGS GESSGITFVD TSLVEVTPTT  1680
FKEEEGLGSV ELSGLPSGEL GVSGTSGLAD VSGLSSGAID SSGFTSQPPE FSGLPSGVTE  1740
VSGEASGAES GSSLPSGAYD SSGLPSGFPT VSFVDRTLVE SVTQAPTAQE AGEGPSGILE  1800
LSGAPSGAPD MSGDHLGSLD QSGLQSGLVE PSGEPASTPY FSGDFSGTTD VSGESSAATS  1860
TSGEASGLPE VTLITSELVE GVTEPTVSQE LGQRPPVTYT PQLFESSGEA SASGDVPRFP  1920
GSGVEVSSVP ESSGETSAYP EAEVGASAAP EASGGASGSP NLSETTSTFH EADLEGTSGL  1980
GVSGSPSAFP EGPTEGLATP EVSGESTTAF DVSVEASGSP SATPLASGDR TDTSGDLSGH  2040
TSGLDIVIST TIPESEWTQQ TQRPAEARLE IESSSPVHSG EESQTADTAT SPTDASIPAS  2100
AGGTDDSEAT TTDIDECLSS PCLNGATCVD AIDSFTCLCL PSYQGDVCEI QKLCEEGWTK  2160
FQGHCYRHFP DRATWVDAES QCRKQQSHLS SIVTPEEQEF VNNNAQDYQW IGLNDKTIEG  2220
DFRWSDGHSL QFENWRPNQP DNFFATGEDC VVMIWHEKGE WNDVPCNYQL PFTCKKGTVA  2280
CGEPPVVEHA RIFGQKKDRY EINALVRYQC TEGFIQGHVP TIRCQPSGHW EEPRITCTDP  2340
ATYKRRLQKR SSRPLRRSHP STAH                                         2364

SEQ ID NO: 128          moltype = AA  length = 2124
FEATURE                 Location/Qualifiers
source                  1..2124
                        mol_type = protein
                        organism = Rattus norvegicus
SEQUENCE: 128
MTTLLLVFVT LRVIAAVISE EVPDHDNSLS VSIPQPSPLK ALLGTSLTIP CYFIDPMHPV  60
TTAPSTAPLT PRIKWSRVSK EKEVVLLVAT EGQVRVNSIY QDKVSLPNYP AIPSDATLEI  120
QNLRSNDSGI YRCEVMHGIE DSEATLEVIV KGIVFHYRAI STRYTLDFDR AQRACLQNSA  180
IIATPEQLQA AYEDGFHQCD AGWLADQTVR YPIHTPREGC YGDKDEFPGV RTYGIRDTNE  240
TYDVYCFAEE MEGEVFYATS PEKFTFQEAA NECRTVGARL ATTGQLYLAW QGGMDMCSAG  300
WLADRSVRYP ISKARPNCGG NLLGVRTVYL HANQTGYPDP SSRYDAICYT GEDFVDIPEN  360
FFGVGGEEDI TIQTVTWPDL ELPLPRNITE GEARGNVILT AKPIFDMSPT VSEPGEALTL  420
APEVGTTVFP EAGERTEKTT RPWGFPEEAT RGPDSATAFA SEDLVVRVTI SPGAVEVPGQ  480
PRLPGGVVFH YRPGSTRYSL TFEEAQQACI RTGAAIASPE QLQAAYEAGY EQCDAGWLQD  540
QTVRYPIVSP RTPCVGDKDS SPGVRTYGVR PSSETYDVYC YVDKLEGEVF FATQMEQFTF  600
QEAQAFCAAQ NATLASTGQL YAAWSQGLDK CYAGWLADGT LRYPIVNPRP ACGGDKPGVR  660
TVYLYPNQTG LPDPLSKHHA FCFRGVSVVP SPGGTPTSPS DIEDWIVTRV EPGVDAVPLE  720
PETTEVPYFT TEPEKQTEWE PAYTPVGTSP LPGIPPTWLP TVPAAEEHTE SPSASQEPSA  780
SQVPSTSEEP YTPSLAVPSG TELPSSGDTS GAPDLSGDFT GSTDTSGRLD SSGEPSGGSE  840
SGLPSGDLDS SGLGPTVSSG LPVESGSASG DGEIPWSSTP TVDRLPSGGE SLEGSASASG  900
TGDLSGLPSG GEITETSASG TEEISGLPSG GDDLETSTSG IDGASVLPTG RGGLETSASG  960
VEDLSGLPSG EEGSETSTSG IEDISVLPTG ESPETSASGV GDLSGLPSGG ESLETSASGV  1020
EDVTQLPTER GGLETSASGI EDITVLPTGR ENLETSASGV EDVSGLPSGK EGLETSASGI  1080
EDISVFPTEA EGLETSASGG YVSGIPSGED GTETSTSGVE GVSGLPSGGE GLETSASGVE  1140
DLGLPTRDSL ETSASGVDVT GYPSGREDTE TSVPGVGDDL SGLPSGQEGL ETSASGAEDL  1200
GGLPSGKEDL VGSASGALDF GKLPSGTLGS GQTPEASGLP SGFSGEYSGV DIGSGPSSGL  1260
PDFSGLPSGF PTVSLVDSTL VEVITATTAS ELEGRGTISV SGSGEESGPP LSELDSSADI  1320
SGLPSGTELS GQTSGSLDVS GETSGFFDVS GQPFGSSGTG EGTSGIPEVS GQAVRSPDTT  1380
EISELSGLSS GQPDVSGEGS GILFGSGQSS GITSVSGETS GISDLSGQPS GFPVLSGTTP  1440
GTPDLASGAM SGSGDSSGIT FVDTSLIEVT PTTFREEEGL GSVELSGLPS GETDLSGTSG  1500
MVDVSGQSSG AIDSSGLISP TPEFSGLPSG VAEVSGEVSG VETGSSLSSG AFDGSGLVSG  1560
FPTVSLVDRT LVESITLAPT AQEAGEGPSS ILEFSGAHSG TPDISGDLSG SLDQSTWQPG  1620
WTEASTEPPS SPYFSGDFSS TTDASGESIT APTGSGETSG LPEVTLITSE LVEGVTEPTV  1680
SQELGHGPSM TYTPRLFEAS GEASASGDLG GPVTIFPGSG VEASVPEGSS DPSAYPEAGV  1740
GVSAAPEASS QLSEFPDLHG ITSASRETDL EMTTPGTEVS SNPWTFQEGT REGSAAPEVS  1800
GESSTTSDID AGTSGVPFAT PMTSGDRTEI SGEWSDHTSE VNVTVSTTVP ESRWAQSTQH  1860
PTETLQEIGS PNPSYSGEET QTAETAKSLT DTPTLASPEG SGETESTAAD QEQCEEGWTK  1920
FQGHCYRHFP DRETWVDAER RCREQQSHLS SIVTPEEQEF VNKNAQDYQW IGLNDRTIEG  1980
DFRWSDGHSL QFEKWRPNQP DNFFATGEDC VVMIWHERGE WNDVPCNYQL PFTCKKGTVA  2040
```

```
CGEPPAVEHA RTLGQKKDRY EISSLVRYQC TEGFVQRHVP TIRCQPSADW EEPRITCTDP  2100
NTYKHRLQKR TMRPTRRSRP SMAH                                         2124

SEQ ID NO: 129          moltype = AA  length = 537
FEATURE                 Location/Qualifiers
VARIANT                 45
                        note = Xaa can be any naturally occurring amino acid
VARIANT                 49
                        note = Xaa can be any naturally occurring amino acid
VARIANT                 146
                        note = Xaa can be any naturally occurring amino acid
source                  1..537
                        mol_type = protein
                        organism = Sus scrofa
SEQUENCE: 129
AISVEVSEPD NSLSVSIPQP SPLRVLLGGS LTIPCYFIDP MHPVXTAPXT APLAPRIKWS  60
RVSKEKEVVL LVATEGQVRV NSAYQDRVTL PNYPAIPSDA TLEIQNLRSN DSGIYRCEVM  120
HGIEDSEATL EVVVKGIVFH YRAISXRYTL DFDRAQRACL QNSAIIATPE QLQAAYEDGF  180
HQCDAGWLAD QTVRYPIHTP REGCYGDKDE FPGVITYGIR DTNETYDVYC FAEEMEGEVF  240
YATSPEKFTF QEAANECRRL GARLATTGQL YLAWRGGMDM CSAGWLADRS VRYPISKARP  300
NCGGNLLGVR TVYLHANQTG YPDPSSRYDA ICYTGEDFVD IPENFFGVGG EEDITIQTVT  360
WPDVELPLPR NITEGEARGT VILTVKPVFE FSPTAPEPEE PFTFAPGTGA TAFPEAENRT  420
GEATRPWAFP EESTPGLGAP TAFTSEDLVV QVTSAATEEG TEGPSATEAP STSEEPFPSE  480
KPFPSEEPFP SEEPFPSEKP SASEEPFPSE QPSTLSAPVP SRTELPGSGE VSGAPEV     537

SEQ ID NO: 130          moltype = AA  length = 2132
FEATURE                 Location/Qualifiers
source                  1..2132
                        mol_type = protein
                        organism = Mus musculus
SEQUENCE: 130
MTTLLLVFVT LRVIAAVISE EVPDHDNSLS VSIPQPSPLK VLLGSSLTIP CYFIDPMHPV  60
TTAPSTAPLT PRIKWSRVSK EKEVVLLVAT EGQVRVNSIY QDKVSLPNYP AIPSDATLEI  120
QNLRSNDSGI YRCEVMHGIE DSEATLEVIV KGIVFHYRAI STRYTLDFDR AQRACLQNSA  180
IIATPEQLQA AYEDGFHQCD AGWLADQTVR YPIHTPREGC YGDKDEFPGV RTYGIRDTNE  240
TYDVYCFAEE MEGEVFYATS PEKFTFQEAA NECRRLGARL ATTGQLYLAW QGGMDMCSAG  300
WLADRSVRYP ISKARPNCGG NLLGVRTVYL HANQTGYPDP SSRYDAICYT GEDFVDIPEN  360
FFGVGGEDDI TIQTVTWPDL ELPLPRNVTE GEALGSVILT AKPIFDLSPT ISEPGEALTL  420
APEVGSTAFP EAEERTGEAT RPWGFPAEVT RGPDSATAFA SEDLVVRVTI SPGAAEVPGQ  480
PRLPGGVVFH YRPGSTRYSL TFEEAQQACM HTGAVIASPE QLQAAYEAGY EQCDAGWLQD  540
QTVRYPIVSP RTPCVGDKDS SPGVRTYGVR PSSETYDVYC YVDKLEGEVF FATRLEQFTF  600
QEARAFCAAQ NATLASTGQL YAAWSQGLDK CYAGWLADGT LRYPIITPRP ACGGDKPGVR  660
TVYLYPNQTG LPDPLSKHHA FCFRGVSVAP SPGEEGGSTP TSPSDIEDWI VTQVGPGVDA  720
VPLEPKTTEV PYFTTEPRKQ TEWEPAYTPV GTSPQPGIPP TWLPTLPAAE EHTESPSASE  780
EPSASAVPST SEEPYTSSFA VPSMTELPGS GEASGAPDLS GDFTGSGDAS GRLDSSGQPS  840
GGIESGLPSG DLDSSGLSPT VSSGLPVESG SASGDGEVPW SHTPTVGRLP SGGESPEGSA  900
SASGTGDLSG LPSGGEITET STSGAEETSG LPSGGDGLET STSGVDDVSG IPTGREGLET  960
SASGVEDLSG LPSGEEGSET STSGIEDISV LPTGGESLET SASGVGDLSG LPSGGESLET  1020
SASGAEDVTQ LPTERGGLET SASGVEDITV LPTGRESLET SASGVEDVSG LPSGREGLET  1080
SASGIEDISV FPTEAEGLDT SASGGYVSGI PSGGDGTETS ASGVEDVSGL PSGGEGLETS  1140
ASGVEDLGPS TRDSLETSAS GVDVTGFPSG RGDPETSVSG VGDDFSGLPS GKEGLETSAS  1200
GAEDLSGLPS GKEDLVGSAS GALDFGKLPP GTLGSGQTPE VNGFPSGFSG EYSGADIGSG  1260
PSSGLPDFSG LPSGFPTVSL VDSTLVEVIT ATTSSELEGR GTIGISGSGE VSGLPLGELD  1320
SSADISGLPS GTELSGQASG SPDSSGETSG FFDVSGQPFG SSGVSEETSG IPEISGQPSG  1380
TPDTTATSGV TELNELSSGQ PDVSGDGSGI LFGSGQSSGI TSVSGETSGI SDLSGQPSGF  1440
PVFSGTATRT PDLASGTISG SGESSGITFV DTSFVEVTPT TFREEEGLGS VELSGFPSGE  1500
TELSGTSGTV DVSEQSSGAI DSSGLTSPTP EFSGLPSGVA EVSGEFSGVE TGSSLPSGAF  1560
DGSGLVSGFP TVSLVDRTLV ESITQAPTAQ EAGEGPSGIL EFSGAHSGTP DISGELSGSL  1620
DLSTLQSGQM ETSTETPSSP YFSGDFSSTT DVSGESIAAT TGSGESSGLP EVTLNTSELV  1680
EGVTEPTVSQ ELGHGPSMTY TPRLFEASGD ASASGDLGGA VTNFPGSGIE ASVPEASSDL  1740
SAYPEAGVGV SAAPEASSKL SEFPDLHGIT SAFHETDLEM TTPSTEVNSN PWTFQEGTRE  1800
GSAAPEVSGE SSTTSDIDTG TSGVPSATPM ASGDRTEISG EWSDHTSEVN VAISSTITES  1860
EWAQPTRYPT ETLQEIESPN PSYSGEETQT AETTMSLTDA PTLSSSEGSG ETESTVADQE  1920
QCEEGWTKFQ GHCYRHFHDR ETWVDAERRC REQQSHLSSI VTPEEQEFVN KNAQDYQWIG  1980
LNDRTIEGDF RWSDGHSLQF EKWRPNQPDN FFATGEDCVV MIWHERGEWN DVPCNYQLPF  2040
TCKKGTVACG DPPVVEHART LGQKKDRYEI SSLVRYQCTE GFVQRHVPTI RCQPSGHWEE  2100
PRITCTDPNT YKHRLQKRSM RPTRRSRPSM AH                                2132

SEQ ID NO: 131          moltype = AA  length = 2167
FEATURE                 Location/Qualifiers
source                  1..2167
                        mol_type = protein
                        organism = Oryctolagus cuniculus
SEQUENCE: 131
MTTLLLVLVA LRVIAAAISG DVSDLDNALS VSIPQPSPVR ALLGTSLTIP CYFIDPVHPV  60
TTAPSTAPLT PRIKWSRISK DKEVVLLVAN EGRVRINSAY QDKVSLPNYP AIPSDATLEI  120
QSLRSNDSGI YRCEVMHGLE DSEATLEVVV KGVVFHYRAI STRYTLDFDR AQRACLQNSA  180
IIATPEQLQA AYEDGFHQCD AGWLADQTVR YPIHTPREGC YGDKDEFPGV RTYGIRDTNE  240
TYDVYCFAEE MEGEVFYATS PEKFTFQEAA SECRRLGARL ATTGQLYLAW QAGMDMCSAG  300
```

```
WLADRSVRYP ISKARPNCGG NLLGVRTVYV HANQTGYPDP SSRYDAICYT GEDFMDIPEN  360
FFGVGGEEDI TVQTVTWPDV ELPVPRNITE GEARGSVVLT AKPVLDVSPT APQPEETFAP  420
GVGATAFPGV ENGTEEATRP RGFADEATLG PSSATAFTSA DLVVQVTAAP GVAEVPGQPR  480
LPGGVVFHYR PGPTRYSLTF EEAQQACLRT GAAMASAEQL QAAYEAGYEQ CDAGWLQDQT  540
VRYPIVSPRT PCVGDKDSSP GVRTYGVRPP SETYDVYCYV DRLEGEVFFA TRLEQFTFQE  600
ALEFCESHNA TLASTGQLYA AWSRGLDRCY AGWLADGSLR YPIVTPRPAC GGDKPGVRTV  660
YLYPNQTGLP DPLSRHHAFC FRGTSEAPSP GPEEGGTATP ASGLEDWIVT QVGPGVAATP  720
RAEERTAVPS FATEPGNQTG WEAASSPVGT SLLPGIPPTW PPTGTAAEGT TEGLSTAAMP  780
SASEGPYTPS SLVARETELP GLGVTSVPPD ISGDLTSSGE ASGLFGPTGQ PLGGSASGLP  840
SGELDSGSLT PTVGSGLPIG SGLASGDEDR IQWSSSTEVG GVTSGAEIPE TSASGVGTDL  900
SGLPSGAEIP ETFASGVGTD LSGLPSGAEI PETFASGVGT DLSGLPSGAE ILETSASGVG  960
TDLSGLPSGA EILETSASGV GTDLSGLPSG AEILETSASG VGTDLSGLPS GAEIPETFAS  1020
GVGTDLSGLP SGAEILETSA SGVGTDLSGL PSGAEIPETS ASGVGTDLSG LPSGAEILET  1080
SASGVGTDLS GLPSGAEILE TSASGVGTDL SGLPSGAEIL ETSASGVGTD LSGLPSGAEI  1140
LETSASGVGT DLSGLPSGAE ILETSASGVG TDLSGLPSGG EIPETFASGV GDLSGLPPGR  1200
EDLETLTSGV GDLSGLSSGK DGLVGSASGA LDFGGTLGSG QIPETSGLPS GYSGEYSEVD  1260
LGSGPSSGLP DFSGLPSGFP TVSLVDTPLV EVVTATTARE LEGRGTIGIS GAGEISGLPS  1320
SELDVSGGTS GADISGEADV GGEASGLIVR GQPSGFPDTS GEAFGVTEVS GLSSGQPDLS  1380
GEASGVLFGS GPPFGITDLS GEPSGQPSGL PEFSGTTHRI PDLVSGATSG SGESSGIAFV  1440
DTSVVEVTPT TLREEEGLGS VEFSGFPSGE TGLSGTPETI DVSGQSSGTI DSSGFTSLAP  1500
EVSGSPSGVA EVSGEASGTE ITSGLPSGVF DSSGLPSGFP TVSLVDRTLV ESVTQAPTAQ  1560
EAEGPSDILE LSGVHSGLPD VSGAHSGFLD PSGLQSGLVE PSGEPPRTPY FSGDFPSTPD  1620
VSGEASAATS SSGDISGLPE VTLVTSEFME GVTRPTVSQE LGQGPPMTHV PKLFESSGEA  1680
LASGDTSGAA PAFPGSGLEA SSVPESHGET SAYAEPGTKA AAAPDASGEA SGSPDSGEIT  1740
SVFREAAGEG ASGLEVSSSS LASQQGPREG SASPEVSGES TTSYEIGTET SGLPLATPAA  1800
SEDRAEVSGD LSGRTPVPVD VVTNVPEAEW IQHSQRPAEM WPETKSSSPS YSGEDTAGTA  1860
ASPASADTPG EPGPTTAAPR SCAEEPCGPG TCQETEGRVT CLCPPGHTGE YCDIDIDECL  1920
SSPCVNGATC VDASDSFTCL CLPSYGGDLC ETDQEVCEEG WTKFQGHCYR HFPDRETWVD  1980
AEGRCREQQS HLSSIVTPEE QEFVNNNAQD YQWIGLNDRT IEGDFRWSDG HPLQFENWRP  2040
NQPDNFFATG EDCVVMIWHE KGEWNDVPCN YHLPFTCKKG TVACGDPPVV EHARTFGQKK  2100
DRYEINSLVR YQCAEGFTQR HVPTIRCQPS GHWEEPRITC THPTTYKRRV QKRSSRTLQR  2160
SQASSAP                                                           2167

SEQ ID NO: 132          moltype = AA  length = 2266
FEATURE                 Location/Qualifiers
source                  1..2266
                        mol_type = protein
                        organism = Macaca fascicularis
SEQUENCE: 132
MTTLLWVFVT LRVIAAAVTV ETSDHDNSLS VSIPQPSPLR VLLGTSLTIP CYFIDPMHPV  60
TTAPSTAPLA PRIKWSRVSK EKEVVLLVAT EGRVRVNSAY QDKVSLPNYP AIPSDATLEI  120
QSLRSNDSGV YRCEVMHGIE DSEATLEVVV KGIVFHYRAI STRYTLDFDR AQRACLQNSA  180
IIATPEQLQA AYEDGFHQCD AGWLADQTVR YPIHTPREGC YGDKDEFPGV RTYGIRDTNE  240
TYDVYCFAEE MEGEVFYATS PEKFTFQEAA NECRRLGARL ATTGQLYLAW QAGMDMCSAG  300
WLADRSVRYP ISKARPNCGG NLLGVRTVYL HANQTGYPDP SSRYDAICYT GEDFVDIPEN  360
FFGVGGEEDI TVQTVTWPDM ELPLPRNITE GEARGSVILT VKPIFDVSPS PLEPEEPFTF  420
APEIGATAFP EVENETGEAT RPWGFPTPGL GPATAFTSED LVVQVTAVPG QPHLPGGVVF  480
HYRPGSTRYS LTFEEAQQAC LRTGAVIASP EQLQAAYEAG YEQCDAGWLR DQTVRYPIVS  540
PRTPCVGDKD SSPGVRTYGV RPSTETYDVY CYVDRLEGEV FFATRLEQFT FQEALEFCES  600
HNATLATTGQ LYAAWSRGLD KCYAGWLADG SLRYPIVTPR PACGGDKPGV RTVYLYPNQT  660
GLPDPLSRHH AFCFRGVSAV PSPGEEEGGT PTSPSGVEDW IATQVVPGVA AVPVEEETTA  720
VPLGETTAIL EFTTEPENQT EWEPAYTPMG TSPLPGILPT WPPTGTATEE STEGPSATEV  780
LTASKEPSPP EVPFPSEEPS PSEEPFPSVR PFPSVEPSPS EEPFPSVEPS PSEEPSASEE  840
PYTPSPPVPS WTELPGSGEE SGAPDVSGDF IGSGDVSGHL DFSGQLSGDR ISGLPSGDLD  900
SSGLTSTVGS GLPVDSGLAS GDEERIEWSS TPTVGELPSG AEILEGSASE VGDLSGLPSG  960
DVLETSASGV GDLSGLPSGE VLETSASGVG DLSGLPSGEV LETSTSGVGD LSGLPSGEVL  1020
ETSTSGVGDL SGLPSAGEVL ETTASGVEDI SGLPSGEVLE TTASGVEDIS GFPSGEVLET  1080
TASGVEDISG LPSGEVLETT ASGVEDISGL PSGEVLETTA SGVGDLGGLP SGEVLETSTS  1140
GVGDLSGLPS GEVVETSTSG VEDLSGLPSG GEVLETSTSG VEDISGLPSG EVLETTASGI  1200
EDVSELPSGE GLETSASGVE DLSRLPSGEV LETSASGVGD ISGLPSGGEV LEISASGVGD  1260
LSGLPSGGEG LETSASGVGT DLSGLPSGRE GLETSASGAE DLSGLPSGKE DLVGPASGDL  1320
DLGKLPSGTL RSGQAPETSG LPSGFSGEYS GVDLGSGPPS GLPDFSGLPS GFPTVSLVDS  1380
TLVEVVTAST ASELEGRGTI GISGAGEISG LPSSELDISG EASGLPSGTE LSGQASGSPD  1440
VSRETPGLFD VSGQPSGFPD ISGGTSGISE VSGQPSGFPD TSGETSGVTE LSGLPSGQPG  1500
VSGEASGVPY GSSQPFGITD LSGETSGVPD LSGQPSGLPG FSGATSGVPD LVSGATSGSG  1560
ESSGITFVDT SLVEVTPTTF KEEEGLGSVE LSGLPSGEAD LSGRSGMVDV SGQFSGTVDS  1620
SGFTSQTPEF SGLPIGIAEV SGESSGAETG SSLPSGAYYG SGLPSGFPTV SLVDRTLVES  1680
VTQAPTAQEA GEGPPGILEL SGTHSGAPDM SGDHSGFLDV SGLQFGLVEP SGEPPSTPYF  1740
SGDFASTTDV SGESSAAMGT SGEASGLPGV TLITSEFMEG VTEPTVSQEL GQRPPVTHTP  1800
QLFESSGEAS AAGDISGATP VLPGSGVEVS SVPESSSETS AYPEAGVGAS AAPETSGEDS  1860
GSPDLSETTS AFHEADLERS SGLGVSGSTL TFQEGEPSAS PEVSGESTTT GDVGTEAPGL  1920
PSATPTASGD RTEISGDLSG HTSGLGVVIS TSIPESEWTQ QTQRPAEAHL ETESSSLLYS  1980
GEETHTAETA TSPTDASIPA SPEWTGESES TVADIDECLS SPCLNGATCV DAIDSFTCLC  2040
LPSYGGDLCE IDQEVCEEGW TKYQGHCYRH FPDRETWVDA ERRCREQQSH LSSIVTPEEQ  2100
EFVNNNAQDY QWIGLNDRTI EGDFRWSDGH PMQFENWRPN QPDNFFAAGE DCVVMIWHEK  2160
GEWNDVPCNY HLPFTCKKGT VACGEPPMVQ HARTFGQKKD RYEINSLVRY QCTEGFVQRH  2220
VPTIRCQPSG HWEEPRITCT DATAYKRRLQ KRSSRHPRRS RPSTAH                2266

SEQ ID NO: 133          moltype = AA  length = 2167
```

```
FEATURE                Location/Qualifiers
VARIANT                1910..1915
                       note = Xaa can be any naturally occurring amino acid
source                 1..2167
                       mol_type = protein
                       organism = Macaca mulatta
SEQUENCE: 133
MTTLLWVFVT LRVIAAAVTV ETSDHDNSLS VSIPQPSPLR VLLGTSLTIP CYFIDPMHPV  60
TTAPSTAPLA PRIKWSRVSK EKEVVLLVAT EGRVRVNSAY QDKVSLPNYP AIPSDATLEI  120
QSLRSNDSGV YRCEVMHGIE DSEATLEVVV KGIVFHYRAI STRYTLDFDR AQRACLQNSA  180
IIATPEQLQA AYEDGFHQCD AGWLADQTVR YPIHTPREGC YGDKDEFPGV RTYGIRDTNE  240
TYDVYCFAEE MEGEVFYATS PEKFTFQEAA NECRRLGARL ATTGQLYLAW QAGMDMCSAG  300
WLADRSVRYP ISKARPNCGG NLLGVRTVYL HANQTGYPDP SSRYDAICYT GEDFVDIPEN  360
FFGVGGEEDI TVQTVTWPDM ELPLPRNITE GEARGSVILT VKPIFDVSPS PLEPEEPFTF  420
APEIGATAFP EVENETGEAT RPWGFPTPGL GPATAFTSED LVVQVTAVPG QPHLPGGVVF  480
HYRPGSTRYS LTFEEAQQAC LRTGAVIASP EQLQAAYEAG YEQCDAGWLR DQTVRYPIVS  540
PRTPCVGDKD SSPGVRTYGV RPSTETYDVY CYVDRLEGEV FFATRLEQFT FQEALEFCES  600
HNATLATTGQ LYAAWSRGLD KCYAGWLADG SLRYPIVTPR PACGGDKPGV RTVYLYPNQT  660
GLPDPLSRHH AFCFRGVSAV PSPGEEEGGT PTSPSGVEDW IATQVVPGVA AVPVEEETTA  720
VPLGETTAIL EFTTEPENQT EWEPAYTPMG TSPLPGILPT WPPTGTATEE STEGPSATEV  780
LTASKEPSPP EVPFPSEEPS PSEEPFPSVR PFPSVEPSPS EEPFPSVEPS PSEEPSASEE  840
PYTPSPPVPS WTELPGSGEE SGAPDVSGDF IGSGDVSGHL DFSGQLSGDR ISGLPSGDLD  900
SSGLTSTVGS GLPVDSGLAS GDEERIEWSS TPTVGELPSG AEILEGSASE VGDLSGLPSG  960
DVLETSASGV GDLSGLPSGE VLETSVSGVG DLSGLPSGEV LETSTSGVGD LSGLPSGEVL  1020
ETSTSGVGDL SGLPSAGEVL ETTASGVEDI SGLPSGEVLE TTASGVEDIS GFPSGEVLET  1080
TASGVEDISG LPSGEVLETT ASGVEDISGL PSGEVLETTA SGVGDLGGLP SGEVLETSTS  1140
GVGDLSGLPS GEVVETSTSG VEDLSGLPSG GEVLETSTSG VEDISGLPSG EVLETTASGI  1200
EDVSELPSGE GLETSASGVE DLSRLPSGEV LETSASGVGD ISGLPSGGEV LEISASGVGD  1260
LSGLPSGGEG LETSASGVGT DLSGLPSGRE GLETSASGAE DLSGLPSGKE DLVGPASGDL  1320
DLGKLPSGTL GSGQAPETSG LPSGFSGEYS GVDLGSGPPS GLPDFSGLPS GFPTVSLVDS  1380
TLVEVVTAST ASELEGRGTI GISGAGEISG LPSSELDISG EASGLPSGTE LSGQASGSPD  1440
VSRETSGLFD VSGQPSGFPD TSGETSGVTE LSGLPSGQPG VSGEASGVPY GSSQPFGITD  1500
LSGETSGVPD LSGQPSGLPG FSGATSGVPD LVSGATSGSG ESSDITFVDT SLVEVTPTTF  1560
KEEEGLGSVE LSGLPSGEAD LSGRSGMVDV SGQFSGTVDS SGFTSQTPEF SGLPIGIAEV  1620
SGESSGAETG SSLPSGAYYG SELPSGFPTV SLVDRTLVES VTQAPTAQEA GEGPPGILEL  1680
SGTHSGAPDM SGDHSGFLDV SGLQFGLVEP SGEPPSTPYF SGDFASTTDV SGESSAAMGT  1740
NGEASGLPEV TLITSEFMEG VTEPTVSQEL GQRPPVTHTP QLFESSGEAS AAGDISGATP  1800
VLPGSGVEVS SVPESSSETS AYPEAGVGAS AAPETSGEDS GSPDLSETTS AFHEADLERS  1860
SGLGVSGSTL TFQEGEPSAS PEVSGESTTT GDVGTEAPGL PSATPTASGX XXXXXPTRSC  1920
AEEPCGAGTC KETEGHVICL CPPGYTGEHC NIDQEVCEEG WTKYQGHCYR HFPDRETWVD  1980
AERRCREQQS HLSSIVTPEE QEFVNNNAQD YQWIGLNDRT IEGDFRWSDG HPMQFENWRP  2040
NQPDNFFAAG EDCVVMIWHE KGEWNDVPCN YHLPFTCKKG TVACGEPPMV QHARTFGQKK  2100
DRYEINSLVR YQCTEGFVQR HVPTIRCQPS GHWEEPRITC TDATAYKRRL QKRSSRHPRR  2160
SRPSTAH                                                           2167

SEQ ID NO: 134         moltype = AA  length = 1321
FEATURE                Location/Qualifiers
source                 1..1321
                       mol_type = protein
                       organism = Homo sapiens
SEQUENCE: 134
MGAPFVWALG LLMLQMLLFV AGEQGTQDIT DASERGLHMQ KLGSGSVQAA LAELVALPCL  60
FTLQPRPSAA RDAPRIKWTK VRTASGQRQD LPILVAKDNV VRVAKSWQGR VSLPSYPRRR  120
ANATLLLGPL RASDSGLYRC QVVRGIEDEQ DLVPLEVTGV VFHYRSARDR YALTFAEAQE  180
ACRLSSAIIA APRHLQAAFE DGFDNCDAGW LSDRTVRYPI TQSRPGCYGD RSSLPGVRSY  240
GRRNPQELYD VYCFARELGG EVFYVGPARR LTLAGARAQC RRQGAALASV GQLHLAWHEG  300
LDQCDPGWLA DGSVRYPIQT PRRRCGGPAP GVRTVYRFAN RTGFPSPAER FDAYCFRAHH  360
PTSQHGDLET PSSGDEGEIL SAEGPPVREL EPTLEEEEVV TPDFQEPLVS SGEEETLILE  420
EKQESQQTLS PTPGDPMLAS WPTGEVWLST VAPSPSDMGA GTAASSHTEV APTDPMPRRR  480
GRFKGLNGRY FQQQEPEPGL QGGMEASAQP PTSEAAVNQM EPPLAMAVTE MLGSGQSRSP  540
WADLTNEVDM PGAGSAGGKS SPEPWLWPPT MVPPSISGHS RAPVLELEKA EGPSARPATP  600
DLFWSPLEAT VSAPSPAPWE AFPVATSPDL PMMAMLRGPK EWMLPHPTPI STEANRVEAH  660
GEATATAPPS PAAETKVYSL PLSLTPTGQG GEAMPTTPES PRADFRETGE TSPAQVNKAE  720
HSSSSPWPSV NRNVAVGFVP TETATEPTGL RGIPGSESGV FDTAESPTSG LQATVDEVQD  780
PWPSVYSKGL DASSPSAPLG SPGVFLVPKV TPNLEPWVAT DEGPTVNPMD STVTPAPSDA  840
SGIWEPGSQV FEEAESTTLS PQVALDTSIV TPLTTLEQGD KVGVPAMSTL GSSSSQPHPE  900
PEDQVETQGT SGASVPPHQS SPLGKPAVPP GTPTAASVGE SASVSSGEPT VPWDPSSTLL  960
PVTLGIEDFE LEVLAGSPGV ESFWEEVASG EEPALPGTPM NAGAEEVHSD PCENNPCLHG  1020
GTCNANGTMY GCSCDQGFAG ENCEIDIDDC LCSPCENGGT CIDEVNGFVC LCLPSYGGSF  1080
CEKDTEGCDR GWHKFQGHCY RYFAHRRAWE DAEKDCRRRS GHLTSVHSPE EHSFINSFGH  1140
ENTWIGLNDR IVERDFQWTD NTGLQFENWR ENQPDNFFAG GEDCVVMVAH ESGRWNDVPC  1200
NYNLPYVCKK GTVLCGPPPA VENASLIGAR KAKYNVHATV RYQCNEGFAQ HHVATIRCRS  1260
NGKWDRPQIV CTKPRRSHRM RRHHHHHQHH HQHHHHKSRK ERRKHKKHPT EDWEKDEGNF  1320
C                                                                 1321

SEQ ID NO: 135         moltype = AA  length = 911
FEATURE                Location/Qualifiers
source                 1..911
                       mol_type = protein
```

```
                        organism = Homo sapiens
SEQUENCE: 135
MAQLFLPLLA ALVLAQAPAA LADVLEGDSS EDRAFRVRIA GDAPLQGVLG GALTIPCHVH  60
YLRPPPSRRA VLGSPRVKWT FLSRGREAEV LVARGVRVKV NEAYRFRVAL PAYPASLTDV  120
SLALSELRPN DSGIYRCEVQ HGIDDSSDAV EVKVKGVVFL YREGSARYAF SFSGAQEACA  180
RIGAHIATPE QLYAAYLGGY EQCDAGWLSD QTVRYPIQTP REACYGDMDG FPGVRNYGVV  240
DPDDLYDVYC YAEDLNGELF LGDPPEKLTL EEARAYCQER GAEIATTGQL YAAWDGGLDH  300
CSPGWLADGS VRYPIVTPSQ RCGGGLPGVK TLFLFPNQTG FPNKHSRFNV YCFRDSAQPS  360
AIPEASNPAS NPASDGLEAI VTVTETLEEL QLPQEATESE SRGAIYSIPI MEDGGGGSST  420
PEDPAEAPRT LLEFETQSMV PPTGFSEEEG KALEEEEKYE DEEEKEEEEE EEEVEDEALW  480
AWPSELSSPG PEASLPTEPA AQEESLSQAP ARAVLQPGAS PLPDGESEAS RPPRVHGPPT  540
ETLPTPRERN LASPSPSTLV EAREVGEATG GPELSGVPRG ESEETGSSEG APSLLPATRA  600
PEGTRELEAP SEDNSGRTAP AGTSVQAQPV LPTDSASRGG VAVVPASGDC VPSPCHNGGT  660
CLEEEEGVRC LCLPGYGGDL CDVGLRFCNP GWDAFQGACY KHFSTRRSWE EAETQCRMYG  720
AHLASISTPE EQDFINNRYR EYQWIGLNDR TIEGDFLWSD GVPLLYENWN PGQPDSYFLS  780
GENCVVMVWH DQGQWSDVPC NYHLSYTCKM GLVSCGPPPE LPLAQVFGRP RLRYEVDTVL  840
RYRCREGLAQ RNLPLIRCQE NGRWEAPQIS CVPRRPARAL HPEEDPEGRQ GRLLGRWKAL  900
LIPPSSPMPG P                                                      911

SEQ ID NO: 136          moltype = AA  length = 115
FEATURE                 Location/Qualifiers
REGION                  1..115
                        note = Nanobody Sequence
source                  1..115
                        mol_type = protein
                        organism = synthetic construct
SEQUENCE: 136
EVQLVESGGG LVQPGNSLRL SCAASGFTFS SFGMSWVRQA PGKGLEWVSS ISGSGSDTLY  60
ADSVKGRFTI SRDNAKTTLY LQMNSLRPED TAVYYCTIGG SLSRSSQGTL VTVSS       115

SEQ ID NO: 137          moltype = AA  length = 115
FEATURE                 Location/Qualifiers
REGION                  1..115
                        note = Nanobody Sequence
source                  1..115
                        mol_type = protein
                        organism = synthetic construct
SEQUENCE: 137
EVQLLESGGG LVQPGGSLRL SCAASGFTFR SFGMSWVRQA PGKGPEWVSS ISGSGSDTLY  60
ADSVKGRFTI SRDNSKNTLY LQMNSLRPED TAVYYCTIGG SLSRSSQGTL VTVSS       115

SEQ ID NO: 138          moltype = AA  length = 116
FEATURE                 Location/Qualifiers
REGION                  1..116
                        note = Nanobody Sequence
source                  1..116
                        mol_type = protein
                        organism = synthetic construct
SEQUENCE: 138
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TATYYCTIGG SLSRSSQGTL VTVSSA      116

SEQ ID NO: 139          moltype = AA  length = 116
FEATURE                 Location/Qualifiers
REGION                  1..116
                        note = Nanobody Sequence
source                  1..116
                        mol_type = protein
                        organism = synthetic construct
SEQUENCE: 139
EVQLVESGGG VVQPGGSLRL SCAASGFTFR SFGMSWVRQA PGKGPEWVSS ISGSGSDTLY  60
ADSVKGRFTI SRDNSKNTLY LQMNSLRPED TATYYCTIGG SLSRSSQGTL VTVSSA      116

SEQ ID NO: 140          moltype = AA  length = 115
FEATURE                 Location/Qualifiers
REGION                  1..115
                        note = Nanobody Sequence
source                  1..115
                        mol_type = protein
                        organism = synthetic construct
SEQUENCE: 140
EVQLVESGGG LVQPGNSLRL SCAASGFTFS SFGMSWVRQA PGKGLEWVSS ISGSGSDTLY  60
ADSVKGRFTI SRDNAKTTLY LQMNSLRPED TAVYYCTIGG SLSRSSQGTL VTVSS       115

SEQ ID NO: 141          moltype = AA  length = 116
FEATURE                 Location/Qualifiers
REGION                  1..116
                        note = Nanobody Sequence
source                  1..116
```

```
                        mol_type = protein
                        organism = synthetic construct
SEQUENCE: 141
EVQLVESGGG LVQPGNSLRL SCAASGFTFS SFGMSWVRQA PGKGLEWVSS ISGSGSDTLY  60
ADSVKGRFTI SRDNAKTTLY LQMNSLRPED TAVYYCTIGG SLSRSSQGTL VKVSSA      116

SEQ ID NO: 142          moltype = AA  length = 115
FEATURE                 Location/Qualifiers
REGION                  1..115
                        note = Nanobody Sequence
source                  1..115
                        mol_type = protein
                        organism = synthetic construct
SEQUENCE: 142
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSS       115

SEQ ID NO: 143          moltype = AA  length = 116
FEATURE                 Location/Qualifiers
REGION                  1..116
                        note = Nanobody Sequence
source                  1..116
                        mol_type = protein
                        organism = synthetic construct
SEQUENCE: 143
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSSA      116

SEQ ID NO: 144          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 144
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSSAA     117

SEQ ID NO: 145          moltype = AA  length = 118
FEATURE                 Location/Qualifiers
REGION                  1..118
                        note = Nanobody Sequence
source                  1..118
                        mol_type = protein
                        organism = synthetic construct
SEQUENCE: 145
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSSAAA    118

SEQ ID NO: 146          moltype = AA  length = 116
FEATURE                 Location/Qualifiers
REGION                  1..116
                        note = Nanobody Sequence
source                  1..116
                        mol_type = protein
                        organism = synthetic construct
SEQUENCE: 146
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSSG      116

SEQ ID NO: 147          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 147
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSSGG     117

SEQ ID NO: 148          moltype = AA  length = 118
FEATURE                 Location/Qualifiers
REGION                  1..118
                        note = Nanobody Sequence
source                  1..118
                        mol_type = protein
                        organism = synthetic construct
```

```
SEQUENCE: 148
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSSGGG    118

SEQ ID NO: 149         moltype = AA  length = 115
FEATURE                Location/Qualifiers
REGION                 1..115
                       note = Nanobody Sequence
source                 1..115
                       mol_type = protein
                       organism = synthetic construct
SEQUENCE: 149
EVQLVESGGG VVQPGGSLRL SCAASGFTFR SFGMSWVRQA PGKGPEWVSS ISGSGSDTLY  60
ADSVKGRFTI SRDNSKNTLY LQMNSLRPED TALYYCTIGG SLSRSSQGTL VTVSS       115

SEQ ID NO: 150         moltype = AA  length = 116
FEATURE                Location/Qualifiers
REGION                 1..116
                       note = Nanobody Sequence
source                 1..116
                       mol_type = protein
                       organism = synthetic construct
SEQUENCE: 150
EVQLVESGGG VVQPGGSLRL SCAASGFTFR SFGMSWVRQA PGKGPEWVSS ISGSGSDTLY  60
ADSVKGRFTI SRDNSKNTLY LQMNSLRPED TALYYCTIGG SLSRSSQGTL VTVSSA      116

SEQ ID NO: 151         moltype = AA  length = 5
FEATURE                Location/Qualifiers
REGION                 1..5
                       note = Nanobody Sequence
source                 1..5
                       mol_type = protein
                       organism = synthetic construct
SEQUENCE: 151
SFGMS                                                              5

SEQ ID NO: 152         moltype = AA  length = 17
FEATURE                Location/Qualifiers
REGION                 1..17
                       note = Nanobody Sequence
source                 1..17
                       mol_type = protein
                       organism = synthetic construct
SEQUENCE: 152
SISGSGSDTL YADSVKG                                                 17

SEQ ID NO: 153         moltype = AA  length = 6
FEATURE                Location/Qualifiers
REGION                 1..6
                       note = Nanobody Sequence
source                 1..6
                       mol_type = protein
                       organism = synthetic construct
SEQUENCE: 153
GGSLSR                                                             6

SEQ ID NO: 154         moltype =   length =
SEQUENCE: 154
000

SEQ ID NO: 155         moltype = AA  length = 5
FEATURE                Location/Qualifiers
REGION                 1..5
                       note = Linker Sequence
source                 1..5
                       mol_type = protein
                       organism = synthetic construct
SEQUENCE: 155
GGGGS                                                              5

SEQ ID NO: 156         moltype = AA  length = 7
FEATURE                Location/Qualifiers
REGION                 1..7
                       note = Linker Sequence
source                 1..7
                       mol_type = protein
                       organism = synthetic construct
SEQUENCE: 156
SGGSGGS                                                            7
```

```
SEQ ID NO: 157          moltype = AA  length = 8
FEATURE                 Location/Qualifiers
REGION                  1..8
                        note = Linker Sequence
source                  1..8
                        mol_type = protein
                        organism = synthetic construct
SEQUENCE: 157
GGGGGGGS                                                        8

SEQ ID NO: 158          moltype = AA  length = 9
FEATURE                 Location/Qualifiers
REGION                  1..9
                        note = Linker Sequence
source                  1..9
                        mol_type = protein
                        organism = synthetic construct
SEQUENCE: 158
GGGGSGGGS                                                       9

SEQ ID NO: 159          moltype = AA  length = 10
FEATURE                 Location/Qualifiers
REGION                  1..10
                        note = Linker Sequence
source                  1..10
                        mol_type = protein
                        organism = synthetic construct
SEQUENCE: 159
GGGGSGGGGS                                                      10

SEQ ID NO: 160          moltype = AA  length = 15
FEATURE                 Location/Qualifiers
REGION                  1..15
                        note = Linker Sequence
source                  1..15
                        mol_type = protein
                        organism = synthetic construct
SEQUENCE: 160
GGGGSGGGGS GGGGS                                                15

SEQ ID NO: 161          moltype = AA  length = 18
FEATURE                 Location/Qualifiers
REGION                  1..18
                        note = Linker Sequence
source                  1..18
                        mol_type = protein
                        organism = synthetic construct
SEQUENCE: 161
GGGGSGGGGS GGGGGGGS                                             18

SEQ ID NO: 162          moltype = AA  length = 20
FEATURE                 Location/Qualifiers
REGION                  1..20
                        note = Linker Sequence
source                  1..20
                        mol_type = protein
                        organism = synthetic construct
SEQUENCE: 162
GGGGSGGGGS GGGGSGGGGS                                           20

SEQ ID NO: 163          moltype = AA  length = 25
FEATURE                 Location/Qualifiers
REGION                  1..25
                        note = Linker Sequence
source                  1..25
                        mol_type = protein
                        organism = synthetic construct
SEQUENCE: 163
GGGGSGGGGS GGGGSGGGGS GGGGS                                     25

SEQ ID NO: 164          moltype = AA  length = 30
FEATURE                 Location/Qualifiers
REGION                  1..30
                        note = Linker Sequence
source                  1..30
                        mol_type = protein
                        organism = synthetic construct
SEQUENCE: 164
```

```
GGGGSGGGGS GGGGSGGGGS GGGGSGGGGS                                  30

SEQ ID NO: 165          moltype = AA  length = 35
FEATURE                 Location/Qualifiers
REGION                  1..35
                        note = Linker Sequence
source                  1..35
                        mol_type = protein
                        organism = synthetic construct
SEQUENCE: 165
GGGGSGGGGS GGGGSGGGGS GGGGSGGGGS GGGGS                            35

SEQ ID NO: 166          moltype = AA  length = 40
FEATURE                 Location/Qualifiers
REGION                  1..40
                        note = Linker Sequence
source                  1..40
                        mol_type = protein
                        organism = synthetic construct
SEQUENCE: 166
GGGGSGGGGS GGGGSGGGGS GGGGSGGGGS GGGGSGGGGS                       40

SEQ ID NO: 167          moltype = AA  length = 15
FEATURE                 Location/Qualifiers
REGION                  1..15
                        note = Linker Sequence
source                  1..15
                        mol_type = protein
                        organism = synthetic construct
SEQUENCE: 167
EPKSCDKTHT CPPCP                                                  15

SEQ ID NO: 168          moltype = AA  length = 24
FEATURE                 Location/Qualifiers
REGION                  1..24
                        note = Linker Sequence
source                  1..24
                        mol_type = protein
                        organism = synthetic construct
SEQUENCE: 168
GGGGSGGGSE PKSCDKTHTC PPCP                                        24

SEQ ID NO: 169          moltype = AA  length = 12
FEATURE                 Location/Qualifiers
REGION                  1..12
                        note = Linker Sequence
source                  1..12
                        mol_type = protein
                        organism = synthetic construct
SEQUENCE: 169
EPKTPKPQPA AA                                                     12

SEQ ID NO: 170          moltype = AA  length = 62
FEATURE                 Location/Qualifiers
REGION                  1..62
                        note = Linker Sequence
source                  1..62
                        mol_type = protein
                        organism = synthetic construct
SEQUENCE: 170
ELKTPLGDTT HTCPRCPEPK SCDTPPPCPR CPEPKSCDTP PPCPRCPEPK SCDTPPPCPR  60
CP                                                                62

SEQ ID NO: 171          moltype = AA  length = 116
FEATURE                 Location/Qualifiers
REGION                  1..116
                        note = Nanobody Sequence
source                  1..116
                        mol_type = protein
                        organism = synthetic construct
```

-continued

```
SEQUENCE: 171
EVQLVESGGG LVQPGNSLRL SCAASGFTFS SFGMSWVRQA PGKGLEWVSS ISGSGSDTLY  60
ADSVKGRFTI SRDNAKTTLY LQMNSLRPED TAVYYCTIGG SLSRSSQGTL VTVKSA      116

SEQ ID NO: 172         moltype = AA  length = 17
FEATURE                Location/Qualifiers
REGION                 1..17
                       note = myc tag
source                 1..17
                       mol_type = protein
                       organism = synthetic construct
SEQUENCE: 172
AAAEQKLISE EDLNGAA                                                 17
```